United States Patent
Bartels et al.

(10) Patent No.: US 9,540,397 B2
(45) Date of Patent: Jan. 10, 2017

(54) BACE1 INHIBITORS

(71) Applicant: Hoffmann-La Roche Inc., Little Falls, NJ (US)

(72) Inventors: Bjoern Bartels, Schopfheim (DE); Philipp Cueni, Therwil (CH); Cosimo Dolente, Allschwil (CH); Wolfgang Guba, Muellheim (DE); Wolfgang Haap, Loerrach (DE); Andreas Kuglstatter, Loerrach (DE); Ulrike Obst Sander, Reinach BL (CH); Jens-Uwe Peters, Grenzach-Wyhlen (DE); Mark Rogers-Evans, Bottmingen (CH); Walter Vifian, Gelterkinden (CH); Thomas Woltering, Freiburg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/877,250

(22) Filed: Oct. 7, 2015

(65) Prior Publication Data

US 2016/0102105 A1 Apr. 14, 2016

(30) Foreign Application Priority Data

Oct. 10, 2014 (EP) .................................... 14188412

(51) Int. Cl.
*C07D 513/04* (2006.01)
*C07D 519/00* (2006.01)

(52) U.S. Cl.
CPC ........... *C07D 513/04* (2013.01); *C07D 519/00* (2013.01)

(58) Field of Classification Search
CPC ........................... C07D 513/04; C07D 519/00
USPC .............................. 544/48; 514/224.2, 226.5
See application file for complete search history.

(56) References Cited

FOREIGN PATENT DOCUMENTS

DE WO 2009103626 A1 * 8/2009 ........... C07D 263/28

* cited by examiner

*Primary Examiner* — Kahsay Habte

(57) ABSTRACT

The present invention provides a compound of formula I, having BACE1 inhibitory activity, their manufacture, pharmaceutical compositions containing them and their use as therapeutically active substances. The active compounds of the present invention are useful in the therapeutic and/or prophylactic treatment of e.g. Alzheimer's disease.

24 Claims, No Drawings

BACE1 INHIBITORS

CROSS-REFERENCE TO RELATED APPLICATIONS

This application claims priority to European Patent Application No. 14188412.2 filed on Oct. 10, 2014, which is incorporated by reference in its entirety herein.

BACKGROUND

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 Jul. 19; 297(5580):353-6, Selkoe, Cell biology of the amyloid beta-protein precursor and the mechanism of Alzheimer's disease, *Annu Rev Cell Biol*. 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFP). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 Oct. 22; 286(5440). 735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci*. 2001 March; 4(3):231-2, Roberds et al., BACE knock-out mice are healthy despite lacking the primary beta-secretase activity in brain: implications for Alzheimer's disease therapeutics, *Hum Mol Genet*. 2001 Jun. 1; 10(12): 1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem*. 2007 Sep. 7; 282(36): 26326). It is thus presumed that inhibitors of BACE1 activity can be useful agents for therapeutic intervention in Alzheimer's disease (AD). Several patent applications have been filed describing BACE 1 inhibitors of various structures, e.g. WO2009103626, WO2010128058, WO2011020806, WO2011029803, WO2011069934, WO2011070029, WO2011138293, WO2012019966, WO2012028563, WO2012098064, WO2012104263, WO2012107371, WO2012110459, WO2012119883, WO2012126791, WO2012136603, WO2012139993, WO2012156284, WO2012163790, WO2012168164, WO2012168175, WO2013004676, WO2013041499, WO2013110622, WO2013174781, WO2014001228, WO2014114532, WO2014150331, WO2014150340, WO2014059185 and WO2014150344.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

The present invention provides novel compounds of formula I, their manufacture, medicaments based on a compound in accordance with the invention and their production as well as the use of compounds of formula I in the control or prevention of illnesses such as Alzheimer's disease.

FIELD OF THE INVENTION

The present invention provides S-imino S-oxo iminothiazines having BACE1 inhibitory properties, their manufacture, pharmaceutical compositions containing them and their use as therapeutically active substances.

SUMMARY OF THE INVENTION

The present invention provides a compound of formula I,

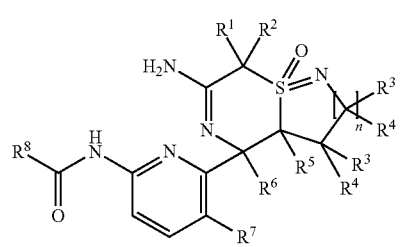

I wherein the substituents and variables are as described below and in the claims, or a pharmaceutically acceptable salt thereof.

The present compounds have Asp2 (β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or β-amyloid plaques and further deposits, particularly Alzheimer's disease.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with inhibition of BACE1, such as Alzheimer's disease. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methylpropyl), 1,2-dimethyl-propyl and the like. Particular "$C_{1-6}$-alkyl" are "$C_{1-3}$-alkyl". Specific groups are methyl and ethyl. Most specific group is methyl.

The term "halogen-$C_{1-6}$-alkyl" or "$C_{1-6}$-alkyl-halogen", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like. A specific group is fluoromethyl.

The term "cyano", alone or in combination with other groups, refers to N≡C—(NC—).

The term "halogen", alone or in combination with other groups, denotes chloro (Cl), iodo (I), fluoro (F) and bromo (Br). Particular "halogen" are Cl, I and F. A specific group is F.

The term "heteroaryl", alone or in combination with other groups, refers to an aromatic carbocyclic group of having a single 4 to 8 membered ring, in particular 5 to 8, or multiple condensed rings comprising 6 to 14, in particular 6 to 10 ring atoms and containing 1, 2 or 3 heteroatoms individually selected from N, O and S, in particular 1N or 2N, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl (pyridyl), pyrimidinyl (pyrimidyl), pyrrolyl, quinolinyl, tetrazolyl, thiazolyl, thienyl, triazolyl, 6,7-dihydro-5H-[1]pyrindinyl and the like. Particular "heteroaryl" groups are pyridyl, pyrazinyl and imidazo[1,2-a]pyridinyl.

The term "aryl" denotes a monovalent aromatic carbocyclic mono- or bicyclic ring system comprising 6 to 10 carbon ring atoms. Examples of aryl moieties include phenyl and naphthyl. Particular "aryl" is phenyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. A specific acid is trifluoroacetic acid.

The term "amino", alone or in combination with other groups, refers to —$NH_2$.

The terms "hydroxyl" or "hydroxyl", alone or in combination with other groups, refer to —OH.

The term "$C_{2-6}$-alkynyl-$C_{1-6}$-alkoxy", alone or in combination with other groups, refers to $C_{1-6}$-alkoxy as defined herein, which is substituted by one or multiple $C_{2-6}$-alkynyl as defined herein, in particular 1 $C_{2-6}$-alkynyl.

The term "$C_{2-6}$-alkynyl", alone or in combination with other groups, denotes a monovalent linear or branched saturated hydrocarbon group of 2 to 6 carbon atoms, in particular from 2 to 4 carbon atoms, and comprising one, two or three triple bonds. Examples of $C_{2-6}$-alkynyl include ethynyl, propynyl, and n-butynyl.

The term "$C_{1-6}$-alkoxy-$C_{1-6}$-alkyl", alone or in combination with other groups, refers to $C_{1-6}$-alkyl as defined herein, which is substituted by one or multiple $C_{1-6}$-alkoxy, as defined herein, particularly 1 $C_{1-6}$-alkoxy. Particular "$C_{1-6}$-alkoxy-$C_{1-6}$-alkyl" is methoxy-$C_{1-6}$-alkyl. Examples are methoxymethyl, methoxyethyl and the like.

The term "$C_{3-6}$-cycloalkyl" refers to a 3 to 8 membered carbon ring, for example cyclopropyl, cyclobutyl, cyclopentyl, cyclohexyl, cycloheptyl or cyclooctyl. Particular are cycloalkyl groups having a 3, 4, 5 or 6 membered carbon ring. Specific is cyclopropyl.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. Specific are ethoxy and methoxy.

The term "halogen-$C_{1-6}$-alkoxy", alone or in combination with other groups, refers to $C_{1-6}$-alkoxy as defined herein, which is substituted by one or multiple halogens, in particular fluoro. Particular "halogen-$C_{1-6}$-alkoxy" are fluoro-$C_{1-6}$-alkoxy. Specific "halogen-$C_{1-6}$-alkoxy" are $CHF_2$—$CF_2$—$CH_2$—O—, $CHF_2$—O— and $CF_2$—O—.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-\log Ki$), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught and A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

One embodiment of the invention provides a compound of formula I,

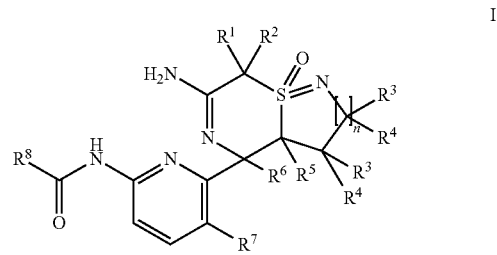

wherein
n is 1, 2 or 3;
$R^1$ is selected from the group consisting of
  i) $C_{1-6}$-alkyl and
  ii) halogen-$C_{1-6}$-alkyl;
$R^2$ is selected from the group consisting of
  i) $C_{1-6}$-alkyl, and
  ii) halogen-$C_{1-6}$-alkyl;
or $R^1$ and $R^2$ form together with the C-atom they are attached to, a $C_{3-6}$-cycloalkyl-, wherein the $C_{3-6}$-cycloalkyl- is optionally substituted by one or more substituents selected from the group consisting of halogen and hydroxyl;
$R^3$ is each independently selected from the group consisting of
  i) hydrogen,
  ii) $C_{1-6}$-alkyl, and
  iii) halogen;
$R^4$ is each independently selected from the group consisting of
  i) hydrogen,
  ii) $C_{1-6}$-alkyl, and
  iii) halogen;
or wherein $R^3$ and $R^4$ together are —$(CH_2)_m$—, wherein m is 2, 3, 4 or 5,
$R^5$ is hydrogen.
$R^6$ is selected from the group consisting of
  i) $C_{1-6}$-alkyl, and
  ii) halogen-$C_{1-6}$-alkyl;
$R^7$ is selected from the group consisting of
  i) hydrogen, and
  ii) halogen;
$R^8$ is selected from the group consisting of
  i) aryl,
  ii) aryl substituted by 1-4 substituents individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, $COOR^9$, wherein $R^9$ is H or $C_{1-6}$-alkyl, CONR$^{10}$R$^{11}$, wherein R$^{10}$ is H or C$_{1-6}$-alkyl C$_{3-6}$-cycloalkyl and R$^{11}$ is H or C$_{1-6}$-alkyl, C$_{3-6}$-cycloalkyl that is optionally substituted by 1 to 4 substituents individually selected from the group consisting of halogen, cyano, C$_{1-6}$-alkyl and C$_{1-6}$-alkoxy, C$_{3-6}$-cycloalkyl-C$_{1-6}$-alkoxy and C$_{3-6}$-cycloalkyl-C$_{1-6}$-alkoxy, wherein the cycloalkyl unit is substituted by 1 to 4 substituents individually selected from the group consisting of halogen, cyano, C$_{1-6}$-alkyl and C$_{1-6}$-alkoxy;
iii) heteroaryl, and
iv) heteroaryl substituted by 1-4 substituents individually selected from amino, cyano, halogen, halogen-C$_{1-6}$-alkyl, halogen-C$_{1-6}$-alkoxy, C$_{1-6}$-alkoxy, C$_{1-6}$-alkoxy-C$_{1-6}$-alkyl, C$_{2-6}$-alkynyl-C$_{1-6}$-alkoxy, C$_{2-6}$-alkynyl, C$_{1-6}$-alkyl, COOR$^9$, wherein R$^9$ is H or C$_{1-6}$-alkyl, CONR$^{10}$R$^{11}$, wherein R$^{10}$ is H or C$_{1-6}$-alkyl C$_{3-6}$-cycloalkyl and R$^{11}$ is H or C$_{1-6}$-alkyl, C$_{3-6}$-cycloalkyl that is optionally substituted by 1 to 4 substituents individually selected from the group consisting of halogen, cyano, C$_{1-6}$-alkyl and C$_{1-6}$-alkoxy, C$_{3-6}$-cycloalkyl-C$_{1-6}$-alkoxy and C$_{3-6}$-cycloalkyl-C$_{1-6}$-alkoxy, wherein the cycloalkyl unit is substituted by 1 to 4 substituents individually selected from the group consisting of halogen, cyano, C$_{1-6}$-alkyl and C$_{1-6}$-alkoxy;
or pharmaceutically acceptable salts thereof.

A certain embodiment of the invention provides a compound of formula I as described herein, wherein
n is 1, 2 or 3;
R$^1$ is selected from the group consisting of
  i) C$_{1-6}$-alkyl and
  ii) halogen-C$_{1-6}$-alkyl;
R$^2$ is selected from the group consisting of
  i) C$_{1-6}$-alkyl, and
  ii) halogen-C$_{1-6}$-alkyl;
or R$^1$ and R$^2$ form together with the C-atom they are attached to, a C$_{3-6}$-cycloalkyl-, wherein the C$_{3-6}$-cycloalkyl- is optionally substituted by one or more substituents selected from the group consisting of halogen and hydroxyl;
R$^3$ is each independently selected from the group consisting of
  i) hydrogen,
  ii) C$_{1-6}$-alkyl, and
  iii) halogen;
R$^4$ is each independently selected from the group consisting of
  i) hydrogen,
  ii) C$_{1-6}$-alkyl, and
  iii) halogen;
R$^5$ is hydrogen.
R$^6$ is selected from the group consisting of
  i) C$_{1-6}$-alkyl, and
  ii) halogen-C$_{1-6}$-alkyl;
R$^7$ is selected from the group consisting of
  i) hydrogen, and
  ii) halogen;
R$^8$ is selected from the group consisting of
  i) aryl,
  ii) aryl substituted by 1-4 substituents individually selected from amino, cyano, halogen, halogen-C$_{1-6}$-alkyl, halogen-C$_{1-6}$-alkoxy, C$_{1-6}$-alkoxy, C$_{1-6}$-alkoxy-C$_{1-6}$-alkyl, C$_{2-6}$-alynyl-C$_{1-6}$-alkoxy, C$_{2-6}$-alkynyl, C$_{1-6}$-alkyl, C$_{3-6}$-cycloalkyl, C$_{3-6}$-cycloalkyl that is optionally substituted by 1 to 4 substituents individually selected from the group consisting of halogen, cyano, C$_{1-6}$-alkyl and C$_{1-6}$-alkoxy, C$_{3-6}$-cycloalkyl-C$_{1-6}$-alkoxy and C$_{3-6}$-cycloalkyl-C$_{1-6}$-alkoxy, wherein the cycloalkyl unit is substituted by 1 to 4 substituents individually selected from the group consisting of halogen, cyano, C$_{1-6}$-alkyl and C$_{1-6}$-alkoxy;
iii) heteroaryl, and
iv) heteroaryl substituted by 1-4 substituents individually selected from amino, cyano, halogen, halogen-C$_{1-6}$-alkyl, halogen-C$_{1-6}$-alkoxy, C$_{1-6}$-alkoxy, C$_{1-6}$-alkoxy-C$_{1-6}$-alkyl, C$_{2-6}$-alkynyl-C$_{1-6}$-alkoxy, C$_{2-6}$-alkynyl, C$_{1-6}$-alkyl, C$_{3-6}$-cycloalkyl, C$_{3-6}$-cycloalkyl that is optionally substituted by 1 to 4 substituents individually selected from the group consisting of halogen, cyano, C$_{1-6}$-alkyl and C$_{1-6}$-alkoxy, C$_{3-6}$-cycloalkyl-C$_{1-6}$-alkoxy and C$_{3-6}$-cycloalkyl-C$_{1-6}$-alkoxy, wherein the cycloalkyl unit is substituted by 1 to 4 substituents individually selected from the group consisting of halogen, cyano, C$_{1-6}$-alkyl and C$_{1-6}$-alkoxy;
or pharmaceutically acceptable salts thereof.

A certain embodiment of the invention provides a compound of formula I as described herein, wherein n, R$^1$, R$^2$, R$^3$, R$^4$, R$^5$, R$^6$, R$^7$ and R$^8$ are as described herein and when n=1, then the ring configuration is cis.

A certain embodiment of the invention provides a compound of formula I as described herein, which is of formula Ia, wherein n, R$^1$, R$^2$, R$^3$, R$^4$, R$^5$, R$^6$, R$^7$ and R$^8$ are as described in as described herein Ia A certain embodiment of the invention provides a compound of formula I as described herein, wherein R$^1$ is methyl.

A certain embodiment of the invention provides a compound of formula I as described herein, wherein R$^2$ is methyl.

A certain embodiment of the invention provides a compound of formula I as described herein, wherein R$^3$ is hydrogen.

A certain embodiment of the invention provides a compound of formula I as described herein, wherein R$^4$ is hydrogen.

A certain embodiment of the invention provides a compound of formula I as described herein, wherein R$^3$ and R$^4$ together are —(CH$_2$)$_2$—.

A certain embodiment of the invention provides a compound of formula I as described herein, wherein R$^5$ is hydrogen.

A certain embodiment of the invention provides a compound of formula I as described herein, wherein R$^6$ is methyl.

A certain embodiment of the invention provides a compound of formula I as described herein, wherein R$^7$ is F.

A certain embodiment of the invention provides a compound of formula I as described herein, wherein R$^8$ is aryl substituted by 1-2 substituents individually selected from cyano and halogen.

A certain embodiment of the invention provides a compound of formula I as described herein, wherein R$^8$ is phenyl substituted by 1-2 substituents individually selected from cyano and Cl.

A certain embodiment of the invention provides a compound of formula I as described herein, wherein $R^8$ is heteroaryl, substituted by 1-2 substituents individually selected from cyano, halogen, halogen-$C_{1-6}$-alkoxy, halogen-$C_{1-6}$-alkyl, $C_{1-6}$-alkoxy, $C_{2-6}$-alkylnyl and $C_{1-6}$-alkyl.

A certain embodiment of the invention provides a compound of formula I as described herein, wherein $R^8$ is heteroaryl, substituted by 1-2 substituents individually selected from cyano, halogen, halogen-$C_{1-6}$-alkoxy, $C_{1-6}$-alkoxy and $C_{1-6}$-alkyl.

A certain embodiment of the invention provides a compound of formula I as described herein, wherein $R^8$ is 1H-pyrazolyl, pyridinyl, pyrazinyl or imidazo[1,2-a]pyridinyl, substituted by 1-2 substituents individually selected from cyano, halogen, halogen-$C_{1-6}$-alkoxy, halogen-$C_{1-6}$-alkyl, $C_{1-6}$-alkoxy, $C_{2-6}$-alkylnyl and $C_{1-6}$-alkyl A certain embodiment of the invention provides a compound of formula I as described herein, wherein $R^8$ is pyridinyl, pyrazinyl or imidazo[1,2-a]pyridinyl, each substituted by 1-2 substituents individually selected from cyano, halogen, halogen-$C_{1-6}$-alkoxy, $C_{1-6}$-alkoxy and $C_{1-6}$-alkyl.

A certain embodiment of the invention provides a compound of formula I as described herein wherein n is 1 or 2.

A certain embodiment of the invention provides a compound of formula I as described herein wherein n is 1 or 2, $R^1$ is methyl, $R^2$ is methyl, $R^3$ at each occurrence is H, $R^4$ at each occurrence is H, $R^5$ is H, $R^6$ is methyl and $R^7$ is F.

A certain embodiment of the invention provides a compound of formula I as described herein that is selected from the group consisting of N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-(difluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3,5-dichloropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-4-cyanobenzamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-2-chloro-4-cyanobenzamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-cyanopicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)-picolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-fluoropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-chloro-3-methylpicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-chloropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-(difluoromethoxy)-picolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2-difluoroethoxy)pyrazine-2-carboxamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(prop-1-yn-1-yl)picolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-6-chloro-3-methylimidazo[1,2-a]pyridine-2-carboxamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aR,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-6-chloro-3-methylimidazo[1,2-a]
pyridine-2-carboxamide,
N-(6-((4aR,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(difluoromethoxy)picolinamide,
N-(6-((4aR,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(2,2,3,3-tetrafluoropropoxy)picolinamide,
N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-cyano-3-methylpicolinamide,
N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-methoxypyrazine-2-carboxamide,
N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-3,5-dichloropicolinamide,
N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-fluoro-3-methylpicolinamide,
N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-3-chloro-5-cyanopicolinamide,
N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-6-chloro-3-methylimidazo[1,2-a]
pyridine-2-carboxamide,
N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(difluoromethoxy)picolinamide,
N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(2,2,3,3-tetrafluoropropoxy)picolinamide,
N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-cyano-3-methylpicolinamide,
N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-methoxypyrazine-2-carboxamide,
N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-3,5-dichloropicolinamide,
N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-fluoro-3-methylpicolinamide,
N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-3-chloro-5-cyanopicolinamide,
N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-6-chloro-3-methylimidazo[1,2-a]
pyridine-2-carboxamide,
N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(difluoromethoxy)picolinamide,
N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(2,2,3,3-tetrafluoropropoxy)picolinamide,
N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-cyano-3-methylpicolinamide,
N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-fluoro-3-methylpicolinamide,
N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-3-chloro-5-fluoropicolinamide,
N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-chloro-3-methylpicolinamide,
N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-(fluoromethoxy)picolinamide,
N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-(difluoromethoxy)picolinamide,
N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide,
N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-methoxypyrazine-2-carboxamide,
N-(6-((5aR,6R,10S)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-cyano-3-methylpicolinamide,
N-(6-((5aR,6R,10S)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-fluoro-3-methylpicolinamide,
N-(6-((5aR,6R,10S)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-3-chloro-5-fluoropicolinamide,
N-(6-((5aR,6R,10S)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-chloro-3-methylpicolinamide,
N-(6-((5aR,6R,10S)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-(fluoromethoxy)picolinamide,
N-(6-((5aR,6R,10S)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-(difluoromethoxy)picolinamide,
N-(6-((5aR,6R,10S)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide,
N-(6-((5aR,6R,10S)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((4aR,5R,9R)-7-amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-5-cyano-3-methylpicolinamide, N-(6-((4aS,5R,9R)-7-amino-5,8,8-trimethyl-9-oxido-4,4a,5,8-tetrahydro-2H-spiro[[1,4]-thiazino[2,1-f][1,2]thiazine-3,1'-cyclopropan]-5-yl)-5-fluoropyridin-2-yl)-5-cyano-3-methylpicolinamide, N-(6-((4aR,5R,9R)-7-amino-5,8,8-trimethyl-9-oxido-4,4a,5,8-tetrahydro-2H-spiro[[1,4]-thiazino[2,1-f][1,2]thiazine-3,1'-cyclopropan]-5-yl)-5-fluoropyridin-2-yl)-3-chloro-5-cyanopicolinamide, N-(6-((4aR,5R,9R)-7-amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-3-chloro-5-(difluoro-methoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-4-chloro-1-(difluoromethyl)-1H-pyrazole-3-carboxamide, and 6-((6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)carbamoyl)nicotinic acid, or pharmaceutically acceptable salts thereof.

A certain embodiment of the invention provides a compound of formula I as described herein that is selected from the group consisting of N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide, N-(6-((3aS,4R,5R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-(difluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3,5-dichloropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-4-cyanobenzamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-2-chloro-4-cyanobenzamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-cyanopicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)-picolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-fluoropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-chloro-3-methylpicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-chloropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-(difluoromethoxy)-picolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2-difluoroethoxy)pyrazine-2-carboxamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(prop-1-yn-1-yl)picolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-6-chloro-3-methylimidazo[1,2-a]pyridine-2-carboxamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aR,5R,9R)-7-amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-5-cyano-3-methylpicolinamide, N-(6-((4aS,5R,9R)-7-amino-5,8,8-trimethyl-9-oxido-4,4a,5,8-tetrahydro-2H-spiro[[1,4]-thiazino[2,1-f][1,2]thiazine-3,1'-cyclopropan]-5-yl)-5-fluoropyridin-2-yl)-5-cyano-3-methylpicolinamide, N-(6-((4aR,5R,9R)-7-amino-5,8,8-trimethyl-9-oxido-4,4a,5,8-tetrahydro-2H-spiro[[1,4]-thiazino[2,1-f][1,2]thiazine-3,1'-cyclopropan]-5-yl)-5-fluoropyridin-2-yl)-3-chloro-5-cyanopicolinamide, N-(6-((4aR,5R,9R)-7-amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-3-chloro-5-(difluoro-methoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-4-chloro-1-(difluoromethyl)-1H-pyrazole-3-carboxamide, and 6-((6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)carbamoyl)nicotinic acid, or pharmaceutically acceptable salts thereof.

A certain embodiment of the invention provides a compound of formula I as described herein that is selected from the group consisting of N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-7-chloro-3-methylimidazo[1,2-a]pyridine-2-carboxamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-7-chloro-3-methylimidazo[1,2-a]pyridine-2-carboxamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-7-chloro-3-methylimidazo[1,2-a]pyridine-2-carboxamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-7-chloro-3-methylimidazo[1,2-a]pyridine-2-carboxamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, N-(6-((4aR,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(2,2,3,3-tetrafluoropropoxy)picolinamide, N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(2,2,3,3-tetrafluoropropoxy)picolinamide, N-(6-((3aR,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-cyano-3-methylpicolinamide, N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-cyano-3-methylpicolinamide, N-(6-((3aR,4R,8S)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-cyano-3-methylpicolinamide, N-(6-((3aS,4R,8S)-6-amino-4,7,7-trimethyl-8-oxido-3,3a,4,
7-tetrahydro-2H-isothiazolo[1,5-a][1,4]thiazin-4-yl)-5-
fluoropyridin-2-yl)-5-cyano-3-methylpicolinamide, N-(6-((3aR,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-fluoro-3-methylpicolinamide, N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-fluoro-3-methylpicolinamide, N-(6-((3aR,4R,8S)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-fluoro-3-methylpicolinamide, N-(6-((3aS,4R,8S)-6-amino-4,7,7-trimethyl-8-oxido-3,3a,4,
7-tetrahydro-2H-isothiazolo[1,5-a][1,4]thiazin-4-yl)-5-
fluoropyridin-2-yl)-5-fluoro-3-methylpicolinamide, N-(6-((3aR,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-3-chloro-5-fluoropicolinamide, N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-3-chloro-5-fluoropicolinamide, N-(6-((3aR,4R,8S)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-3-chloro-5-fluoropicolinamide, N-(6-((3aS,4R,8S)-6-amino-4,7,7-trimethyl-8-oxido-3,3a,4,
7-tetrahydro-2H-isothiazolo[1,5-a][1,4]thiazin-4-yl)-5-
fluoropyridin-2-yl)-3-chloro-5-fluoropicolinamide, N-(6-((3aR,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-chloro-3-methylpicolinamide, N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-chloro-3-methylpicolinamide, N-(6-((3aR,4R,8S)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-chloro-3-methylpicolinamide, N-(6-((3aS,4R,8S)-6-amino-4,7,7-trimethyl-8-oxido-3,3a,4,
7-tetrahydro-2H-isothiazolo[1,5-a][1,4]thiazin-4-yl)-5-
fluoropyridin-2-yl)-5-chloro-3-methylpicolinamide, N-(6-((3aR,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-(fluoromethoxy)picolinamide, N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-(fluoromethoxy)picolinamide, N-(6-((3aR,4R,8S)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-(fluoromethoxy)picolinamide, N-(6-((3aS,4R,8S)-6-amino-4,7,7-trimethyl-8-oxido-3,3a,4,
7-tetrahydro-2H-isothiazolo[1,5-a][1,4]thiazin-4-yl)-5-
fluoropyridin-2-yl)-5-(fluoromethoxy)picolinamide, N-(6-((3aR,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-(difluoromethoxy)picolinamide, N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-(difluoromethoxy)picolinamide, N-(6-((3aR,4R,8S)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-(difluoromethoxy)picolinamide, N-(6-((3aS,4R,8S)-6-amino-4,7,7-trimethyl-8-oxido-3,3a,4,
7-tetrahydro-2H-isothiazolo[1,5-a][1,4]thiazin-4-yl)-5-
fluoropyridin-2-yl)-5-(difluoromethoxy)picolinamide, N-(6-((3aR,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-(2,2,3,3-tetrafluoropropoxy)picolinamide, N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-(2,2,3,3-tetrafluoropropoxy)picolinamide, N-(6-((3aR,4R,8S)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-(2,2,3,3-tetrafluoropropoxy)picolinamide, N-(6-((3aS,4R,8S)-6-amino-4,7,7-trimethyl-8-oxido-3,3a,4,
7-tetrahydro-2H-isothiazolo[1,5-a][1,4]thiazin-4-yl)-5-
fluoropyridin-2-yl)-5-(2,2,3,3-tetrafluoropropoxy)picolinamide, N-(6-((3aR,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-methoxypyrazine-2-carboxamide, N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-methoxypyrazine-2-carboxamide, N-(6-((3aR,4R,8S)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-methoxypyrazine-2-carboxamide, N-(6-((3aS,4R,8S)-6-amino-4,7,7-trimethyl-8-oxido-3,3a,4,
7-tetrahydro-2H-isothiazolo[1,5-a][1,4]thiazin-4-yl)-5-
fluoropyridin-2-yl)-5-methoxypyrazine-2-carboxamide, N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aS,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aR,6R,10S)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aS,6R,10S)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aS,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, and N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide or pharmaceutically acceptable salts thereof.

A certain embodiment of the invention provides a compound of formula I as described herein that is selected from the group consisting of N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aR,4R,8S)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-methoxypyrazine-2-carboxamide,
N-(6-((3aR,4R,8S)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-(difluoromethoxy)pyrazine-2-carboxamide,
N-(6-((3aR,4R,8S)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-fluoropicolinamide,
N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-cyano-3-methylpicolinamide,
N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-3-chloro-5-cyanopicolinamide,
N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-fluoro-3-methylpicolinamide,
N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-3-chloro-5-fluoropicolinamide,
N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-chloro-3-methylpicolinamide,
N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-(fluoromethoxy)picolinamide,
N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-(difluoromethoxy)picolinamide,
N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-(2,2,3,3-tetrafluoropropoxy)picolinamide,
N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-methoxypyrazine-2-carboxamide,
N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-(difluoromethoxy)pyrazine-2-carboxamide,
N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-5-fluoropicolinamide,
N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-3-chloro-5-(difluoromethoxy)picolinamide,
N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-3,5-dichloropicolinamide,
N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-4-cyanobenzamide,
N-(6-((3aS,4R,8R)-6-amino-4,7,7-trimethyl-8-oxido-3,3a,
4,7-tetrahydro-2H-isothiazolo[1,5-a][1,4]thiazin-4-yl)-5-
fluoropyridin-2-yl)-2-chloro-4-cyanobenzamide,
N-(6-((4aR,5R,9R)-7-amino-3,3-difluoro-5,8,8-trimethyl-9-
oxido-2,3,4,4a,5,8-hexahydro-[1,4]thiazino[2,1-f][1,2]
thiazin-5-yl)-5-fluoropyridin-2-yl)-5-cyano-3-methylpicolinamide,
N-(6-((4aR,5R,9R)-7-amino-3,3-difluoro-5,8,8-trimethyl-9-
oxido-2,3,4,4a,5,8-hexahydro-[1,4]thiazino[2,1-f][1,2]
thiazin-5-yl)-5-fluoropyridin-2-yl)-5-fluoropicolinamide,
N-(6-((4aR,5R,9R)-7-amino-3,3-difluoro-5,8,8-trimethyl-9-
oxido-2,3,4,4a,5,8-hexahydro-[1,4]thiazino[2,1-f][1,2]
thiazin-5-yl)-5-fluoropyridin-2-yl)-5-cyanopicolinamide,
N-(6-((4aR,5R,9R)-7-amino-3,3-difluoro-5,8,8-trimethyl-9-
oxido-2,3,4,4a,5,8-hexahydro-[1,4]thiazino[2,1-f][1,2]
thiazin-5-yl)-5-fluoropyridin-2-yl)-5-(difluoromethoxy)
picolinamide,
N-(6-((4aR,5R,9R)-7-amino-3,3-difluoro-5,8,8-trimethyl-9-
oxido-2,3,4,4a,5,8-hexahydro-[1,4]thiazino[2,1-f][1,2]
thiazin-5-yl)-5-fluoropyridin-2-yl)-5-(2,2,3,3-tetrafluoropropoxy)-picolinamide,
N-(6-((4aR,5R,9R)-7-amino-3,3-difluoro-5,8,8-trimethyl-9-
oxido-2,3,4,4a,5,8-hexahydro-[1,4]thiazino[2,1-f][1,2]
thiazin-5-yl)-5-fluoropyridin-2-yl)-3-chloro-5-cyanopicolinamide,
N-(6-((4aR,5R,9R)-7-amino-3,3-difluoro-5,8,8-trimethyl-9-
oxido-2,3,4,4a,5,8-hexahydro-[1,4]thiazino[2,1-f][1,2]
thiazin-5-yl)-5-fluoropyridin-2-yl)-5-methoxypyrazine-2-carboxamide,
N-(6-((4aR,5R,9R)-7-amino-3,3-difluoro-5,8,8-trimethyl-9-
oxido-2,3,4,4a,5,8-hexahydro-[1,4]thiazino[2,1-f][1,2]
thiazin-5-yl)-5-fluoropyridin-2-yl)-5-fluoro-3-methylpicolinamide,
N-(6-((4aR,5R,9R)-7-amino-3,3-difluoro-5,8,8-trimethyl-9-
oxido-2,3,4,4a,5,8-hexahydro-[1,4]thiazino[2,1-f][1,2]
thiazin-5-yl)-5-fluoropyridin-2-yl)-3,5-dichloropicolinamide,
N-(6-((4aR,5R,9R)-7-amino-3,3-difluoro-5,8,8-trimethyl-9-
oxido-2,3,4,4a,5,8-hexahydro-[1,4]thiazino[2,1-f][1,2]
thiazin-5-yl)-5-fluoropyridin-2-yl)-3-chloro-5-fluoropicolinamide,
N-(6-((4aR,5R,9R)-7-amino-3,3-difluoro-5,8,8-trimethyl-9-
oxido-2,3,4,4a,5,8-hexahydro-[1,4]thiazino[2,1-f][1,2]
thiazin-5-yl)-5-fluoropyridin-2-yl)-5-chloro-3-methylpicolinamide,
N-(6-((4aR,5R,9R)-7-amino-3,3-difluoro-5,8,8-trimethyl-9-
oxido-2,3,4,4a,5,8-hexahydro-[1,4]thiazino[2,1-f][1,2]
thiazin-5-yl)-5-fluoropyridin-2-yl)-5-chloropicolinamide,
N-(6-((4aR,5R,9R)-7-amino-3,3-difluoro-5,8,8-trimethyl-9-
oxido-2,3,4,4a,5,8-hexahydro-[1,4]thiazino[2,1-f][1,2]
thiazin-5-yl)-5-fluoropyridin-2-yl)-3-chloro-5-(difluoromethoxy)-picolinamide,
N-(6-((4aR,5R,9R)-7-amino-3,3-difluoro-5,8,8-trimethyl-9-
oxido-2,3,4,4a,5,8-hexahydro-[1,4]thiazino[2,1-f][1,2]
thiazin-5-yl)-5-fluoropyridin-2-yl)-5-(2,2-difluoroethoxy)pyrazine-2-carboxamide,
N-(6-((4aR,5R,9R)-7-amino-3,3-difluoro-5,8,8-trimethyl-9-
oxido-2,3,4,4a,5,8-hexahydro-[1,4]thiazino[2,1-f][1,2]
thiazin-5-yl)-5-fluoropyridin-2-yl)-5-(prop-1-yn-1-yl)picolinamide,
N-(6-((4aR,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-cyano-3-methylpicolinamide,
N-(6-((4aR,5R,9R)-7-amino-5,8,8-trimethyl-9-oxido-2,3,4,
4a,5,8-hexahydro-[1,4]thiazino[2,1-f]i[1,2]thiazin-5-yl)-
5-fluoropyridin-2-yl)-5-methoxypyrazine-2-carboxamide,
N-(6-((4aR,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-3,5-dichloropicolinamide,
N-(6-((4aR,5R,9R)-7-amino-5,8,8-trimethyl-9-oxido-2,3,4,
4a,5,8-hexahydro-[1,4]thiazino[2,1-f]i[1,2]thiazin-5-yl)-
5-fluoropyridin-2-yl)-5-fluoro-3-methylpicolinamide,
N-(6-((4aR,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-3-chloro-5-cyanopicolinamide, N-(6-((4aR,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-6-chloro-3-methylimidazo[1,2-a]
pyridine-2-carboxamide, N-(6-((4aR,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(difluoromethoxy)picolinamide, N-(6-((4aR,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(2,2,3,3-tetrafluoropropoxy)picolinamide, N-(6-((4aR,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-cyano-3-methylpicolinamide, N-(6-((4aR,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-methoxypyrazine-2-carboxamide, N-(6-((4aR,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-3,5-dichloropicolinamide, N-(6-((4aR,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-fluoro-3-methylpicolinamide, N-(6-((4aR,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-3-chloro-5-cyanopicolinamide, N-(6-((4aR,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-6-chloro-3-methylimidazo[1,2-a]
pyridine-2-carboxamide, N-(6-((4aR,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(difluoromethoxy)picolinamide, N-(6-((4aR,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(2,2,3,3-tetrafluoropropoxy)picolinamide, N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-cyano-3-methylpicolinamide, N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-methoxypyrazine-2-carboxamide, N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-3,5-dichloropicolinamide, N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-fluoro-3-methylpicolinamide, N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-3-chloro-5-cyanopicolinamide, N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-6-chloro-3-methylimidazo[1,2-a]
pyridine-2-carboxamide, N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(difluoromethoxy)picolinamide, N-(6-((4aS,5R,9R)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(2,2,3,3-tetrafluoropropoxy)picolinamide, N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-cyano-3-methylpicolinamide, N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-methoxypyrazine-2-carboxamide, N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-3,5-dichloropicolinamide, N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-fluoro-3-methylpicolinamide, N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-3-chloro-5-cyanopicolinamide, N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-6-chloro-3-methylimidazo[1,2-a]
pyridine-2-carboxamide, N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(difluoromethoxy)picolinamide, N-(6-((4aS,5R,9S)-7-amino-5,8,8-trimethyl-9-oxido-2,3,4,
4a,5,8-hexahydro-[1,4]thiazino[2,1-f][1,2]thiazin-5-yl)-
5-fluoropyridin-2-yl)-5-(2,2,3,3-tetrafluoropropoxy)picolinamide, N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aR,6R,10R)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((5aR,6R,10S)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aR,6R,10S)-8-amino-6,9,9-trimethyl-10-oxido-3,4,
5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((4aR,5R,9R)-7-amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-5-cyano-3-methylpicolinamide, N-(6-((4aS,5R,9R)-7-amino-5,8,8-trimethyl-9-oxido-4,4a,5,8-tetrahydro-2H-spiro[[1,4]-thiazino[2,1-f][1,2]thiazine-3,1'-cyclopropan]-5-yl)-5-fluoropyridin-2-yl)-5-cyano-3-methylpicolinamide, N-(6-((4aR,5R,9R)-7-amino-5,8,8-trimethyl-9-oxido-4,4a,5,8-tetrahydro-2H-spiro[[1,4]-thiazino[2,1-f][1,2]thiazine-3,1'-cyclopropan]-5-yl)-5-fluoropyridin-2-yl)-3-chloro-5-cyanopicolinamide, N-(6-((4aR,5R,9R)-7-amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-3-chloro-5-(difluoro-methoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-4-chloro-1-(difluoromethyl)-1H-pyrazole-3-carboxamide, and 6-((6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)carbamoyl)nicotinic acid, or pharmaceutically acceptable salts thereof.

A certain embodiment of the invention provides a compound of formula I as described herein whenever prepared by a process as described herein.

A certain embodiment of the invention provides a compound of formula I as described herein for use as therapeutically active substance.

A certain embodiment of the invention provides a compound of formula I as described herein for the use as inhibitor of BACE1 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides a compound of formula I as described herein for the use in inhibition of BACE1 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a method for the use in inhibition of BACE1 activity, particularly for the therapeutic and/or prophylactic treatment of diseases and disorders characterized by elevated β-amyloid levels and/or β-amyloid oligomers and/or β-amyloid plaques and further deposits or Alzheimer's disease, which method comprises administering compound of formula I as described herein to a human being or animal.

A certain embodiment of the invention provides a method for the use in the therapeutic and/or prophylactic treatment of Alzheimer's disease, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric form

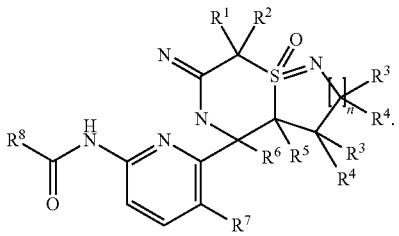

If

All tautomeric forms are encompassed in the present invention.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

Certain embodiments are the following specific forms:

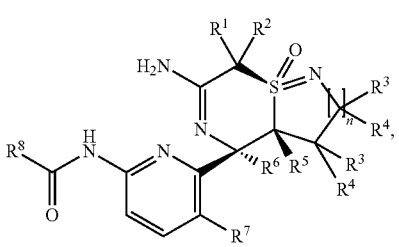

Ib

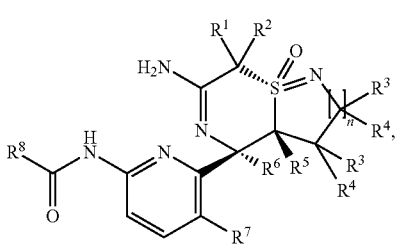

Ic

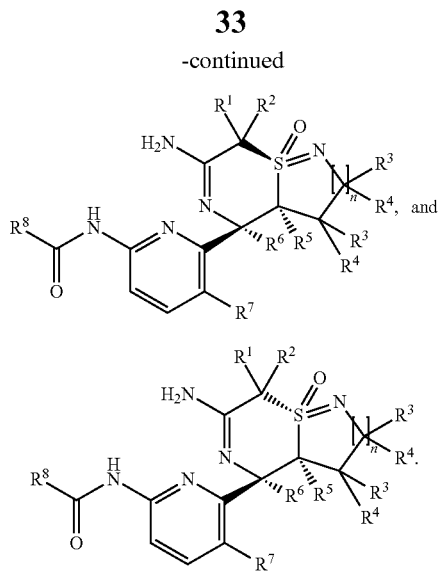

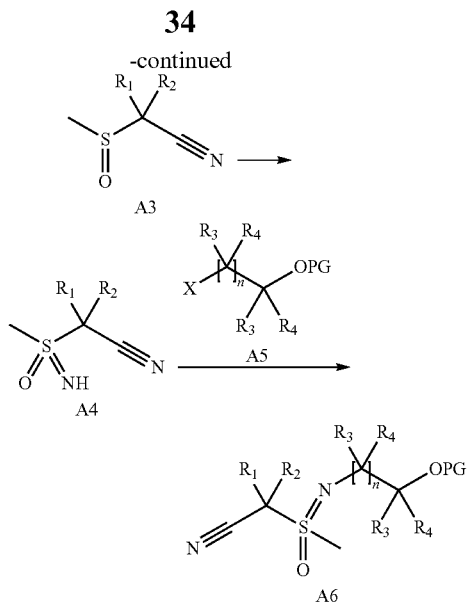

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I can be prepared through a number of synthetic routes for example as illustrated in schemes 1-14. The preparation of compounds of formula I of the present invention may be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

Key intermediate A6 can be prepared via the intermediates depicted in Scheme 1. Commercially available 2-(methylthio)acetonitrile (A1) can be alkylated using a base, such as e.g. sodium hydride, in the presence of an appropriate alkylating agent, e.g. alkyl iodide or alkyl bromide, in a suitable aprotic solvent, e.g. tetrahydrofuran, to give the corresponding intermediate A2. Alternatively, the alkylation agent can be an appropriate aldehyde, e. g. paraformaldehyde. The resulting hydroxy compounds can thereafter be transformed into the corresponding halogen compounds be methods known in the art, e.g. using suitable fluorinating agents, such as diethylaminosulfurtrifluoride, to obtain intermediates A2. The alkylations can be run stepwise, or, if R=R², in one pot using appropriate reagent excesses.

Intermediate A2 can be oxidized to the corresponding sulfoxide A3 using suitable oxidation procedures known in the art, e.g. using sodium periodate, m-chloroperbenzoic acid or oxone. The following formation of the sulfoximine moiety to obtain intermediate A4 can be achieved by methods known in the art, e.g. in two steps using, e.g. catalytic amounts of dirhodiumtetraacetate, and stoichiometric amounts of diacetoxyiodosobenzene, trifluoroacetamide and magnesium oxide, followed by hydroylsis, e.g. using potassium carbonate in lower alcohols, or, alternatively, using catalytic amounts of 4,4',4"-tri-tert-butyl-2,2':6',2"-terpyridine and silver nitrate, and stoichiometric amounts of 4-nitrobenzenesulfonamide and diacetoxyiodosobenzene, and subsequent hydrolysis using thiophenol and cesium carbonate, both steps in appropriate solvents. Alternatively, intermediate A4 can be synthesized in one step using stoichiometric amounts of sodium azide in Eaton's reagent (i.e. a solution of diphosphorouspentoxide in methanesulfonic acid). Intermediate A4 can thereafter be reacted with an appropriate alkylation reagent A5 in the presence of a suitable base, e.g. sodium hydride, potassium hydride or cesium carbonate, and optionally a catalytic amount of a quaternary ammonium salt, e.g. tetra-n-butyl ammonium bromide or tetra-n-butyl ammonium iodide, in a suitable aprotic solvent, e.g. dimethoxyethane, tetrahydrofurane or acetonitrile, to give intermediate A6. The alkylation reagent A5 is a protected halo-alcohol, in which X means a leaving group, e.g. halogen, (substituted) arene- or (substituted) alkanesulfonate, preferably bromine, iodine or triflouromethanesulfonate, and PG means a protecting group, e.g. tetrahydropyranyl.

Scheme 2

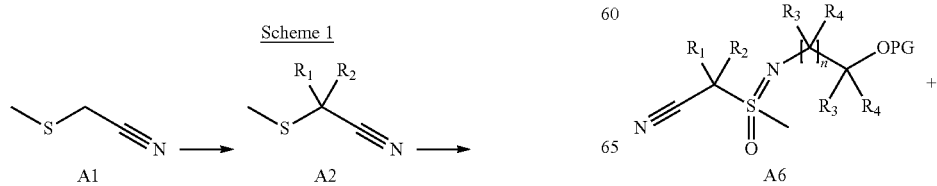

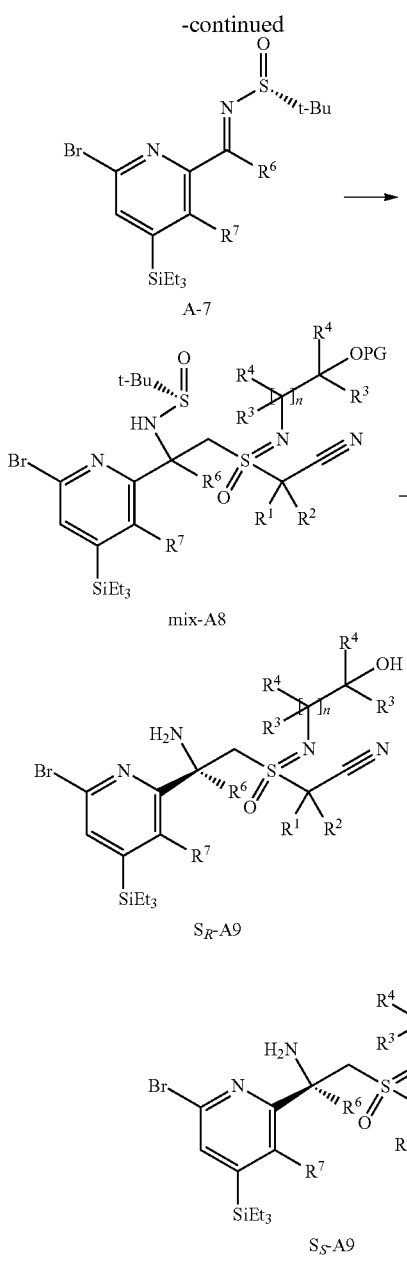

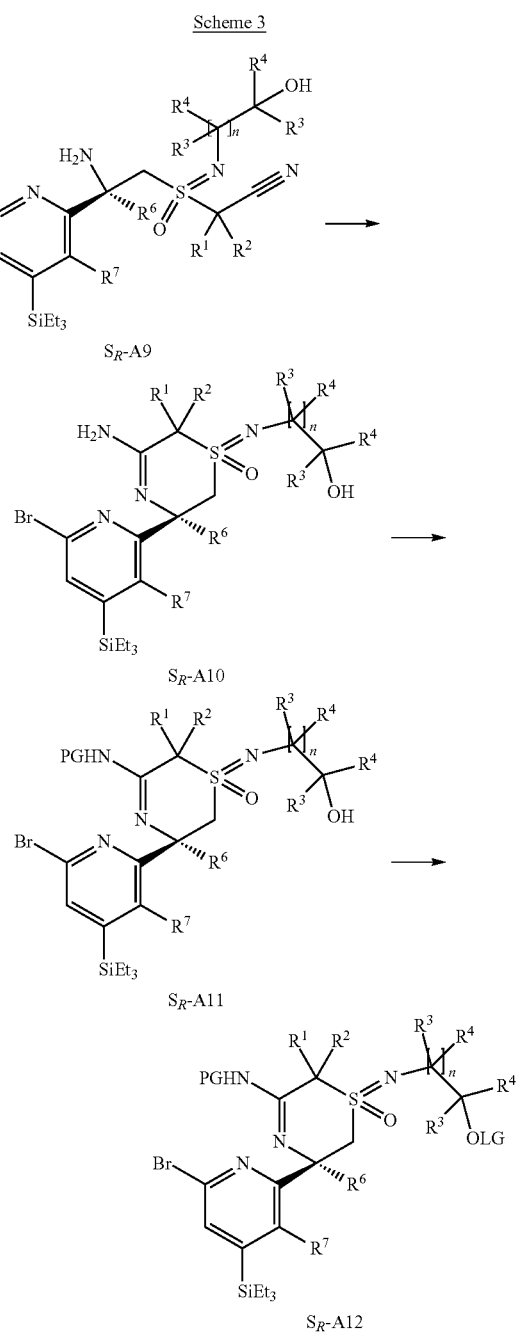

Scheme 3 labile, e.g. tetrahydropyranyl, the two cleavages mentioned above can be carried out in one step under acidic conditions, e.g. using solutions of hydrogen chloride in alcohols, such as methanol or ethanol. The two enantioenriched diastereoisomers $S_R$-A9 and $S_S$-A9 can be separated by chromatography or by other means known in the art. Alternatively, the mixture of diastereoisomers can be carried through the synthesis and the respective resulting mixtures can be separated at later stages by chromatography or by other means known in the art.

Key intermediate A6 can then be reacted with sulfoximine A7 in the presence of a strong base, e.g. alkali hexamethyldisilazide, such as lithium hexamethyldisilazide, alkali diisopropylamide, such as lithium diisopropylamide, or alkyl lithium, such as n-butyl lithium, under anhydrous conditions in a suitable aprotic solvent, e.g. tetrahydrofuran or dichloromethane, to form intermediate mix-A8 as a mixture of stereoisomers (Scheme 2). The single stereoisomers can be separated at this stage by chromatography and the route as depicted in Scheme 2 and the following schemes can be followed analogously employing the separated single isomers. Alternatively, the mixture of stereoisomers can be deprotected and the sulfoxamide moiety can be cleaved to give the corresponding aminoalcohols A9 as a mixture of enantiomerically enriched diastereomers $S_R$-A9 and $S_S$-A9. The prefix $S_X$ indicates the absolute configuration ($S_S$- for (S) and $S_R$- for (R), respectively) at the sulfur atom. In case the protecting group PG in intermediate mix-A8 is acid Subsequently, intermediate $S_R$-A9 can be cyclised to intermediate $S_R$-A10 using methods known in the art, e.g. using stoichiometric amounts of copper(I) salts, e.g. copper (I) chloride or copper(I) bromide, in suitable solvents, e.g. alcohols, such as ethanol, at elevated temperatures, such as 20° C. to 130° C., preferably at 70° C. to 90° C. (Scheme 3). Alternatively, the transformation can be achieved using stoichiometric amounts of a Lewis acid, like trimethyl aluminium, in a suitable aprotic solvent, such as toluene. The amidine function in intermediate $S_R$-A10 is then protected by an appropriate protecting group PG to give intermediate $S_R$-A11. The protecting group PG should be stable towards basic conditions and can be, e.g. tert-butoxycarbonyl (BOC). In case PG is BOC, the transformation to intermediate $S_R$-A11 can be achieved using conditions known in the art, e.g. di-tert-butyl dicarbonate in the presence of a suitable base, such as sodium hydrogencarbonate, and optionally in the presence of catalytic amounts of a suitable Lewis base, e.g. 4-(dimethylamino)-pyridine, followed by addition of a suitable nucleophile, e.g. aqueous ammonia, to eliminate the excess of di-tert-butyl dicarbonate prior to concentration of the reaction mixture. Thereafter, the hydroxy group in intermediate $S_R$-A11 is transformed into a leaving group OLG in intermediate $S_R$-A12. Suitable leaving groups include arenesulfonoyl, e.g. p-toluenesulfonoyl alkanesulfonoyl, e.g. triflourmethanesulfonoyl, or halogen, e.g. iodine. If OLG is p-toluenesulfonoyl, the transformation to intermediate $S_R$-A12 can be achieved under standard conditions known in the art, using, e. g., p-toluenesulfonyl chloride in the presence of a suitable base, e. g. a tertiary amine, such as triethylamine or diisopropylethylamine, and, optionally, catalytic amounts of a suitable Lewis base, e. g. 4-(dimethylamino)-pyridine. If OLG is iodide, the transformation to intermediate $S_R$-A12 can be achieved under standard conditions known in the art, using, e. g., tetraalkylammonium iodide, e.g. tetra-n-butylammonium iodide, in the presence of a suitable phosphine, e. g. triphenylphosphine, and a suitable activator, such as 2,3-dichloro-5,6-dicyano-1,4-benzoquinone (DDQ), in an aprotic solvent, e.g. dichloromethane.

In analogy to the chemistry described above and in Scheme 3 for the transformation of intermediate $S_R$-A9 into intermediate $S_R$-A12, intermediate $S_S$-A9 can be transformed into intermediate $S_S$-A12 (Scheme 4).

Scheme 4

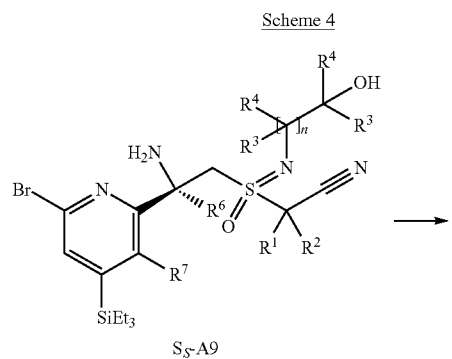

$S_S$-A9

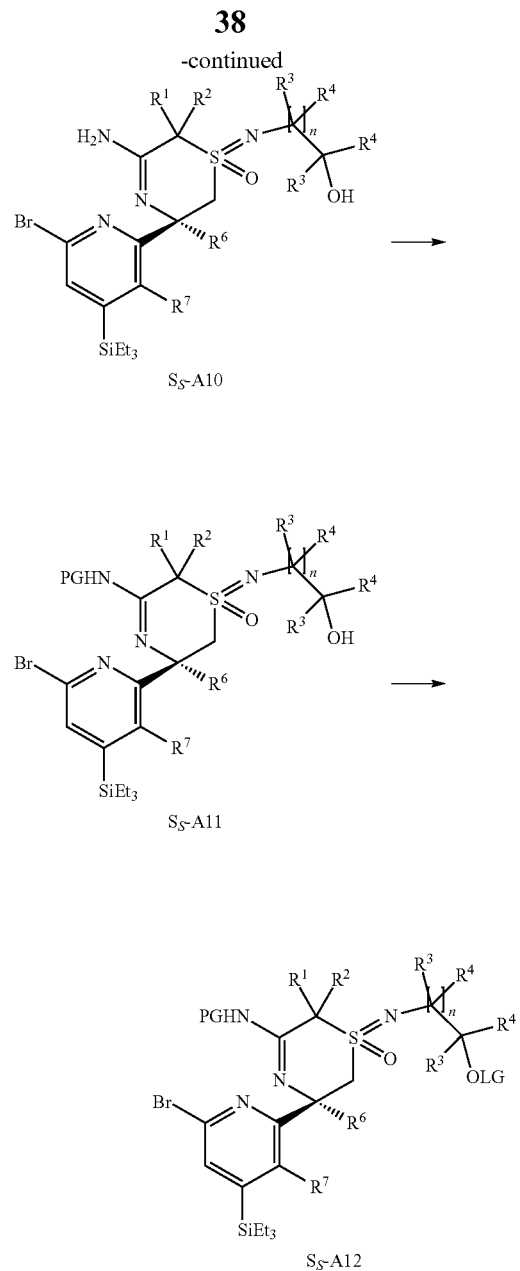

$S_S$-A10

$S_S$-A11

$S_S$-A12

The following cyclisation step starting from intermediate $S_R$-A12 gives rise to two diastereoisomers $S_R$-A13 and $S_R$-A14 (Scheme 5). The two diastereoisomers can either be separated by means of chromatography or other means known in the art, or the mixture can be reacted in the following steps and the reaction products separated at later stages by means of chromatography, or other means known in the art. Alternatively, the mixture of diastereoisomers $S_R$-A13 and $S_R$-A14 can be reacted in the following steps exploiting reactivity differences. Likewise, if one of the two diastereoisomers $S_R$-A13 or $S_R$-A14 has a higher reactivity in the following step, this difference can be used to separate the two diastereoisomers by chromatographic means. The transformation can be achieved using a strong base, such as, e. g., lithium hexamethyldisilazide or lithium diisopropylamide, under anhydrous conditions in an aprotic solvent, e. g. tetrahydrofuran, at temperatures of −80° C. to 0° C. In certain cases, one of the two possible diastereoisomers is strongly favoured, due to steric or thermodynamic reasons.

Scheme 5

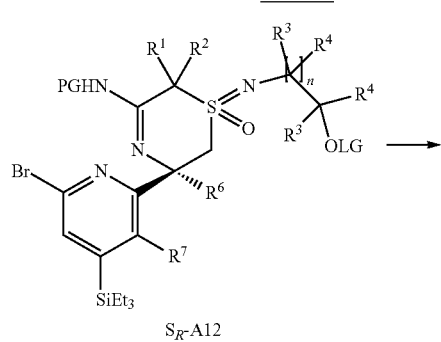

$S_R$-A12

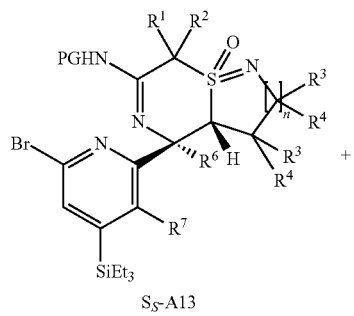

$S_S$-A13

+

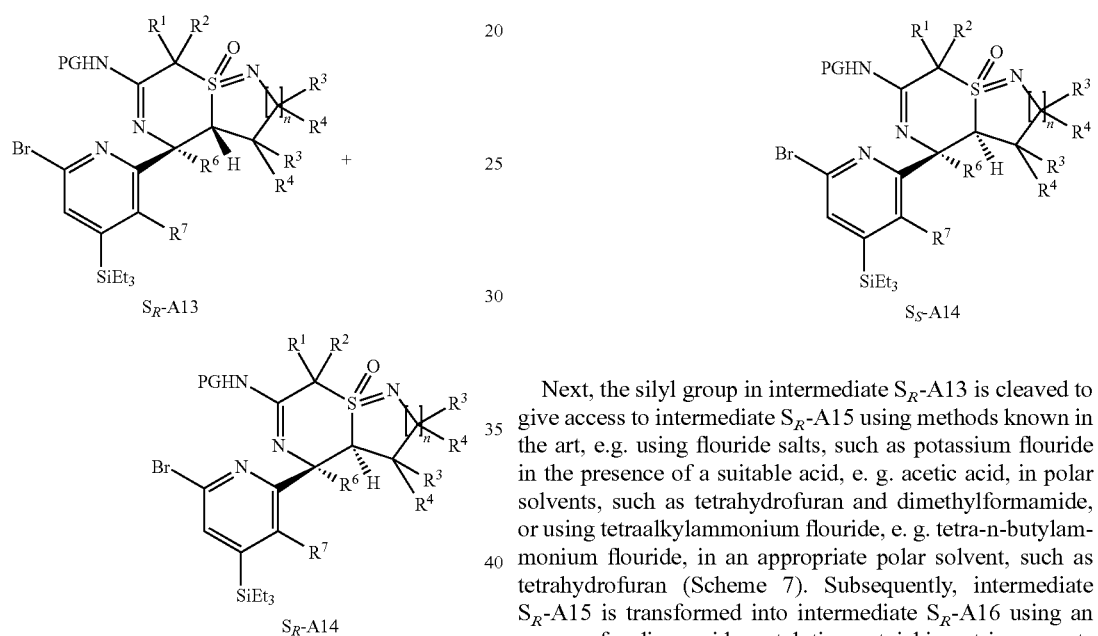

$S_R$-A13

$S_S$-A14

$S_R$-A14

In analogy to the chemistry described above and in Scheme 5 for the transformation of intermediate $S_R$-A12 into intermediates $S_R$-A13 and $S_R$-A14, intermediate $S_S$-A12 can be transformed into intermediates $S_S$-A13 and $S_S$-A14 (Scheme 6).

Next, the silyl group in intermediate $S_R$-A13 is cleaved to give access to intermediate $S_R$-A15 using methods known in the art, e.g. using flouride salts, such as potassium flouride in the presence of a suitable acid, e. g. acetic acid, in polar solvents, such as tetrahydrofuran and dimethylformamide, or using tetraalkylammonium flouride, e. g. tetra-n-butylammonium flouride, in an appropriate polar solvent, such as tetrahydrofuran (Scheme 7). Subsequently, intermediate $S_R$-A15 is transformed into intermediate $S_R$-A16 using an excess of sodium azide, catalytic or stoichiometric amounts of a suitable copper(I) salt, such as copper(I) iodide, and a suitable diamino ligand, such as trans-N,N'-dimethylcyclohexane-1,2-diamine, and substoichiometric amounts of sodium ascorbate, in appropriate polar solvents, such as dioxane and water, at elevated temperatures, e.g. 60° C. to 80° C.

Scheme 6

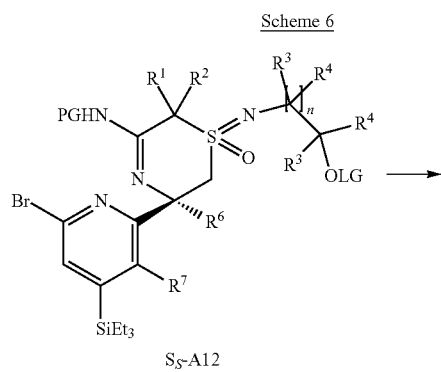

$S_S$-A12

Scheme 7

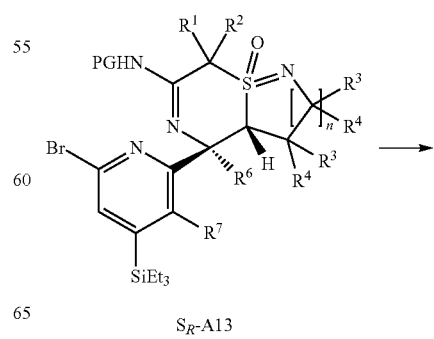

$S_R$-A13

-continued

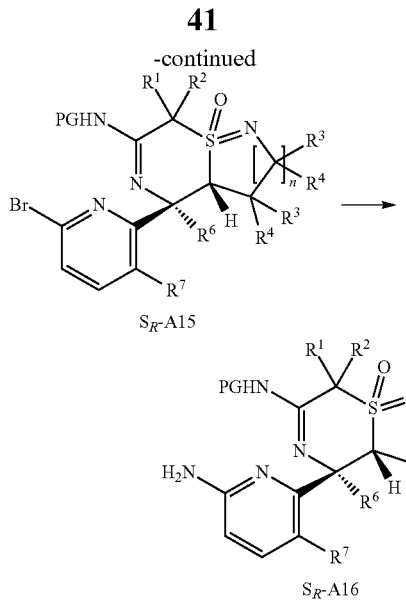

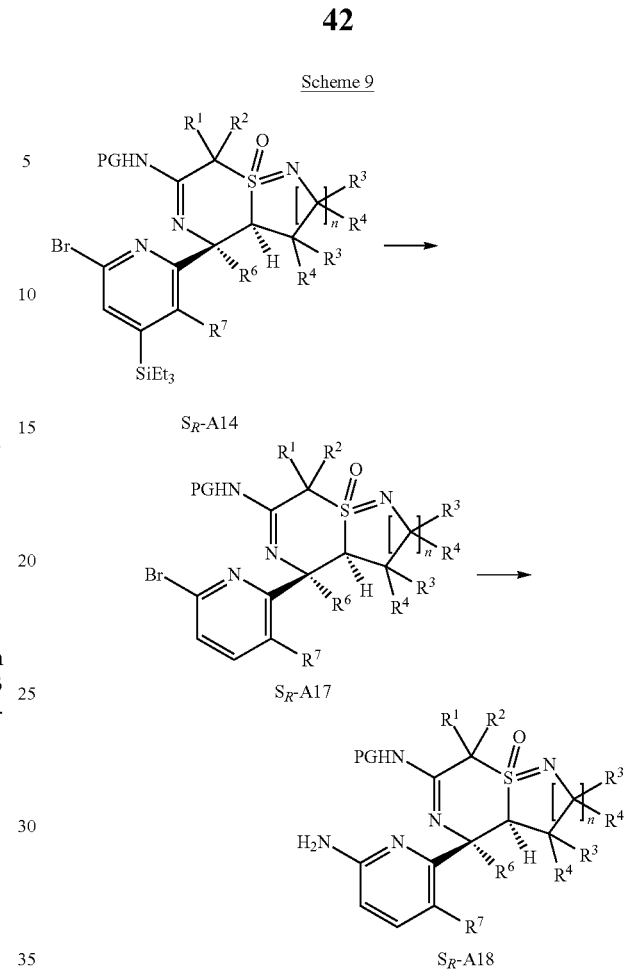

In analogy to the chemistry described above and in Scheme 7 for the transformation of intermediate S$_R$-A13 into intermediate S$_R$-A16, intermediate S$_S$-A13 can be transformed into intermediate S$_S$-A16 (Scheme 8).

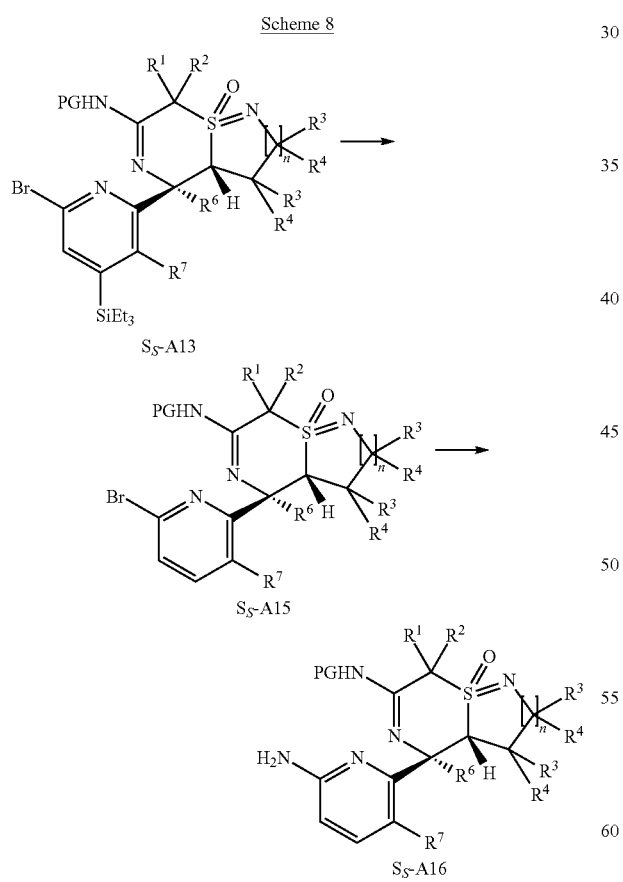

In analogy to the chemistry described above and in Scheme 7 for the transformation of intermediate S$_R$-A13 into intermediate S$_R$-A16, intermediate S$_R$-A14 can be transformed into intermediate S$_R$-A18 (Scheme 9).

In analogy to the chemistry described above and in Scheme 7 for the transformation of intermediate S$_R$-A13 into intermediate S$_R$-A16, intermediate S$_S$-A14 can be transformed into intermediate S$_S$-A18 (Scheme 10).

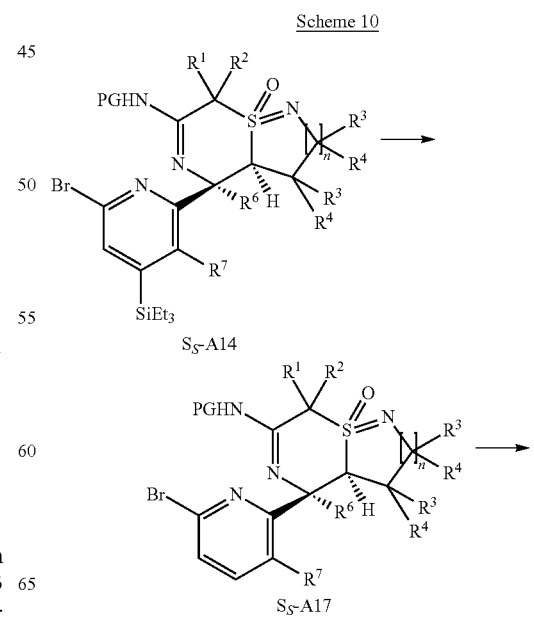

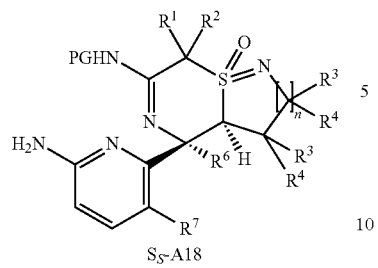

$S_S$-A18

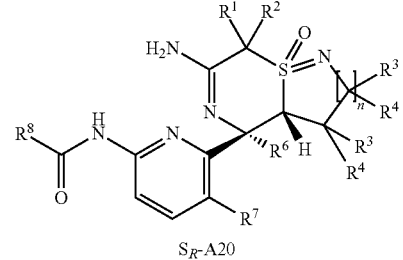

$S_R$-A20

Thereafter, intermediate $S_R$-A16 is acylated to form intermediate $S_R$-A19 by suitable amide bond forming methods known in the art using appropriate acids $R^8COOH$, wherein $R^8$ is as defined above (Scheme 11). These methods include, as example, the reaction of intermediate $S_R$-A16 with acid $R^8COOH$ in the presence of stoichiometric amounts of 1-chloro-N,N,2-trimethylpropenylamine and a suitable base, e. g. a tertiary amine, such as diisopropylethylamine, in an aprotic solvent, e. g. dichloromethane, at temperatures of −10° C. to 30° C. Alternatively, acid $R^8COOH$ can be transformed into the corresponding acid chloride $R^8COCl$ using methods known in the art, e. g. using oxalyl chloride or thionyl chloride in aprotic solvents, such as dichloromethane or toluene. The isolated acid chloride $R^8COCl$ can then be reacted with intermediate $S_R$-A16 in the presence of a suitable base, e.g. a tertiary amine, such as diisopropylethylamine, in an aprotic solvent, e. g. dichloromethane, at temperatures of −10° C. to 30° C. to form intermediate $S_R$-A19. Finally, intermediate $S_R$-A19 is deprotected by methods known in the art to give access to final compounds $S_R$-A20. If PG is BOC, the deprotection is achieved by stirring intermediate $S_R$-A19 in the presence of an excess of a strong acid, such as triflouroacetic acid or hydrogen chloride either in a suitable solvent, such as dichloromethane or tetrahydrofuran or without a solvent under neat conditions, if feasible. Subsequently, the enantiomerically enriched products of formula $S_R$-A20 are purified to their enantiopure form by chromatography using suitable chiral stationary phases.

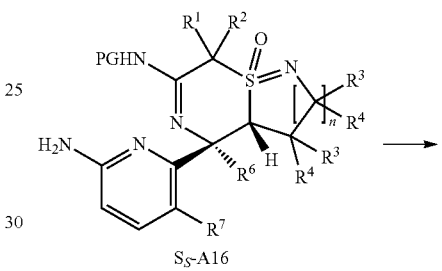

$S_R$-A16

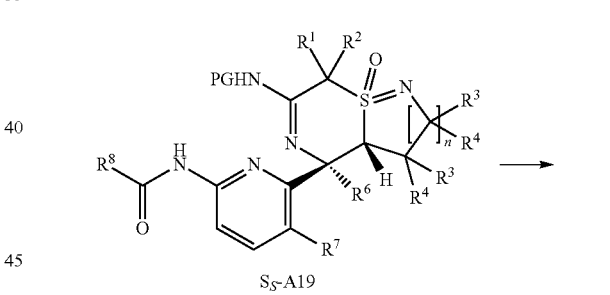

$S_R$-A19

In analogy to the chemistry described above and in Scheme 11 for the transformation of intermediate $S_R$-A16 into enantiopurified final compound $S_R$-A20, intermediate $S_S$-A16 can be transformed into enantiopurified final compound $S_S$-A20 (Scheme 12).

Scheme 12

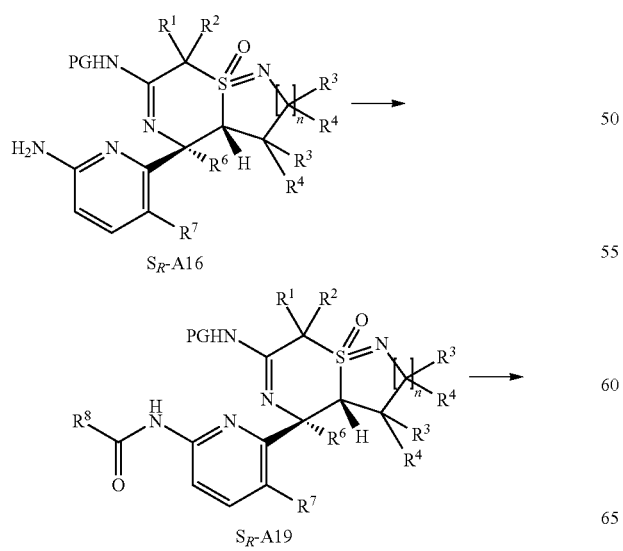

$S_S$-A16

$S_S$-A19

$S_S$-A20

In analogy to the chemistry described above and in Scheme 11 for the transformation of intermediate $S_R$-A16 into enantiopurified final compound $S_R$-A20, intermediate $S_R$-A18 can be transformed into enantiopurified final compound $S_R$-A22 (Scheme 13).

Scheme 13

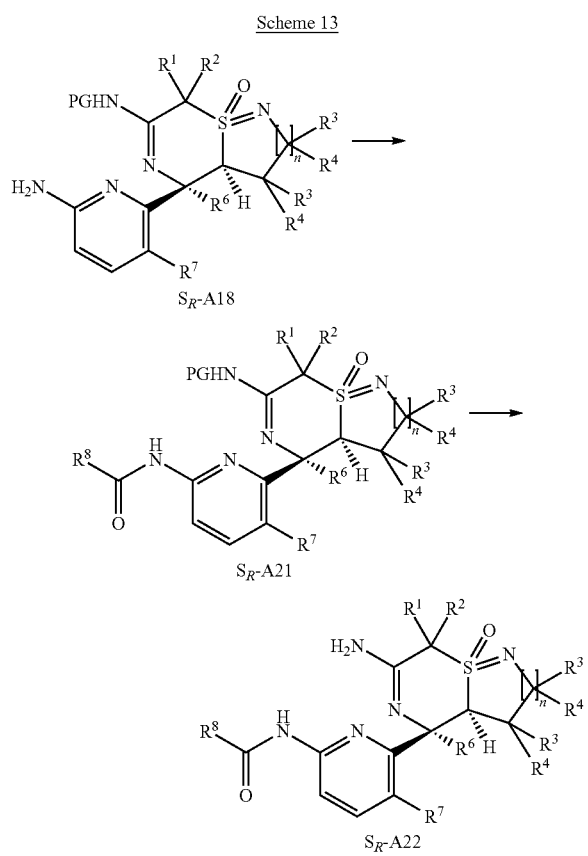

In analogy to the chemistry described above and in Scheme 11 for the transformation of intermediate $S_R$-A16 into enantiopurified final compound $S_R$-A20, intermediate $S_S$-A18 can be transformed into enantiopurified final compound $S_S$-A22 (Scheme 14).

Scheme 14

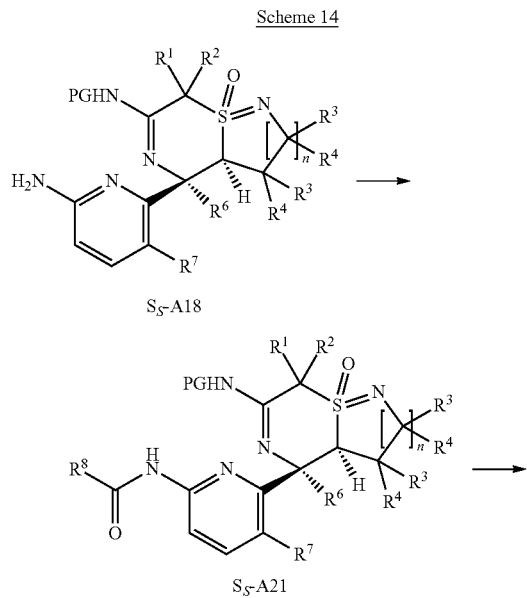

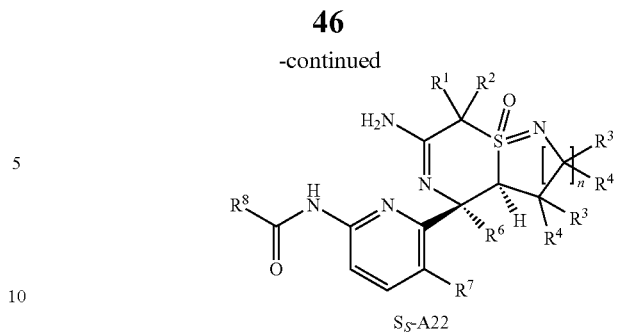

The order of the synthetic steps that are depicted in the schemes 7 and 11 to obtain final compounds of formula $S_R$-A20 can be changed as appropriate. Likewise, the desilation step in Scheme 7 may be carried out, e. g., at the end of the sequence in Scheme 11.

The order of the synthetic steps that are depicted in the schemes 8 and 12 to obtain final compounds of formula $S_S$-A20 can be changed as appropriate. Likewise, the desilation step in Scheme 8 may be carried out, e. g., at the end of the sequence in Scheme 12.

The order of the synthetic steps that are depicted in the schemes 9 and 13 to obtain final compounds of formula $S_R$-A22 can be changed as appropriate. Likewise, the desilation step in Scheme 9 may be carried out, e. g., at the end of the sequence in Scheme 13.

The order of the synthetic steps that are depicted in the schemes 10 and 14 to obtain final compounds of formula $S_S$-A22 can be changed as appropriate. Likewise, the desilation step in Scheme 10 may be carried out, e. g., at the end of the sequence in Scheme 14.

The corresponding pharmaceutically acceptable salts with acids can be obtained by standard methods known to the person skilled in the art, e.g. by dissolving the compound of formula I in a suitable solvent such as e.g. dioxane or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The compounds of formula I and their pharmaceutically acceptable salts possess valuable pharmacological properties. It has been found that the compounds of the present invention are associated with inhibition of BACE1 activity.

The compounds were investigated in accordance with the test given hereinafter.

Cellular Aβ-lowering assay:

The Abeta 40 AlphaLISA Assay can be used. The HEK293 APP cells were seeded in 96 well Microtiter plates in cell culture medium (Iscove's, plus 10% (v/v) fetal bovine serum, penicillin/streptomycin) to about 80% confluency and the compounds were added at a 3× concentration in ⅓ volume of culture medium (final DMSO concentration was kept at 1% v/v). After 18-20 hrs incubation at 37° C. and 5% $CO_2$ in a humidified incubator, the culture supernatants were harvested for the determination of AP 40 concentrations using Perkin-Elmer Human Amyloid beta 1-40 (high specificity) Kit (Cat#AL275C).

In a Perkin-Elmer White Optiplate-384 (Cat#6007290), 2 ul culture supernatants were combined with 2 μl of a 10× AlphaLISA Anti-hAβ Acceptor beads+Biotinylated Antibody Anti-Aβ 1-40 Mix (50 g/mL/5 nM). After 1 hour room temperature incubation, 16 μl of a 1.25× preparation of Streptavidin (SA) Donor beads (25 μg/mL) were added and incubated for 30 minutes in the Dark. Light Emission at 615 nm was then recorded using EnVision-Alpha Reader. Levels of Aβ 40 in the culture supernatants were calculated as percentage of maximum signal (cells treated with 1% DMSO without inhibitor). The $IC_{50}$ values were calculated using the Excel XLfit software.

Lowering of Aβ40 in Brain of Wild-Type Mice:

Animals and Housing Conditions.

Animals were maintained in a 12/12 h light/dark cycle, with lights starting at 6 a.m., and experiments were conducted during the light phase. Animal housing and experimental procedures were in line with ethical and legal guidelines and were authorized by local veterinary authorities.

Experiment. Female C57Bl/6J mice were treated with a dose of 30 mg/kg of the compounds, 3-4 animals per treatment group. The test compound was dissolved in 5% EtOH, 10% Solutol, and was applied per os at 10 mL/kg. After 4 h, the animals were sacrificed and brain and plasma were collected. The brain was cut into halves and immediately frozen on dry ice. Brain was used for measurement of Aβ40 and plasma was used for determination of compound exposure. The method for Aβ40 determination in brain lysates followed the known procedure (Lanz, T. A.; Schachter, J. B. Demonstration of a common artifact in immunosorbent assays of brain extracts: development of a solidphase extraction protocol to enable measurement of amyloid-3 from wild-type rodent brain. J. Neurosci. Methods 2006, 157, 71-81.). Brain tissue was homogenized in 2% DEA buffer in a Roche MagnaLyser (20", 4000 rpm) and subsequently centrifuged for 1 h at 100000 g. DEA was reduced to 0.2% in 50 mM NaCl and one-half of the DEA lysate was passed over an Oasis Solid phase extraction plate (Waters; cat. no. 186000679), which had been activated with MeOH and equilibrated in dH2O (1 mL each). After washes in 10% and 30% MeOH (1 mL each), the Aβ-peptides were eluted in 0.8 mL of 2% NH4OH in 90% MeOH. The eluate was dried over a N2 flow, and the dried sample was reconstituted in 30 μL of AlphaLISA assay buffer. Aβ40 was determined by an AlphaLISA assay (Perkin-Elmer). In a white 96-well, half area microplate (Perkin-Elmer cat. no. 6005561), 20 μL of the reconstituted sample were mixed with 5 μL of biotinylated BAP-24 (specific for C-terminus of Aβ40) (Brockhaus, M.; Grunberg, J.; Rohrig, S.; Loetscher, H.; Wittenburg, N.; Baumeister, R.; Jacobsen, H.; Haass, C. Caspasemediated cleavage is not required for the activity of presenilins in amyloidogenesis and NOTCH signaling. NeuroReport 1998, 9, 1481-1486.) stock=4.4 mg/mL, f.c.5.5 μg/mL), and 5 μL 252Q6 acceptor beads (252Q6 antibody, Invitrogen AMB0062) had been previously conjugated with AlphaLISA Acceptor beads (Perkin-Elmer cat. no. 6772002); final dilution 1:500). The mix was incubated for 1 h at RT in the dark. Then 20 μL of Streptavin-coated Donor Beads (Perkin-Elmer cat. no. 6760002, final dilution 1:125) were added and this final mix was incubated in the dark for another 30 min at RT before RFU was measured in an AlphaScreen Reader (Perkin-Elmer Envision 2104). The value obtained for Aβ40 in the treated animals was related to the value in the vehicle group and is given in %. Alternatively a commercial ELISA was used for Aβ40 determination (Wako ELISA: ("Human/Rat β Amyloid (40) ELISA kit Wako II"; cat nr. 294-64701) following the manufacture's instruction. Also here the Aβ-lowering efficacy was calculated as percentage of the vehicle group.

TABLE 1

| | | Pharmacological data | | |
|---|---|---|---|---|
| Ex. | Structure | BACE1 cell act. Aβ40 $IC_{50}$ [nM] | Aβ40 (wt mice, brain) [%] | Name |
| 1AA | 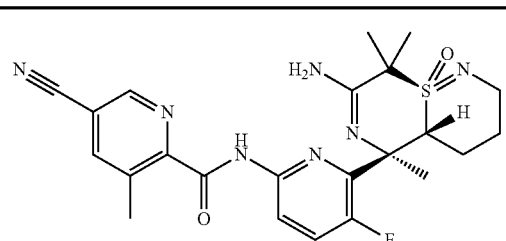 | 0.6 | 38 | N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 1AB | 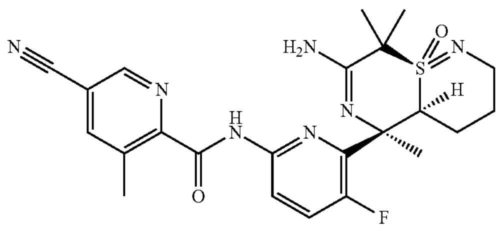 | 2.3 | 79 | N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, |
| 1BA | 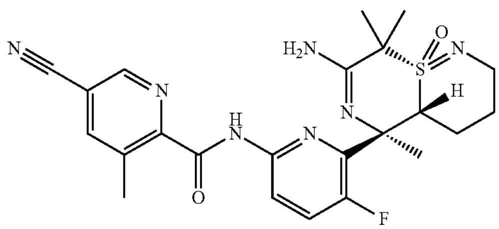 | 0.5 | 95 | N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, |
| 1BB | 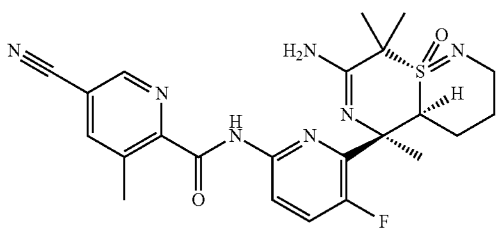 | 3.9 | 93 | N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, |
| 2AA | 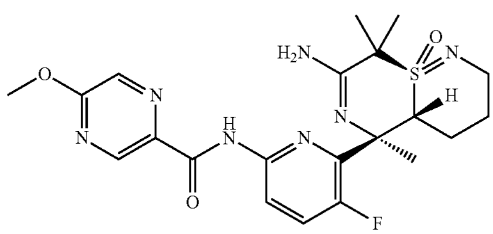 | 19.7 | 83 | N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, |
| 2AB | 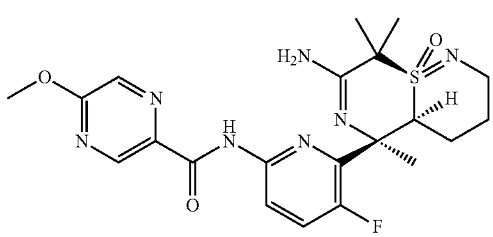 | 18.7 | 92 | N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, |
| 2BA | 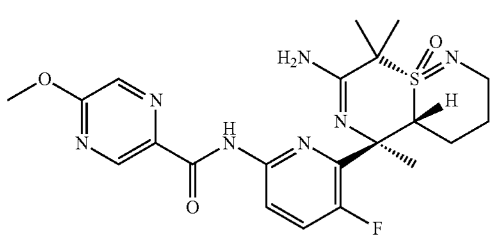 | 21.7 | 87 | N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 2BB | 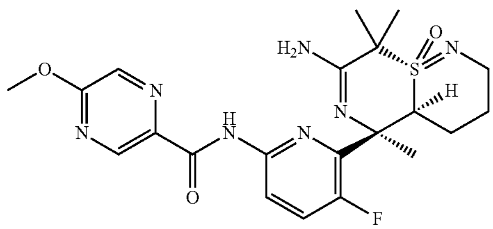 | | | N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, |
| 3AA | 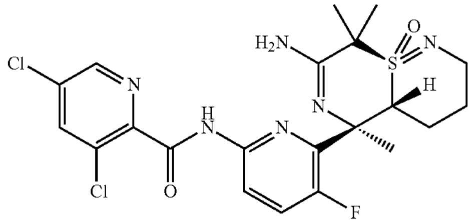 | 1.3 | 76 | N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, |
| 3AB | 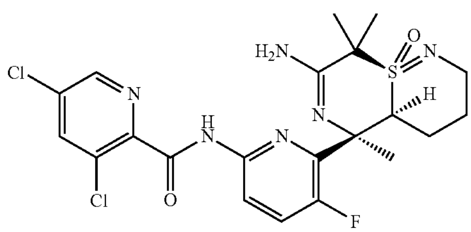 | | | N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, |
| 3BA | 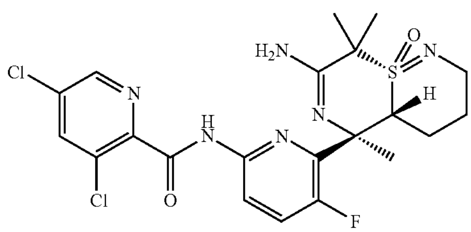 | | | N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, |
| 3BB | 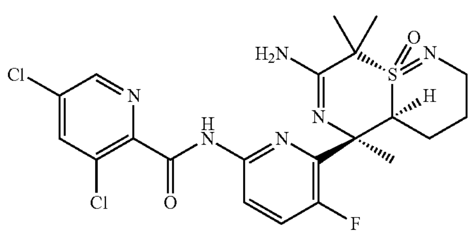 | | | N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, |
| 4AA | 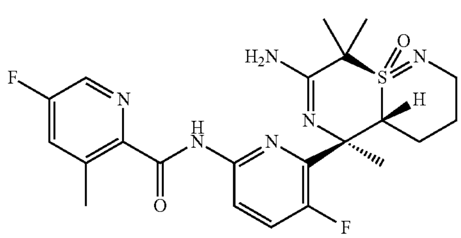 | 18.1 | 80 | N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 4AB | 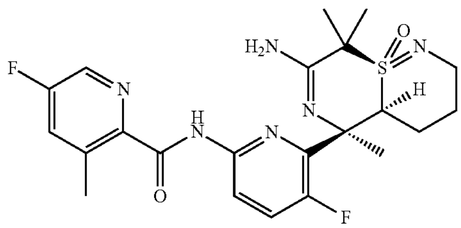 | | | N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, |
| 4BA | 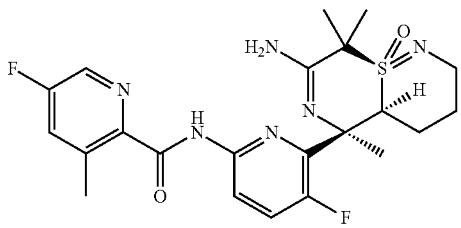 | | | N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, |
| 4BB | 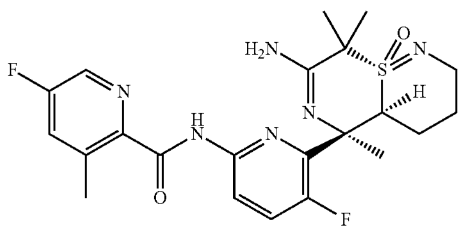 | | | N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, |
| 5AA | 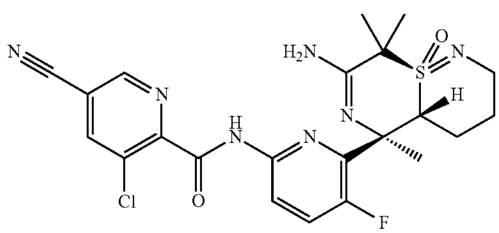 | | | N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, |
| 5AB | 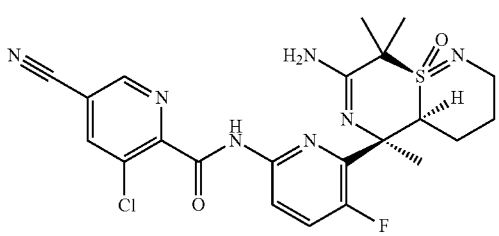 | | | N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, |
| 5BA | 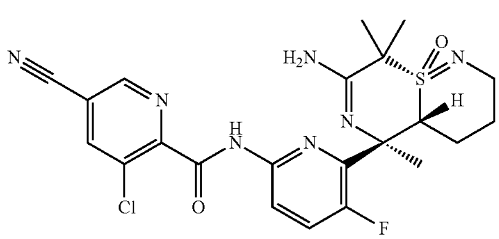 | | | N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 5BB | 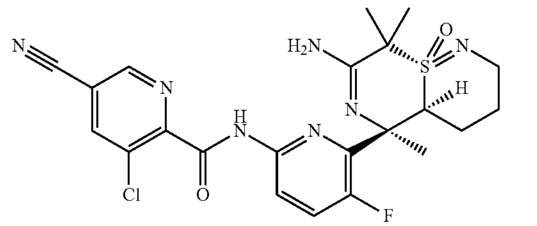 | | | N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, |
| 6AA | 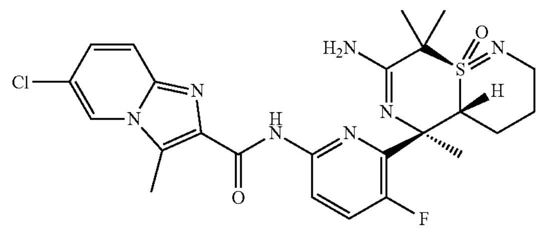 | 28.5 | 103 | N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-6-chloro-3-methylimidazo[1,2-a]pyridine-2-carboxamide, |
| 6AB | 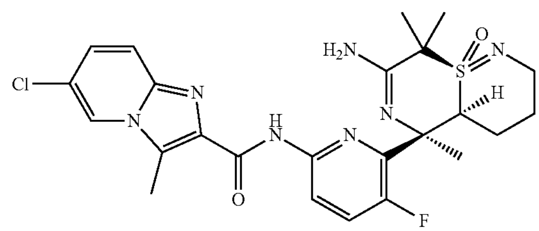 | | | N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-6-chloro-3-methylimidazo[1,2-a]pyridine-2-carboxamide, |
| 6BA | 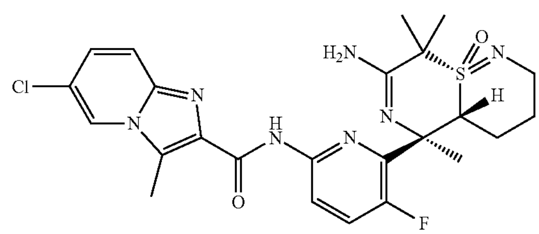 | | | N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-6-chloro-3-methylimidazo[1,2-a]pyridine-2-carboxamide, |
| 6BB | 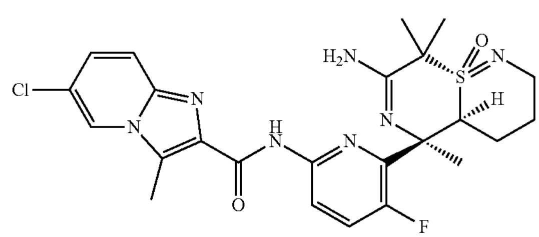 | | | N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-6-chloro-3-methylimidazo[1,2-a]pyridine-2-carboxamide, |
| 7AA | 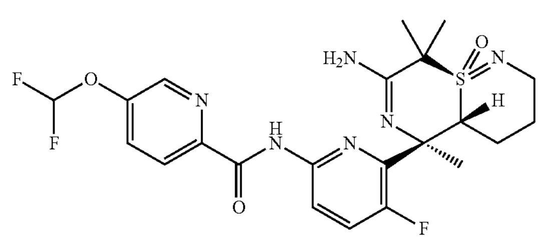 | 2.7 | 65 | N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 7AB | 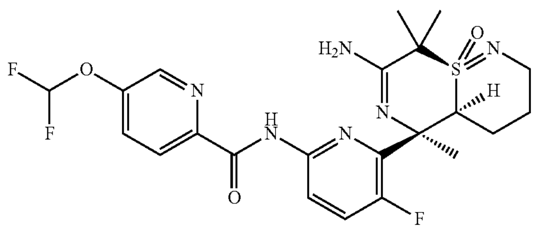 | | | N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, |
| 7BA | 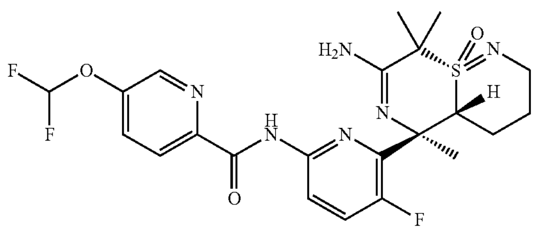 | | | N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, |
| 7BB | 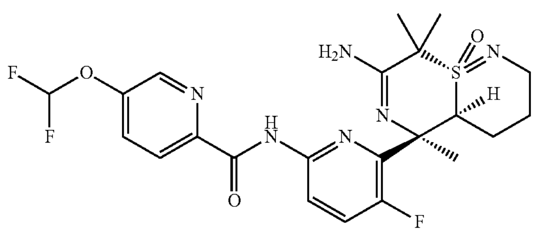 | | | N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, |
| 8AA | 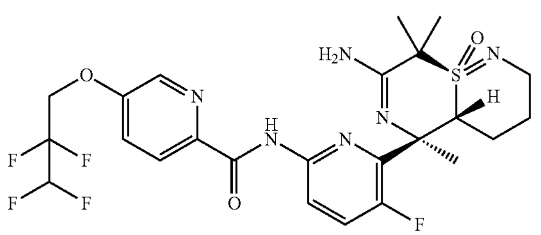 | 35.4 | 61 | N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, |
| 8AB | 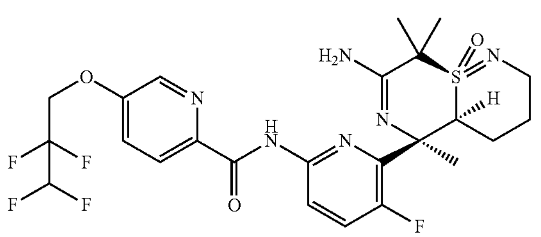 | | | N-(6-((4sS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, |
| 8BA | 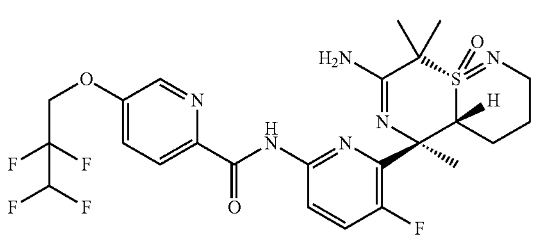 | | | N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 8BB | 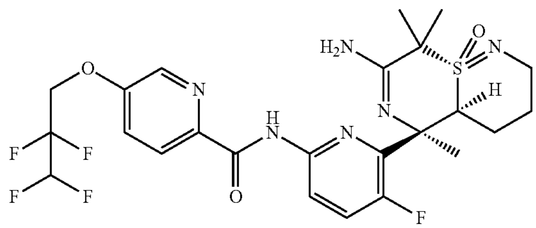 | | | N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, |
| 9AA | 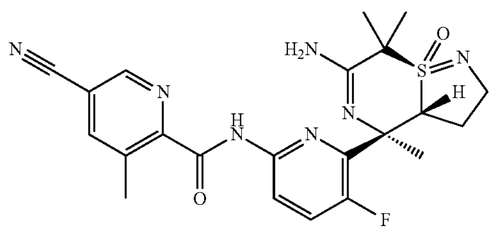 | | | N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, |
| 9AB | 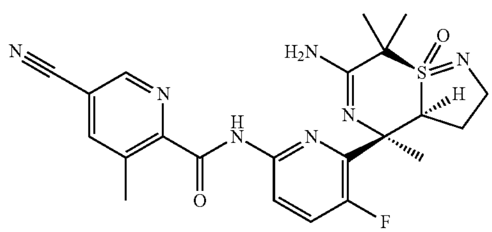 | 0.6 | 40 | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, |
| 9BA | 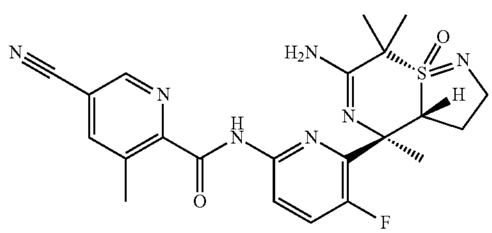 | 14.9 | 86 | N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, |
| 9BB | 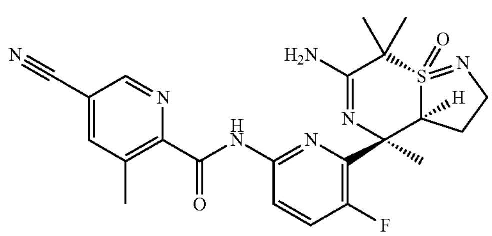 | | | N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, |
| 10AA | 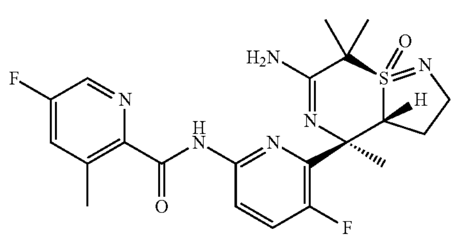 | | | N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 10AB | 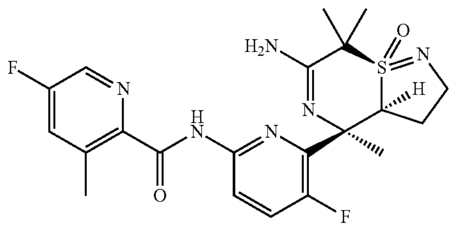 | 10 | 71 | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide |
| 10BA | 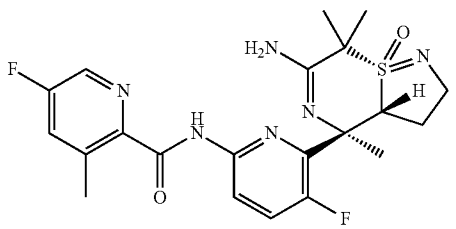 | 420 | | N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide |
| 10BB | 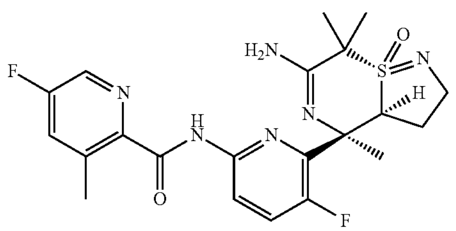 | | | N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, |
| 11AA | 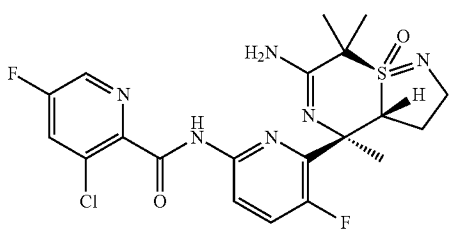 | | | N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, |
| 11AB | 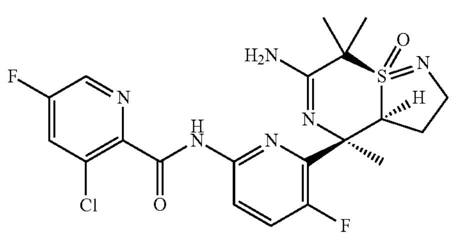 | 3.5 | 100 | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide |
| 11BA | 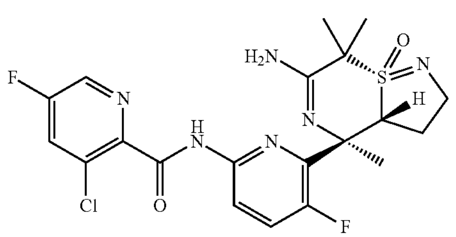 | 117 | | N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 11BB | 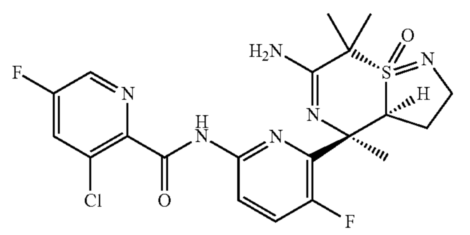 | | | N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, |
| 12AA | 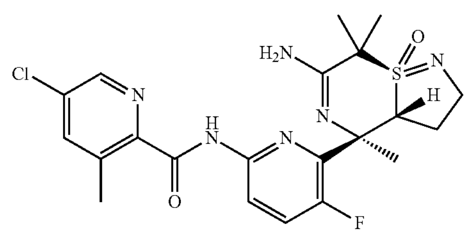 | | | N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, |
| 12AB | 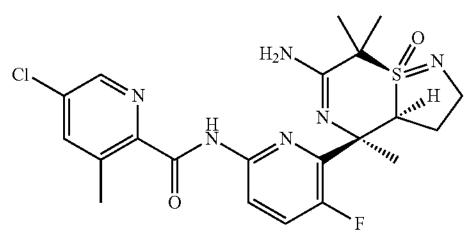 | 1.3 | 38 | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide |
| 12BA | 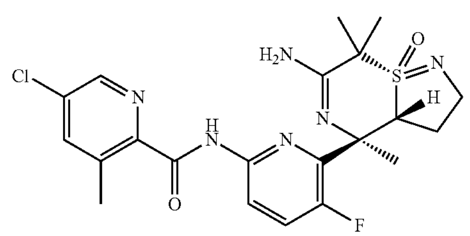 | 24.2 | | N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide |
| 12BB | 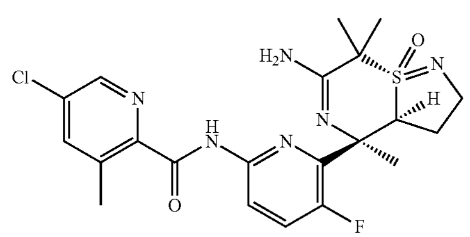 | | | N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, |
| 13AA | 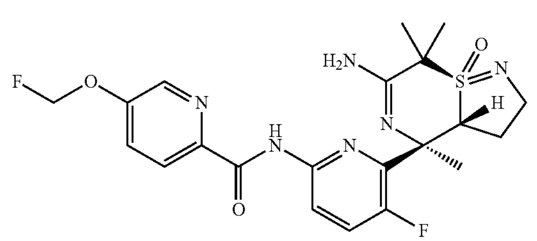 | | | N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 13AB | 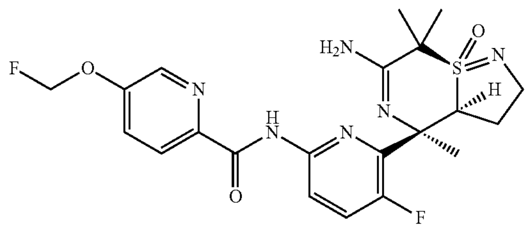 | 9.8 | 86 | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide |
| 13BA | 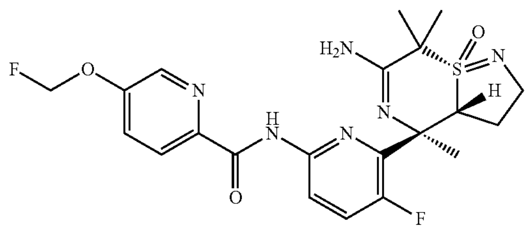 | 382 | | N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide |
| 13BB | 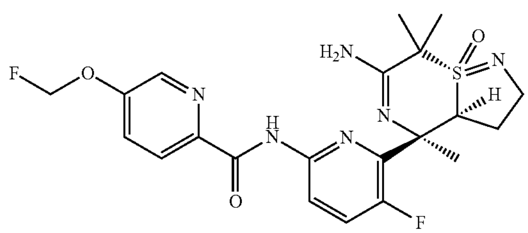 | | | N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, |
| 14AA | 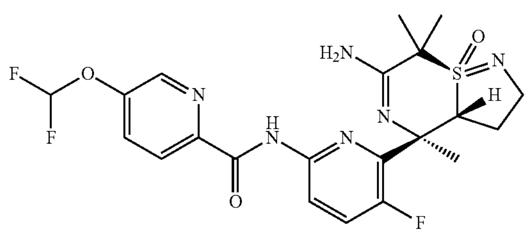 | | | N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, |
| 14AB | 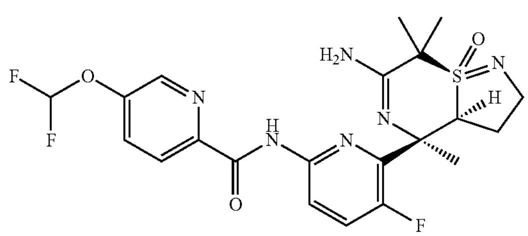 | 6.3 | 61 | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide |
| 14BA | 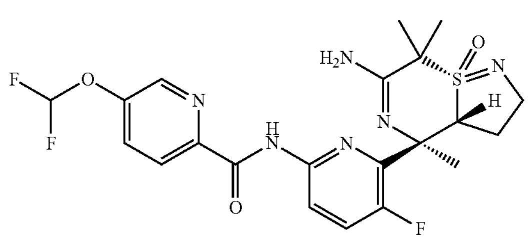 | 52.6 | | N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 14BB | 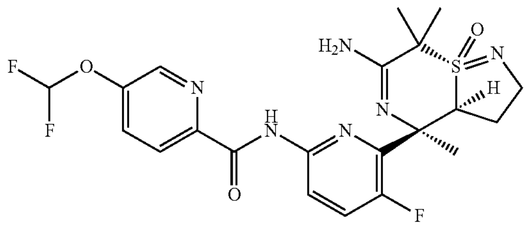 | | | N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, |
| 15AA | 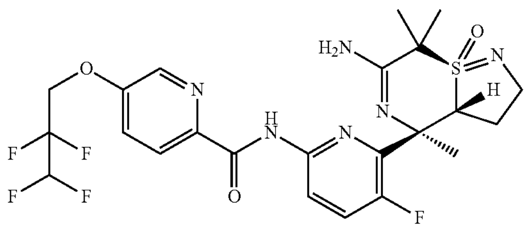 | | | N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, |
| 15AB | 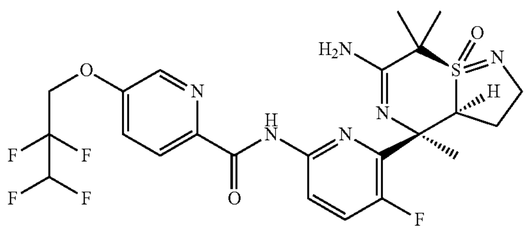 | 146 | 100 | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide |
| 15BA | 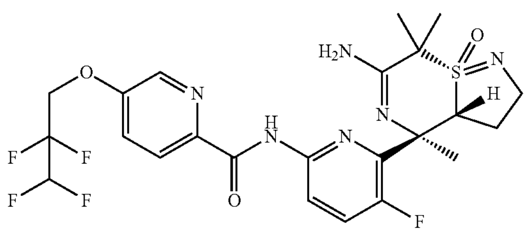 | 557 | | N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide |
| 15BB | 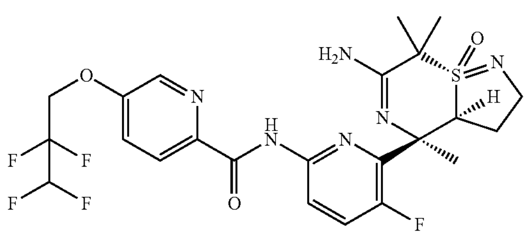 | | | N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, |
| 16AA | 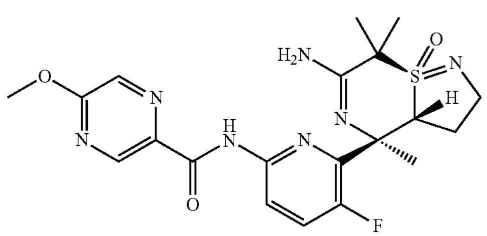 | | | N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 16AB | 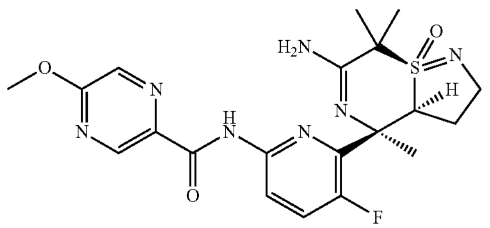 | 8.6 | 89 | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide |
| 16BA | 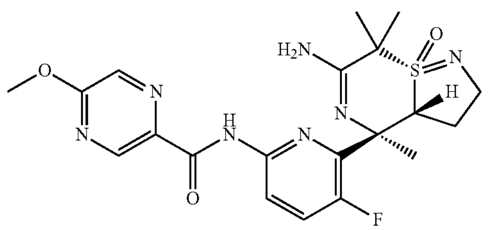 | 115 | | N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide |
| 16BB | 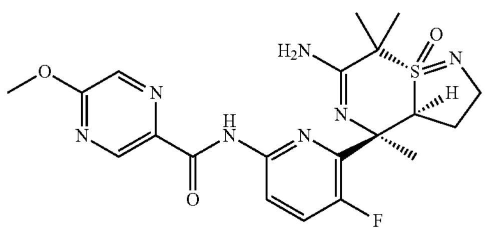 | | | N-(6-((3aS,4R,8S)-6-amino-4,7,7-trimethyl-8-oxido-3,3a,4,7-tetrahydro-2H-isothiazolo[1,5-a][1,4]thiazin-4-yl)-5 fluoropyiridin-2-yl)-5-methoxypyrazine-2-carboxamide, |
| 17AA | 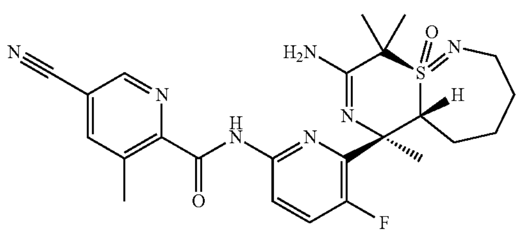 | | | N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, |
| 17AB | 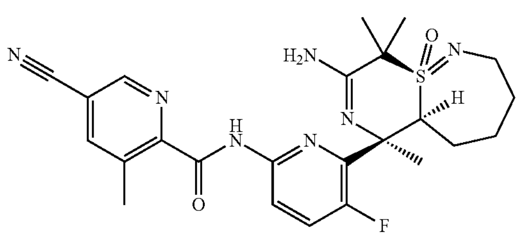 | | | N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, |
| 17BA | 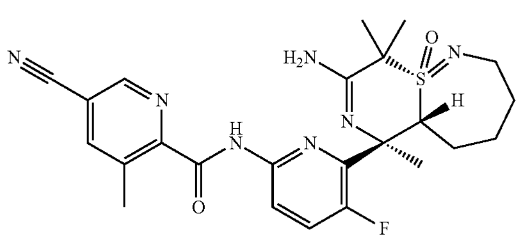 | | | N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 17BB | 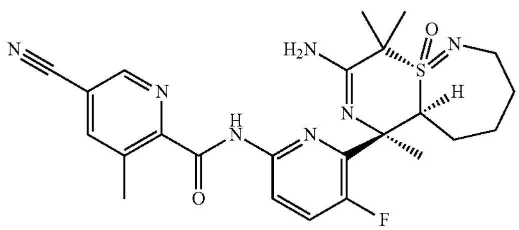 | | | N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, |
| 18AA | 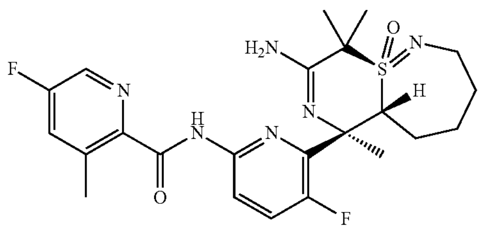 | | | N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, |
| 18AB | 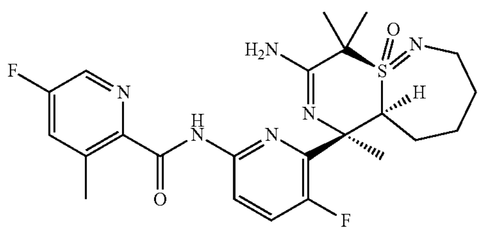 | | | N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, |
| 18BA | 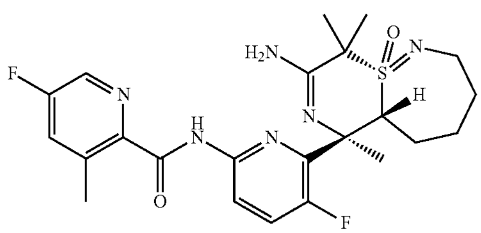 | | | N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, |
| 18BB | 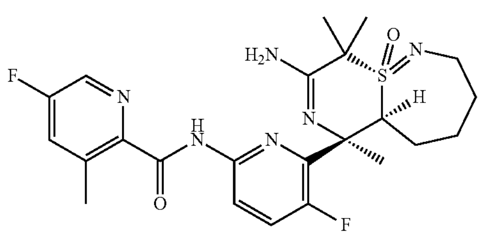 | | | N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, |
| 19AA | 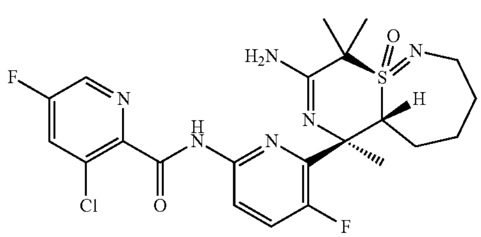 | | | N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 19AB | 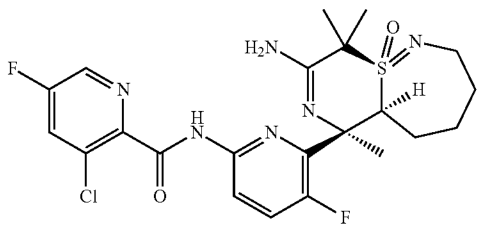 | | | N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, |
| 19BA | 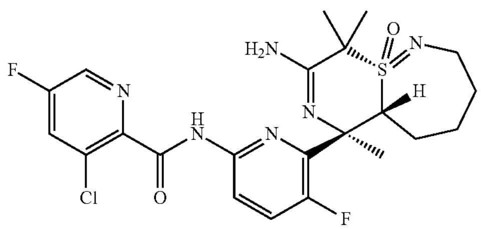 | | | N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, |
| 19BB | 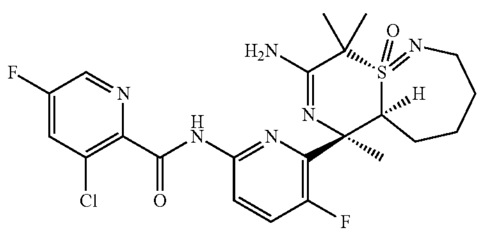 | | | N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, |
| 20AA | 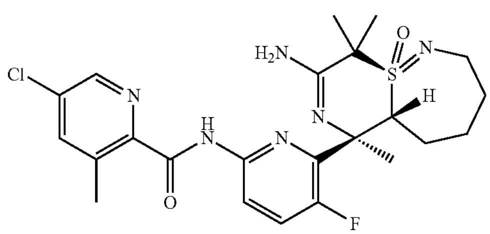 | | | N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, |
| 20AB | 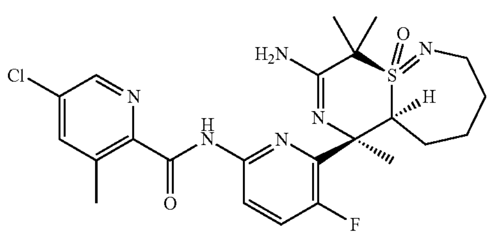 | | | N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, |
| 20BA | 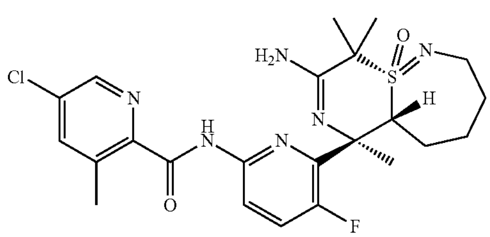 | | | N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 20BB | 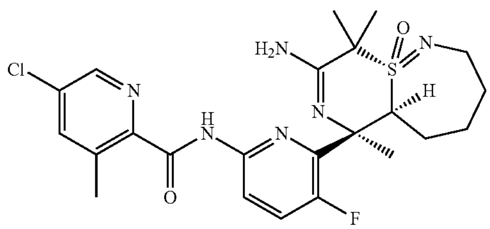 | | | N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, |
| 21AA | 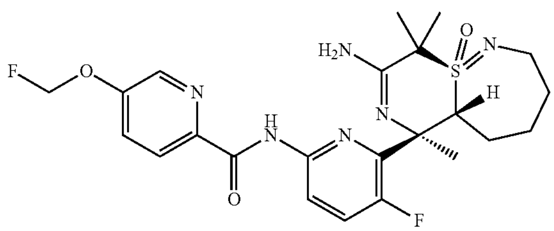 | | | N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, |
| 21AB | 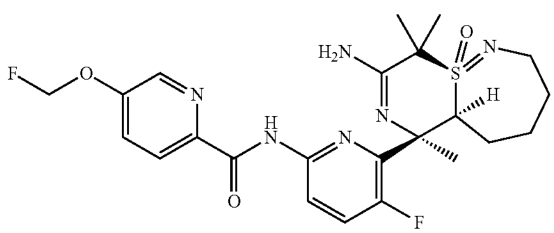 | | | N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, |
| 21BA | 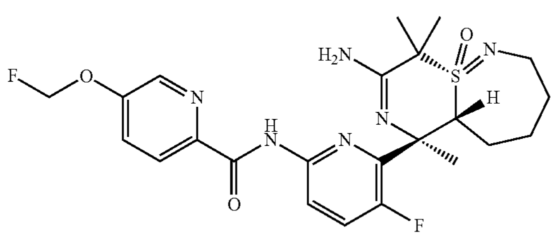 | | | N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, |
| 21BB | 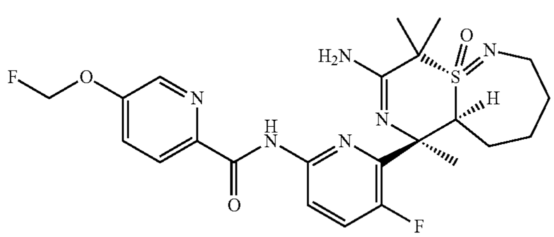 | | | N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, |
| 22AA | 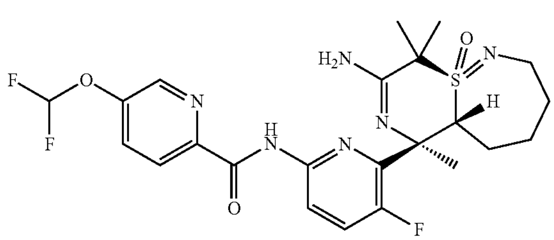 | | | N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 22AB | 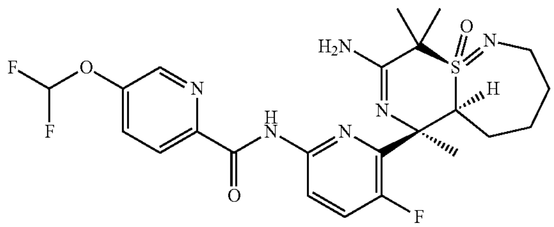 | | | N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, |
| 22BA | 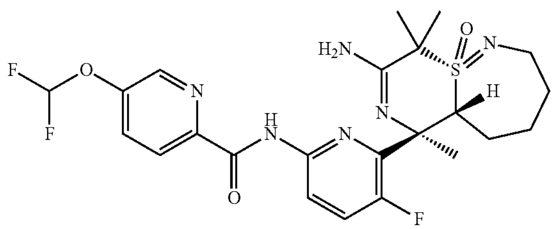 | | | N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, |
| 22BB | 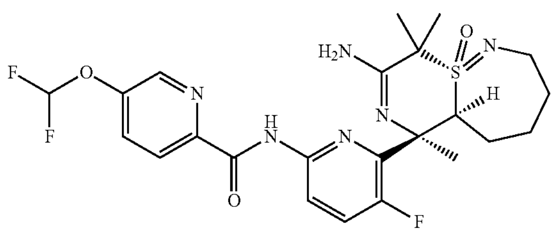 | | | N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, |
| 23AA | 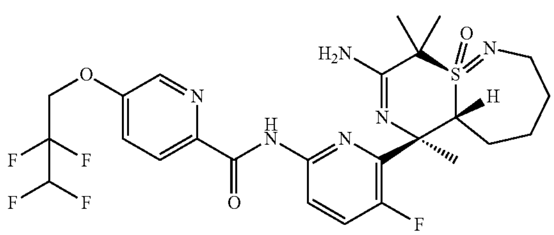 | | | N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, |
| 23AB | 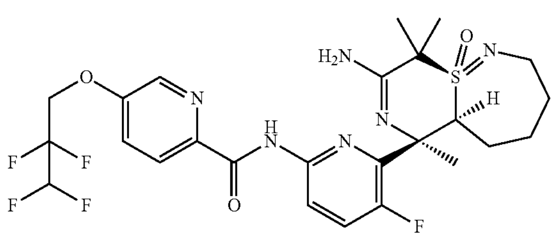 | | | N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, |
| 23BA | 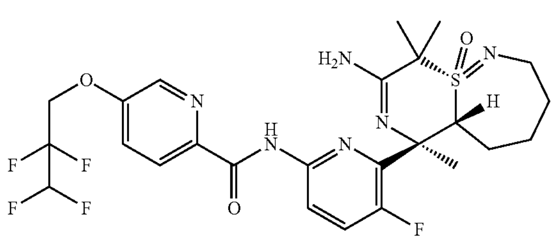 | | | N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 23BB | 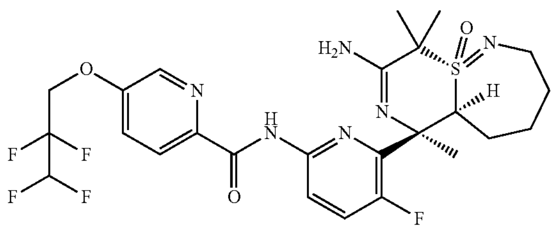 | | | N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, |
| 24AA | 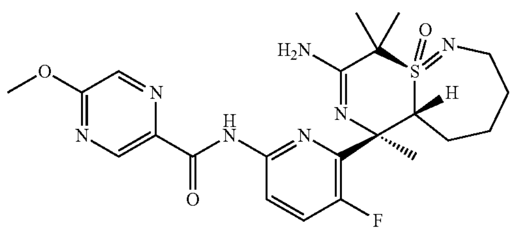 | | | N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, |
| 24AB | 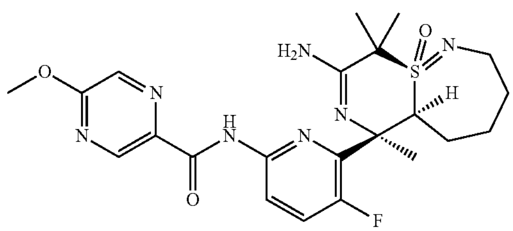 | | | N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, |
| 24BA | 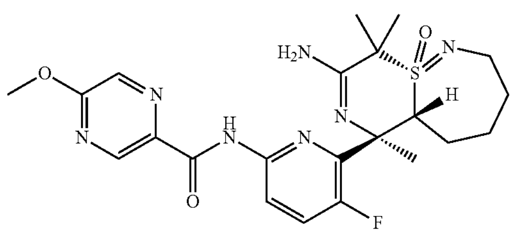 | | | N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, |
| 24BB | 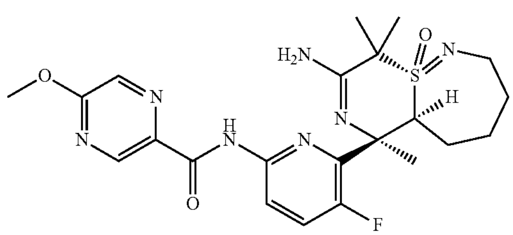 | | | N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide |
| 25AB | 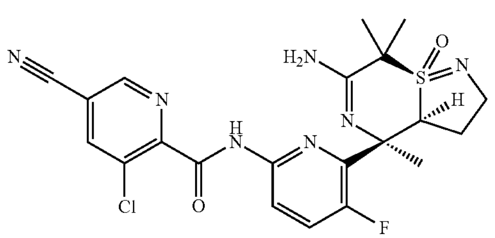 | 0.5 | 56 | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide |

// TABLE 1-continued
// Pharmacological data

| Ex. | Structure | BACE1 cell act. Aβ40 IC$_{50}$ [nM] | Aβ40 (wt mice, brain) [%] | Name |
|---|---|---|---|---|
| 25BA | 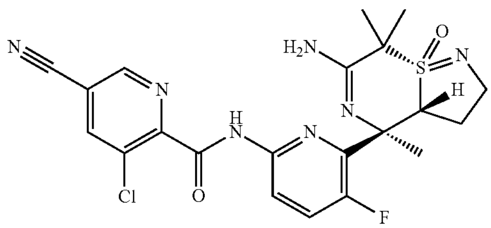 | 15.5 | 117 | N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide |
| 26AB | 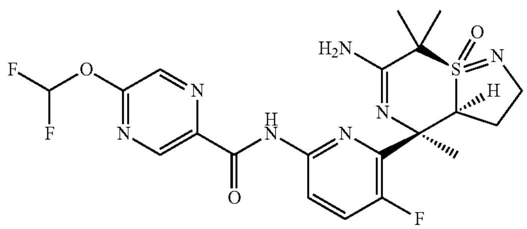 | 7.7 | 82 | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide |
| 26BA | 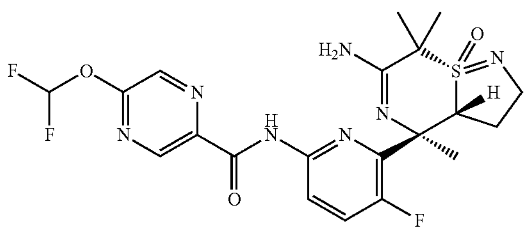 | 152 | | N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide |
| 27AB | 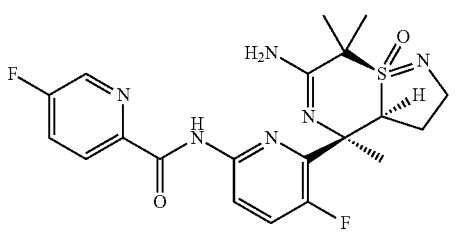 | 15 | 92 | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoropicolinamide |
| 27BA | 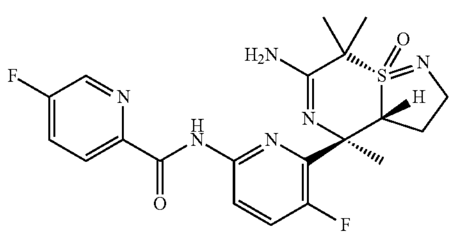 | 118 | | N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoropicolinamide |
| 28AB | 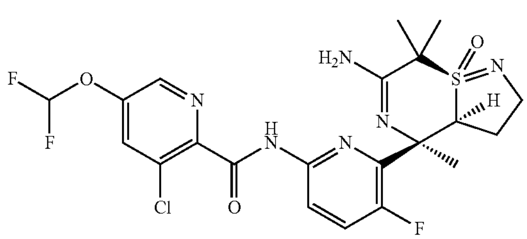 | 2.8 | 100 | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-(difluoromethoxy)picolinamide |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 29AB | 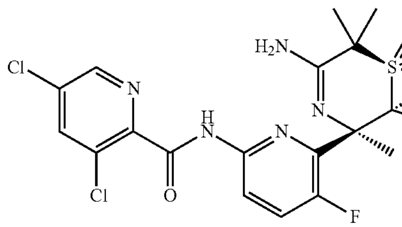 | 0.6 | 88 | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3,5-dichloropicolinamide |
| 30AB | 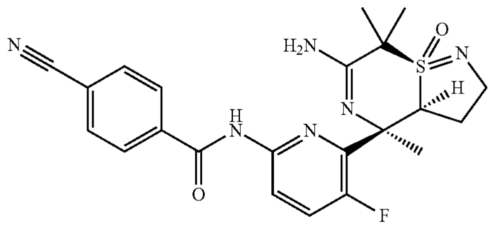 | 14 | | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-4-cyanobenzamide |
| 31AB | 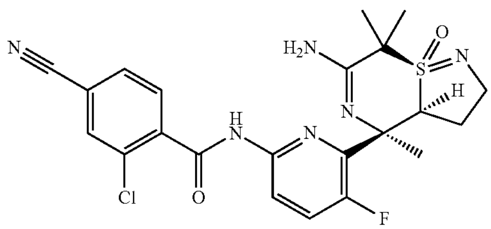 | 34 | | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-2-chloro-4-cyanobenzamide |
| 32AA | 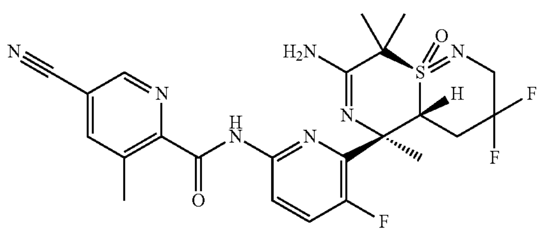 | 1.2 | 53 | N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide |
| 33AA | 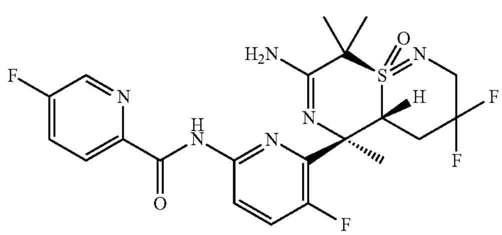 | 90 | 83 | N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoropicolinamide |
| 34AA | 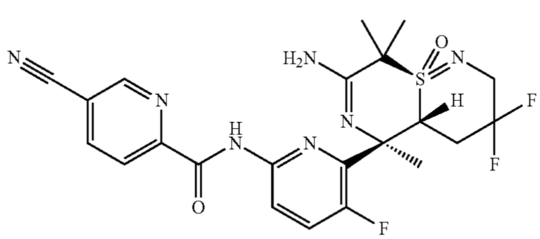 | 9.8 | 113 | N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-cyanopicolinamide |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 35AA | 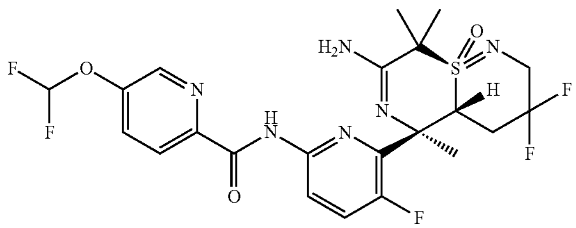 | 87.4 | 101 | N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide |
| 36AA | 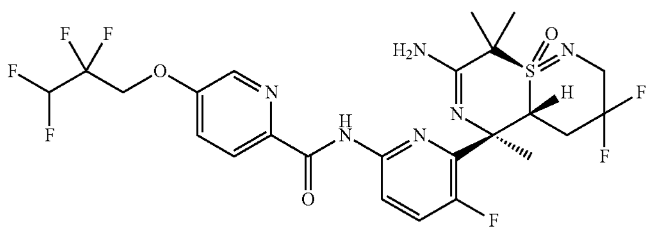 | 416 | 84 | N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)-picolinamide |
| 37AA | 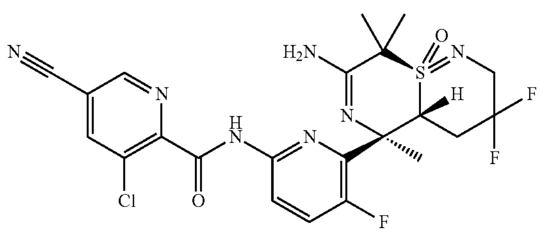 | 1.6 | 73 | N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide |
| 38AA | 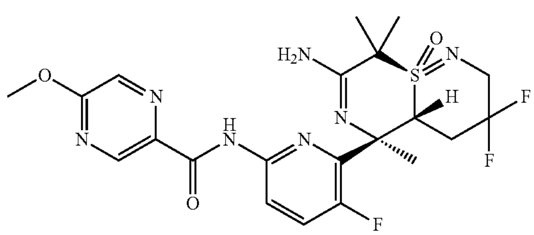 | 295 | | N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide |
| 39AA | 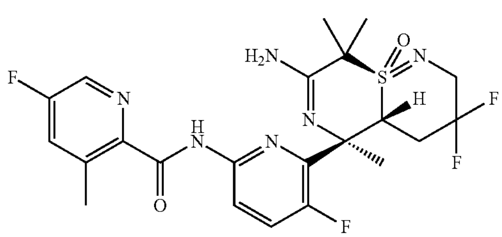 | 114 | | N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide |
| 40AA | 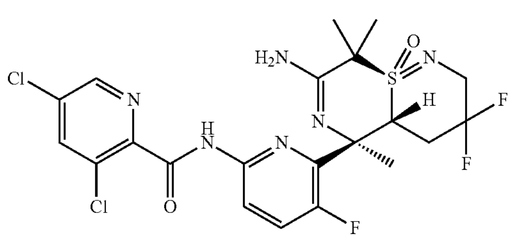 | 4.9 | 77 | N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 41AA | 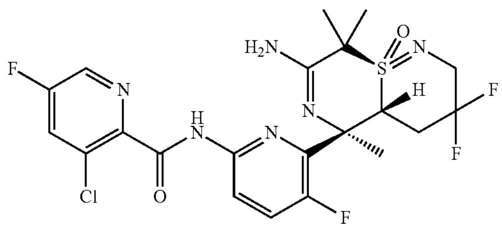 | 30.4 | 78 | N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-fluoropicolinamide |
| 42AA | 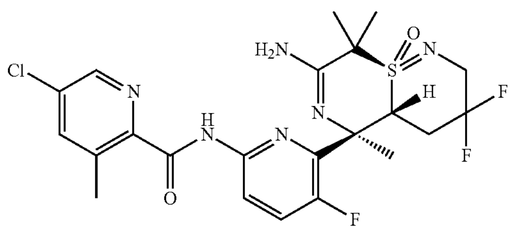 | 19.4 | 85 | N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-chloro-3-methylpicolinamide |
| 43AA | 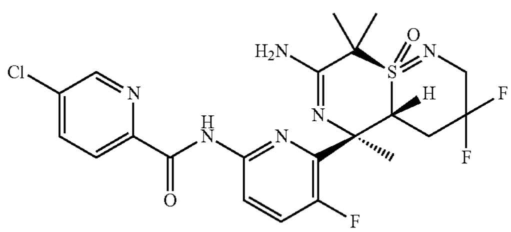 | 56 | 80 | N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-chloropicolinamide |
| 44AA | 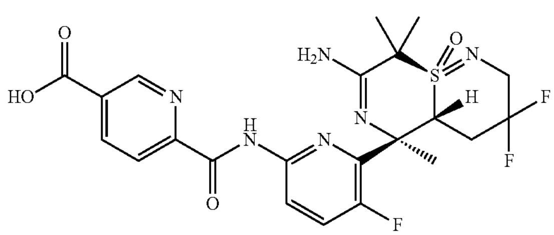 | >40 | | 6-((6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)carbamoyl)nicotinic acid |
| 45AA | 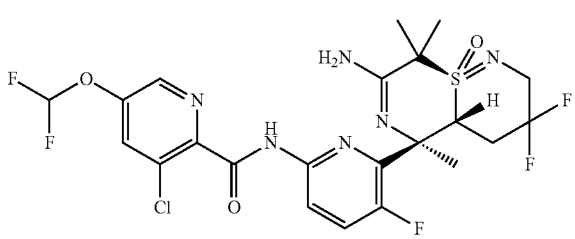 | 26.6 | 85 | N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-(difluoromethoxy)-picolinamide |
| 46AA | 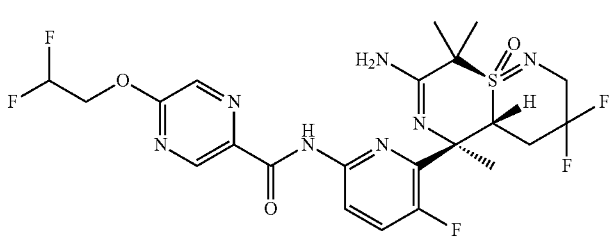 | 144 | | N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2-difluoroethoxy)pyrazine-2-carboxamide |

TABLE 1-continued

Pharmacological data

| Ex. | Structure | BACE1 cell act. Aβ40 IC$_{50}$ [nM] | Aβ40 (wt mice, brain) [%] | Name |
|---|---|---|---|---|
| 47AA | 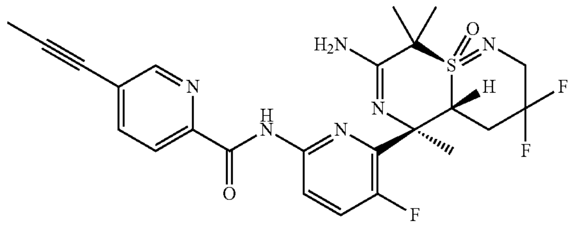 | 147 | | N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(prop-1-yn-1-yl)picolinamide |
| 48AA | 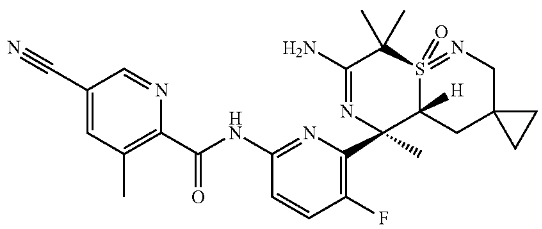 | 0.3 | 61 | N-(6-((4aR,5R,9R)-7-amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-5-cyano-3-methylpicolinamide |
| 48AB | 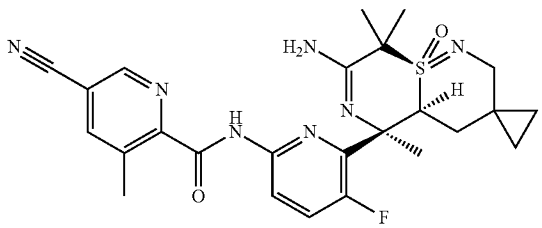 | 13 | | N-(6-((4aS,5R,9R)-7-amino-5,8,8-trimethyl-9-oxido-4,4a,5,8-tetrahydro-2H-spiro[[1,4]-thiazino[2,1-f][1,2]thiazine-3,1'-cyclopropan]-5-yl)-5-fluoropyridin-2-yl)-5-cyano-3-methylpicolinamide |
| 49AA | 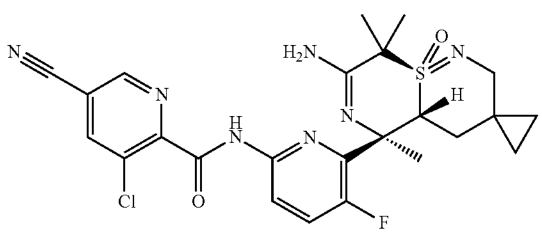 | 0.1 | 106 | N-(6-((4aR,5R,9R)-7-amino-5,8,8-trimethyl-9-oxido-4,4a,5,8-tetrahydro-2H-spiro[[1,4]-thiazino[2,1-f][1,2]thiazine-3,1'-cyclopropan]-5-yl)-5-fluoropyridin-2-yl)-3-chloro-5-cyanopicolinamide |
| 50AA | 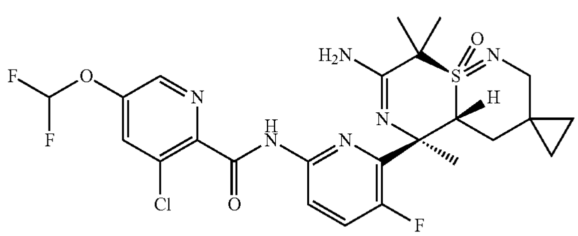 | 15.9 | 117 | N-(6-((4aR,5R,9R)-7-amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-3-chloro-5-(difluoromethoxy)picolinamide |
| 51AB | 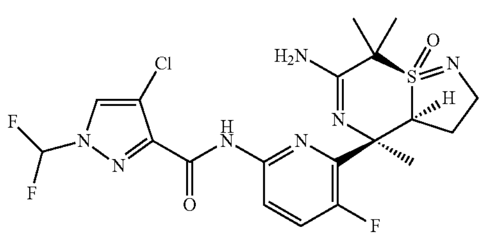 | <10 | | N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-4-chloro-1-(difluoromethyl)-1H-pyrazole-3-carboxamide |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |

TABLE 4-continued possible soft gelatin capsule ingredient composition

| ingredient | mg/capsule |
| --- | --- |
| Partially hydrogenated plant oils | 34 |
| Soya bean oil | 110 |
| Total | 165 |

TABLE 5 possible soft gelatin capsule composition

| ingredient | mg/capsule |
| --- | --- |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
| --- | --- |
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7 possible injection solution composition

| ingredient | mg/injection solution. |
| --- | --- |
| Compound of formula I | 3 |
| Polyethylene Glycol 400 | 150 |

TABLE 7-continued possible injection solution composition

| ingredient | mg/injection solution. |
| --- | --- |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8 possible sachet composition

| ingredient | mg/sachet |
| --- | --- |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

General

Analytical Methods

Gas chromatograms (GC) were recorded using an Agilent 6850 Series II single channel GC system. Column: Agilent HP-1, 30 m×0.32 mm×0.25 μm film, SN USC174642H, PN 190917-413E; Carrier gas: Helium in constant flow mode, pressure 25 psi; nominal initial flow 7.8 mL/min, injection volume 1 μL; Inlet: Split (ratio 20:1); Detector: Temperature 300° C., hydrogen flow 30 mL/min, air flow 400 mL/min.

Oven Temperature Program:

| Time [min] | Start-Temp. [° C.] | Rate [° C./min] | End-Temperature [° C.] |
| --- | --- | --- | --- |
| 0.0 | 40 | 5.0 | 80 |
| 8.0 | 80 | 20.0 | 250 |
| 16.5 | -end of method- | | |

HPLC (method LCMS_fglm)

Column: Agilent Zorbax Eclipse Plus C18, Rapid Resolution HT, 2.1×30 mm, 1.8 μm, Part. no. 959731-902

Solvent A: Water 0.01% Formic Acid; Solvent B: acetonitrile (MeCN)

Gradients:

| Time [min] | Flow Rate [ml/min] | % A | % B |
|---|---|---|---|
| Initial | 0.8 | 97 | 3 |
| 0.2 | 1.0 | 97 | 3 |
| 1.7 | 1.0 | 3 | 97 |
| 2.0 | 1.0 | 3 | 97 |
| 2.1 | 1.0 | 97 | 3 |

HPLC (method LCMS_gradient)

Column: Agilent Zorbax Eclipse Plus C18, Rapid Resolution HT, 2.1×30 mm, 1.8 μm, Part. no. 959731-902

Solvent A: Water 0.01% Formic Acid; Solvent B: MeCN

Gradients:

| Time [min] | Flow Rate [ml/min] | % A | % B |
|---|---|---|---|
| Initial | 1.0 | 97 | 3 |
| 0.2 | 1.0 | 97 | 3 |
| 5.2 | 1.0 | 3 | 97 |
| 6.0 | 1.0 | 3 | 97 |
| 6.2 | 1.0 | 97 | 3 |

HPLC (method 7626L05)

Column: Agilent Poroshell 120 EC-C18, 4.6×50 mm, 2.7 μm, Part. no. 699975-902

Solvent A: MeCN; Solvent B: water/MeCN 95:5 v/v; Solvent C: solution of 1 g tetra n-butylammonium hydrogensulfate in 1 L of water/MeCN 1:4 v/v.

Gradients:

| Time [min] | Flow Rate [ml/min] | % A | % B | % C |
|---|---|---|---|---|
| Initial | 1.0 | 10 | 85 | 5 |
| 1.0 | 1.0 | 10 | 85 | 5 |
| 7.0 | 1.0 | 85 | 10 | 5 |
| 12.0 | 1.0 | 85 | 10 | 5 |
| 13.0 | 1.0 | 10 | 85 | 5 |

ABBREVIATIONS

The following abbreviations were used in the experimental part: THF, tetrahydrofurane; MTBE, methyl-tert-butylether; DMF, dimethylformamide; TLC, thin layer chromatography.

Intermediates

Synthesis of Int-7: 2-Methyl-2-[S-methyl-N-(3-tetrahydropyran-2-yloxypropyl)sulfonimidoyl]propanenitrile

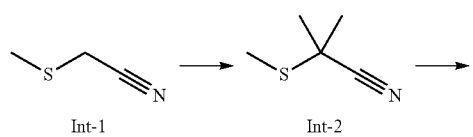

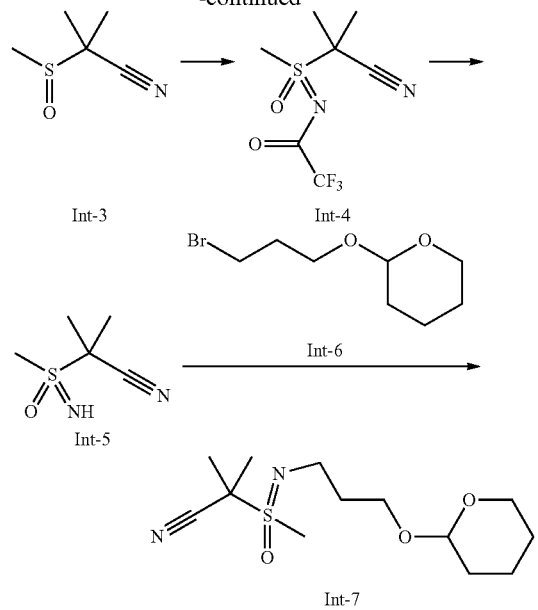

Step 1: 2-Methyl-2-methylsulfanyl-propanenitrile (Int-2)

Sodium hydride (24.0 g, 60% suspension in mineral oil, 600 mmol) was washed with n-heptane (3×100 mL) and suspended in THF (300 mL) at 0-5° C. A solution of 2-(methylthio)acetonitrile (Int-1, 20 g, 230 mmol) in THF (100 mL) was added and the resulting suspension was stirred for 15 min at 0-5° C. (ice bath). Then, a solution of methyl iodide (90.8 g, 40.0 mL, 640 mmol) in THF was added over 15 min. The mixture was allowed to warm and stirred for 3 h at room temperature. After that, the reaction mixture was poured carefully onto water (200 mL) and extracted with MTBE (1×500 mL, 3×150 mL). The combined extracts were washed with saturated aqueous sodium hydrogencarbonate solution (100 mL) and brine (100 mL), dried (sodium sulfate) and concentrated in vacuo to afford, after drying in vacuo (10 mbar, 40° C., 45 min), the title compound as a yellow oil (23.4 g, 89%), that was used in the next step without further purification. GC (method 7626G01) $t_R$=2.5 min. $^1$H NMR (CDCl$_3$, 400 MHz): δ 1.65 (s, 6H), 2.32 (s, 3H).

Step 2: 2-Methyl-2-methylsulfinyl-propanenitrile (Int-3)

2-Methyl-2-(methylthio)propanenitrile (Int-2, 23 g, 200 mmol) was dissolved in 1,4-dioxane (115 mL) and water (345 mL) was added. The emulsion was cooled to 0-5° C. (ice bath) and sodium periodate (44.8 g, 210 mmol) was added with water (115 mL). The resulting white suspension was warmed to room temperature and stirred vigorously for 16 h. Then, the mixture was filtered, the residue washed with ethyl acetate (400 mL). After phase separation of the filtrate, the aqueous phase was saturated with sodium chloride, extracted with ethyl acetate (5×200 mL). The combined extracts were washed with brine (100 mL), dried (sodium sulfate) and concentrated in vacuo to afford, after drying (50° C., 5 mbar), the title compound as yellow oil (25 g). The crude product was purified by column chromatography (silica gel, 100 g, eluting with ethyl acetate/n-heptane, gradient 50:50 to 0:100) to give the title compound as yellow oil (23.3 g, 89%). $^1$H NMR (CDCl$_3$, 400 MHz): δ 1.59 (s, 3H), 1.68 (s, 3H), 2.74 (s, 3H).

Step 3: 2-Methyl-2-(S-methylsulfon(trifluoracetylimidoyl))propanenitrile (Int-4)

2-Methyl-2-(methylsulfinyl)propanenitrile (Int-3, 9.8 g, 74.7 mmol) was dissolved in dichloromethane (390 mL) at 0-5° C. (ice bath) and 2,2,2-trifluoroacetamide (17.0 g, 151 mmol), magnesium oxide (12.7 g, 307 mmol) and rhodium (II) acetate dimer (850 mg, 1.92 mmol) were added subsequently. Finally, a solution of iodobenzene diacetate (36.3 g, 113 mmol) in dichloromethane (98.0 mL) was added and the mixture was stirred for 1 h at 0-5° C., followed by 6 h at room temperature. Then, a second portion of rhodium(II) acetate dimer (850 mg, 1.92 mmol) was added and the suspension stirred for additional 95 h at room temperature. The reaction mixture was filtered, the residue was washed with dichloromethane (100 mL) and the combined filtrate was concentrated in vacuo to afford a dark oil as crude product. After column chromatography (silica gel, 100 g, eluting with ethyl acetate/n-heptane, gradient 10:90 to 50:50) and drying in vacuo (50° C., 5 mbar) the title compound was isolated as a light yellow oil, that solidified upon standing (13.74 g, 76%). HPLC (method LCMS_fglm) $t_R$=0.97 min. $^1$H NMR (CDCl$_3$, 400 MHz): δ 1.91 (s, 3H), 1.91 (s, 3H), 3.65 (s, 3H). MS (ES−) m/z 241.1 [M−H].

Step 4: 2-Methyl-2-(S-methylsulfonimidoyl)propanenitrile (Int-5)

2-Methyl-2-(S-methylsulfon(trifluoracetylimidoyl))propanenitrile (Int-4, 9.90 g, 40.9 mmol) was dissolved in methanol (100 mL) at 0-5° C. (ice bath). Potassium carbonate (28.2 g, 204 mmol) was added with methanol (20 mL) and the resulting suspension was stirred at room temperature for 0.5 h. The reaction mixture was diluted with MTBE (250 mL) and silica gel (25 g) was added, the mixture was stirred for 15 min. After that, it was filtered over a plug of silica gel (35 g), the residue was washed with MTBE/methanol 2:1 (v/v, 250 mL). The combined filtrate was concentrated in vacuo to give a yellow oil. This material was again dissolved in ethyl acetate (200 mL) and filtered over a plug of silica gel (40 g), the residue was washed with ethyl acetate (200 mL). The combined filtrate was again concentrated in vacuo to afford the crude product as a yellow oil (5.98 g). The crude was purified by column chromatography (silica gel, 100 g, eluting with ethyl acetate/n-heptane, gradient 50:50 to 100:0) to yield, after drying in vacuo (50° C., 5 mbar), the title compound as a light yellow solid (4.54 g, 76%). GC (method 7626G01) $t_R$=9.7 min. $^1$H NMR (CDCl$_3$, 400 MHz): δ 1.75 (s, 3H), 1.76 (s, 3H), 2.79 (br s, 1H), 3.15 (s, 3H).

Step 5: 2-Methyl-2-[S-methyl-N-(3-tetrahydropyran-2-yloxypropyl)sulfonimidoyl]propanenitrile (Int-7)

Potassium hydride (30% w/w in mineral oil, 2.2 g, 16.5 mmol) was suspended in 1,2-dimethoxyethane (20.0 mL) and the suspension cooled to 0-5° C. (ice bath). A solution of 2-methyl-2-(methylsulfonimidoyl)propanenitrile (Int-5, 2.0 g, 13.7 mmol) in 1,2-dimethoxyethane (15 mL) was added dropwise over 10 min. The ice bath was removed and the mixture was stirred for 3 h at room temperature. After that, it was cooled again to 0-5° C. and tetrabutylammonium bromide (235 mg, 730 µmol) followed by 2-(3-bromopropoxy)tetrahydro-2H-pyran (Int-6, 3.95 g, 3.00 mL, 17.7 mmol) was added. The reaction mixture was stirred for 16 h at room temperature. Then, the mixture was poured onto a saturated aqueous solution of sodium hydrogencarbonate (60 mL) and diluted with ethyl acetate (180 mL). After phase separation, the aqueous phase was extracted with ethyl acetate (2×50 mL), the combined organic extracts were dried (sodium sulfate) and concentrated in vacuo to afford a yellow biphasic oil as crude product. This was purified by column chromatography (silica gel, 100 g, eluting with ethyl acetate/n-heptane, gradient 40:60 to 100:0) to yield, after drying in vacuo (50° C., 5 mbar), the title compound as mixture of diastereoisomers as a colorless viscous oil (3.28 g, 83%). HPLC (method LCMS_gradient) $t_R$=1.6 min. $^1$H NMR (CDCl$_3$, 400 MHz): δ 1.47-1.60 (m, 4H), 1.68-1.77 (m, 1H), 1.76 (br s, 6H), 1.78-1.88 (m, 3H), 3.06 & 3.07 (2s, 3H, diast.), 3.20-3.41 (m, 2H), 3.45-3.54 (m, 2H), 3.79-3.91 (m, 2H), 4.56-4.60 (m, 1H). MS (ES+) m/z 205.1 [M+H—(C$_5$H$_8$O)].

Synthesis of Int-11A and Int-11B: 2-((R,2R)-2-Amino-2-(6-bromo-3-fluoro-4-(triethylsilyl)pyridin-2-yl)-N-(3-hydroxypropyl)propylsulfonimidoyl)-2-methylpropanenitrile (Int-11A) and 2-((S,2R)-2-amino-2-(6-bromo-3-fluoro-4-(triethylsilyl)pyridin-2-yl)-N-(3-hydroxypropyl)propylsulfonimidoyl)-2-methylpropanenitrile (Int-11B)

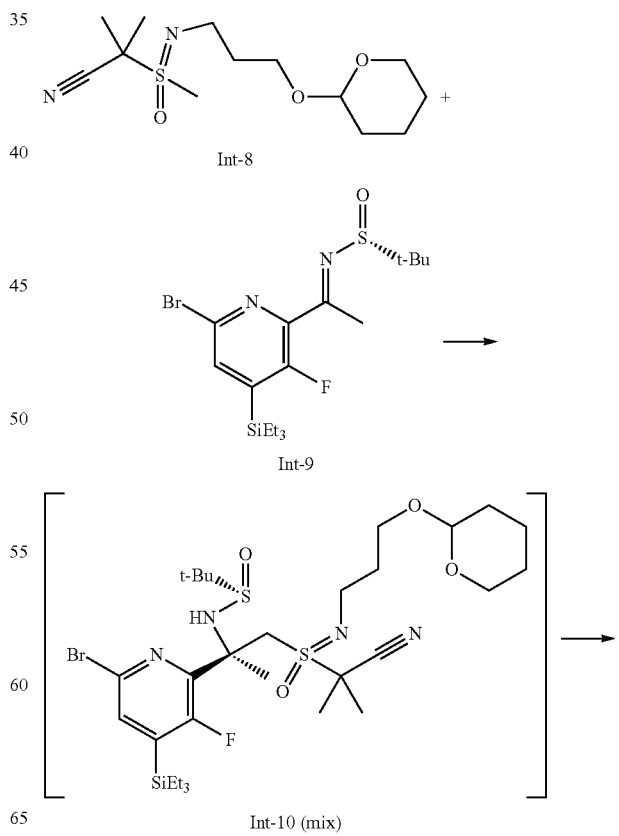

-continued

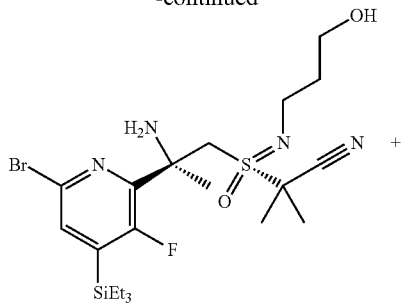

Int-11A

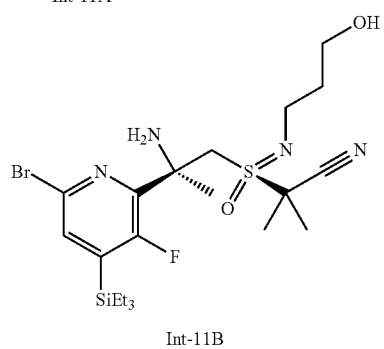

Int-11B

Step 1: N-[1-(6-Bromo-3-fluoro-4-triethylsilyl-2-pyridyl)-2-[S-(1-cyano-1-methyl-ethyl)-N-(3-tetrahydropyran-2-yloxypropyl)sulfonimidoyl]-1-methyl-ethyl]-2-methyl-propane-2-sulfinamide (Int-10 (mix))

2-Methyl-2-(S-methyl-N-(3-(tetrahydro-2H-pyran-2-yloxy)propyl)sulfonimidoyl)propanenitrile (Int-8, 3.31 g, 11.5 mmol) was dissolved in THF (45 mL) and the solution was cooled to <−70° C. (acetone/dry ice bath). N-Butyl lithium (1.6 M in hexanes, 7.0 mL, 11.2 mmol) was added dropwise over 10 min, and the resulting solution was stirred for 50 min at <−70° C. Then, a solution of (R,E)-N-(1-(6-bromo-3-fluoro-4-(triethylsilyl)-pyridin-2-yl)ethylidene)-2-methylpropane-2-sulfinamide (Int-9, 3.90 g, 8.96 mmol) in THF (45.0 mL) was added over 20 min at that temperature. After 30 min stirring at <70° C., the reaction mixture was poured onto a 2M aqueous solution of ammonium chloride (75 mL) and extracted with MTBE (1×300 mL, 2×100 mL). The combined organic extracts were concentrated in vacuo to give a yellow, viscous oil (2.46 g), that was used in the following step without further purification.

Step 2: 2-((R,2R)-2-Amino-2-(6-bromo-3-fluoro-4-(triethylsilyl)pyridin-2-yl)-N-(3)propylsulfonimidoyl)-2-methylpropanenitrile (Int-11A) and 2-((S,2R)-2-amino-2-(6-bromo-3-fluoro-4-(triethylsilyl)pyridin-2-yl)-N-(3)propylsulfonimidoyl)-2-methylpropanenitrile (Int-11B)

N-[1-(6-Bromo-3-fluoro-4-triethylsilyl-2-pyridyl)-2-[S-(1-cyano-1-methyl-ethyl)-N-(3-tetrahydropyran-2-yloxypropyl)sulfonimidoyl]-1-methyl-ethyl]-2-methyl-propane-2-sulfinamide (Int-10 (mix), 7.40 g, 10.2 mmol) was dissolved in ethanol (74 mL) and a solution of hydrogen chloride in methanol (ca. 20% w/w, 30 g, 30 mL, 165 mmol) was added at 0-5° C. (ice bath). The mixture was stirred for 30 min at room temperature. After that, it was poured onto a 2M aqueous solution of sodium carbonate (200 mL) and diluted with MTBE (300 mL). The resulting suspension was filtered, the residue was washed with MTBE (100 mL). Phases of the combined filtrate were separated, the aqueous phase was extracted with ethyl acetate (2×100 mL), the combined organic extracts were dried (sodium sulfate) and concentrated in vacuo to afford a brownish oil as crude product. The crude was purified by column chromatography (silica gel, 100 g, eluting with ethyl acetate/methanol, gradient 100:0 to 90:10) to yield, after drying in vacuo (55° C., 5 mbar), the title compound as separated diastereomers. The first eluting, minor diastereomer (Int-11B) was isolated as a colorless viscous oil (920 mg, 17%), the second eluting, major diastereomer (Int-11A) was obtained as a colorless oil (3.42 g, 62%). The overall yield is 79% over two steps.

Int-11A: HPLC (method LCMS_gradient) $t_R$=2.1 min. $^1$H NMR (CDCl$_3$, 400 MHz): δ 0.82-0.91 (m, 6H), 0.94-1.01 (m, 9H), 1.57 (d, J=0.8 Hz, 3H), 1.59-1.66 (m, 2H), 1.68 (s, 3H), 1.72 (s, 3H), 2.77 (br s, 3H), 3.10-3.18 (m, 1H), 3.24-3.31 (m, 1H), 3.57-3.71 (m, 2H), 3.80 (dd, J=1.1, 13.7 Hz, 1H), 4.08 (d, J=13.7 Hz, 1H), 7.35 (d, J=2.7 Hz, 1H). MS (ES+) m/z 537.3 & 535.3 [M+H].

Int-11B: HPLC (method LCMS_gradient) $t_R$=2.1 min. $^1$H NMR (CDCl$_3$, 400 MHz): δ 0.82-0.90 (m, 6H), 0.93-1.00 (m, 9H), 1.31-1.40 (m, 1H), 1.42-1.51 (m, 1H), 1.62 (d, J=1.1 Hz, 3H), 1.71 (s, 3H), 1.75 (s, 3H), 2.31 (br s, 3H), 3.05 (ddd, J=5.5, 6.3, 11.9 Hz, 1H), 3.26 (ddd, J=5.1, 7.5, 12.4 Hz, 1H), 3.54 (t, J=5.9 Hz, 2H), 3.63 (d, J=13.7 Hz, 1H), 4.22 (d, J=13.4 Hz, 1H), 7.33 (d, J=2.7 Hz, 1H). MS (ES+) m/z 537.3 & 535.3 [M+H].

Synthesis of Int-14A: 3-(((1R,3R)-3-(6-Bromo-3-fluoro-4-(triethylsilyl)pyridin-2-yl)-5-((tert-butoxycarbonyl)amino)-3,6,6-trimethyl-1-oxido-3,6-dihydro-2H-1,4-thiazin-1-ylidene)amino)propyl 4-methylbenzenesulfonate

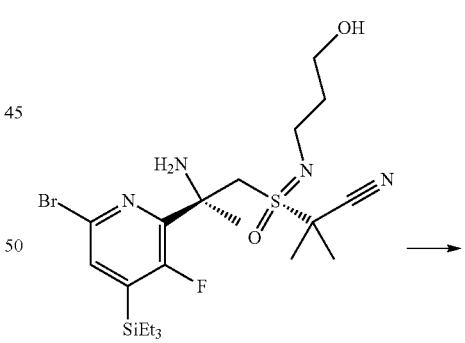

Int-11A

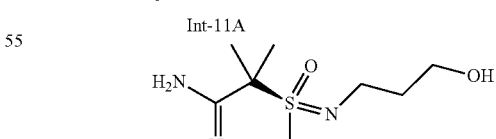

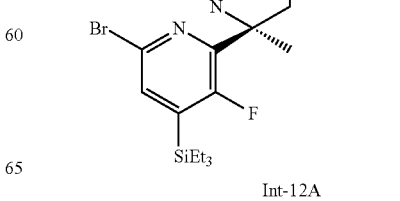

Int-12A

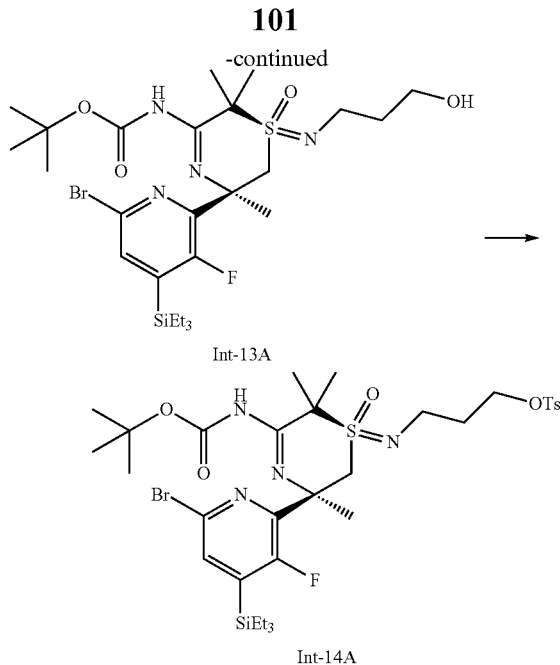

Int-13A

Int-14A

Step 1: (1R,3R)(6-bromo-3-fluoro-4-(triethylsilyl) pyridin-2-yl)-1-((3-hydro-xypropyl)imino)-3,6,6-trimethyl-3,6-dihydro-2H-1,4-thiazine 1-oxide (Int-12A)

2-((R,2R)-2-Amino-2-(6-bromo-3-fluoro-4-(triethylsilyl) pyridin-2-yl)-N-(3-hydroxypro-pyl)propylsulfonimidoyl)-2-methylpropanenitrile (Int-11A, 3.40 g, 6.35 mmol) was dissolved in ethanol (59 mL) and copper (I) chloride (660 mg, 6.67 mmol) was added. The mixture was heated to 75-80° C. and stirred for 45 min at that temperature. After that, it was cooled to 5° C. (ice bath) and poured onto a mixture of brine (40 mL) and aqueous ammonia (25% w/w, 20 mL). The resulting mixture was extracted with MTBE (200 mL) and ethyl acetate (2×50 mL), the combined extracts were dried (sodium sulfate) and concentrated in vacuo to give a yellow oil as crude product. The crude was purified by column chromatography (silica gel, 100 g, eluting with ethyl acetate/methanol, gradient 95:5 to 85:15) to afford, after drying in vacuo (55° C., 5 mbar), the title compound as a white solid (2.79 g, 82%). HPLC (method LCMS_gradient) $t_R$=1.8 min. $^1$H NMR (CDCl$_3$, 400 MHz): δ 0.81-0.89 (m, 6H), 0.92-0.99 (m, 9H), 1.40-1.65 (m, 2H), 1.63 (s, 3H), 1.73 (s, 3H), 1.78 (s, 3H), 2.78-2.88 (m, 1H), 3.16-3.24 (m, 1H), 3.28-3.36 (m, 1H), 3.39 (d, J=14.8 Hz, 1H), 3.41-3.49 (m, 1H), 3.56-3.70 (m, 2H), 3.78-3.82 (m, 1H), 4.24 (d, J=14.8 Hz, 1H), 7.32 (d, J=2.4 Hz, 1H). MS (ES+) m/z 537.3 & 535.3 [M+H, Br].

Step 2: tert-Butyl ((1R,5R)-5-(6-bromo-3-fluoro-4-(triethylsilyl)pyridin-2-yl)-1-((3-hydroxypropyl) imino)-2,2,5-trimethyl-1-oxido-5,6-dihydro-2H-1,4-thiazin-3-yl)carbamate (Int-13A)

(1R,3R)(6-bromo-3-fluoro-4-(triethylsilyl)pyridin-2-yl)-1-((3-hydroxypro-pyl)imino)-3,6,6-trimethyl-3,6-dihydro-2H-1,4-thiazine 1-oxide (Int-12A, 2.20 g, 4.11 mmol) was dissolved in THF (22 mL) and water (4.4 mL) and Boc-anhydride (1 g, 1.06 ml, 4.58 mmol), sodium hydrogencarbonate (440 mg, 5.24 mmol) and 4-dimethylaminopyridine (26 mg, 213 μmol) were added. The mixture was stirred for 1.5 h at room temperature. After that, aqueous ammonia (25% w/w, 198 mg, 220 μl, 2.91 mmol) was added and the mixture was stirred for additional 30 min. The reaction mixture was then poured onto water (50 mL) and extracted with MTBE (1×150 mL, 1×50 mL). The combined extracts were dried and concentrated in vacuo. The crude product was purified by column chromatography (silica gel, 100 g, eluting with ethyl acetate/n-heptane, gradient 40:60 to 60:40) to yield, after drying in vacuo (50° C., 5 mbar), the title compound as a colorless gum (2.06 g, 79%). HPLC (method LCMS_gradient) $t_R$=3.9 min. $^1$H NMR (CDCl$_3$, 400 MHz): δ 0.82-0.90 (m, 6H), 0.93-0.99 (m, 9H), 1.37-1.61 (m, 2H), 1.54 (s, 9H), 1.60 (s, 3H), 1.63 (s, 3H), 1.77 (s, 3H), 2.65-2.74 (m, 2H), 3.13-3.20 (m, 1H), 3.54 (d, J=15.0 Hz, 1H), 3.57-3.69 (m, 2H), 4.48 (d, J=15.3 Hz, 1H), 7.37 (d, J=2.7 Hz, 1H), 11.14 (br s, 1H, exch). MS (ES+) m/z 637.4 & 635.6 [M+H, Br].

Step 3: 3-((((1R,3R)-3-(6-Bromo-3-fluoro-4-(triethylsilyl)pyridin-2-yl)-5-((tert-butoxy-carbonyl)amino)-3,6,6-trimethyl-1-oxido-3,6-dihydro-2H-1,4-thiazin-1-ylidene)amino)propyl 4-methylbenzenesulfonate (Int-14A)

tert-Butyl ((1R,5R)-5-(6-bromo-3-fluoro-4-(triethylsilyl) pyridin-2-yl)-1-((3-hydroxy-propyl)imino)-2,2,5-trimethyl-1-oxido-5,6-dihydro-2H-1,4-thiazin-3-yl)carbamate (Int-13A, 2.0 g, 3.15 mmol) was dissolved in dichloromethane (20 mL), the solution was cooled to 0-5° C. (ice bath) and triethylamine (799 mg, 1.1 mL, 7.89 mmol), a solution of tosyl chloride (925 mg, 4.85 mmol) in dichloromethane (10 ml) and 4-dimethylaminopyridine (30 mg, 246 μmol) were added subsequently at that temperature. The resulting clear solution was stirred for 16 h at room temperature. Then, the reaction mixture was poured onto an aqueous saturated solution of ammonium chloride (50 mL), and, after phase separation, the aqueous phase extracted with MTBE (1×200 mL, 1×50 mL). The combined extracts were washed with sat. aqueous sodium hydrogencarbonate solution (50 mL), dried (sodium sulfate) and concentrated in vacuo to give a turbid brownish oil as crude product. The crude was purified by column chromatography (silica gel, 100 g, eluting with ethyl acetate/n-heptane, gradient 25:75 to 40:60) to afford, after drying in vacuo (50° C., 5 mbar), the title compound as a white solid (2.29 g, 92%). HPLC (method LCMS_gradient) $t_R$=4.6 min. $^1$H NMR (CDCl$_3$, 400 MHz): δ 0.81-0.89 (m, 6H), 0.92-0.98 (m, 9H), 1.46 (s, 3H), 1.48-1.69 (m, 2H), 1.54 (s, 9H), 1.59 (s, 3H), 1.70 (s, 3H), 2.44 (s, 3H), 2.50-2.60 (m, 1H), 2.93-3.02 (m, 1H), 3.49 (d, J=15.0 Hz, 1H), 3.95-4.02 (m, 2H), 4.39 (d, J=15.3 Hz, 1H), 7.33 (d, J=8.1 Hz, 2H), 7.36 (d, J=2.4 Hz, 1H), 7.76 (d, J=8.3 Hz, 2H), 11.10 (br s, 1H, exch). MS (ES+) m/z 791.4 & 789.6 [M+H, Br].

Synthesis of Int-14B: 3-(((1S,3R)-3-(6-Bromo-3-fluoro-4-(triethylsilyl)pyridin-2-yl)-5-((tert-butoxycarbonyl)amino)-3,6,6-trimethyl-1-oxido-3,6-dihydro-2H-1,4-thiazin-1-ylidene)amino)propyl 4-methylbenzenesulfonate

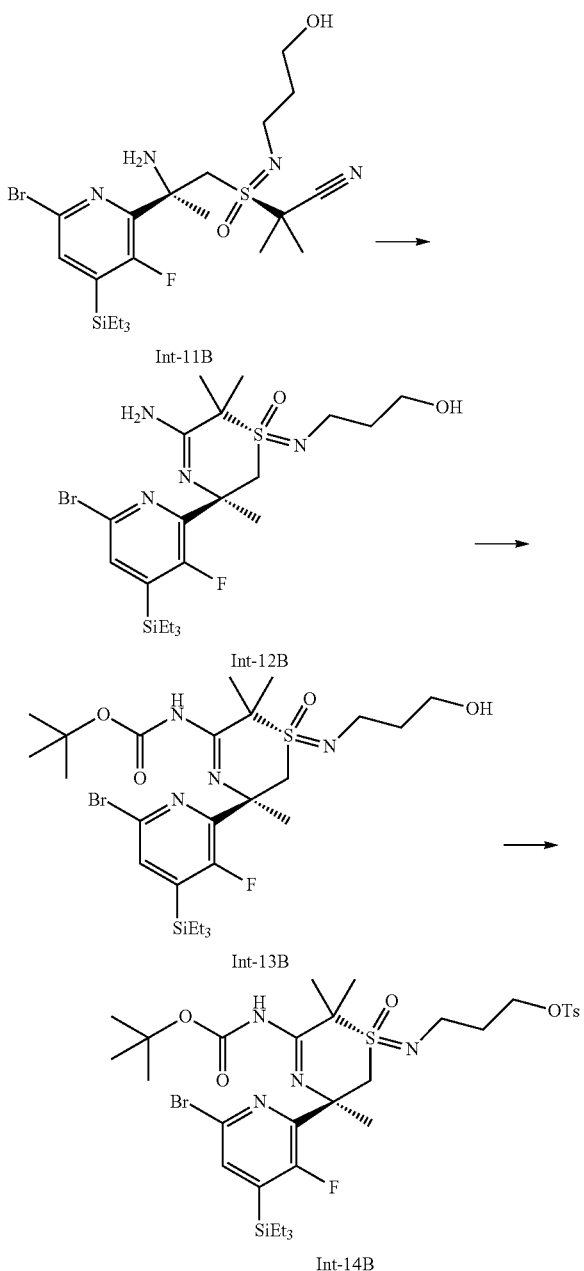

Step 1: (1S,3R)(6-bromo-3-fluoro-4-(triethylsilyl)pyridin-2-yl)-1-((3-hydro-xypropyl)imino)-3,6,6-trimethyl-3,6-dihydro-2H-1,4-thiazine 1-oxide (Int-12B)

2-((S,2R)-2-Amino-2-(6-bromo-3-fluoro-4-(triethylsilyl)pyridin-2-yl)-N-(3-hydroxypro-pyl)propylsulfonimidoyl)-2-methylpropanenitrile (Int-11B, 970 mg, 1.81 mmol) was dissolved in ethanol (20 mL) and copper (I) bromide (275 mg, 1.92 mmol) was added. The mixture was heated to 75-80° C. and stirred for 1.5 h at that temperature. After that, it was cooled to 5° C. (ice bath) and poured onto a mixture of brine (10 mL) and aqueous ammonia (25% w/w, 5 mL). The resulting mixture was extracted with MTBE (60 mL) and ethyl acetate (2×25 mL), the combined extracts were dried (sodium sulfate) and concentrated in vacuo to give a yellow oil as crude product. The crude was purified by column chromatography (silica gel, 100 g, eluting with ethyl acetate/methanol, gradient 95:5 to 70:30) to yield, after drying in vacuo (55° C., 5 mbar), the title compound as a white foam (670 mg, 69%). HPLC (method 7626L05) $t_R$=4.7 min.

Step 2: tert-Butyl ((1S,5R)-5-(6-bromo-3-fluoro-4-(triethylsilyl)pyridin-2-yl)-1-((3-hydroxypropyl)imino)-2,2,5-trimethyl-1-oxido-5,6-dihydro-2H-1,4-thiazin-3-yl)carbamate (Int-13B)

(1S,3R)(6-bromo-3-fluoro-4-(triethylsilyl)pyridin-2-yl)-1-((3-hydroxy-propyl)imino)-3,6,6-trimethyl-3,6-dihydro-2H-1,4-thiazine 1-oxide (Int-12B, 670 mg, 1.25 mmol) was dissolved in THF (8 mL) and water (1.7 mL) and Boc-anhydride (350 mg, 372 µl, 1.6 mmol), sodium hydrogencarbonate (135 mg, 1.61 mmol) and 4-dimethylaminopyridine (8 mg, 65 µmol) were added. The mixture was stirred for 2 h at room temperature. After that, aqueous ammonia (25% w/w, 54 mg, 60 µl, 0.79 mmol) was added and the mixture was stirred for additional 30 min. The reaction mixture was then poured onto water (15 mL) and extracted with MTBE (1×40 mL, 1×20 mL). The combined extracts were washed with brine (10 mL), dried (sodium sulfate) and concentrated in vacuo (50° C., 5 mbar) to afford the title compound as a light brown gum (770 mg, 97% yield), that was used in the next step without further purification. HPLC (method 7626L05) $t_R$=8.6 min.

Step 3: 3-(((1S,3R)-3-(6-Bromo-3-fluoro-4-(triethylsilyl)pyridin-2-yl)-5-((tert-butoxy-carbonyl)amino)-3,6,6-trimethyl-1-oxido-3,6-dihydro-2H-1,4-thiazin-1-ylidene)amino)propyl 4-methylbenzenesulfonate (Int-14B)

tert-Butyl ((1S,5R)-5-(6-bromo-3-fluoro-4-(triethylsilyl)pyridin-2-yl)-1-((3-hydroxy-propyl)imino)-2,2,5-trimethyl-1-oxido-5,6-dihydro-2H-1,4-thiazin-3-yl)carbamate (Int-13B, 1.22 g, 1.92 mmol) was dissolved in dichloromethane (12 mL), the solution was cooled to 0-5° C. (ice bath) and triethylamine (486 mg, 670 µL, 4.81 mmol), a solution of tosyl chloride (560 mg, 2.94 mmol) in dichloromethane (6 ml) and 4-dimethylaminopyridine (15 mg, 123 µmol) were added subsequently at that temperature. The resulting clear solution was stirred for 16 h at room temperature. Then, the reaction mixture was poured onto an aqueous saturated solution of ammonium chloride (25 mL), and, after phase separation, the aqueous phase extracted with MTBE (1×100 mL, 1×50 mL). The combined extracts were washed with sat. aqueous sodium hydrogencarbonate solution (25 mL), dried (sodium sulfate) and concentrated in vacuo to give a turbid brownish oil as crude product. The crude was purified by column chromatography (silica gel, 50 g, eluting with ethyl acetate/n-heptane, gradient 25:75 to 50:50) to yield, after drying in vacuo (50° C., 5 mbar), the title compound as a light brown gum (1.25 g, 83% yield). HPLC (method 7626L05) $t_R$=11.1 min.

Synthesis of Int-15AA and Int-15AB: tert-Butyl ((4aR,5R,9R)-5-(6-bromo-3-fluoro-4-(triethylsilyl)pyridin-2-yl)-5,8,8-trimethyl-9-oxido-2,3,4,4a,5,8-hexahydro-[1,4]thiazino[2,1-f][1,2]thiazin-7-yl)carbamate (Int-15AA) and tert-butyl ((4aS,5R,9R)-5-(6-bromo-3-fluoro-4-(triethylsilyl)pyridin-2-yl)-5,8,8-trimethyl-9-oxido-2,3,4,4a,5,8-hexahydro-[1,4]thiazino[2,1-f][1,2]thiazin-7-yl)carbamate (Int-15AB)

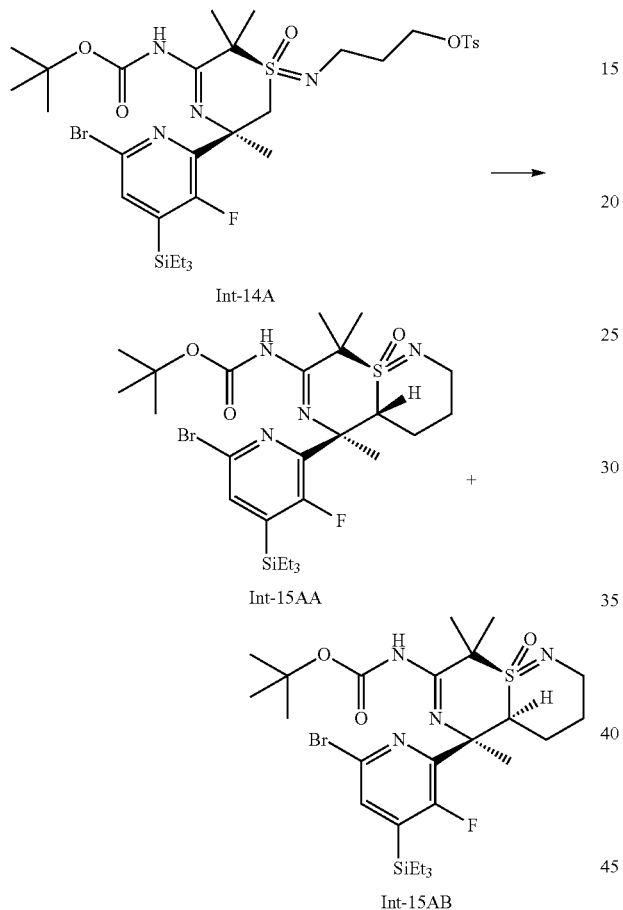

3-(((1R,3R)-3-(6-Bromo-3-fluoro-4-(triethylsilyl)pyridin-2-yl)-5-((tert-butoxycarbonyl)-amino)-3,6,6-trimethyl-1-oxido-3,6-dihydro-2H-1,4-thiazin-1-ylidene)amino)propyl 4-methylbenzenesulfonate (Int-14A, 2.28 g, 2.89 mmol) was dissolved in THF (50 mL) and the solution was cooled to <−70° C. (acetone/dry ice bath). A solution of LHMDS in THF (1.0 M, 7.6 ml, 7.6 mmol) was added over 10 min at that temperature. Then, the resulting clear, yellow solution was allowed to warm to 0-5° C. (ice bath) and stirred for 1.5 h at that temperature. The reaction mixture was poured onto a 2 M aqueous ammonium chloride solution (50 mL) and extracted with MTBE (1×150 mL, 1×50 mL). The combined extracts were washed with brine (30 mL), dried (sodium sulfate) and concentrated in vacuo. The crude was purified by column chromatography (silica gel, 100 g, eluting with ethyl acetate/n-heptane, gradient 30:70 to 60:40) to afford, after drying in vacuo (55° C., 5 mbar), the title compounds as separated diastereoisomers. The first eluting diastereoisomer (Int-15AA) was isolated as a white foam (800 mg, 45%) and the second eluting diastereoisomer (Int-15AB) was obtained as a white foam (670 mg, 37%).

Int-15AA: HPLC (method LCMS_gradient) $t_R$=4.4 min. $^1$H NMR (CDCl$_3$, 400 MHz): δ 0.82-0.91 (m, 6H), 0.94-1.00 (m, 9H), 1.48 (s, 9H), 1.77 (s, 3H), 1.79 (s, 3H), 1.81-2.01 (m, 2H), 1.91 (d, J=1.3 Hz, 3H), 2.07-2.14 (m, 1H), 2.38 (dddd, J=3.0, 12.9, 13.2, 13.2 Hz, 1H), 3.36-3.44 (m, 1H), 3.62 (ddd, J=3.5, 12.7, 12.7 Hz, 1H), 4.17 (dd, J=3.4, 12.5 Hz, 1H), 7.42 (d, J=2.4 Hz, 1H), 11.37 (br s, 1H, exch). MS (ES+) m/z 619.3 & 617.6 [M+H, Br].

Int-15AB: HPLC (method LCMS_gradient) $t_R$=4.2 min. $^1$H NMR (CDCl$_3$, 400 MHz): δ 0.83-0.91 (m, 6H), 0.93-0.99 (m, 9H), 1.49-1.69 (m, 2H), 1.59 (s, 9H), 1.71-1.82 (m, 2H), 1.78 (s, 3H), 1.89 (s, 3H), 2.02 (d, J=0.8 Hz, 3H), 3.37-3.47 (m, 1H), 3.56-3.70 (m, 2H), 7.45 (d, J=2.7 Hz, 1H), 11.82 (br s, 1H, exch). MS (ES+) m/z 619.3 & 617.6 [M+H, Br].

Synthesis of Int-15BA and Int-15BB: tert-Butyl ((4aR,5R,9S)-5-(6-bromo-3-fluoro-4-(triethylsilyl)pyridin-2-yl)-5,8,8-trimethyl-9-oxido-2,3,4,4a,5,8-hexahydro-[1,4]thiazino[2,1-f][1,2]thiazin-7-yl)carbamate (Int-15BA) and tert-butyl ((4aS,5R,9S)-5-(6-bromo-3-fluoro-4-(triethylsilyl)pyridin-2-yl)-5,8,8-trimethyl-9-oxido-2,3,4,4a,5,8-hexahydro-[1,4]thiazino[2,1-f][1,2]thiazin-7-yl)carbamate (Int-15BB)

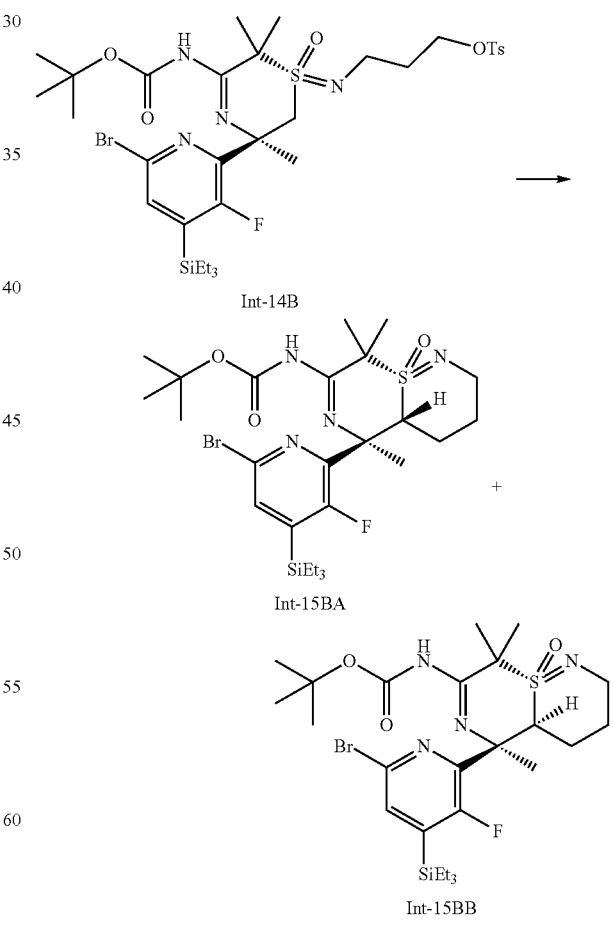

3-(((1S,3R)-3-(6-Bromo-3-fluoro-4-(triethylsilyl)pyridin-2-yl)-5-((tert-butoxycarbonyl)-amino)-3,6,6-trimethyl- 1-oxido-3,6-dihydro-2H-1,4-thiazin-1-ylidene)amino)propyl 4-methylbenzenesulfonate (Int-14B, 1.25 g, 1.58 mmol) was dissolved in THF (28 mL) and the solution was cooled to <−70° C. (acetone/dry ice bath). A solution of LHMDS in THF (1.0 M, 4.2 ml, 4.2 mmol) was added over 10 min at that temperature. Then, the resulting clear, yellow solution was allowed to warm to 0-5° C. (ice bath) and stirred for 2.5 h at that temperature. The reaction mixture was poured onto a 2 M aqueous ammonium chloride solution (50 mL) and extracted with MTBE (1×100 mL, 1×50 mL). The combined extracts were washed with brine (30 mL), dried (sodium sulfate) and concentrated in vacuo to give a yellow foam as crude product (1.06 g). The crude product contained two diastereoisomers in a ratio of ca. 7:3 (Int-15BA/Int-15BB, by HPLC) and was used in the following step without further purification.

Int-15BA: HPLC (method LCMS_gradient) $t_R$=4.1 min. MS (ES+) m/z 619.3 & 617.3 [M+H, Br].

Int-15BB: HPLC (method LCMS_gradient) $t_R$=4.3 min. MS (ES+) m/z 619.3 & 617.3 [M+H, Br].

Synthesis of Int-17AA: tert-Butyl ((4aR,5R,9R)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate

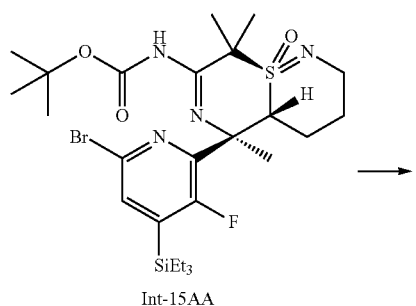

Int-15AA

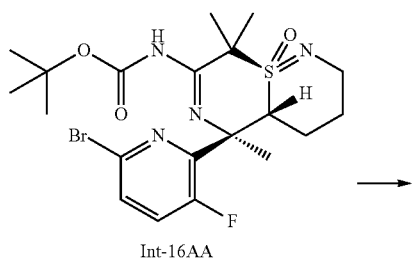

Int-16AA

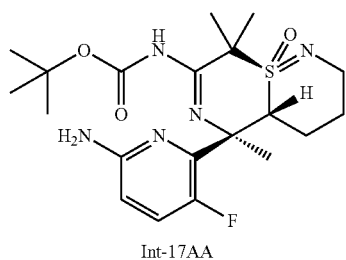

Int-17AA

Step 1: tert-Butyl ((4aR,5R,9R)-5-(6-bromo-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-16AA)

tert-Butyl ((4aR,5R,9R)-5-(6-bromo-3-fluoro-4-(triethylsilyl)pyridin-2-yl)-5,8,8-trimethyl-9-oxido-2,3,4,4a,5,8-hexahydro-[1,4]thiazino[2,1-f][1,2]thiazin-7-yl)carbamate (Int-15AA, 780 mg, 1.26 mmol) was dissolved in THF (9.6 mL) and DMF (2.4 mL). Acetic acid (157 mg, 150 µl, 2.62 mmol) and potassium fluoride (150 mg, 2.58 mmol) were added at room temperature and the resulting fine suspension was stirred for 2 h at that temperature. After that, it was poured upon a saturated aqueous solution of sodium hydrogencarbonate (20 mL) and extracted with MTBE (1×80 mL, 1×40 mL). The combined extracts were washed with brine (20 mL), dried (sodium sulfate) and concentrated in vacuo to give a white foam as crude product (650 mg). The crude was purified by column chromatography (silica gel, 50 g, eluting with ethyl acetate/n-heptane, gradient 60:40 to 80:20) to yield, after drying in vacuo (50° C., 5 mbar), the title compound as a white solid (550 mg, 86%). HPLC (method LCMS_gradient) $t_R$=2.8 min. $^1$H NMR (CDCl$_3$, 400 MHz): δ 1.48 (s, 9H), 1.77 (s, 3H), 1.81 (s, 3H), 1.82-1.95 (m, 2H), 1.92 (d, J=1.6 Hz, 3H), 1.95-2.05 (m, 1H), 2.38 (dddd, J=3.5, 12.4, 12.6, 13.4 Hz, 1H), 3.36-3.43 (m, 1H), 3.61 (ddd, J=3.5, 12.5, 12.5 Hz, 1H), 4.08-4.14 (m, 1H), 7.38 (dd, J=8.3, 10.8 Hz, 1H), 7.51 (dd, J=3.1, 8.5 Hz, 1H), 11.23 (br s, 1H, exch). MS (ES+) m/z 505.3 & 503.4 [M+H, Br].

Step 2: tert-Butyl ((4aR,5R,9R)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-17AA)

tert-Butyl ((4aR,5R,9R)-5-(6-bromo-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-16AA, 300 mg, 596 µmol) was dissolved in 1,4-dioxane (5 mL) and water (1.7 mL) and sodium azide (400 mg, 6.15 mmol) was added. Copper (I) iodide (63 mg, 331 µmol), sodium ascorbate (33 mg, 167 µmol) and trans-N,N-dimethyl-1,2-cyclohexanediamine (72.2 mg, 80 µl, 507 µmol) were added subsequently and the dark blue mixture was stirred for 1 h at 70° C. Then, the reaction mixture was allowed to cool to room temperature and poured onto a saturated aqueous solution of sodium hydrogencarbonate (20 mL). It was extracted with ethyl acetate (1×60 mL, 1×30 mL), the combined extracts were dried over sodium sulfate and silica gel (2 g) was added to the solution. After filtration, the filtrate was concentrated in vacuo to give a green solid as crude product. The crude was purified by column chromatography (silica gel, 50 g, eluting with ethyl acetate/n-heptane, gradient 80:20 to 100:0) to afford, after drying in vacuo (50° C., 5 mbar), the title compound as an off-white solid (150 mg, 57%). HPLC (method LCMS_gradient) $t_R$=2.2 min $^1$H NMR (CDCl$_3$, 400 MHz): δ 1.48 (s, 9H), 1.76 (s, 3H), 1.79-1.95 (m, 2H), 1.82 (s, 3H), 1.87 (d, J=1.9 Hz, 3H), 2.01-2.08 (m, 1H), 2.35 (dddd, J=3.8, 12.6, 13.2, 13.2

Hz, 1H), 3.34-3.42 (m, 1H), 3.61 (ddd, J=3.9, 12.4, 12.4 Hz, 1H), 4.09-4.16 (m, 1H), 4.38 (s, 2H), 6.47 (dd, J=2.4, 8.9 Hz, 1H), 7.24 (dd, J=8.7, 11.1 Hz, 1H), 11.12 (br s, 1H, exch). MS (ES+) m/z 440.3 [M+H].

Synthesis of Int-17AB: tert-Butyl ((4aS,5R,9R)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate

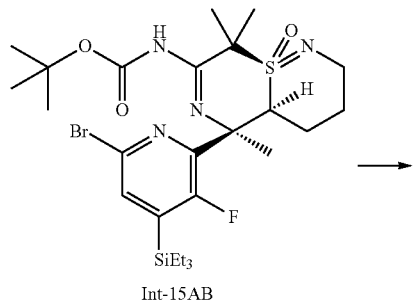

Int-15AB

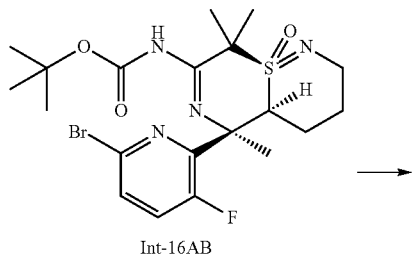

Int-16AB

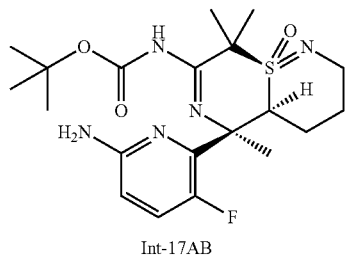

Int-17AB p 1: tert-Butyl ((4aS,5R,9R)-5-(6-bromo-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-16AB)

tert-Butyl ((4a S,5R,9R)-5-(6-bromo-3-fluoro-4-(triethylsilyl)pyridin-2-yl)-5,8,8-trimethyl-9-oxido-2,3,4,4a,5,8-hexahydro-[1,4]thiazino[2,1-f][1,2]thiazin-7-yl)carbamate (Int-15AB, 650 mg, 1.05 mmol) was dissolved in THF (8 mL) and DMF (2 mL). Acetic acid (131 mg, 125 µl, 2.18 mmol) and potassium fluoride (125 mg, 2.15 mmol) were added at room temperature and the resulting fine suspension was stirred for 2 h at that temperature. After that, it was poured upon a saturated aqueous solution of sodium hydrogencarbonate (20 mL) and extracted with MTBE (1×60 mL, 1×30 mL). The combined extracts were washed with brine (15 mL), dried (sodium sulfate) and concentrated in vacuo to give a white solid as crude product. The crude was suspended in MTBE (10 mL) and stirred for 10 min at room temperature. N-Heptane (10 mL) was added, the precipitate was filtered, washed with n-heptane (10 mL) and dried in vacuo (50° C., mbar) to afford the title compound as white powder (410 mg, 77%). HPLC (method LCMS_gradient) $t_R$=2.6 min. $^1$H NMR (CDCl$_3$, 400 MHz): δ 1.58 (s, 9H), 1.59-1.70 (m, 2H), 1.72-1.82 (m, 2H), 1.79 (s, 3H), 1.90 (s, 3H), 2.03 (d, J=1.1 Hz, 3H), 3.38-3.48 (m, 1H), 3.54-3.61 (m, 1H), 3.63-3.70 (m, 1H), 7.39 (dd, J=8.5, 10.5 Hz, 1H), 7.55 (dd, J=3.1, 8.5 Hz, 1H), 11.86 (br s, 1H, exch). MS (ES+) nm/z 505.3 & 503.4 [M+H, Br].

Step 2: tert-Butyl ((4aS,5R,9R)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-17AB)

tert-Butyl ((4aS,5R,9R)-5-(6-bromo-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-16AB, 180 mg, 358 µmol) was dissolved in 1,4-dioxane (3 mL) and water (1 mL) and sodium azide (240 mg, 3.69 mmol) was added. Copper (I) iodide (38 mg, 200 mol), sodium ascorbate (20 mg, 101 mol) and trans-N,N'-dimethyl-1,2-cyclohexanediamine (45.1 mg, 50 µl, 317 µmol) were added subsequently and the dark blue mixture was stirred for 1 h at 70° C. After that, a second portion of sodium azide (120 mg, 1.85 mmol), and a suspension of copper (I) iodide (38 mg, 200 mol), sodium ascorbate (20 mg, 101 mol) and trans-N,N'-dimethyl-1,2-cyclohexanediamine (45.1 mg, 50 µl, 317 µmol) in dioxane (0.5 mL) were added and the mixture was stirred for additional 45 min at 70° C. Then, the reaction mixture was allowed to cool to room temperature and poured onto a saturated aqueous solution of sodium hydrogencarbonate (15 mL). It was extracted with ethyl acetate (1×60 mL, 1×30 mL), the combined extracts were dried over sodium sulfate and silica gel (2 g) was added to the solution. After filtration, the filtrate was concentrated in vacuo to give a green sticky solid as crude product (200 mg). The crude was purified by column chromatography (silica gel, 50 g, eluting with dichloromethane/methanol, gradient 98:1 to 95:5) to afford, after drying in vacuo (50° C., 5 mbar), the title compound as an off-white solid (140 mg, 89%). HPLC (method LCMS_gradient) $t_R$=1.8 min. $^1$H NMR (CDCl$_3$, 400 MHz): δ 1.56 (s, 9H), 1.62-1.84 (m, 4H), 1.79 (s, 3H), 1.89 (s, 3H), 1.98 (d, J=0.8 Hz, 3H), 3.35-3.45 (m, 1H), 3.56-3.69 (m, 2H), 4.57 (s, 2H), 6.48 (dd, J=2.4, 8.9 Hz, 1H), 7.26 (dd, J=8.6, 10.5 Hz, 1H), 12.07 (br s, 1H, exch). MS (ES+) m/z 440.3 [M+H].

Synthesis of Int-17BA: tert-Butyl ((4aR,5R,9S)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate Int-16BA: HPLC (method LCMS_gradient) $t_R$=2.6 min. $^1$H NMR (CDCl$_3$, 400 MHz): δ 1.44 (s, 3H), 1.55 (s, 9H), 1.77 (s, 3H), 1.85 (s, 3H), 1.87-1.95 (m, 2H), 2.12-2.24 (m, 1H), 2.51-2.59 (m, 1H), 3.49-3.57 (m, 1H), 3.63-3.72 (m,

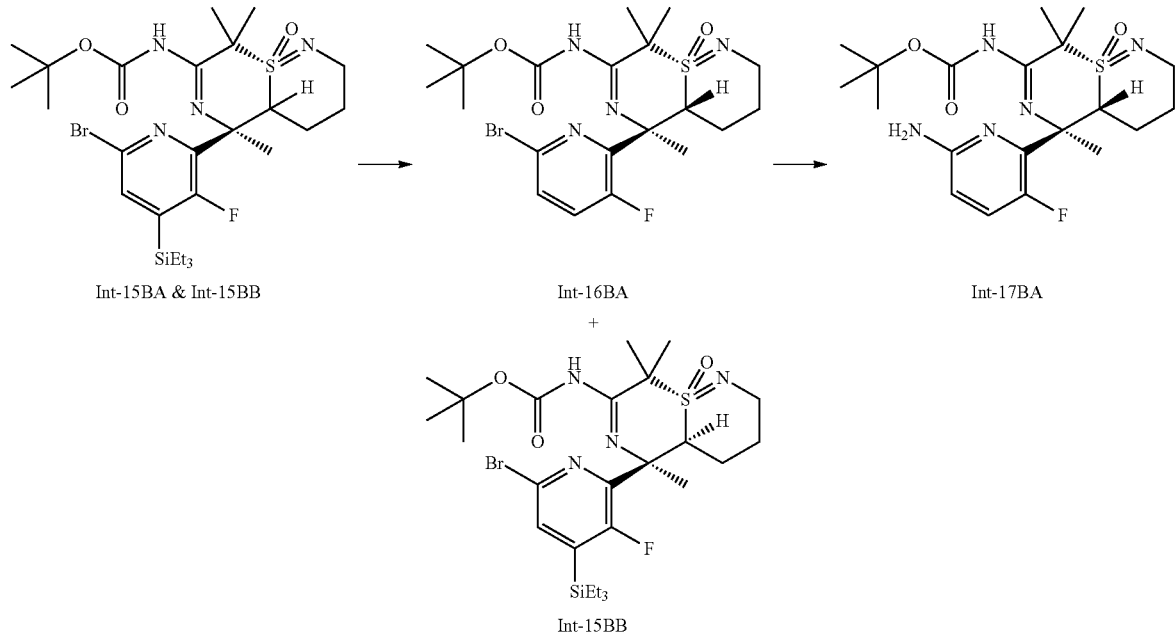

Step 1: tert-Butyl ((4aR,5R,9S)-5-(6-bromo-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-16BA)

A mixture of tert-butyl ((4aR,5R,9S)-5-(6-bromo-3-fluoro-4-(triethylsilyl)pyridin-2-yl)-5,8,8-trimethyl-9-oxido-2,3,4,4a,5,8-hexahydro-[1,4]thiazino[2,1-f][1,2]thiazin-7-yl)carbamate and tert-butyl ((4aS,5R,9S)-5-(6-bromo-3-fluoro-4-(triethylsilyl)pyridin-2-yl)-5,8,8-trimethyl-9-oxido-2,3,4,4a,5,8-hexahydro-[1,4]thiazino[2,1-f][1,2]thiazin-7-yl)carbamate (Int-15BA/Int-15BB ca. 7:3, 1.00 g, 1.62 mmol) was dissolved in THF (12 mL) and DMF (3 mL). Acetic acid (315 mg, 300 µl, 5.24 mmol) and potassium fluoride (300 mg, 5.16 mmol) were added at room temperature and the resulting fine suspension was stirred for 2 h at that temperature. After that, it was poured upon a saturated aqueous solution of sodium hydrogencarbonate (25 mL) and extracted with MTBE (1×100 mL, 1×50 mL). The combined extracts were washed with brine (25 mL), dried (sodium sulfate) and concentrated in vacuo to give a yellow viscous oil as crude product. The reaction control by HPLC and tlc showed that only Int-15BA was converted to the desilated product, the other diastereomer (Int-15BB) did not react. The crude was purified by column chromatography (silica gel, 50 g, eluting with ethyl acetate/n-heptane, gradient 60:40 to 80:20) to afford, after drying in vacuo (50° C., 5 mbar), desilated compound (Int-16BA) as white foam (460 mg, 56% yield). The remaining starting material was also isolated as pure Int-15BB as yellow oil (210 mg, 21%).

2H), 7.25 (dd, J=8.5, 10.6 Hz, 1H), 7.40 (dd, J=3.1, 8.5 Hz, 1H), 10.69 (br s, 1H, exch). MS (ES+) m/z 505.3 & 503.4 [M+H, Br].

Step 2: tert-Butyl ((4aR,5R,9S)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-17BA)

tert-Butyl ((4aR,5R,9S)-5-(6-bromo-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-16BA, 450 mg, 894 mol) was dissolved in 1,4-dioxane (7.5 mL) and water (2.5 mL) and sodium azide (600 mg, 9.23 mmol) was added. Copper (I) iodide (90 mg, 473 µmol), sodium ascorbate (45 mg, 227 µmol) and trans-N,N'-dimethyl-1,2-cyclohexanediamine (108 mg, 120 µl, 761 µmol) were added subsequently and the dark blue mixture was stirred for 1 h at 70° C. After that, a second portion of sodium azide (200 mg, 3.08 mmol), copper (I) iodide (45 mg, 236 µmol), sodium ascorbate (25 mg, 126 mol) and trans-N,N'-dimethyl-1,2-cyclohexanediamine (60 µl, 380 µmol) were added and the mixture was stirred for additional 20 min at 70° C. Then, the reaction mixture was allowed to cool to room temperature and poured onto a saturated aqueous solution of sodium hydrogencarbonate (25 mL). It was extracted with ethyl acetate (1×100 mL, 1×50 mL), the combined extracts were dried over sodium sulfate and silica gel (4 g) was added to the solution. After filtration, the filtrate was concentrated in vacuo to give a green sticky solid as crude product. The crude was purified by column chromatography (silica gel, 50 g, eluting with ethyl acetate/n-heptane, gradient 80:20 to 100:0) to afford, after drying in vacuo (50° C., 5 mbar), the title compound as a white solid (290 mg, 74%). HPLC (method LCMS_gradient) $t_R$=2.0 min. $^1$H NMR (CDCl$_3$, 400 MHz): δ 1.34 (s, 3H), 1.54 (s, 9H), 1.73 (s, 3H), 1.79 (s, 3H), 1.81-1.92 (m, 2H), 2.15-2.26 (m, 1H), 2.47-2.57 (m, 1H), 3.40 (ddd, J=5.0, 8.6, 13.3 Hz, 1H), 3.64 (ddd, J=4.8, 4.8, 13.2 Hz, 1H), 3.98 (dd, J=4.8, 10.2 Hz, 1H), 4.31 (s, 2H), 6.38 (dd, J=2.4, 8.6 Hz, 1H), 7.15 (dd, J=8.7, 10.9 Hz, 1H), 10.47 (br s, 1H, exch). MS (ES+) m/z 440.4 [M+H].

Synthesis of Int-9: (R,E)-N-(1-(6-Bromo-3-fluoro-4-(triethylsilyl)pyridin-2-yl)ethylidene)-2-methyl-propane-2-sulfinamide

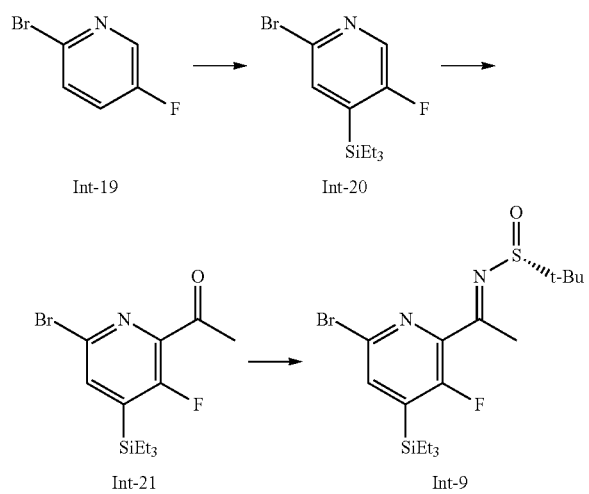

Step 1: 2-Bromo-5-fluoro-4-(triethylsilyl)pyridine (Int-20)

To a solution of diisopropylamine (130 g, 183 mL, 1.28 mol) in tetrahydrofuran (1500 mL) was added 1.6 M n-butyllithium in tetrahydrofuran (800 mL, 1.28 mol) at −20° C. The reaction mixture was allowed to warm to 0° C. and stirred for additional 30 minutes. A solution consisting of 2-bromo-5-fluoropyridine (Int-19, 205 g, 1.16 mol) in tetrahydrofuran (200 mL) was added at −70° C. After 60 minutes triethylchlorosilane (193 g, 217 mL, 1.28 mol) was added drop wise in 30 minutes. Stirring was continued for 1 h at −70° C. and then allowed to warm to −30° C. The reaction mixture was poured onto a mixture of 1 M aqueous hydrogen chloride solution (1000 mL) and β-% aqueous ammonium chloride solution. The layers were separated. The aqueous layer was extracted with tert-butyl methyl ether (2000 mL). The combined organic layers were washed with one 1500-mL portion of water and concentrated in vacuo to give the crude title compound (345 g, quantitative) as orange oil, which was used in the next step without further purification. MS (ES+) m/z 290.1 & 292.1 [M+H, Br].

Step 2: 1-(6-Bromo-3-fluoro-4-(triethylsilyl)pyridin-2-yl)ethanone (Int-21)

To a solution of diisopropylamine (160 g, 225 mL, 1.55 mol) in tetrahydrofuran (2200 mL) was added 1.6 M n-butyllithium in tetrahydrofuran (950 mL, 1.52 mol) at −20° C. The reaction mixture was allowed to warm to 0° C. and stirred for additional 30 minutes. A solution of 2-bromo-5-fluoro-4-(triethylsilyl)pyridine (338 g, 1.16 mol) in tetrahydrofuran (300 mL) was added drop wise in 30 minutes at −70° C. After 80 minutes N,N-dimethylacetamide (107 g, 115 mL, 1.22 mol) was added drop wise in 10 minutes. The cooling bath was removed and the reaction mixture was poured onto a mixture of 25-% aqueous hydrogen chloride solution (255 g, 227 mL, 1.75 mol), 10-% aqueous sodium chloride solution (2500 mL). The layers were separated. The aqueous layer was extracted with tert-butyl methyl ether (2500 mL). The combined organic layers were concentrated in vacuo to give the crude title compound (392 g, quantitative) as dark brown viscous oil, which was used in the next step without further purification. MS (ES+) m/z 332.1 & 334.1 [M+H, Br].

Step 3: (R,E)-N-(1-(6-Bromo-3-fluoro-4-(triethylsilyl)pyridin-2-yl)ethylidene)-2-methyl-propane-2-sulfimamide (Int-9)

To a mixture of 1-(6-bromo-3-fluoro-4-(triethylsilyl)pyridin-2-yl)ethanone (200 g, 512 mmol) and (R)-2-methylpropane-2-sulfinamide (77.5 g, 640 mmol) in ethyl acetate (2000 mL) was added titanium (IV) ethoxide (187 g, 171 mL, 819 mmol). The reaction mixture was heated at 60° C. and stirred over night. The heating bath was removed and the excess of titanium (IV) ethoxide was quenched by addition of water (24.0 g, 24 mL, 1.33 mol) at 40° C. The solids were removed by filtration and washed with two 500-mL portions of water. The filtrate was washed with one 1000-mL portion of 5-% aqueous hydrogen chloride solution and one 5-% aqueous sodium hydrogencarbonate solution. The organic layer was dried over anhydrous sodium sulfate, filtrated and concentrated in vacuo. Purification by flash-chromatography with n-heptane/ethyl acetate as eluent gave the title compound as brown viscous oil. MS (ES+) m/z 435.2 & 437.2 [M+H, Br].

Synthesis of Int-24BB: tert-Butyl ((4aS,5R,9S)-5-(6-amino-3-fluoro-4-(triethylsilyl)pyridin-2-yl)-5,8,8-trimethyl-9-oxido-2,3,4,4a,5,8-hexahydro-[1,4]thiazino[2,1-f][1,2]thiazin-7-yl)carbamate

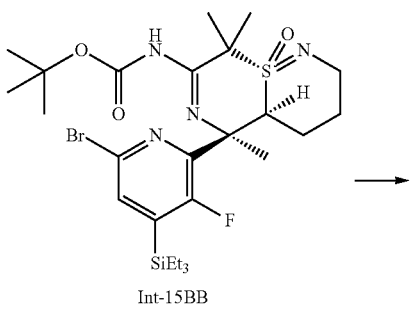

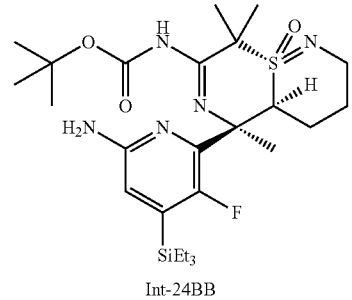

tert-Butyl ((4aS,5R,9S)-5-(6-bromo-3-fluoro-4-(triethyl-silyl)pyridin-2-yl)-5,8,8-trimethyl-9-oxido-2,3,4,4a,5,8-hexahydro-[1,4]thiazino[2,1-f][1,2]thiazin-7-yl)carbamate (Int-15BB, 210 mg, 340 μmol) was dissolved in 1,4-dioxane (4 mL) and water (1 mL) and sodium azide (225 mg, 3.46 mmol) was added. Copper (I) iodide (35 mg, 184 μmol), sodium ascorbate (17.5 mg, 88.3 μmol) and trans-N,N'-dimethyl-1,2-cyclohexanediamine (45.1 mg, 50 μl, 317 μmol) were added subsequently and the dark blue mixture was stirred for 1 h at 70° C. After that, it was cooled to room temperature and second portions of sodium azide (225 mg, 3.46 mmol), copper (I) iodide (40 mg, 210 μmol), sodium ascorbate (20 mg, 101 μmol) and trans-N,N'-dimethyl-1,2-cyclohexanediamine (60 μl, 380 μmol) were added and the mixture was stirred for additional 1 h min at 70° C. After that, it was cooled to room temperature and third portions of sodium azide (225 mg, 3.46 mmol), copper (I) iodide (40 mg, 210 μmol), sodium ascorbate (20 mg, 101 μmol) and trans-N,N'-dimethyl-1,2-cyclohexanediamine (60 μl, 380 μmol) were added and the mixture was stirred for additional 1 h min at 70° C. Then, the reaction mixture was allowed to cool to room temperature and poured onto a saturated aqueous solution of sodium hydrogencarbonate (25 mL). It was extracted with ethyl acetate (1×100 mL, 1×50 mL), the combined extracts were dried over sodium sulfate and silica gel (4 g) was added to the solution. After filtration, the filtrate was concentrated in vacuo to give a green solid as crude product. The crude was purified by column chromatography (silica gel, 50 g, eluting with ethyl acetate/n-heptane, gradient 80:20 to 100:0) to afford, after drying in vacuo (50° C., 5 mbar), the title compound as a brown oil (50 mg, 27%). HPLC (method LCMS_gradient) $t_R$=3.4 min. MS (ES+) m/z 554.5 [M+H].

Synthesis of Int-31: 2-Methyl-2-[S-methyl-N-(2-tetrahydropyran-2-yloxyethyl)sulfonimidoyl]pro-panenitrile

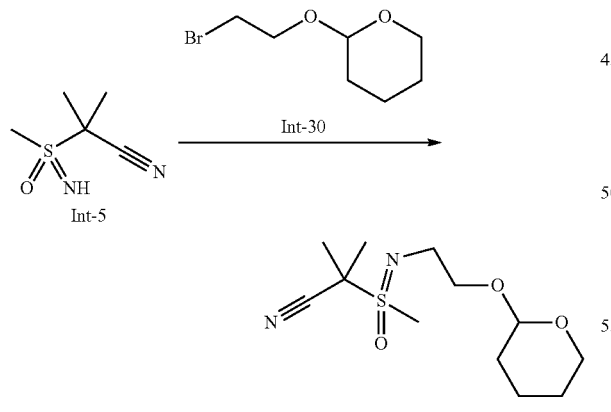

A suspension of potassium hydride (30% suspension in mineral oil, 54.7 g, 410.4 mmol) in DME (200.0 mL) was cooled to 0-5° C. (ice bath). Then a solution of 2-methyl-2-(methylsulfonimidoyl)propanenitrile (Int-5, 30.0 g, 205.2 mmol) in DME (100.0 mL) was added dropwise to the mixture. After that, the mixture was allowed to warm to 23° C. and stirred for 3 h. Then tetra-n-butylammonium bromide (3.3 g, 10.26 mmol) and 2-(2-bromoethoxy)tetrahydropyran (Int-30, 85.8 g, 410.4 mmol) in DME (100.0 mL) was added to the reaction mixture. The mixture was stirred at 23° C. for 16 h. After complete consumption of starting material had been detected by tlc, the mixture was poured into a saturated aqueous solution of sodium hydrogencarbonate (500 mL) and diluted with ethyl acetate (300 mL). After phase separation, the aqueous phase was extracted with ethyl acetate (2×200 mL), the combined organic extracts were dried over sodium sulfate, filtered and concentrated to give a crude product which was purified by column chromatography (silica gel, eluting with ethyl acetate/petroleum ether 50:50) to give the title compound as yellow oil (45.0 g, 80% yield). $^1$H NMR (CDCl$_3$, 400 MHz): δ 1.46-1.61 (m, 4H), 1.67-1.86 (m, 2H), 1.76 (s, 6H), 3.09 & 3.10 (2s, 3H, diast.), 3.31-3.54 (m, 4H), 3.77-3.91 (m, 2H), 4.60-4.64 (m, 1H).

Synthesis of Int-33 (mix): 2-((2R)-2-Amino-2-(6-bromo-3-fluoro-4-(triethylsilyl)pyridin-2-yl)-N-(2-hydroxyethyl)propylsulfonimidoyl)-2-methylpro-panenitrile

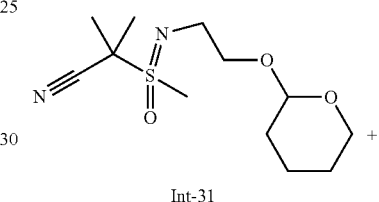

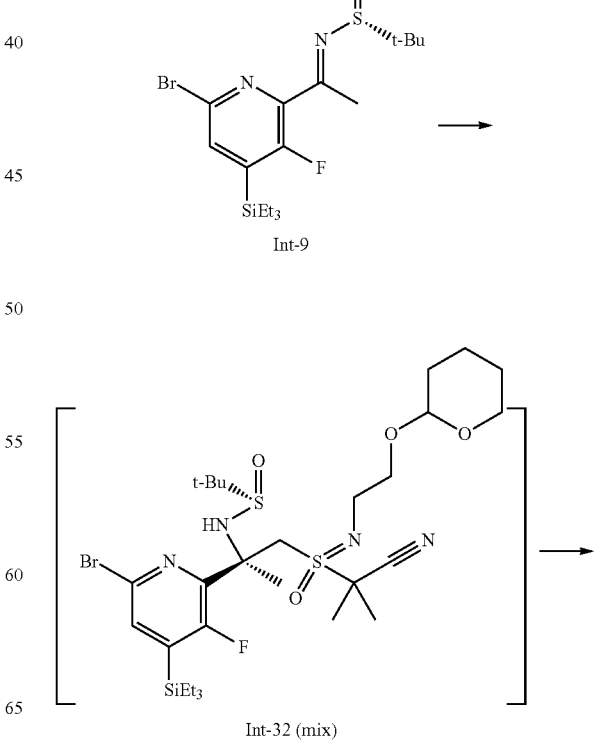

-continued

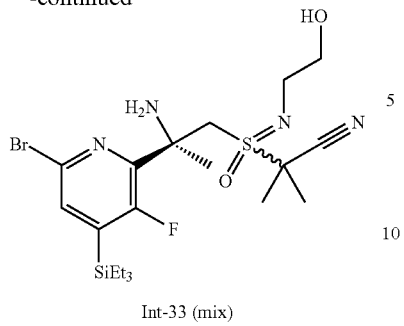

Int-33 (mix)

Step 1: (R)—N-((2R)-2-(6-Bromo-3-fluoro-4-(triethylsilyl)pyridin-2-yl)-1-(2-cyano-N-(2-((tetrahydro-2H-pyran-2-yl)oxy)ethyl)propan-2-ylsulfonimidoyl)propan-2-yl)-2-methylpropane-2-sulfinamide (Int-32 (mix))

To a solution of 2-methyl-2-[S-methyl-N-(2-tetrahydropyran-2-yloxyethyl)sulfonimidoyl]propanenitrile (Int-31, 8.0 g, 29.16 mmol) in THF (120.0 mL) was added n-BuLi (11.6 mL, 29.16 mmol, 2.5 N) at −70° C. over 10 min, the mixture was stirred at −70° C. for 1 h. Then a solution of (R,E)-N-(1-(6-bromo-3-fluoro-4-(triethylsilyl)pyridin-2-yl)ethylidene)-2-methyl-propane-2-sulfinamide (Int-9, 12.7 g, 29.16 mmol) in THF (30.0 mL) was added to the reaction mixture over 10 min. Then the mixture was stirred at −70° C. for 4 h. The reaction mixture was quenched by addition of an aqueous saturated solution of ammonium chloride (100 mL) and extracted with ethyl acetate (2×100 mL). The organic layer was washed with brine (100 mL), dried over sodium sulfate. After filtration, the filtrate was concentrated to give a crude product. The crude product was purified by column chromatography (silica gel, eluting with ethyl acetate/petroleum ether 50:50) to give the title compound (5.0 g, 24% yield) as a yellow oil and as a mixture of diastereoisomers.

Step 2: 2-42R)-2-Amino-2-(6-bromo-3-fluoro-4-(triethylsilyl)pyridin-2-yl)-N-(2-hydroxyethyl)propylsulfonimidoyl)-2-methylpropanenitrile (Int-33 (mix))

To a solution of (R)—N-((2R)-2-(6-bromo-3-fluoro-4-(triethylsilyl)pyridin-2-yl)-1-(2-cyano-N-(2-((tetrahydro-2H-pyran-2-yl)oxy)ethyl)propan-2-ylsulfonimidoyl)propan-2-yl)-2-methylpropane-2-sulfinamide (Int-32 (mix), 25.0 g, 35.2 mmol) in methanol (200 mL) was added a solution of hydrogen chloride in methanol (4 N, 40.0 mL) at 0° C. The reaction mixture was stirred for 1 h at 15° C. After that, the reaction mixture was basified by addition of an aqueous solution of sodium carbonate (2 M) until pH 8-9, and extracted with ethyl acetate (2×200 mL). The combined organic layers were dried over sodium sulfate, filtered and concentrated in vacuo. The crude product was purified by column chromatography (silica gel, eluting with ethyl acetate) to afford the title compound (16.3 g, 75% yield) as a yellow solid and as mixture of diastereoisomers.

Synthesis of Int-35A & Int-35B: tert-Butyl ((1R,5R)-5-(6-bromo-3-fluoro-4-(triethylsilyl)pyridin-2-yl)-1-((2-hydroxyethyl)imino)-2,2,5-trimethyl-1-oxido-5,6-dihydro-2H-1,4-thiazin-3-yl)carbamate (Int-35A) and tert-butyl ((1S,5R)-5-(6-bromo-3-fluoro-4-(triethylsilyl)pyridin-2-yl)-1-((2-hydroxyethyl)imino)-2,2,5-trimethyl-1-oxido-5,6-dihydro-2H-1,4-thiazin-3-yl)carbamate (Int-35B)

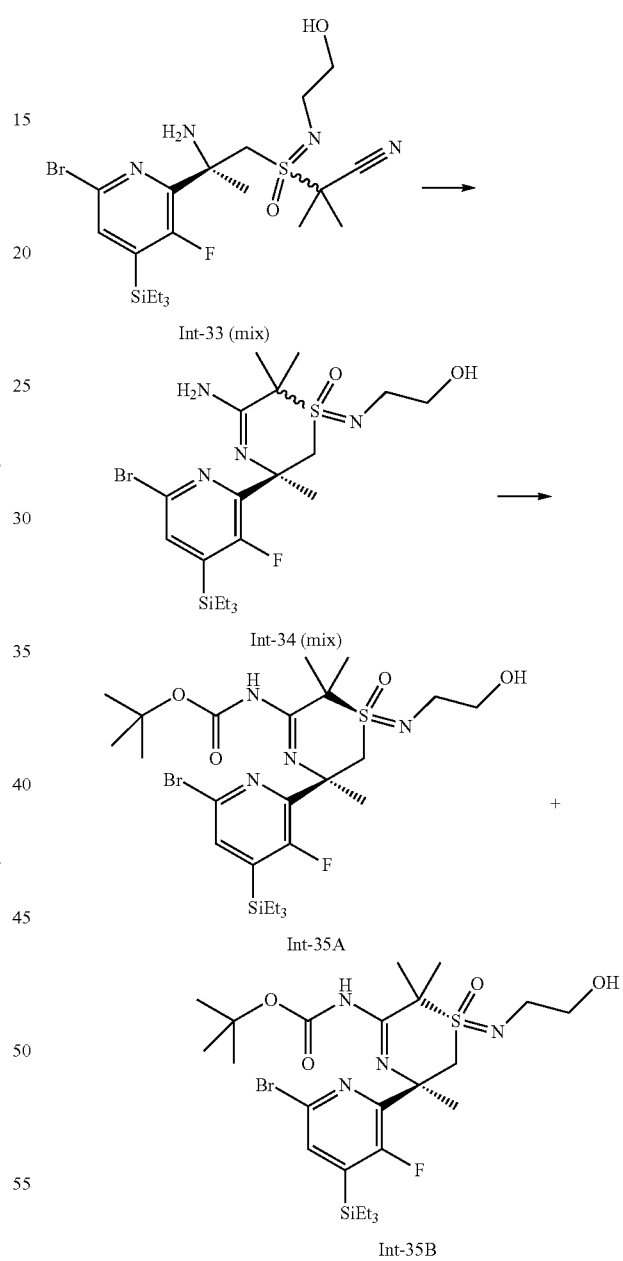

Step 1: (3R)-5-Amino-3-(6-bromo-3-fluoro-4-(triethylsilyl)pyridin-2-yl)-1-((2-hydroxyethyl)imino)-3,6,6-trimethyl-3,6-dihydro-2H-1,4-thiazine 1-oxide (Int-34 (mix))

To a suspension of 2-((2R)-2-amino-2-(6-bromo-3-fluoro-4-(triethylsilyl)pyridin-2-yl)-N-(2)propylsulfonimidoyl)-2-methylpropanenitrile (Int-33 (mix), 15.0 g, 28.7 mmol) in ethanol (200 mL) was added copper(I) chloride (3.13 g, 31.6 mmol). Then, the mixture was stirred at 70° C. for 2 h. The reaction mixture was poured into a mixture of brine (100 mL) and aqueous ammonia (100 mL). The resulting mixture was extracted with ethyl acetate (2×100 mL), the combined organic layers were dried over Na₂SO₄, filtered and concentrated in vacuo to give the crude product as a yellow gum which was used for the next step without further purification (15 g).

Step 2: tert-Butyl ((1R,5R)-5-(6-bromo-3-fluoro-4-(triethylsilyl)pyridin-2-yl)-1-((2-hydroxyethyl)imino)-2,2,5-trimethyl-1-oxido-5,6-dihydro-2H-1,4-thiazin-3-yl)carbamate (Int-35A) and tert-butyl ((1S,5R)-5-(6-bromo-3-fluoro-4-(triethylsilyl)pyridin-2-yl)-1-((2-hydroxyethyl)imino)-2,2,5-trimethyl-1-oxido-5,6-dihydro-2H-1,4-thiazin-3-yl)carbamate (Int-35B)

To a suspension of (3R)-5-amino-3-(6-bromo-3-fluoro-4-(triethylsilyl)pyridin-2-yl)-1-((2-hydroxyethyl)imino)-3,6,6-trimethyl-3,6-dihydro-2H-1,4-thiazine 1-oxide (Int-34 (mix), crude from preceeding step, 30.0 g, 57.2 mmol) in tetrahydrofuran (400 mL) and water (80 mL), solid sodium hydrogencarbonate (6.3 g, 74.7 mmol), followed by Boc-anhydride (13.8 g, 63.3 mmol) and 4-(dimethylamino)-pyridine (351 mg, 2.8 mmol) were added. The mixture was stirred at 15° C. for 18 h. The reaction mixture was diluted with water (200 mL) and extracted with ethyl acetate (2×200 mL). The combined extracts were dried over sodium sulfate, filtered and concentrated in vacuo. The crude was purified by column chromatography (silica gel, eluting with ethyl acetate/petroleum ether 25:75) to yield the title compounds as separated diastereoisomers. The first eluting diastereoisomer (Int-35A) was isolated as a yellow solid (9.0 g, 25%) and the second eluting diastereoisomer (Int-35B) was obtained as a yellow gum (11.0 g, 31%). The combined yield was 56% over 2 steps.

Int-35A: ¹H NMR (CDCl₃, 400 MHz): δ 0.82-0.90 (m, 6H), 0.93-1.00 (m, 9H), 1.55 (s, 9H), 1.64 (s, 3H), 1.79 (s, 3H), 1.83 (s, 3H), 2.12 (t, J=6.3 Hz, 1H), 2.67 (ddd, J=3.5, 6.0, 12.5 Hz, 1H), 3.09 (ddd, J=3.5, 6.8, 12.5 Hz, 1H), 3.24-3.34 (m, 1H), 3.37-3.46 (m, 1H), 3.60 (d, J=15.1 Hz, 1H), 4.49 (d, J=15.1 Hz, 1H), 7.36 (d, J=2.5 Hz, 1H), 11.11 (s, 1H).

Int-35B: ¹H NMR (CDCl₃, 400 MHz): δ 0.80-0.90 (m, 6H), 0.91-1.00 (m, 9H), 1.53 (s, 9H), 1.66 (s, 3H), 1.73 (s, 3H), 1.85 (s, 3H), 2.39-2.47 (m, 1H), 3.29-3.33 (m, 2H), 3.58 (d, J=15.3 Hz, 1H), 3.62-3.68 (m, 2H), 4.31 (d, J=15.1 Hz, 1H), 7.36 (d, J=2.5 Hz, 1H), 11.16 (s, 1H).

Synthesis of Int-37AB: tert-Butyl ((3aS,4R,8R)-4-(6-bromo-3-fluoro-4-(triethylsilyl)pyridin-2-yl)-4,7,7-trimethyl-8-oxido-3,3a,4,7-tetrahydro-2H-isothiazolo[1,5-a][1,4]thiazin-6-yl)carbamate

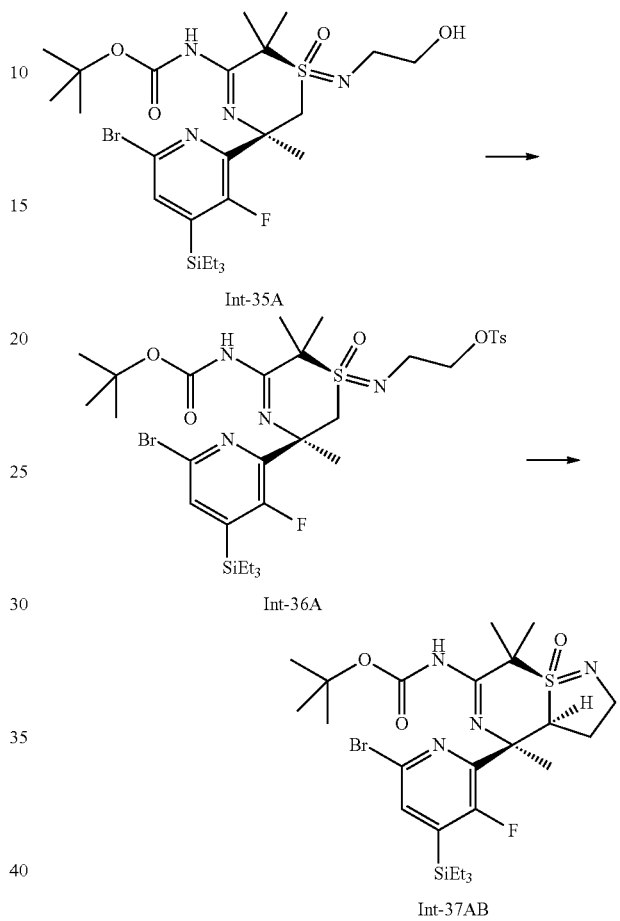

Step 1: 2-(((1R,3R)-3-(6-Bromo-3-fluoro-4-(triethylsilyl)pyridin-2-yl)-5-(((tert-butoxycarbonyl)amino)-3,6,6-trimethyl-1-oxido-3,6-dihydro-2H-1,4-thiazin-1-ylidene)amino)ethyl 4-methylbenzenesulfonate (Int-36A)

To a solution of tert-butyl ((1R,5R)-5-(6-bromo-3-fluoro-4-(triethylsilyl)pyridin-2-yl)-1-((2-hydroxyethyl)imino)-2,2,5-trimethyl-1-oxido-5,6-dihydro-2H-1,4-thiazin-3-yl)carbamate (Int-35A, 9.0 g, 14.5 mmol) in dichloromethane (150 mL) was added tosyl chloride (3.3 g, 17.4 mmol), triethylamine (2.9 g, 29.0 mmol) and 4-(dimethylamino)-pyridine (88.5 mg, 0.73 mmol) at 0° C. The resulting mixture was stirred at 15° C. for 16 h. After that, the mixture was poured into water (200 mL) and extracted with ethyl acetate (2×100 mL). The combined organic layers were dried over sodium sulfate, filtered and concentrated to give the crude product. The crude product was purified by column chromatography (silica gel, eluting with ethyl acetate/petroleum ether 25:75) to yield the title compound as a yellow solid (10.5 g, 95%). ¹H NMR (CDCl₃, 400 MHz): δ 0.81-0.90 (m, 6H), 0.92-1.00 (m, 9H), 1.54 (s, 9H), 1.59 (s, 3H), 1.82 (s, 3H), 2.44 (s, 3H), 2.86-2.94 (m, 1H), 3.16-3.24 (m, 1H), 3.50 (d, J=15.1 Hz, 1H), 3.70-3.78 (m, 1H), 3.82-3.89 (m, 1H), 4.46 (d, J=15.1 Hz, 1H), 7.33 (d, J=8.0 Hz, 2H), 7.39 (d, J=2.5 Hz, 1H), 7.74 (d, J=8.3 Hz, 2H), 11.14 (s, 1H).

Step 2: tert-Butyl ((3aS,4R,8R)-4-(6-bromo-3-fluoro-4-(triethylsilyl)pyridin-2-yl)-4,7,7-trimethyl-8-oxido-3,3a,4,7-tetrahydro-2H-isothiazolo[1,5-a][1,4]thiazin-6-yl)carbamate (Int-37AB)

To a solution of 2-(((1R,3R)-3-(6-bromo-3-fluoro-4-(triethylsilyl)pyridin-2-yl)-5-((tert-butoxycarbonyl)amino)-3,6,6-trimethyl-1-oxido-3,6-dihydro-2H-1,4-thiazin-1-ylidene)amino)-ethyl 4-methylbenzenesulfonate (Int-36A, 8.5 g, 10.9 mmol) in dry THF (150 mL) a solution of lithium hexamethyldisilazide (LHMDS) in THF (1 M, 32.7 mL, 32.7 mmol) was added dropwise at −70° C. over 5 min. Then, the yellow solution was allowed to warm to 0° C. (ice bath) and stirred for 2 h. After that, the reaction mixture was poured into an aqueous saturated ammonium chloride solution (150 mL) and extracted with ethyl acetate (2×150 mL). The combined extracts were washed with brine (200 mL), dried over sodium sulfate and concentrated to give the crude product (6.48 g) as single diastereoisomer, which was used in the next step without further purification. $^1$H NMR (CDCl$_3$, 400 MHz): δ 0.84-0.91 (m, 6H), 0.93-0.99 (m, 9H), 1.57 (s, 9H), 1.70-1.80 (m, 1H), 1.83 (s, 3H), 1.91-2.01 (m, 1H), 1.95 (s, 3H), 2.11 (s, 3H), 3.54 (dd, J=7.5, 10.5 Hz, 1H), 3.69 (ddd, J=5.0, 10.5, 10.5 Hz, 1H), 4.24 (ddd, J=2.5, 7.3, 12.0 Hz, 1H), 7.47 (d, J=2.5 Hz, 1H), 12.09 (s, 1H).

Synthesis of Int-37BA: tert-Butyl ((3aR,4R,8S)-4-(6-bromo-3-fluoro-4-(triethylsilyl)pyridin-2-yl)-4,7,7-trimethyl-8-oxido-3,3a,4,7-tetrahydro-2H-isothiazolo[1,5-a][1,4]thiazin-6-yl)carbamate

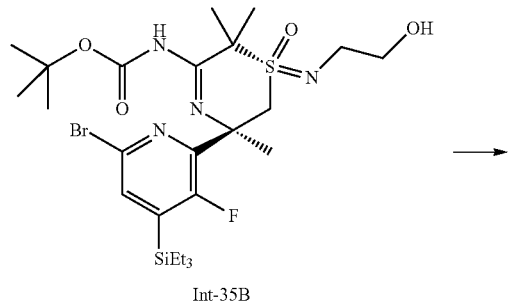

Int-35B

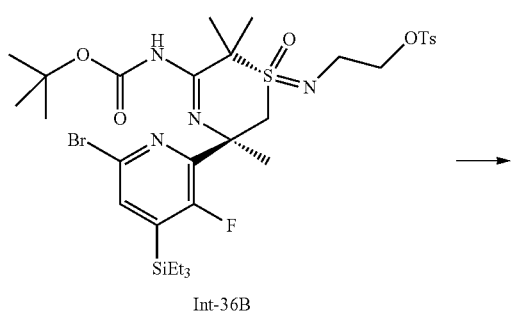

Int-36B

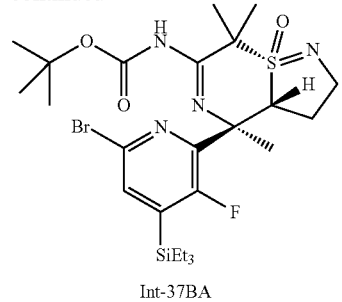

Int-37BA

Step 1: 2-(((1S,3R)-3-(6-Bromo-3-fluoro-4-(triethylsilyl)pyridin-2-yl)-5-((tert-butoxycarbonyl)amino)-3,6,6-trimethyl-1-oxido-3,6-dihydro-2H-1,4-thiazin-1-ylidene)amino)ethyl 4-methylbenzenesulfonate (Int-36B)

To a solution of tert-butyl ((1S,5R)-5-(6-bromo-3-fluoro-4-(triethylsilyl)pyridin-2-yl)-1-((2-hydroxyethyl)imino)-2,2,5-trimethyl-1-oxido-5,6-dihydro-2H-1,4-thiazin-3-yl)carbamate (Int-35B, 11.0 g, 17.7 mmol) in dichloromethane (150 mL) was added tosyl chloride (4.0 g, 21.2 mmol), triethylamine (3.6 g, 35.4 mmol) and 4-(dimethylamino)pyridine (107.9 mg, 0.89 mmol) at 0° C. The resulting mixture was stirred at 15° C. for 16 h. After that, the mixture was poured into water (200 mL) and extracted with ethyl acetate (2×100 mL). The combined organic layers were dried over sodium sulfate, filtered and concentrated to give the crude product. The crude product was purified by column chromatography (silica gel, eluting with ethyl acetate/petroleum ether 25:75) to yield the title compound as a yellow solid (13.0 g, 95%). $^1$H NMR (CDCl$_3$, 400 MHz): δ 0.81-0.91 (m, 6H), 0.92-1.00 (m, 9H), 1.54 (s, 9H), 1.59 (s, 3H), 1.64 (s, 3H), 1.82 (s, 3H), 2.45 (s, 3H), 3.30-3.43 (m, 2H), 3.47 (d, J=15.1 Hz, 1H), 4.03-4.13 (m, 2H), 4.24 (d, J=15.1 Hz, 1H), 7.34-7.38 (m, 3H), 7.80 (d, J=8.3 Hz, 2H), 11.15 (s, 1H).

Step 2: tert-Butyl ((3aR,4R,8S)-4-(6-bromo-3-fluoro-4-(triethylsilyl)pyridin-2-yl)-4,7,7-trimethyl-8-oxido-3,3a,4,7-tetrahydro-2H-isothiazolo[1,5-a][1,4]thiazin-6-yl)carbamate (Int-37BA)

To a solution of 2-(((1S,3R)-3-(6-bromo-3-fluoro-4-(triethylsilyl)pyridin-2-yl)-5-((tert-butoxycarbonyl)amino)-3,6,6-trimethyl-1-oxido-3,6-dihydro-2H-1,4-thiazin-1-ylidene)amino)ethyl 4-methylbenzenesulfonate (Int-36B, 11.0 g, 14.2 mmol) in dry THF (150 mL) a solution of lithium hexamethyldisilazide (LHMDS) in THF (1 M, 42.6 mL, 42.6 mmol) was added dropwise at −70° C. over 5 min. Then, the yellow solution was allowed to warm to 0° C. (ice bath) and stirred for 2 h. After that, the reaction mixture was poured into an aqueous saturated ammonium chloride solution (150 mL) and extracted with ethyl acetate (2×150 mL). The combined extracts were washed with brine (200 mL), dried over sodium sulfate and concentrated to give the crude product (6.77 g) as single diastereoisomer, which was used in the next step without further purification.

Synthesis of Int-39AB: tert-Butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate

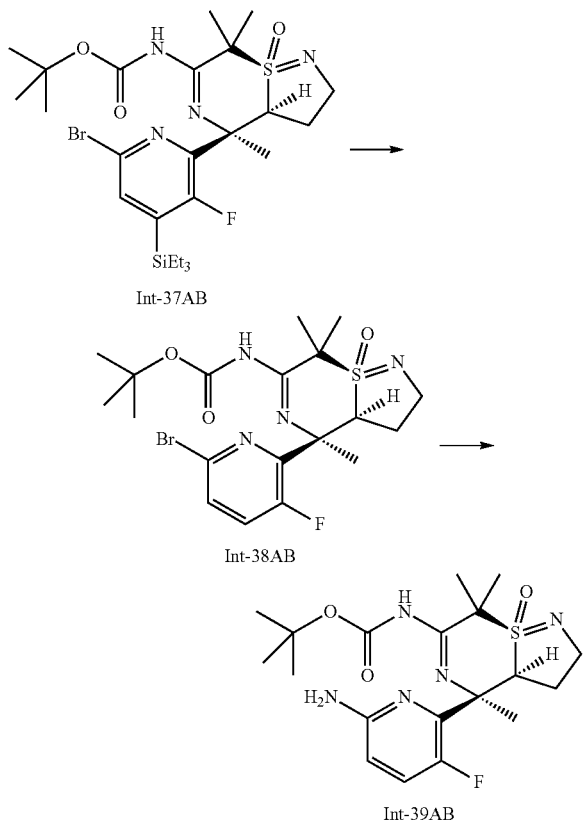

Step 1: tert-Butyl ((3aS,4R,8R)-4-(6-bromo-3-fluoropyridin-2-yl)-4,7,7-trimethyl-8-oxido-3,3a,4,7-tetrahydro-2H-isothiazolo[1,5-a][1,4]thiazin-6-yl)carbamate (Int-38AB)

To a suspension of tert-butyl ((3aS,4R,8R)-4-(6-bromo-3-fluoro-4-(triethylsilyl)pyridin-2-yl)-4,7,7-trimethyl-8-oxido-3,3a,4,7-tetrahydro-2H-isothiazolo[1,5-a][1,4]thiazin-6-yl)carbamate (Int-37AB, 6.0 g, crude from preceeding step, ca. 9.94 mmol) in THF (60 mL) and DMF (10 mL) was added potassium fluoride (1.15 g, 19.8 mmol) and acetic acid (1.18 g, 19.8 mmol) at 16° C., the mixture was stirred at 30° C. for 3 h. The reaction mixture was diluted with aqueous sodium hydrogencarbonate solution (100 mL), extracted with ethyl acetate (2×100 mL). The organic layer was washed with brine (100 mL) and dried over sodium sulfate. After filtration, the filtrate was concentrated in vacuo to give a crude product. The crude was suspended in a mixture of ethyl acetate (15 mL) and petroleum ether (60 mL) and stirred for 30 min at 15° C. The precipitate was filtered off, washed with a mixture of ethyl acetate/petroleum ether (1:5 v/v, 30 mL) and dried in vacuo to afford the title compound as a yellow solid (4.87 g, 85% over 2 steps). $^1$H NMR (CDCl$_3$, 400 MHz): δ 1.59 (s, 9H), 1.61-1.65 (m, 1H), 1.85 (s, 3H), 1.96 (s, 3H), 2.01-2.09 (m, 1H), 2.14 (s, 3H), 3.56 (dd, J=7.7, 10.6 Hz, 1H), 3.70 (dd, J=4.9, 10.6 Hz, 1H), 4.24 (ddd, J=. 2.5, 7.1, 12.1 Hz, 1H), 7.42 (dd, J=8.5, 10.5 Hz, 1H), 7.57 (dd, J=3.3, 8.5 Hz, 1H), 12.13 (s, 1H).

Step 2: tert-Butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB)

To a mixture of tert-butyl ((3aS,4R,8R)-4-(6-bromo-3-fluoropyridin-2-yl)-4,7,7-trimethyl-8-oxido-3,3a,4,7-tetrahydro-2H-isothiazolo[1,5-a][1,4]thiazin-6-yl)carbamate (Int-38AB, 3.0 g, 6.13 mmol) in dioxane (30.0 mL) and water (10.0 mL) was added copper(I) iodide (1.27 g, 6.7 mmol), sodium ascorbate (0.73 g, 3.7 mmol), sodium azide (6.0 g, 92.0 mmol) and trans-N,N'-dimethyl-1,2-cyclohexanediamine (1.57 g, 11.03 mmol). Then the dark blue mixture was stirred for 1 h at 70° C. The reaction mixture was diluted with aqueous sodium hydrogencarbonate solution (100 mL) and extracted with ethyl acetate (2×100 mL). The combined organic layers were dried over sodium sulfate, filtered and concentrated to give the crude product. The crude was purified by column chromatography (silica gel, eluting with ethyl acetate/petroleum ether 2:1) to yield, after drying in vacuo, the title compound as yellow solid (2.3 g, 89% yield). $^1$H NMR (CDCl$_3$, 400 MHz): δ 1.53-1.63 (m, 1H), 1.57 (s, 9H), 1.84 (s, 3H), 1.95 (s, 3H), 2.06-2.15 (m, 1H), 2.09 (s, 3H), 3.53 (dd, J=7.6, 10.6 Hz, 1H), 3.68 (ddd, J=4.8, 10.5, 10.5 Hz, 1H), 4.25 (ddd, J=1.9, 7.0, 12.2 Hz, 1H), 4.60 (s, 2H), 6.50 (dd, J=2.5, 8.8 Hz, 1H), 7.28 (dd, J=8.9, 10.5 Hz, 1H), 12.29 (s, 1H).

Synthesis of Int-39BA: tert-Butyl ((3aR,4R,8S)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate

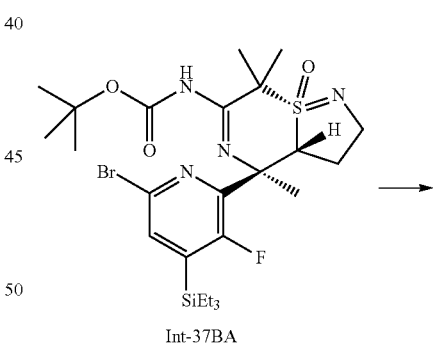

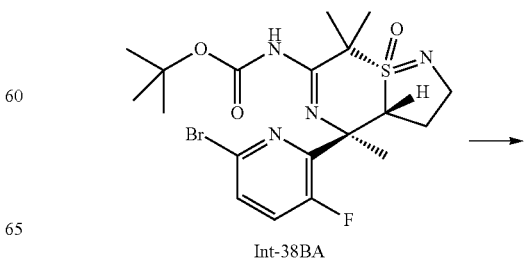

-continued

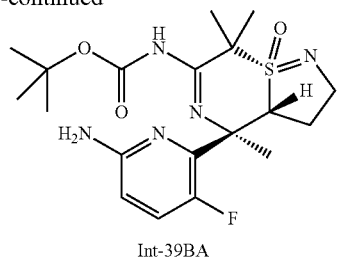

Int-39BA

Step 1: tert-Butyl ((3aR,4R,8S)-4-(6-bromo-3-fluoropyridin-2-yl)-4,7,7-trimethyl-8-oxido-3,3a,4,7-tetrahydro-2H-isothiazolo[1,5-a][1,4]thiazin-6-yl)carbamate (Int-38BA)

To a suspension of tert-butyl ((3aR,4R,8S)-4-(6-bromo-3-fluoro-4-(triethylsilyl)pyridin-2-yl)-4,7,7-trimethyl-8-oxido-3,3a,4,7-tetrahydro-2H-isothiazolo[1,5-a][1,4]thiazin-6-yl)carbamate (Int-37BA, 6.0 g, crude from preceeding step, ca. 9.94 mmol) in THF (60 mL) and DMF (10 mL) was added potassium fluoride (1.15 g, 19.8 mmol) and acetic acid (1.18 g, 19.8 mmol) at 16° C., the mixture was stirred at 30° C. for 3 h. The reaction mixture was diluted with aqueous sodium hydrogencarbonate solution (100 mL), extracted with ethyl acetate (2×100 mL). The organic layer was washed with brine (100 mL) and dried over sodium sulfate. After filtration, the filtrate was concentrated in vacuo to give a crude product. The crude was suspended in a mixture of ethyl acetate (15 mL) and petroleum ether (60 mL) and stirred for 30 min at 15° C. The precipitate was filtered off, washed with a mixture of ethyl acetate/petroleum ether (1:5 v/v, 30 mL) and dried in vacuo to afford the title compound as a yellow solid (4.12 g, 68% over 2 steps). $^1$H NMR (CDCl$_3$, 400 MHz): δ 0.91 (s, 3H), 1.55 (s, 9H), 1.72 (s, 3H), 1.75 (s, 3H), 2.07-2.19 (m, 1H), 2.54-2.62 (m, 1H), 3.71-3.85 (m, 2H), 5.07 (dd, J=7.2, 10.9 Hz, 1H), 7.36 (dd, J=8.5, 10.3 Hz, 1H), 7.53 (dd, J=3.0, 8.5 Hz, 1H), 10.99 (s, 1H).

Step 2: tert-Butyl ((3aR,4R,8S)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39BA)

To a mixture of tert-butyl ((3aR,4R,8S)-4-(6-bromo-3-fluoropyridin-2-yl)-4,7,7-trimethyl-8-oxido-3,3a,4,7-tetrahydro-2H-isothiazolo[1,5-a][1,4]thiazin-6-yl)carbamate (Int-38BA, 5.5 g, 11.2 mmol) in dioxane (100.0 mL) and water (30.0 mL) was added copper(I) iodide (2.3 g, 12.3 mmol), sodium ascorbate (1.3 g, 6.7 mmol), sodium azide (11.0 g, 168.0 mmol) and trans-N,N'-dimethyl-1,2-cyclohexanediamine (2.88 g, 20.23 mmol). Then the dark blue mixture was stirred for 1 h at 70° C. The reaction mixture was diluted with aqueous sodium hydrogencarbonate solution (200 mL) and extracted with ethyl acetate (2×150 mL). The combined organic layers were dried over sodium sulfate, filtered and concentrated to give the crude product. The crude was purified by column chromatography (silica gel, eluting with ethyl acetate/petroleum ether 2:1) to yield, after drying in vacuo, the title compound as yellow solid (4.5 g, 94% yield). $^1$H NMR (CDCl$_3$, 400 MHz): δ 0.93 (s, 3H), 1.52 (s, 9H), 1.66 (s, 3H), 1.73 (s, 3H), 2.03-2.15 (m, 1H), 2.47-2.57 (m, 1H), 3.69-3.79 (m, 2H), 4.54 (s, 2H), 5.16 (dd, J=7.2, 10.9 Hz, 1H), 6.46 (dd, J=2.3, 8.8 Hz, 1H), 7.20 (dd, J=8.8, 10.8 Hz, 1H), 10.90 (s, 1H).

Synthesis of Int-43: 2-(N-(2,2-Difluoro-3-((tetrahydro-2H-pyran-2-yl)oxy)propyl)-S-methylsulfonimidoyl)-2-methylpropanenitrile

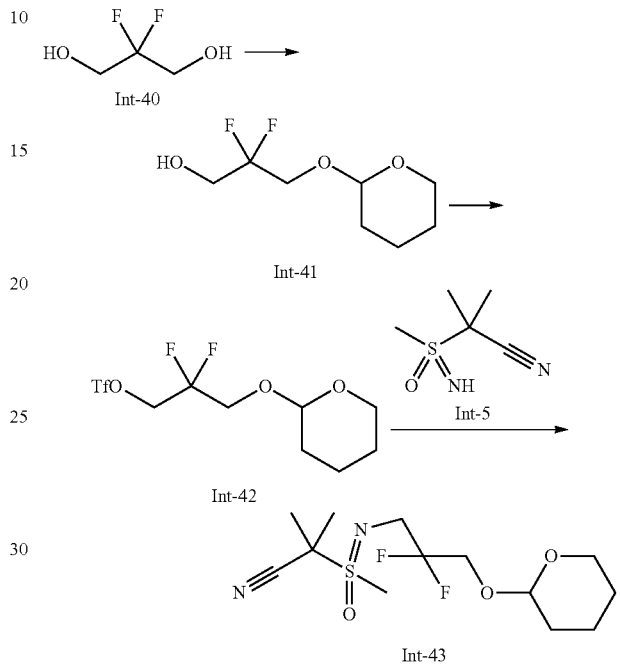

Step 1: 2,2-Difluoro-3-((tetrahydro-2H-pyran-2-yl)oxy)propan-1-ol (Int-41)

2,2-Difluoropropane-1,3-diol (1.00 g, 8.92 mmol) was suspended in cyclohexane (50 mL), 2,3-dihydropyrane (2.48 g, 2.7 ml, 29.5 mmol) followed by an aqueous solution of sodium hydrogensulfate (5 mol/L, 1.8 mL, 9 mmol) were added and the biphasic mixture was stirred for 90 min at 30° C. After that, solid sodium carbonate (8 g, 75.5 mmol) was added, the reaction mixture diluted by addition of tert-butylmethylether (20 mL) and stirred for 30 min at room temperature. It was filtered and the filtrate was concentrated in vacuo (55° C./5 mbar). The crude product was purified by column chromatography (silica gel, 50 g, eluting with ethyl acetate/n-heptane, gradient 20:80 to 40:60) to give, after drying in vacuo (50° C., 5 mbar), the title compound as colorless oil (1.2 g, 69%). $^1$H NMR (CDCl$_3$, 400 MHz): δ 1.49-1.65 (m, 4H), 1.72-1.88 (m, 2H), 2.58 (dd, J=7.1, 7.7 Hz, 1H), 3.51-3.59 (m, 1H), 3.74-4.07 (m, 5H), 4.62-4.66 (m, 1H).

Step 2: 2,2-Difluoro-3-hydroxypropyl trifluoromethanesulfonate (Int-42)

2,2-Difluoro-3-((tetrahydro-2H-pyran-2-yl)oxy)propan-1-ol (Int-41, 1.20 g, 6.12 mmol) was dissolved in dichloromethane (15 mL) and the solution was cooled to 0-5° C. (ice bath). Pyridine (685 mg, 700 μl, 8.65 mmol) followed by a solution of trifluoromethanesulfonic anhydride (2 g, 1.2 ml, 6.96 mmol) in dichloromethane (2 mL) were added over 15 min. The reaction mixture was stirred for 45 min. After that, it was poured into an aqueous saturated solution of sodium hydrogencarbonate (50 mL) and extracted with tert-butylmethylether (1×100 mL, 1×50 mL). The combined organic extracts were washed with brine (50 mL), dried (sodium sulfate) and concentrated in vacuo to give a brown oil as crude product. The crude product was purified by column chromatography (silica gel, 50 g, eluting with ethyl acetate/n-heptane, gradient 2:98 to 10:90) to afford, after drying in vacuo (40° C., 5 mbar) the title compound as viscous, colorless oil (1.54 g, 77%). $^1$H NMR (CDCl$_3$, 400 MHz): δ 1.48-1.68 (m, 4H), 1.69-1.86 (m, 2H), 3.52-3.60 (m, 1H), 3.68-3.84 (m, 2H), 4.02 (ddd, J=10.7, 11.5, 14.5 Hz, 1H), 4.63-4.76 (m, 3H).

Step 3: 2-(N-(2,2-Difluoro-3-((tetrahydro-2H-pyran-2-yl)oxy)propyl)-S-methylsulfonimidoyl)-2-methyl-propanenitrile (Int-43)

Potassium hydride (30% w/w in mineral oil, 700 mg, 5.24 mmol) was suspended in 1,2-dimethoxyethane (12 mL) and the suspension cooled to 0-5° C. (ice bath). A solution of 2-methyl-2-(methylsulfonimidoyl)propanenitrile (Int-5, 650 mg, 4.45 mmol) in 1,2-dimethoxyethane (5 mL) was added dropwise over 5 min. The ice bath was removed and the mixture was stirred for 30 min at room temperature. After that, it was cooled again to 0-5° C. and tetrabutylammonium bromide (80 mg, 248 μmol) followed by a solution of 2,2-difluoro-3-hydroxypropyl trifluoromethanesulfonate (Int-42, 1.53 g, 4.66 mmol) in 1,2-dimethoxyethane (5 mL) were added. The reaction mixture was stirred for 16 h at room temperature. Then, the mixture was poured into a saturated aqueous solution of sodium hydrogencarbonate (15 mL) and diluted with tert-butylmethylether (60 mL). After phase separation, the aqueous phase was extracted with tert-butylmethylether (2×30 mL), the combined organic extracts were dried (sodium sulfate) and concentrated in vacuo to afford the crude product. This was purified by column chromatography (silica gel, 50 g, eluting with ethyl acetate/n-heptane, gradient 40:60 to 60:40) to yield, after drying in vacuo (40° C., 5 mbar), the title compound as mixture of diastereoisomers as a light yellow viscous oil (980 mg, 68%). HPLC (method LCMS_gradient) t$_R$=2.0 min. $^1$H NMR (CDCl$_3$, 400 MHz): δ 1.49-1.87 (m, 6H), 1.78 (s, 6H), 3.11 & 3.12 (2s, 3H, diast.), 3.50-3.77 (m, 4H), 3.83-4.03 (m, 2H), 4.72 (t, J=3.2 Hz, 1H). MS (ES+) m/z 241.1 [M+H—(C$_5$H$_8$O)].

Synthesis of Int-45A and Int-45B: 2-((R,2R)-2-Amino-2-(6-bromo-3-fluoro-4-(triethylsilyl)pyridin-2-yl)-N-(2,2-difluoro-3-hydroxypropyl)propylsulfonimidoyl)-2-methylpropanenitrile (Int-45A) and 2-((S,2R)-2-amino-2-(6-bromo-3-fluoro-4-(triethylsilyl)pyridin-2-yl)-N-(2,2-difluoro-3-hydroxypropyl) propylsulfonimidoyl)-2-methylpropanenitrile (Int-45B)

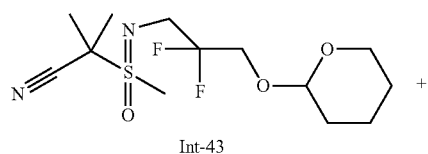

Int-43

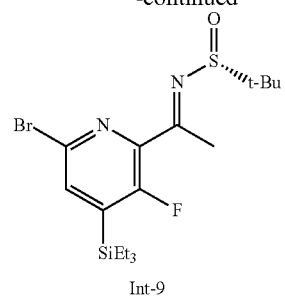

Int-9

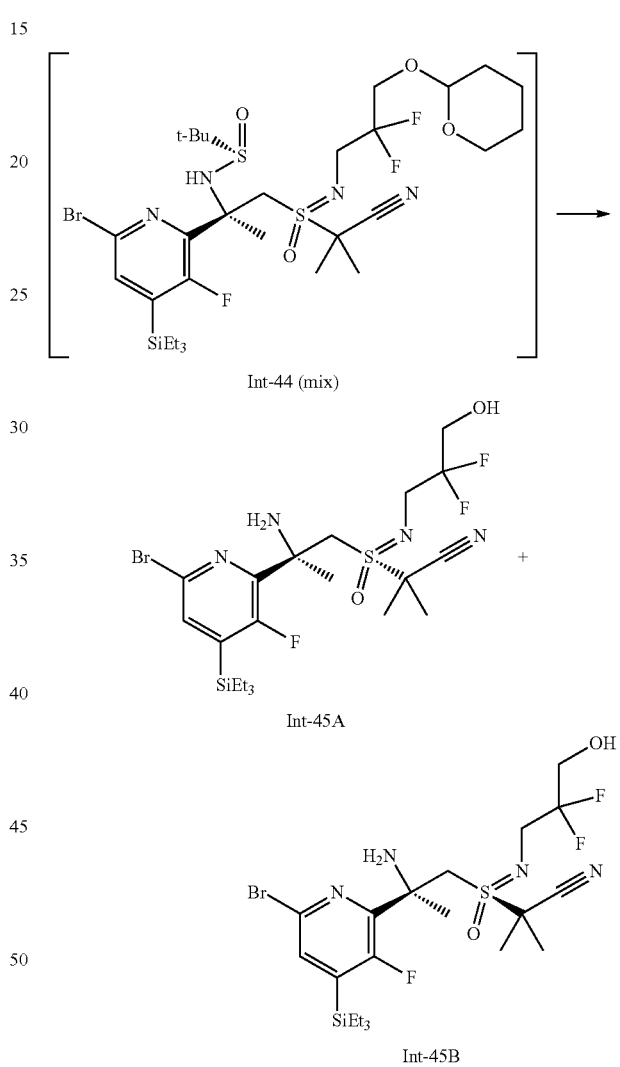

Step 1: N-(2-(6-Bromo-3-fluoro-4-(triethylsilyl) pyridin-2-yl)-1-(2-cyano-N-(2,2-difluoro-3-((tetra-hydro-2H-pyran-2-yl)oxy)propyl)propan-2-ylsulfon-imidoyl)propan-2-yl)-2-methylpropane-2-sulfinamide (Int-44 (mix))

2-(N-(2,2-Difluoro-3-((tetrahydro-2H-pyran-2-yl)oxy) propyl)-S-methylsulfonimidoyl)-2-methylpropanenitrile (Int-43, 960 mg, 2.96 mmol) was dissolved in THF (8 mL) and the solution was cooled to <−70° C. (acetone/dry ice bath). N-Butyl lithium (1.6 M in hexanes, 1.8 mL, 2.88 mmol) was added dropwise over 10 min, and the resulting solution was stirred for 50 min at <−70° C. Then, a solution of (R,E)-N-(1-(6-bromo-3-fluoro-4-(triethylsilyl)pyridin-2-yl)ethylidene)-2-methylpropane-2-sulfinamide (Int-9, 1.0 g, 2.3 mmol) in THF (6.0 mL) was added over 5 min at that temperature. After 30 min stirring at <−70° C., the reaction was not complete by tlc and HLPC. A solution of lithium hexamethyldisilazide in THF (1 M, 2.9 mL, 2.9 mmol) was added over 5 min and the reaction mixture was stirred for further 15 min at <−70° C. After that, it was poured into a 2M aqueous solution of ammonium chloride (20 mL) and extracted with tert-butylmethylether (1×80 mL, 1×40 mL). The combined organic extracts were concentrated in vacuo to give a yellow, viscous oil (2.1 g), that was used in the following step without further purification.

Step 2: 2-((R,2R)-2-Amino-2-(6-bromo-3-fluoro-4-(triethylsilyl)pyridin-2-yl)-N-(2,2-difluoro-3-hydroxypropyl)propylsulfonimidoyl)-2-methylpropanenitrile (Int-45A) and 2-((S,2R)-2-amino-2-(6-bromo-3-fluoro-4-(triethylsilyl)pyridin-2-yl)-N-(2,2-difluoro-3-hydroxypropyl)propylsulfonimidoyl)-2-methylpropanenitrile (Int-45B)

N-(2-(6-Bromo-3-fluoro-4-(triethylsilyl)pyridin-2-yl)-1-(2-cyano-N-(2,2-difluoro-3-((tetrahydro-2H-pyran-2-yl)oxy)propyl)propan-2-ylsulfonimidoyl)propan-2-yl)-2-methyl-propane-2-sulfinamide (Int-44 (mix), 2.10 g, 2.76 mmol) was dissolved in ethanol (21 mL) and a solution of hydrogen chloride in methanol (ca. 20% w/w, 8.5 g, 8.5 mL, 46.6 mmol) was added at 0-5° C. (ice bath). The mixture was stirred for 30 min at room temperature. After that, it was poured onto a 2M aqueous solution of sodium carbonate (100 mL) and diluted with MTBE (150 mL). The resulting suspension was filtered, the residue was washed with MTBE (50 mL). Phases of the combined filtrate were separated, the aqueous phase was extracted with ethyl acetate (2×50 mL), the combined organic extracts were dried (sodium sulfate) and concentrated in vacuo to afford a brownish oil as crude product. The crude was purified by column chromatography (silica gel, 100 g, eluting with ethyl acetate/methanol, gradient 100:0 to 90:10) to yield, after drying in vacuo (40° C., 5 mbar), the title compound Int-45A as single diastereomer and as a colorless oil 600 mg, 39% over two steps). HPLC (method LCMS_gradient) $t_R$=2.2 min. $^1$H NMR (CDCl$_3$, 400 MHz): δ 0.82-0.90 (m, 6H), 0.94-1.00 (m, 9H), 1.59 (s, 3H), 1.72 (s, 3H), 1.73 (s, 3H), 2.86 (br s, 3H), 3.46 (ddd, J=10.1, 13.0, 13.0 Hz, 1H), 3.60 (ddd, J=9.1, 13.4, 19.1 Hz, 1H), 3.75-3.85 (m, 3H), 4.25 (d, J=13.7 Hz, 1H), 7.36 (d, J=2.7 Hz, 1H). MS (ES+) m/z 573.1 & 571.2 [M+H, Br].

The minor diastereomer Int-45B was not isolated.

Synthesis of Int-48A: 3-(((1R,3R)-3-(6-Bromo-3-fluoro-4-(triethylsilyl)pyridin-2-yl)-5-((tert-butoxycarbonyl)amino)-3,6,6-trimethyl-1-oxido-3,6-dihydro-2H-1,4-thiazin-1-ylidene)amino)-2,2-difluoropropyl trifluoromethanesulfonate

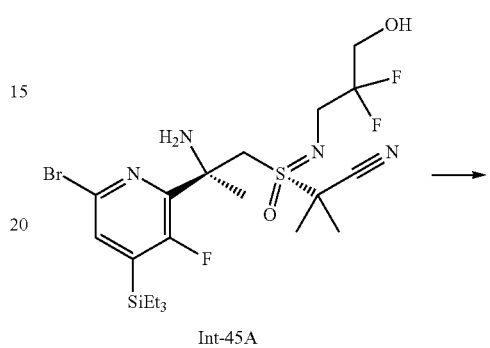

Int-45A

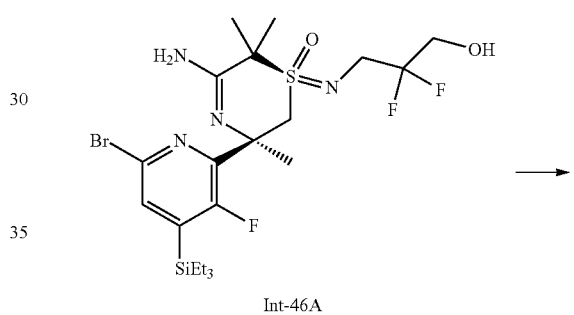

Int-46A

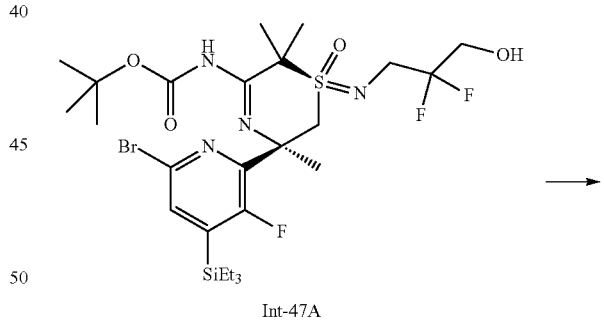

Int-47A

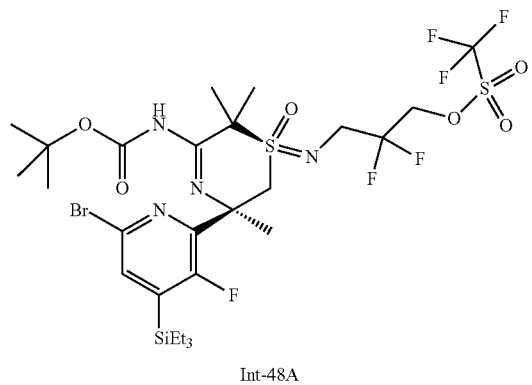

Int-48A

Step 1: (1R,3R)-5-Amino-3-(6-bromo-3-fluoro-4-(triethylsilyl)pyridin-2-yl)-1-((2,2-difluoro-3-hydroxypropyl)imino)-3,6,6-trimethyl-3,6-dihydro-2H-1,4-thiazine 1-oxide (Int-46A)

2-(2-amino-2-(6-bromo-3-fluoro-4-(triethylsilyl)pyridin-2-yl)-N-(2,2-difluoro-3-hydroxypropyl)propylsulfoninidoyl)-2-methylpropanenitrile (Int-45A, 600 mg, 1.05 mmol) was dissolved in ethanol (9 mL) and copper (I) bromide (160 mg, 1.12 mmol) was added. The mixture was heated to 75-80° C. and stirred for 45 min at that temperature. After that, it was cooled to 5° C. (ice bath) and poured into a mixture of brine (10 mL) and aqueous ammonia (25% w/w, 5 mL). The resulting mixture was extracted with MTBE (60 mL) and ethyl acetate (2×25 mL), the combined extracts were dried (sodium sulfate) and concentrated in vacuo to give a yellow oil as crude product. The crude was purified by column chromatography (silica gel, 50 g, eluting with ethyl acetate/methanol, gradient 95:5 to 85:15) to yield, after drying in vacuo (60° C., 5 mbar), the title compound as a white foam (490 mg, 82%). HPLC (method LCMS_gradient) $t_R$=2.1 min. $^1$H NMR (CDCl$_3$, 400 MHz): δ 0.80-0.90 (m, 6H), 0.93-1.00 (m, 9H), 1.65 (s, 3H), 1.73 (s, 3H), 1.75 (s, 3H), 2.96-3.09 (m, 1H), 3.40 (d, J=15.0 Hz, 1H), 3.40-3.52 (m, 1H), 3.64-3.80 (m, 2H), 4.30 (d, J=14.8 Hz, 1H), 7.33 (d, J=2.4 Hz, 1H). MS (ES+) m/z 573.1 & 571.2 [M+H, Br].

Step 2: tert-Butyl ((1R,5R)-5-(6-bromo-3-fluoro-4-(triethylsilyl)pyridin-2-yl)-1-((2,2-difluoro-3-hydroxypropyl)imino)-2,2,5-trimethyl-1-oxido-5,6-dihydro-2H-1,4-thiazin-3-yl)carbamate (Int-47A)

(1R,3R)(6-bromo-3-fluoro-4-(triethylsilyl)pyridin-2-yl)-1-((2,2-difluoro-3-hydroxypropyl)imino)-3,6,6-trimethyl-3,6-dihydro-2H-1,4-thiazine 1-oxide (Int-46A, 490 mg, 857 µmol) was dissolved in THF (5 mL) and water (1 mL) and Boc-anhydride (280 mg, 298 µL, 1.28 mmol), sodium hydrogencarbonate (100 mg, 1.19 mmol) and 4-dimethylaminopyridine (5 mg, 41 µmol) were added. The mixture was stirred for 3.75 h at room temperature. After that, aqueous ammonia (25% w/w, 90 mg, 100 µL, 1.32 mmol) was added and the mixture was stirred for additional 30 min. The reaction mixture was then poured onto water (10 mL) and extracted with MTBE (1×80 mL, 1×40 mL). The combined extracts were dried and concentrated in vacuo. The crude product was purified by column chromatography (silica gel, 100 g, eluting with ethyl acetate/n-heptane, gradient 40:60 to 60:40) to yield, after drying in vacuo (55° C., 5 mbar), the title compound as a white foam (520 mg, 90%). HPLC (method LCMS_gradient) $t_R$=4.1 min. $^1$H NMR (CDCl$_3$, 400 MHz): δ 0.82-0.90 (m, 6H), 0.93-0.99 (m, 9H), 1.54 (s, 9H), 1.64 (s, 3H), 1.78 (s, 3H), 1.83 (s, 3H), 2.66 (t, J=7.5 Hz, 1H), 2.86 (ddd, J=10.5, 13.2, 13.2 Hz, 1H), 3.42 (ddd, J=8.9, 13.4, 18.5 Hz, 1H), 3.57 (d, J=15.3 Hz, 1H), 3.60-3.80 (m, 2H), 4.56 (d, J=15.0 Hz, 1H), 7.38 (d, J=2.7 Hz, 1H), 11.15 (s, 1H). MS (ES+) m/z 673.2 & 671.2 [M+H, Br].

Step 3: 3-(((1R,3R)-3-(6-Bromo-3-fluoro-4-(triethylsilyl)pyridin-2-yl)-5-((tert-butoxycarbonyl)amino)-3,6,6-trimethyl-1-oxido-3,6-dihydro-2H-1,4-thiazin-1-ylidene)amino)-2,2-difluoropropyl trifluoromethanesulfonate (Int-48A)

tert-Butyl ((1R,5R)-5-(6-bromo-3-fluoro-4-(triethylsilyl)pyridin-2-yl)-1-((2,2-difluoro-3-hydroxypropyl)imino)-2,2,5-trimethyl-1-oxido-5,6-dihydro-2H-1,4-thiazin-3-yl)carbamate (Int-47A, 2.05 g, 3.05 mmol) was dissolved in dichloromethane (25 mL), the solution was cooled to 0-5° C. (ice bath) and pyridine (302 mg, 309 µL, 3.82 mmol) and a solution of triflic anhydride (947 mg, 3.36 mmol) in dichloromethane (8 ml) were added subsequently at that temperature. The resulting yellow solution was stirred for 30 min at 0-5° C. After that, an aqueous solution of sodium hydrogencarbonate (5%, 100 mL) was added and the pH of the aqueous phase was verified to be 8-9. The phases were separated and the aqueous phase was extracted with dichloromethane (2×60 mL). The combined extracts were dried (sodium sulfate) and concentrated in vacuo to give the crude product. The crude was purified by column chromatography (silica gel, 40 g, eluting with ethyl acetate/n-heptane, gradient 5:95 to 30:70) to afford, after drying in vacuo (40° C., 5 mbar), the title compound as a light yellow foam (2.15 g, 88%). HPLC (method LCMS_fglm) $t_R$=1.86 min. $^1$H NMR (CDCl$_3$, 300 MHz): δ 0.81-0.91 (m, 6H), 0.93-1.01 (m, 9H), 1.55 (s, 9H), 1.62 (s, 3H), 1.78 (s, 3H), 1.83 (s, 3H), 3.07 (ddd, J=9.9, 13.9, 13.9 Hz, 1H), 3.44 (ddd, J=9.5, 13.5, 17.1 Hz, 1H), 3.57 (d, J=15.1 Hz, 1H), 4.46-4.56 (m, 2H), 4.56 (d, J=15.1 Hz, 1H), 7.39 (d, J=2.6 Hz, 1H), 11.20 (s, 1H). MS (ES+) m/z 803.2 & 805.2 [M+H, Br].

Synthesis of Int-49AA and Int-49AB: tert-Butyl ((4aR,5R,9R)-5-(6-bromo-3-fluoro-4-(triethylsilyl)pyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-49AA) and tert-butyl ((4aS,5R,9R)-5-(6-bromo-3-fluoro-4-(triethylsilyl)pyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-49AB)

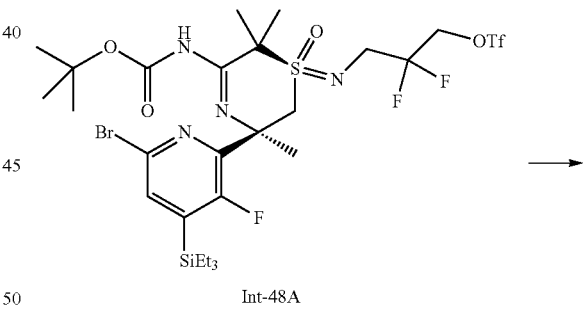

Int-48A

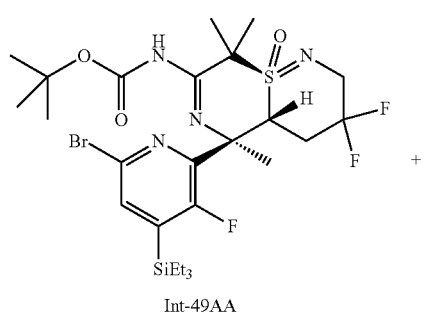

Int-49AA

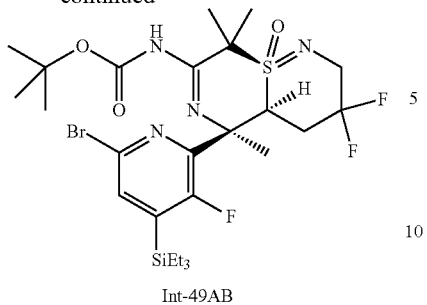

Int-49AB 3-(((1R,3R)-3-(6-Bromo-3-fluoro-4-(triethylsilyl)pyridin-2-yl)-5-((tert-butoxycarbonyl)amino)-3,6,6-trimethyl-1-oxido-3,6-dihydro-2H-1,4-thiazin-1-ylidene)amino)-2,2-difluoropropyl trifluoromethanesulfonate (Int-48A, 2.13 g, 2.65 mmol) was dissolved in THF (25 mL) under anhydrous conditions and the solution was cooled to <−70° C. (acetone/dry ice bath). A solution of LHMDS in THF (1.0 M, 6.89 ml, 6.89 mmol) was added over 15 min and stirred for 15 min at that temperature. Then, the resulting clear, yellow solution was allowed to warm to −20° C. (ice/ethanol bath) and stirred for 90 min at that temperature TLC showed complete conversion. The reaction was stopped by addition of a saturated aqeuous solution of ammonium chloride (60 mL) and, after phase separation, the aqueous phase was extracted with ethyl acetate (2×60 mL). The combined extracts were dried (sodium sulfate) and concentrated in vacuo. The crude was purified by column chromatography (silica gel, 40 g, eluting with ethyl acetate/n-heptane, gradient 5:95 to 35:65) to yield, after drying in vacuo (55° C., 5 mbar), the title compound Int-49AA as single diastereoisomer and as colorless viscous oil (1.57 g, 91%). HPLC (method LCMS_gradient) $t_R$=4.5 min. $^1$H NMR (CDCl$_3$, 400 MHz): δ 0.83-0.91 (m, 6H), 0.94-1.00 (m, 9H), 1.47 (s, 9H), 1.79 (s, 3H), 1.82 (s, 3H), 1.93 (br s, 3H), 2.55-2.77 (m, 2H), 3.63-3.86 (m, 2H), 4.50-4.57 (m, 1H), 7.45 (d, J=2.7 Hz, 1H), 11.45 (s, 1H). MS (ES+) m/z 555.1 & 553.1 [M+H—CO$_2$—CH$_2$=CMe$_2$, Br]. The minor diastereomer was not isolated.

Synthesis of Int-51AA: tert-Butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate Int-49AA Int-50AA Int-51AA Step 1: tert-Butyl ((4aR,5R,9R)-5-(6-bromo-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-50AA)

tert-Butyl ((4aR,5R,9R)-5-(6-bromo-3-fluoro-4-(triethylsilyl)pyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-49AA, 170 mg, 260 mop was dissolved in THF (4 mL) and DMF (1 mL). Acetic acid (52.5 mg, 50 μl, 873 μmol) and potassium fluoride (50 mg, 861 μmol) were added at room temperature and the resulting fine suspension was stirred for 2.5 h at that temperature. After that, it was poured into a saturated aqueous solution of sodium hydrogencarbonate (10 mL) and extracted with MTBE (1×60 mL, 1×30 mL). The combined extracts were washed with brine (10 mL), dried (sodium sulfate) and concentrated in vacuo. The residue was treated with o-xylene (8 mL) and concentrated again in vacuo to give a yellow viscous oil as crude product. The crude was purified by column chromatography (silica gel, 50 g, eluting with ethyl acetate/n-heptane, gradient 20:80 to 40:60) to yield, after drying in vacuo (55° C., 5 mbar), the title compound as a white foam (130 mg, 93%). HPLC (method LCMS_gradient) $t_R$=3.1 min. $^1$H NMR (CDCl$_3$, 400 MHz): δ 1.49 (s, 9H), 1.80 (s, 3 II), 1.82 (s, 3H), 1.93 (d, J=1.1 Hz, 3H), 2.49-2.60 (m, 1H), 2.61-2.78 (m, 1H), 3.63-3.86 (m, 2H), 4.45-4.51 (m, 1H), 7.41 (dd, J=8.6, 10.7 Hz, 1H), 7.54 (dd, J=3.1, 8.5 Hz, 1H), 11.31 (s, 1H). MS (ES+) m/z 541.1 & 539.1 [M+H, Br].

Step 2: tert-Butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AA)

tert-Butyl ((4aR,5R,9R)-5-(6-bromo-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-50AA, 120 mg, 222 μmol) was dissolved in 1,4-dioxane (3 mL) and water (1 mL) and sodium azide (200 mg, 3.08 mmol) was added. Copper (I) iodide (30 mg, 158 μmol), sodium ascorbate (15 mg, 76 μmol) and trans-N,N'-dimethyl-1,2-cyclohexanediamine (36.1 mg, 40 μl, 254 mol) were added subsequently and the dark blue mixture was stirred for 1 h at 70° C. Since the conversion was not complete, further portions of sodium azide (100 mg, 1.54 mmol), copper (I) iodide (30 mg, 158 μmol), sodium ascorbate (15 mg, 76 μmol) and trans-N,N'-dimethyl-1,2-cyclohexanediamine (36.1 mg, 40 μl, 254 μmol) were added subsequently and the mixture was stirred at 70° C. for further 30 min. Then, the reaction mixture was allowed to cool to room temperature and poured into a saturated aqueous solution of sodium hydrogencarbonate (10 mL). It was extracted with ethyl acetate (1×50 mL, 2×30 mL), the combined extracts were washed with a mixture of brine (10 mL) and ammonia (25% w/w, 1 mL), dried over sodium sulfate and silica gel (2 g) was added to the solution. After filtration, the filtrate was concentrated in vacuo to give a yellow solid as crude product. The crude was purified by column chromatography (silica gel, 50 g, eluting with ethyl acetate/n-heptane, gradient 30:70 to 50:50) to afford, after drying in vacuo (55° C., 5 mbar), the title compound as a white solid (70 mg, 66%). HPLC (method LCMS_gradient) $t_R$=2.6 min. $^1$H NMR (CDCl$_3$, 400 MHz): δ 1.49 (s, 9H), 1.78 (s, 3H), 1.80 (s, 3H), 1.87 (d, J=1.6 Hz, 3H), 2.58-2.75 (m, 2H), 3.62-3.86 (m, 2H), 4.41 (s, 2H), 4.59-4.65 (m, 1H), 6.49 (dd, J=2.6, 8.6 Hz, 1H), 7.28 (dd, J=8.7, 10.9 Hz, 1H), 11.23 (s, 1H). MS (ES+) m/z 476.2 [M+H].

Synthesis of Int-51AAp: Enantiopure tert-Butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate

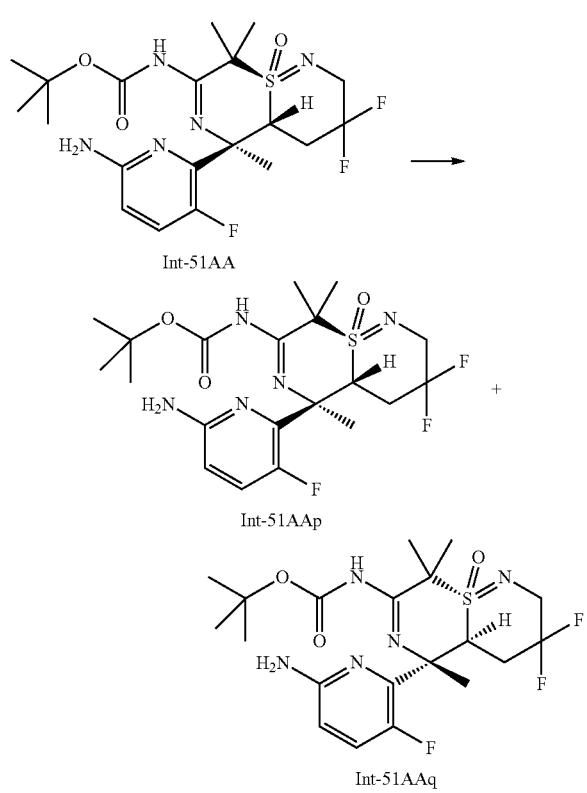

Enantiomeric purification of tert-butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AA, 1.68 g, 3.53 mmol) was performed by chiral preparative HPLC (Chiralpak AD, 250*4.6 mm*5 μm, isocratic, n-heptane/ethanol 90/10, flow 1.0 mL/min) to yield the desired (−)-rotating first eluting enantiomer as a white solid (Int-51AAp, 979 mg, 58%), and the opposite (+)-rotating enantiomer as a white solid (Int-51AAq, 366 mg, 22%).

Synthesis of Int-55: 2-Methyl-2-(S-methyl-N-((1-(((tetrahydro-2H-pyran-2-yl)oxy)methyl)cyclopropyl)methyl)sulfonimidoyl)propanenitrile

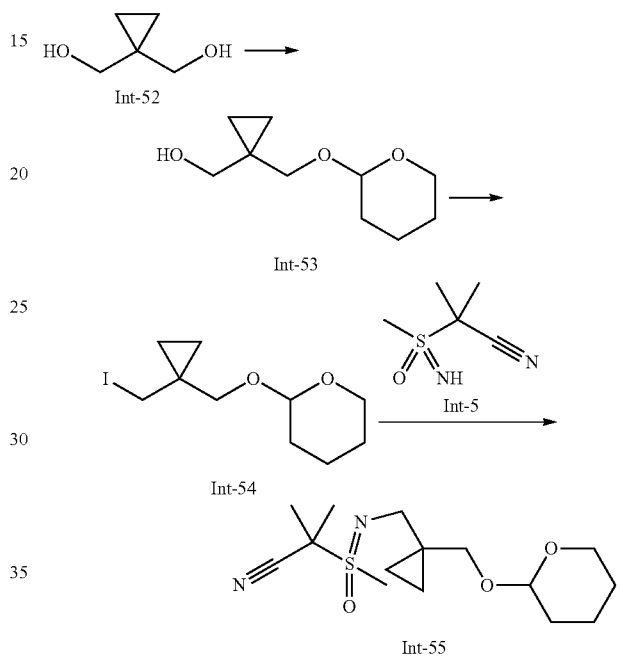

Step 1: (1-(((Tetrahydro-2H-pyran-2-yl)oxy)methyl)cyclopropyl)methanol (Int-53)

Cyclopropane-1,1-diyldimethanol (16.0 g, 157 mmol) was suspended in toluene (312 mL) at 30° C., 2,3-dihydropyrane (43.6 g, 47.0 ml, 519 mmol) followed by an aqueous solution of sodium hydrogensulfate (5 mol/L, 31.6 mL, 158 mmol) were added and the biphasic mixture was stirred for 1 h at 30° C. After that, solid sodium carbonate (140 g, 1.33 mol) was added, the resulting suspension was stirred for 30 min at room temperature and filtered. The precipitate was washed with toluene (4×125 mL), and the combined filtrates were concentrated in vacuo (40° C./5 mbar). The crude product was purified by column chromatography (silica gel, 330 g, eluting with tert-butylmethyl ether/n-heptane, gradient 20:80 to 35:65) to give, after drying in vacuo (40° C., 5 mbar), the title compound as light yellow liquid (21.1 g, 72%). $^1$H NMR (CDCl$_3$, 300 MHz): δ 0.48-0.58 (m, 4H), 1.51-1.64 (m, 4H), 1.72-1.78 (m, 1H), 1.79-1.87 (m, 1H), 2.63 (br s, 1H), 3.40 (d, J=10.3 Hz, 1H), 3.49-3.55 (m, 1H), 3.51 (d, J=11.3 Hz, 1H), 3.63 (d, J=11.2 Hz, 1H), 3.76 (d, J=10.2 Hz, 1H), 3.87-3.92 (m, 1H), 4.61-4.63 (m, 1H).

Step 2: 2-((1-(Iodomethyl)cyclopropyl)methoxy)tetrahydro-2H-pyran (Int-54)

2,3-Dichloro-5,6-dicyano-1,4-benzoquinone (6.67 g, 29.4 mmol) was dissolved in dichloromethane (200 mL) and triphenyl phosphine (7.71 g, 29.4 mmol) was added. The brown suspension was cooled to 0-5° C. (ice bath) and tetra-n-butylammonium iodide (10.9 g, 29.4 mmol) was added in one portion, followed by a solution of (1-(((tetrahydro-2H-pyran-2-yl)oxy)methyl)cyclopropyl)methanol (Int-53, 5.21 g, 28 mmol) in dichloromethane (50 mL). The reaction mixture was stirred for 15 min at 0-5° C. and for 1 h at room temperature. After that, it was concentrated in vacuo and purified directly by column chromatography (silica gel, 220 g, eluting with ethyl acetate/n-heptane, gradient 2:98 to 15:85) to afford, after drying in vacuo (40° C., 5 mbar) the title compound as colorless liquid (6.0 g, 72%). $^1$H NMR (CDCl$_3$, 600 MHz): δ 0.60-0.72 (m, 4H), 0.83-0.98 (m, 2H), 1.48-1.91 (m, 6H), 3.29 (d, AB, J=9.9 Hz, 1H), 3.38-3.45 (m, 2H), 3.49-3.57 (m, 1H), 3.62 (d, AB, J=10.5 Hz, 1H), 3.85-3.94 (m, 1H), 4.64-4.68 (m, 1H).

Step 3: 2-Methyl-2-(S-methyl-N-((1-(((tetrahydro-2H-pyran-2-yl)oxy)methyl)cyclo-propyl)methyl)sulfonimidoyl)propanenitrile (Int-55)

Potassium hydride (30% w/w in mineral oil, 758 mg, 5.67 mmol) was suspended in tetrahydrofuran (5 mL) and the suspension cooled to 0-5° C. (ice bath). A solution of 2-methyl-2-(methylsulfonimidoyl)propanenitrile (Int-5, 829 mg, 5.67 mmol) in tetrahydrofuran (3 mL) was added dropwise over 5 min. The mixture was stirred for 15 min at 0-5° C. and for 90 min at room temperature. After that, it was cooled again to 0-5° C. and tetrabutylammonium bromide (45.1 mg, 140 μmol) followed by a solution of 2-((1-(iodomethyl)cyclopropyl)methoxy)tetrahydro-2H-pyran (Int-54, 829 mg, 2.8 mmol) in tetrahydrofuran (3 mL) were added. The reaction mixture was stirred for 14 h at room temperature, followed by 24 h at 65° C. (reflux). After cooling to room temperature, the mixture was poured into a saturated aqueous solution of sodium hydrogencarbonate (5% m/m, 40 mL) and extracted with ethyl acetate (2×50 mL). The combined organic extracts were dried (sodium sulfate) and concentrated in vacuo to afford the crude product. This was purified by column chromatography (silica gel, 40 g, eluting with ethyl acetate/n-heptane, gradient 25:75 to 75:25) to yield, after drying in vacuo (40° C., 5 mbar), the title compound as mixture of diastereoisomers as a yellow viscous oil (404 mg, 46%). $^1$H NMR (CDCl$_3$, 300 MHz): δ 0.43-0.58 (m, 4H), 1.48-1.65 (m, 4H), 1.68-1.91 (m, 2H), 1.76 (s, 6H), 3.08 (2s, 3H, diast.), 3.10-3.54 (m, 4H), 3.60 (dd, J=6.0, 10.2 Hz, 1H), 3.84-3.93 (m, 1H), 4.61-4.66 (m, 1H). MS (ES+) m/z 315.2 [M+H].

Synthesis of Int-57A and Int-57B: 2-((R,2R)-2-Amino-2-(6-bromo-3-fluoro-4-(triethylsilyl)pyridin-2-yl)-N-((1-(hydroxymethyl)cyclopropyl)methyl)propylsulfonimidoyl)-2-methylpropanenitrile (Int-57A) and 2-((S,2R)-2-amino-2-(6-bromo-3-fluoro-4-(triethylsilyl)pyridin-2-yl)-N-((1-(hydroxymethyl)cyclopropyl)methyl)propylsulfonimidoyl)-2-methylpropanenitrile (Int-57B)

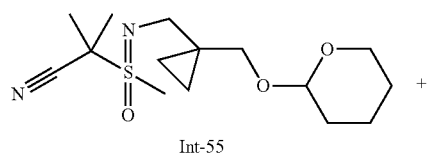

Int-55

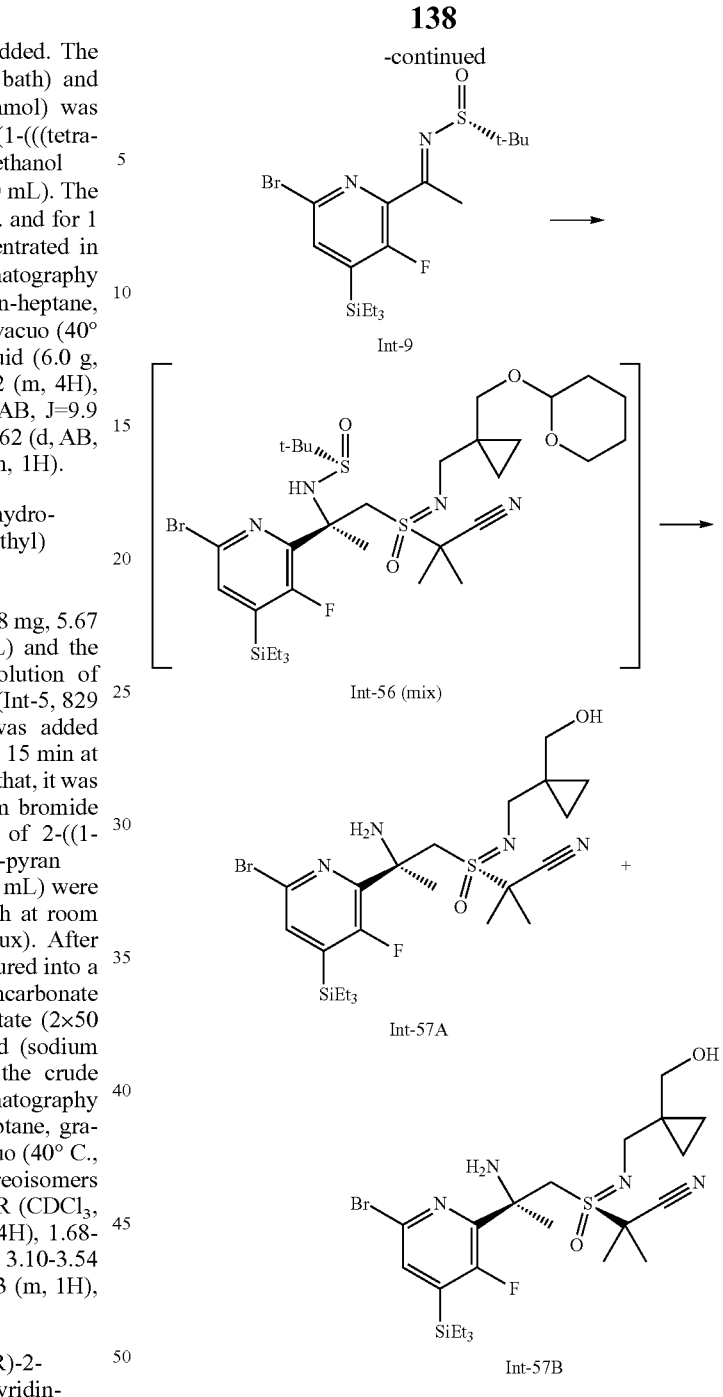

Step 1: N-(2-(6-Bromo-3-fluoro-4-(triethylsilyl)pyridin-2-yl)-1-(2-cyano-N-((1-(((tetrahydro-2H-pyran-2-yl)oxy)methyl)cyclopropyl)methyl)propan-2-ylsulfonimidoyl)propan-2-yl)-2-methylpropane-2-sulfinamide (Int-56 (mix))

2-Methyl-2-(S-methyl-N-((1-(((tetrahydro-2H-pyran-2-yl)oxy)methyl)cyclopropyl)-methyl)sulfonimidoyl)propanenitrile (Int-55, 2.34 g, 7.44 mmol) was dissolved in THF (40 mL) and the solution was cooled to <−70° C. (acetone/dry ice bath). N-Butyl lithium (1.6 M in hexanes, 4.65 mL, 7.44 mmol) was added dropwise over 10 min, and the resulting solution was stirred for 1 h at <−70° C. Then, a solution of (R,E)-N-(1-(6-bromo-3-fluoro-4-(triethylsilyl)

pyridin-2-yl)ethylidene)-2-methylpropane-2-sulfinamide (Int-9, 2.7 g, 6.2 mmol) in THF (20 mL) was added over 20 min at that temperature. After 90 min stirring at <−70° C., a saturated aqueous solution of ammonium chloride (100 mL) was added and the mixture was allowed to warm to room temperature. Then, it was diluted with water (50 mL) and extracted with ethyl acetate (2×100 mL). The combined organic extracts were dried (sodium sulfate) and concentrated in vacuo to give a yellow, viscous oil (6.08 g), that was used in the following step without further purification.

Step 2: 2-((R,2R)-2-Amino-2-(6-bromo-3-fluoro-4-(triethylsilyl)pyridin-2-yl)-N-((1-(hydroxymethyl)cyclopropyl)methyl)propylsulfonimidoyl)-2-methyl-propanenitrile (Int-57A) and 2-((S,2R)-2-amino-2-(6-bromo-3-fluoro-4-(triethylsilyl)pyridin-2-yl)-N-((1-(hydroxymethyl)-cyclopropyl)methyl)propylsulfonimidoyl)-2-methylpropanenitrile (Int-57B)

N-(2-(6-Bromo-3-fluoro-4-(triethylsilyl)pyridin-2-yl)-1-(2-cyano-N-((1-(((tetrahydro-2H-pyran-2-yl)oxy)methyl)cyclopropyl)methyl)propan-2-ylsulfonimidoyl)propan-2-yl)-2-methylpropane-2-sulfinamide (Int-56 (mix), 6.08 g, 6.2 mmol) was dissolved in ethanol (25 mL) and a solution of hydrogen chloride in methanol (ca. 20% w/w, 41.9 g, 45.6 mL, 676 mmol) was added at 0-5° C. (ice bath). The mixture was stirred for 40 min at 0-5° C. After that, an aqueous solution of sodium carbonate (10% m/m, 300 mL) was added, and the resulting mixture was extracted with ethyl acetate (2×150 mL). The combined organic extracts were dried (sodium sulfate) and concentrated in vacuo to afford a yellow oil as crude product. The crude was purified by column chromatography (silica gel, 120 g, eluting with ethyl acetate/methanol, gradient 100:0 to 90:10) to yield, after drying in vacuo (40° C., 5 mbar), the title compound Int-57A as single diastereomer and as light yellow solid (1.8 g, 52% over 2 steps). The minor diastereomer Int-57B was not isolated. Int-57A: $^1$H NMR (CDCl$_3$, 300 MHz): δ 0.30-0.50 (m, 4H), 0.81-0.93 (m, 6H), 0.94-1.03 (m, 9H), 1.56 (s, 3H), 1.67 (s, 3H), 1.72 (s, 3H), 2.77 (br s, 3H), 3.01 (d, AB, J=12.5 Hz, 1H), 3.14 (d, AB, J=12.3 Hz, 1H), 3.42 (d, AB, J=11.5 Hz, 1H), 3.51 (d, AB, J=11.5 Hz, 1H), 3.77 (dd, AB, J=1.2, 13.5 Hz, 1H), 4.13 (d, AB, J=13.5 Hz, 1H), 7.36 (d, J=2.6 Hz, 1H). MS (ES+) m/z 563.2 & 561.2 [M+H, Br].

Synthesis of Int-60A: tert-Butyl ((1R,5R)-5-(6-bromo-3-fluoro-4-(triethylsilyl)pyridin-2-yl)-1-(((1-(iodomethyl)cyclopropyl)methyl)imino)-2,2,5-trimethyl-1-oxido-5,6-dihydro-2H-1,4-thiazin-3-yl)carbamate

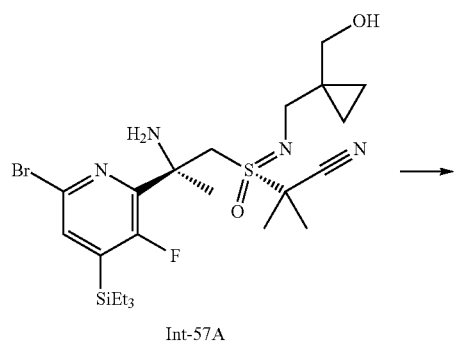

Int-57A

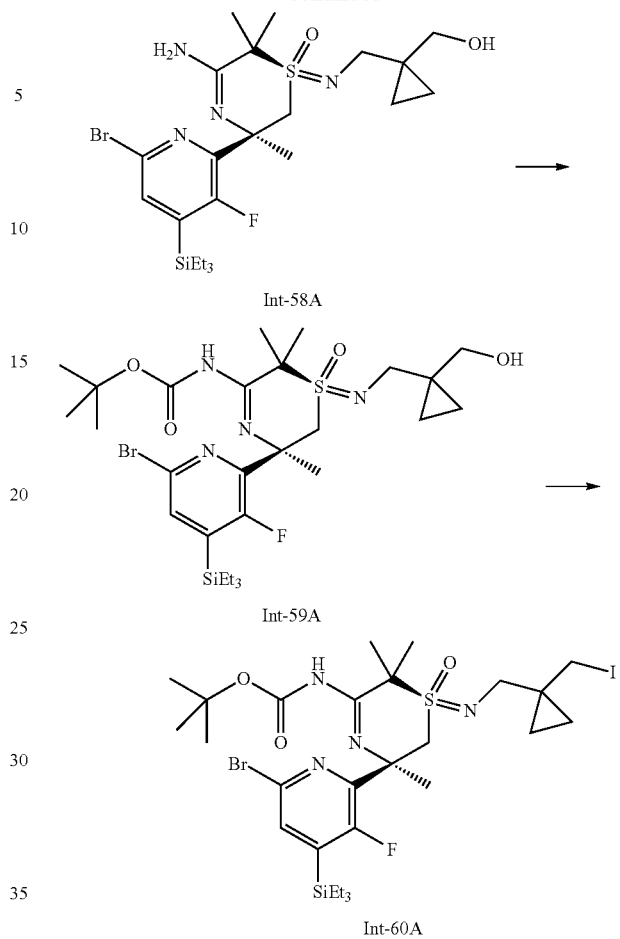

Int-58A

Int-59A

Int-60A

Step 1: (1R,3R)(6-bromo-3-fluoro-4-(triethylsilyl)pyridin-2-yl)-1-(((1-(hydroxymethyl)cyclopropyl)methyl)imino)-3,6,6-trimethyl-3,6-dihydro-2H-1,4-thiazine 1-oxide (Int-58A)

2-((R,2R)-2-Amino-2-(6-bromo-3-fluoro-4-(triethylsilyl)pyridin-2-yl)-N-((1-(hydroxy-methyl)cyclopropyl)methyl)propylsulfonimidoyl)-2-methylpropanenitrile (Int-57A, 1.8 g, 3.2 mmol) was dissolved in ethanol (30 mL) and copper (I) bromide (460 mg, 3.2 mmol) was added. The mixture was heated to 85° C. and stirred for 90 min at that temperature. After that, it was cooled to room temperature and poured into a mixture of brine (100 mL) and aqueous ammonia (32% w/w, 40 mL). The resulting mixture was extracted with ethyl acetate (2×100 mL), the combined extracts were dried (sodium sulfate) and concentrated in vacuo to give a light yellow foam as crude product. The crude was purified by column chromatography (silica gel, 40 g, eluting with ethyl acetate/2N ammonia in methanol, gradient 98:2 to 90:10) to yield, after drying in vacuo (40° C., 5 mbar), the title compound as a white foam (1.4 g, 78%). $^1$H NMR (CDCl$_3$, 300 MHz): δ 0.25-0.49 (m, 4H), 0.81-0.92 (m, 6H), 0.93-1.02 (m, 9H), 1.66 (s, 3H), 1.72 (s, 3H), 1.77 (s, 3H), 2.80 (br s, 1H), 3.02 (d, J=11.9 Hz, 1H), 3.18-3.51 (m, 4H), 4.20 (d, J=14.7 Hz, 1H), 7.33 (d, J=2.4 Hz, 1H). MS (ES+) m/z 563.2 & 561.2 [M+H, Br].

Step 2: tert-Butyl ((1R,5R)-5-(6-bromo-3-fluoro-4-(triethylsilyl)pyridin-2-yl)-1-(((1-(hydroxymethyl)cyclopropyl)methyl)imino)-2,2,5-trimethyl-1-oxido-5,6-dihydro-2H-1,4-thiazin-3-yl)carbamate (Int-59A)

(1R,3R)(6-bromo-3-fluoro-4-(triethylsilyl)pyridin-2-yl)-1-(((1-(hydroxy-methyl)cyclopropyl)methyl)imino)-3,6,6-trimethyl-3,6-dihydro-2H-1,4-thiazine 1-oxide (Int-58A, 1.4 mg, 2.49 mmol) was dissolved in THF (30 mL) and water (6 mL) and Boc-anhydride (816 mg, 3.74 mmol), sodium hydrogencarbonate (293 mg, 3.49 mmol) and 4-dimethylaminopyridine (15.2 mg, 125 µmol) were added. The mixture was stirred for 90 min at room temperature. After that, aqueous ammonia (25% w/w, 255 mg, 324 µL, 3.74 mmol) was added and the mixture was stirred for additional 10 min. The reaction mixture was then diluted with water (80 mL) and extracted with ethyl acetate (2×80 mL). The combined extracts were dried (sodium sulfate) and concentrated in vacuo. The crude product was purified by column chromatography (silica gel, 24 g, eluting with ethyl acetate/n-heptane, gradient 5:95 to 50:50) to yield, after drying in vacuo (40° C., 5 mbar), the title compound as a white foam (1.52 g, 92%). HPLC (method LCMS_fglm) $t_R$=1.70 min. $^1$H NMR (CDCl$_3$, 300 MHz): δ 0.21-0.46 (m, 4H), 0.80-0.92 (m, 6H), 0.93-1.03 (m, 9H), 1.54 (s, 9H), 1.65 (s, 3H), 1.77 (s, 3H), 1.85 (s, 3H), 2.61 (d, J=12.5 Hz, 1H), 2.94 (dd, J=5.7, 6.3 Hz, 1H), 3.01 (d, J=12.5 Hz, 1H), 3.35 (dd, J=6.4, 11.3 Hz, 1H), 3.54 (d, J=15.1 Hz, 1H), 4.45 (d, J=15.1 Hz, 1H), 7.38 (d, J=2.4 Hz, 1H). MS (ES+) m/z 663.2 & 661.2 [M+H, Br].

Step 3: tert-Butyl ((1R,5R)-5-(6-bromo-3-fluoro-4-(triethylsilyl)pyridin-2-yl)-1-(((1-(iodomethyl)cyclopropyl)methyl)imino)-2,2,5-trimethyl-1-oxido-5,6-dihydro-2H-1,4-thiazin-3-yl)carbamate (Int-60A)

2,3-Dichloro-5,6-dicyano-1,4-benzoquinone (626 mg, 2.76 mmol) was dissolved in dichloromethane (25 mL) and triphenyl phosphine (723 mg, 2.76 mmol) was added. The brown suspension was cooled to 0-5° C. (ice bath) and tetra-n-butylammonium iodide (1.02 g, 2.76 mmol) was added in one portion, followed by a solution of tert-butyl ((1R,5R)-5-(6-bromo-3-fluoro-4-(triethylsilyl)pyridin-2-yl)-1-(((1-(hydroxymethyl)cyclopropyl)methyl)imino)-2,2,5-trimethyl-1-oxido-5,6-dihydro-2H-1,4-thiazin-3-yl)carbamate (Int-59A, 1.52 g, 2.3 mmol) in dichloromethane (5 mL). The reaction mixture was stirred for 15 min at 0-5° C. and for 1 h at room temperature. After that, it was concentrated in vacuo and purified directly by column chromatography (silica gel, 40 g, eluting with ethyl acetate/n-heptane, gradient 5:95 to 30:70) to afford, after drying in vacuo (40° C., 5 mbar) the title compound as colorless oil (1.36 g, 73%). HPLC (method LCMS_gradient) $t_R$=4.8 min. $^1$H NMR (CDCl$_3$, 300 MHz): δ 0.40-0.50 (m, 2H), 0.63-0.79 (m, 2H), 0.81-0.92 (m, 6H), 0.93-1.02 (m, 9H), 1.56 (s, 9H), 1.63 (s, 3H), 1.77 (s, 3H), 1.82 (s, 3H), 2.55 (d, J=12.3 Hz, 1H), 2.91 (d, J=12.5 Hz, 1H), 3.15 (d, AB, J=9.7 Hz, 1H), 3.26 (d, AB, J=9.7 Hz, 1H), 3.57 (d, J=15.1 Hz, 1H), 4.41 (d, J=14.9 Hz, 1H), 7.38 (d, J=2.6 Hz, 1H), 11.15 (s, 1H). MS (ES+) m/z 771.4 & 773.4 [M+H, Br].

Synthesis of Int-61AA and Int-61AB: tert-Butyl ((4aR,5R,9R)-5-(6-bromo-3-fluoro-4-(triethylsilyl)pyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-61AA) and tert-butyl ((4aS,5R,9R)-5-(6-bromo-3-fluoro-4-(triethylsilyl)pyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-61AB)

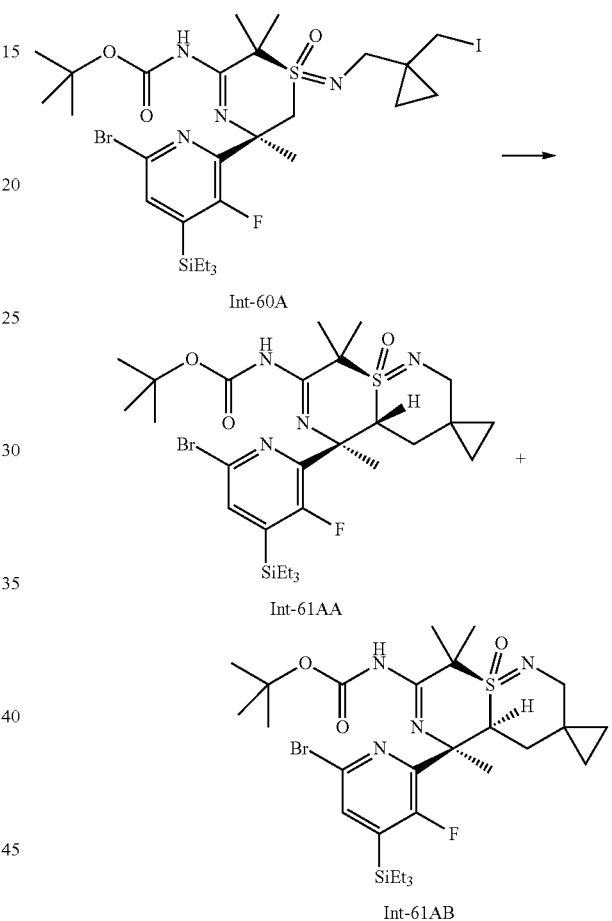

tert-Butyl ((1R,5R)-5-(6-bromo-3-fluoro-4-(triethylsilyl)pyridin-2-yl)-1-(((1-(iodomethyl)cyclopropyl)methyl)imino)-2,2,5-trimethyl-1-oxido-5,6-dihydro-2H-1,4-thiazin-3-yl)carbamate (Int-60A, 1.36 g, 1.76 mmol) was dissolved in THF (20 mL) under anhydrous conditions and the solution was cooled to <−70° C. (acetone/dry ice bath). A solution of LHMDS in THF (1.0 M, 4.58 ml, 4.58 mmol) was added over 15 min and stirred for 45 min at that temperature. Then, the resulting clear, yellow solution was allowed to warm to −20° C. (ice/ethanol bath) and stirred for 45 min at that temperature TLC showed complete conversion. The reaction was stopped by addition of a saturated aqeuous solution of ammonium chloride (80 mL) and, after phase separation, the aqueous phase was extracted with ethyl acetate (2×80 mL). The combined extracts were dried (sodium sulfate) and concentrated in vacuo. The crude was purified by column chromatography (silica gel, 40 g, eluting with ethyl acetate/n-heptane, gradient 10:90 to 50:50) to yield, after drying in vacuo (40° C., 5 mbar), the title compounds Int-61AA (first eluting, 608 mg, 54%, white waxy solid) and Int-61AB (second eluting, 408 mg, 36%, colorless viscous oil) as separated diastereoisomers.

Int-61AA: HPLC (method LCMS_gradient) $t_R$=4.55 min. MS (ES+) m/z 643.3 & 645.3 [M+H, Br].

Int-61AB: HPLC (method LCMS_gradient) $t_R$=4.31 min. MS (ES+) m/z 643.4 & 645.4 [M+H, Br].

Synthesis of Int-63AA and Int-63AB: tert-Butyl ((4aR,5R,9R)-5-(6-amino-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-63AA) and tert-butyl ((4aS,5R,9R)-5-(6-amino-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-63AB)

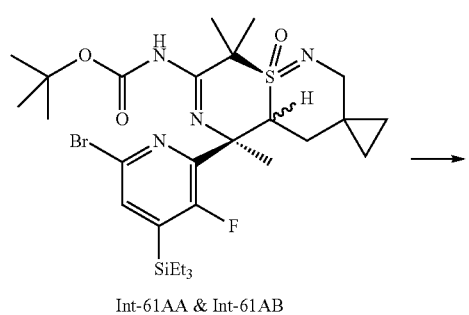

Int-61AA & Int-61AB

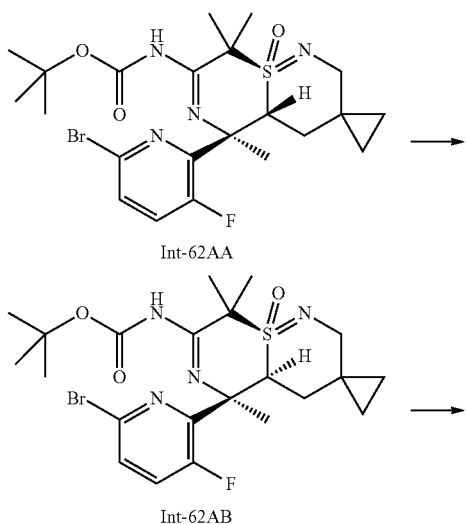

Int-62AA

Int-62AB

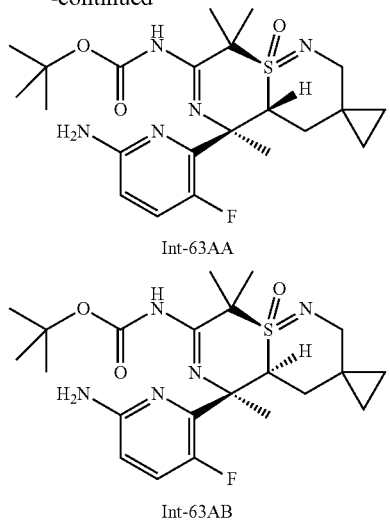

Int-63AA

Int-63AB

Step 1: tert-Butyl ((4aR,5R,9R)-5-(6-bromo-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-62AA) and tert-butyl ((4aS,5R,9R)-5-(6-amino-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-62AA)

Note: It was noticed, that during this reaction epimerisation at $C_4a$ occurs (AB to AA). Therefore, it was decided to carry on a mixture of Int-61AA and Int-61AB in step 1 and separate the diastereomers afterwards.

tert-Butyl ((4aRS,5R,9R)-5-(6-bromo-3-fluoro-4-(triethylsilyl)pyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-61AA & Int-61AB, 1016 mg, 1.58 mmol) was dissolved in THF (24 mL) and DMF (6 mL). Acetic acid (319 mg, 304 µl, 5.3 mmol) and potassium fluoride (304 mg, 5.23 mmol) were added at room temperature and the resulting fine suspension was stirred for 3 h at that temperature. After that, an aqueous solution of sodium hydrogencarbonate (5% m/m, 120 mL) was added and the mixture was extracted with tert-butylmethyl ether (2×150 mL). The combined extracts were washed with brine (2×100 mL), dried (sodium sulfate) and concentrated in vacuo. The crude was purified by column chromatography (silica gel, 40 g, eluting with ethyl acetate/n-heptane, gradient 20:80 to 90:10) to yield, after drying in vacuo (40° C., 5 mbar), the title compounds Int-62AA (first eluting, 532 mg, 64%, white solid) and Int-62AB (second eluting, 246 mg, 29%, white solid) as separated diastereoisomers.

Int-62AA: HPLC (method LCMS_gradient) $t_R$=3.1 min. $^1$H NMR (CDCl$_3$, 300 MHz): δ 0.37-0.55 (m, 2H), 0.62-0.75 (m, 2H), 1.29-1.40 (m, 1H), 1.50 (s, 9H), 1.80 (2s, 6H), 1.89 (s, 3H), 2.52 (d, J=13.1 Hz, 1H), 2.76-2.90 (m, 1H), 4.06 (d, J=12.7 Hz, 1H), 4.54-4.64 (m, 1H), 7.36-7.46 (m, 1H), 7.47-7.55 (m, 1H), 11.33 (s, 1H). MS (ES+) m/z 529.3 & 531.3 [M+H, Br].

Int-62AB: HPLC (method LCMS_gradient) $t_R$=2.8 min. $^1$H NMR (CDCl$_3$, 300 MHz): δ 0.24-0.46 (m, 3H), 0.60-0.76 (m, 2H), 1.59 (s, 9H), 1.80 (s, 3H), 1.94 (s, 3H), 2.03 (d, J=0.8 Hz, 3H), 2.27-2.39 (m, 1H), 2.79 (dd, J=1.9, 13.4 Hz, 1H), 3.81-3.91 (m, 2H), 7.38 (dd, J=8.5, 10.5 Hz, 1H), 7.54 (dd, J=3.2, 8.5 Hz, 1H), 11.86 (s, 1H). MS (ES+) m/z 529.3 & 531.3 [M+H, Br].

Step 2a: tert-Butyl ((4aR,5R,9R)-5-(6-amino-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-63AA)

tert-Butyl ((4aR,5R,9R)-5-(6-bromo-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-62AA, 527 mg, 995 μmol) was dissolved in 1,4-dioxane (14 mL) and water (4.5 mL) and sodium azide (893 mg, 13.7 mmol) were added. Copper (I) iodide (134 mg, 705 mol), sodium ascorbate (67 mg, 338 μmol) and trans-N,N'-dimethyl-1,2-cyclohexanediamine (161 mg, 181 μl, 1.13 mmol) were added subsequently and the dark green mixture was stirred for 75 min at 70° C. Then, the reaction mixture was allowed to cool to room temperature and poured into an aqueous solution of sodium hydrogencarbonate (5% m/m, 120 mL). It was extracted with ethyl acetate (1×120 mL), the combined extracts were washed with brine (100 mL), dried over sodium sulfate and concentrated in vacuo to give a yellow solid as crude product. The crude was purified by column chromatography (silica gel, 24 g, eluting with ethyl acetate/n-heptane, gradient 35:65 to 100:0) to afford, after drying in vacuo (40° C., 5 mbar), the title compound as a white solid (305 mg, 66%). HPLC (method LCMS_gradient) $t_R$=2.5 min. $^1$H NMR (CDCl$_3$, 300 MHz): δ 0.31-0.42 (m, 2H), 0.44-0.50 (m, 1H), 0.60-0.67 (m, 2H), 1.17-1.26 (m, 1H), 1.49 (s, 9H), 1.79 (s, 3H), 1.83 (s, 3H), 1.86 (d, J=1.6 Hz, 3H), 2.48 (dd, J=2.1, 13.0 Hz, 1H), 2.74-2.86 (m, 1H), 4.03 (dd, J=1.2, 12.9 Hz, 1H), 4.35 (br s, 2H), 4.46 (dd, J=3.4, 12.3 Hz, 1H), 6.47 (dd, J=2.5, 8.0 Hz, 1H), 7.26 (dd, J=8.7, 11.1 Hz, 1H), 11.16 (s, 1H). MS (ES+) m/z 466.3 [M+H].

Step 2b: tert-Butyl ((4aS,5R,9R)-5-(6-amino-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-63AB)

tert-Butyl ((4aS,5R,9R)-5-(6-bromo-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-62AB, 240 mg, 453 μmol) was dissolved in 1,4-dioxane (15 mL) and water (2.5 mL) and sodium azide (407 mg, 6.26 mmol) were added. Copper (I) iodide (61 mg, 321 μmol), sodium ascorbate (30 mg, 154 μmol) and trans-N,N'-dimethyl-1,2-cyclohexanediamine (74 mg, 83 μl, 0.52 mmol) were added subsequently and the dark green mixture was stirred for 75 min at 70° C. Then, the reaction mixture was allowed to cool to room temperature and poured into an aqueous solution of sodium hydrogencarbonate (5% m/m, 120 mL), stirred for 5 min. A suspension was formed, which was filtered, and washed with water (4×10 mL). The precipitate was dissolved in tetrahydrofuran (50 mL), dried (sodium sulfate) and concentrated in vacuo give a yellow green solid as crude product. The crude was purified by column chromatography (silica gel, 24 g, eluting with dichloromethane/2N ammonia in methanol, gradient 99:1 to 95:5) to afford, after drying in vacuo (40° C., 5 mbar), the title compound as a white solid (123 mg, 58%). HPLC (method LCMS_gradient) $t_R$=2.13 min. $^1$H NMR (CDCl$_3$, 300 MHz): δ 0.24-0.33 (m, 1H), 0.35-0.44 (m, 2H), 0.64-0.84 (m, 2H), 1.57 (s, 9H), 1.80 (s, 3H), 1.93 (s, 3H), 1.98 (m, 3H), 2.18-2.30 (m, 1H), 2.78 (dd, J=1.8, 13.5 Hz, 1H), 3.79-3.92 (m, 2H), 7.57 (s, 2H), 6.47 (dd, J=2.5, 8.8 Hz, 1H), 7.24 (dd, J=8.7, 10.5 Hz, 1H), 12.07 (s, 1H). MS (ES+) m/z 466.3 [M+H].

Examples

N-(6-((4aR,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide (1AA)

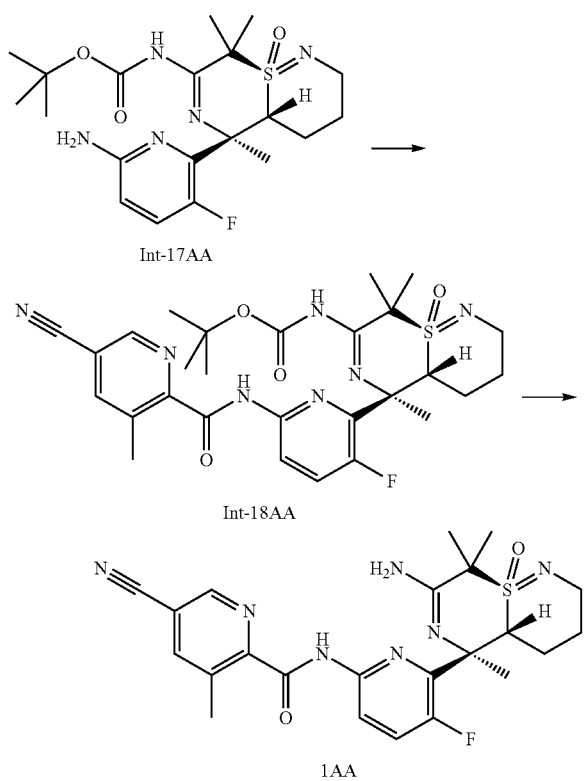

Step 1: tert-Butyl ((4aR,5R,9R)-5-(6-(5-cyano-3-methylpicolinamido)-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-18AA)

5-Cyano-3-methylpicolinic acid (200 mg, 1.23 mmol) was suspended in dichloromethane (4 mL), the suspension was cooled to 0-5° C. (ice bath) and oxalyl chloride (203 mg, 140 μL, 1.6 mmol) as well as a drop of a mixture of dimethylformamide and dichloromethane (2:1, v/v) were added. The mixture was stirred for 1.5 h at room temperature. Then, it was concentrated in vacuo, the residue was treated with n-heptane (3 mL) and again concentrated and dried in vacuo (40° C., mbar) to afford 5-cyano-3-methylpicolinoyl chloride as red oil (220 mg, 99%). After that, tert-butyl ((4aR,5R,9R)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-17AA, 150 mg, 341 mol) was dissolved in dichloromethane (4 mL), the solution cooled to 0-5° C. (ice bath) and N,N-diisopropylethylamine (75.5 mg, 100 μl, 584 μmol) was added, followed by a solution of 5-cyano-3-methylpicolinoyl chloride (vide supra, 80 mg, 443 mol) in dichloromethane (2.5 mL). The reaction mixture was stirred at 0-5° C. for 1.5 h. Then, the mixture was poured onto a saturated aqueous solution of sodium hydrogencarbonate (20 mL) and extracted with dichloromethane (1×50 mL, 2×20 mL). The combined extracts were dried (sodium sulfate) and concentrated in vacuo. The crude was triturated with ethyl acetate (100 mL), and filtered over a plug silica gel (10 g), that was washed with ethyl acetate (50 mL). The combined filtrate was concentrated in vacuo. The crude was purified by column chromatography (silica gel, 50 g, eluting with ethyl acetate/n-heptane, gradient 60:40 to 80:20) to yield, after drying in vacuo (50° C., 5 mbar), the title compound as a yellow solid (190 mg, 95%). HPLC (method LCMS_gradient) $t_R$=3.1 min. $^1$H NMR (CDCl$_3$, 400 MHz): δ 1.47 (s, 9H), 1.79 (s, 3H), 1.82-2.02 (m, 3H), 1.84 (s, 3H), 1.95 (s, 3H), 2.34-2.46 (m, 1H), 2.86 (s, 3H), 3.36-3.42 (m, 1H), 3.57-3.66 (m, 1H), 4.04-4.10 (m, 1H), 7.57 (dd, J=8.9, 10.7 Hz, 1H), 7.96-7.99 (m, 1H), 8.41 (dd, J=3.1, 9.0 Hz, 1H), 8.79 (d, J=1.3 Hz, 1H), 10.41 (br s, 1H, exch), 11.23 (br s, 1H, exch). MS (ES+) m/z 484.3 [M+H—CO$_2$tBu].

Step 2: N-(6-((4aR,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide (1AA)

tert-Butyl ((4aR,5R,9R)-5-(6-(5-cyano-3-methylpicolinamido)-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-18AA, 180 mg, 308 mol) was dissolved in dichloromethane (10 mL) and trifluoroacetic acid (2.66 g, 1.8 mL, 23.4 mmol) was added. The solution was stirred for 0.5 h at room temperature. After that, it was concentrated in vacuo (25° C., 5 mbar). The residue, a brown viscous oil, was dissolved in dichloromethane (40 mL), and saturated aqueous sodium hydrogencarbonate solution (20 mL) was added. After stirring for 5 min, phases were separated and the aqueous phase was extracted with dichloromethane (2×15 mL). The combined extracts were dried (sodium sulfate) and concentrated in vacuo. The residue was dissolved in dichloromethane (1 mL), MTBE (5 mL) was added and again concentrated in vacuo to give, after drying in vacuo (50° C., 5 mbar), an off white solid as crude product, which was purified by chiral preparative HPLC (Chiralpak AD-H, 250*4.6 mm*5 μm, isocratic, (n-heptane+0.2% triethylamine)/(ethanol+0.1% triethylamine) 60/40, flow 1.0 mL/min) to yield the title compound as a white powder (79 mg, 53%). For transfer purpose, the material was dissolved in dichloromethane (2 mL) and MTBE (8 mL) and concentrated and dried in vacuo at 50° C./5 mbar. HPLC (method LCMS_gradient) $t_R$=1.4 min. $^1$H NMR (CDCl$_3$, 400 MHz): δ 1.65-1.90 (m, 3H), 1.72 (s, 3H), 1.82 (s, 3H), 1.85 (s, 3H), 2.25-2.42 (m, 1H), 2.87 (s, 3H), 3.36 (br d, J=12.4 Hz, 1H), 3.52-3.68 (m, 1H), 3.80 (br d, J=12.1 Hz, 1H), 4.36 (br s, 2H, exch), 7.47 (dd, J=9.8, 9.8 Hz, 1H), 7.97 (s, 1H), 8.31 (dd, J=2.4, 8.6 Hz, 1H), 8.79 (s, 1H), 10.38 (br s, 1H, exch). MS (ES+) m/z 484.3 [M+H].

N-(6-((4aS,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide (1AB)

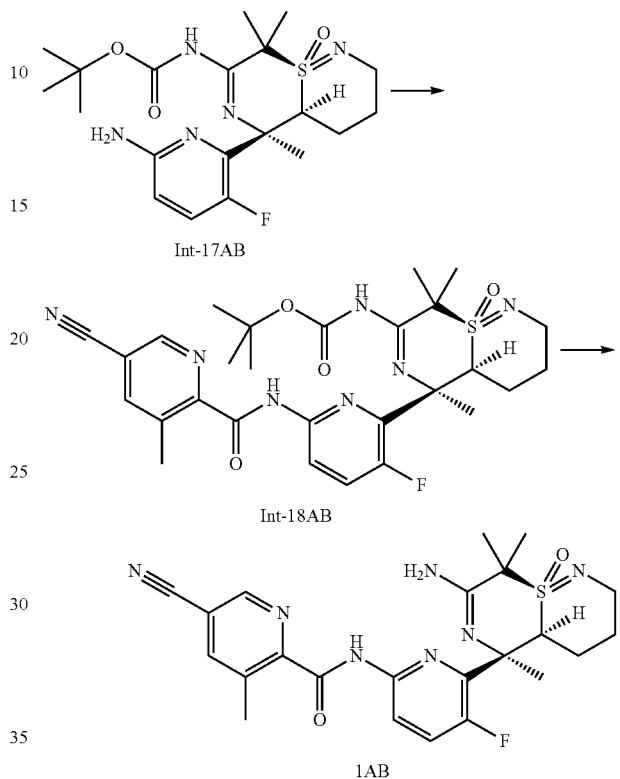

Step 1: tert-Butyl ((4aS,5R,9R)-5-(6-(5-cyano-3-methylpicolinamido)-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-18AB)

5-Cyano-3-methylpicolinic acid (85 mg, 524 mol) was suspended in dichloromethane (3 mL), the suspension cooled to 0-5° C. (ice bath) and 1-chloro-N,N,2-trimethylpropenylamine (140 mg, 140 μl, 1.05 mmol) was added. After 30 min stirring at 0° C., a solution of tert-butyl ((4aS,5R,9R)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-17AB, 150 mg, 341 μmol) and N,N-diisopropylethylamine (148 mg, 200 μL, 1.15 mmol) in dichloromethane (3 mL) was added over 5 min at −5° C. The reaction mixture was stirred at 0-5° C. for 15 min and allowed to warm to room temperature. Then, the mixture was poured onto a saturated aqueous solution of sodium hydrogencarbonate (20 mL) and extracted with dichloromethane (1×50 mL, 2×20 mL). The combined extracts were dried (sodium sulfate) and concentrated in vacuo. The crude was triturated with ethyl acetate (100 mL), and filtered over a plug silica gel (10 g), that was washed with ethyl acetate (50 mL). The combined filtrate was concentrated in vacuo. The crude was purified by column chromatography (silica gel, 50 g, eluting with dichloromethane/methanol, gradient 99:1 to 95:5) to yield, after drying in vacuo (50° C., 5 mbar), a yellow sticky solid. This material was suspended in a mixture of MTBE (3 mL) and n-heptane (2 mL), the precipitate was filtered, washed with a mixture of MTBE/n-heptane (1:3 v/v, 4 mL) and dried in vacuo (50° C., 5 mbar) to afford the title compound as an off-white solid (50 mg, 25%). HPLC (method LCMS_gradient) $t_R$=3.0 min. $^1$H NMR (CDCl$_3$, 400 MHz): δ 1.62-1.71 (m, 2H), 1.65 (s, 9H), 1.74-1.84 (m, 2H), 1.82 (s, 3H), 1.91 (s, 3H), 2.04 (s, 3H), 2.88 (s, 3H), 3.36-3.46 (m, 1H), 3.62-3.71 (m, 2H), 7.59 (dd, J=9.0, 10.0 Hz, 1H), 7.98-8.00 (m, 1H), 8.47 (dd, J=3.2, 8.9 Hz, 1H), 8.71 (d, J=1.3 Hz, 1H), 10.76 (br s, 1H, exch), 12.40 (br s, 1H, exch). MS (ES+) m/z 584.4 [M+H].

Step 2: N-(6-((4aS,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide (1AB)

tert-Butyl ((4aS,5R,9R)-5-(6-(5-cyano-3-methylpicolinamido)-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-18AB, 50 mg, 85.7 µmol) was dissolved in dichloromethane (3 mL) and trifluoroacetic acid (740 mg, 500 µL, 6.49 mmol) was added. The solution was stirred for 2 h at room temperature. After that, it was concentrated in vacuo (25° C., 5 mbar). The residue, a brown viscous oil, was dissolved in dichloromethane (30 mL), saturated aqueous sodium hydrogencarbonate solution (10 mL) was added. After stirring for 5 min, phases were separated and the aqueous phase was extracted with dichloromethane (2×15 mL). The combined extracts were dried (sodium sulfate) and concentrated in vacuo. The residue was dissolved in dichloromethane (1 mL), MTBE (3 mL) was added and again concentrated in vacuo to give, after drying in vacuo (50° C., 5 mbar), an off white solid as crude product, which was purified by chiral preparative HPLC (Chiralpak AD-H, 250*4.6 mm*5 µm, isocratic, n-heptane/(ethanol+0.1% triethylamine) 50/50, flow 1.0 mL/min) to yield the title compound as a white powder (16 mg, 39%). For transfer purpose, the material was dissolved in dichloromethane (1 mL) and MTBE (3 mL) and concentrated and dried in vacuo at 50° C./5 mbar. HPLC (method LCMS_gradient) $t_R$=1.3 min. $^1$H NMR (CDCl$_3$, 400 MHz): δ 1.65-2.06 (m, 4H), 1.70 (s, 3H), 1.86 (s, 3H), 1.92 (s, 3H), 2.87 (s, 3H), 3.45-3.54 (m, 1H), 3.56-3.64 (m, 1H), 3.66-3.74 (m, 1H), 7.55 (dd, J=9.1, 10.0 Hz, 1H), 7.98 (s, 1H), 8.42 (dd, J=3.0, 8.9 Hz, 1H), 8.80 (s, 1H), 10.59 (br s, 1H, exch). MS (ES+) m/z 484.3 [M+H].

N-(6-((4aR,5R,9S)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide (1BA)

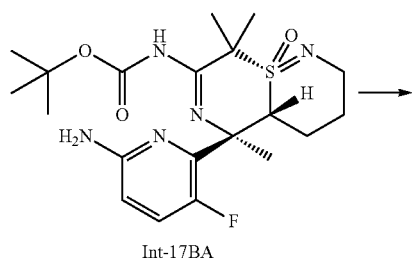

Int-17BA

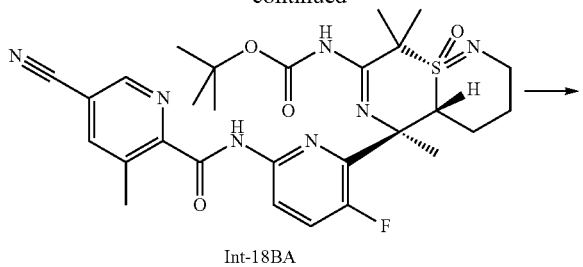

Int-18BA

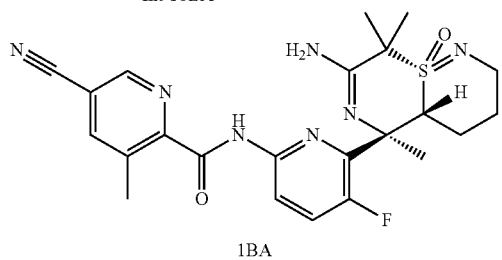

1BA

Step 1: tert-Butyl ((4aR,5R,9S)-5-(6-(5-cyano-3-methylpicolinamido)-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-18BA)

5-Cyano-3-methylpicolinic acid (100 mg, 617 µmol) was suspended in dichloromethane (2 mL), the suspension was cooled to 0-5° C. (ice bath) and oxalyl chloride (102 mg, 70 µL, 0.8 mmol) as well as a drop of a mixture of dimethylformamide and dichloromethane (1:3, v/v) were added. The mixture was stirred for 1 h at room temperature. Then, it was concentrated in vacuo, the residue was treated with n-heptane (2 mL) and again concentrated and dried in vacuo (40° C., mbar) to afford 5-cyano-3-methylpicolinoyl chloride as red oil (110 mg). After that, tert-butyl ((4aR,5R,9S)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-17AB, 150 mg, 341 µmol) was dissolved in dichloromethane (4 mL), the solution cooled to 0-5° C. (ice bath) and N,N-diisopropylethylamine (75.5 mg, 100 µl, 584 µmol) was added, followed by a solution of 5-cyano-3-methylpicolinoyl chloride (vide supra, 80 mg, 443 µmol) in dichloromethane (2.5 mL). The reaction mixture was stirred at 0-5° C. for 1.5 h. Then, the mixture was poured onto a saturated aqueous solution of sodium hydrogencarbonate (20 mL) and extracted with dichloromethane (1×50 mL, 2×20 mL). The combined extracts were dried (sodium sulfate) and concentrated in vacuo. The crude was purified by column chromatography (silica gel, 50 g, eluting with ethyl acetate/n-heptane, gradient 60:40 to 80:20) to yield, after drying in vacuo (50° C., 5 mbar), the title compound as a yellow solid (135 mg, 68% yield). HPLC (method LCMS_gradient) $t_R$=3.0 min. $^1$H NMR (CDCl$_3$, 400 MHz): δ 1.34 (s, 3H), 1.56 (s, 9H), 1.79 (s, 3H), 1.82 (s, 3H), 1.86-1.97 (m, 2H), 2.16-2.29 (m, 1H), 2.53-2.62 (m, 1H), 2.85 (s, 3H), 3.52 (ddd, J=5.6, 7.9, 13.6 Hz, 1H), 3.67 (ddd, J=4.6, 4.6, 13.4 Hz, 1H), 3.98 (dd, J=4.7, 10.6 Hz, 1H), 7.48 (dd, J=9.0, 10.6 Hz, 1H), 7.96 (dd, J=0.8, 1.9 Hz, 1H), 8.36 (dd, J=3.0, 8.9 Hz, 1H), 8.74-8.77 (m, 1H), 10.31 (br s, 1H, exch), 10.78 (br s, 1H, exch). MS (ES+) m/z 584.4 [M+H].

Step 2: N-(6-((4aR,5R,9S)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide (1BA)

tert-Butyl ((4aR,5R,9S)-5-(6-(5-cyano-3-methylpicolinamido)-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-18BA, 130 mg, 223 µmol) was dissolved in dichloromethane (7 mL) and trifluoroacetic acid (1.92 g, 1.3 mL, 16.9 mmol) was added. The solution was stirred for 0.5 h at room temperature. After that, it was concentrated in vacuo (25° C., 5 mbar). The residue, a brown viscous oil, was dissolved in dichloromethane (40 mL), and saturated aqueous sodium hydrogencarbonate solution (20 mL) was added. After stirring for 5 min, phases were separated and the aqueous phase was extracted with dichloromethane (2×15 mL). The combined extracts were dried (sodium sulfate) and concentrated in vacuo. The residue was dissolved in dichloromethane (1 mL), MTBE (5 mL) was added and again concentrated in vacuo to give, after drying in vacuo (50° C., 5 mbar), an off white solid as crude product. The crude was purified by chiral preparative HPLC (ReprosilChiral-NR, 250*4.6 mm*5 µm, isocratic, (n-heptane/(ethanol+0.1% ammonium acetate) 60/40, flow 1.0 mL/min) to yield the title compound as a off white powder (89 mg, 83%). For transfer purpose, the material was dissolved in dichloromethane (2 mL) and MTBE (8 mL) and concentrated and dried in vacuo at 50° C./5 mbar. HPLC (method LCMS_gradient) $t_R$=1.2 min. $^1$H NMR (CDCl$_3$, 400 MHz): δ 1.55 (s, 3H), 1.88-1.99 (m, 2H), 1.99 (s, 3H), 2.01 (s, 3H), 2.07 (s, 3H), 2.08-2.20 (m, 1H), 2.61-2.70 (m, 1H), 2.73 (s, 3H), 3.42-3.54 (m, 2H), 3.66-3.74 (m, 1H), 7.51 (dd, J=9.0, 10.1 Hz, 1H), 7.70-7.74 (m, 1H), 8.08 (dd, J=3.0, 8.6 Hz, 1H), 8.77 (d, J=1.3 Hz, 1H), 10.30 (br s, 1H, exch). MS (ES+) m/z 484.3 [M+H].

N-(6-((4aR,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide (2AA)

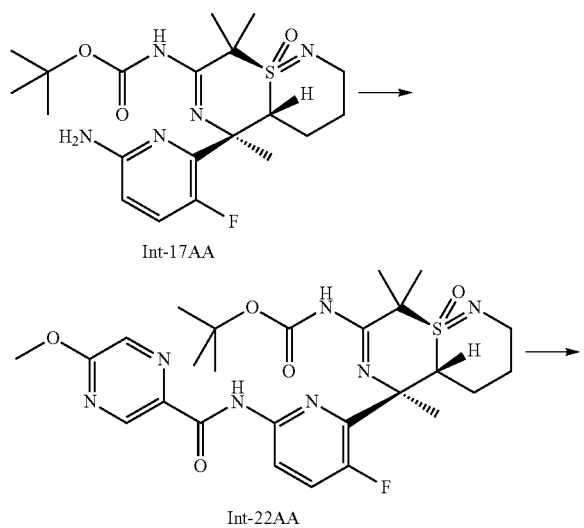

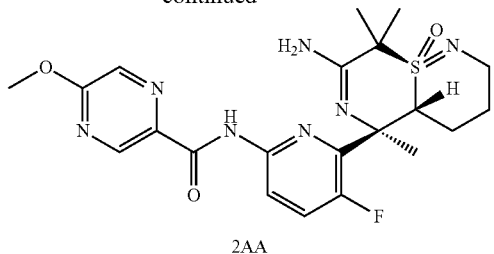

Step 1: tert-Butyl ((4aR,5R,9R)-5-(3-fluoro-6-(5-methoxypyrazine-2-carboxamido)pyridin-2-yl)-5,8,8-trimethyl-9-oxido-2,3,4,4a,5,8-hexahydro-[1,4]thiazino[2,1-f][1,2]thiazin-7-yl)carbamate (Int-22AA)

5-Methoxypyrazine-2-carboxylic acid (100 mg, 649 µmol) was suspended in dichloromethane (2 mL), the suspension was cooled to 0-5° C. (ice bath) and oxalyl chloride (218 mg, 150 µl, 1.71 mmol) as well as a drop of a mixture of dimethylformamide and dichloromethane (1:3, v/v) were added. The mixture was stirred for 1.5 h at room temperature. Then, it was concentrated in vacuo at 40° C., the residue was treated with n-heptane (2 mL) and again concentrated and dried in vacuo (40° C., 5 mbar) to afford 5-methoxypyrazine-2-carboxylic acid chloride as red oil (110 mg). After that, tert-butyl ((4aR,5R,9R)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-17AA, 100 mg, 228 µmol) was dissolved in dichloromethane (4 mL), the solution cooled to 0-5° C. (ice bath) and N,N-diisopropylethylamine (75.5 mg, 100 µl, 584 µmol) was added, followed by a solution of 5-methoxypyrazine-2-carboxylic acid chloride (vide supra, 50 mg, 290 mol) in dichloromethane (1 mL). The reaction mixture was stirred at 0-5° C. for 1.5 h. Then, ethanol (100 µl) was added, the mixture was stirred for 15 min at room temperature, poured onto a saturated aqueous solution of sodium hydrogencarbonate (15 mL) and extracted with dichloromethane (1×30 mL, 2×20 mL). The combined extracts were dried (sodium sulfate) and concentrated in vacuo. The crude was purified by column chromatography (silica gel, 50 g, eluting with ethyl acetate/n-heptane, gradient 60:40 to 80:20) to yield, after drying in vacuo (50° C., 5 mbar), the title compound as a yellow solid (120 mg, 92% yield). HPLC (method LCMS_gradient) $t_R$=3.0 min. $^1$H NMR (CDCl$_3$, 400 MHz): δ 1.48 (s, 9H), 1.79 (s, 3H), 1.82-2.04 (m, 3H), 1.85 (s, 3H), 1.95 (s, 3H), 2.40 (dddd, J=3.8, 12.6, 12.6, 12.6 Hz, 1H), 3.36-3.44 (m, 1H), 3.58-3.66 (m, 1H), 4.05-4.11 (m, 1H), 4.09 (s, 3H), 7.57 (dd, J=9.0, 10.9 Hz, 1H), 8.23 (d, J=1.3 Hz, 1H), 8.44 (dd, J=3.0, 8.9 Hz, 1H), 9.04 (d, J=1.3 Hz, 1H), 9.94 (br s, 1H), 11.24 (br s, 1H, exch). MS (ES+) m/z 576.4 [M+H].

Step 2: N-(6-((4aR,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide (2AA)

tert-Butyl ((4aR,5R,9R)-5-(3-fluoro-6-(5-methoxypyrazine-2-carboxamido)pyridin-2-yl)-5,8,8-trimethyl-9-oxido-2,3,4,4a,5,8-hexahydro-[1,4]thiazino[2,1-f][1,2]thiazin-7-yl)carbamate (Int-22AA, 120 mg, 208 µmol) was dissolved in dichloromethane (6 mL) and trifluoroacetic acid (1.78 g, 1.2 mL, 15.6 mmol) was added. The solution was stirred for 0.5 h at room temperature. After that, it was concentrated in vacuo (25° C., 5 mbar). The residue, a brown viscous oil, was dissolved in dichloromethane (40 mL), and saturated aqueous sodium hydrogencarbonate solution (15 mL) was added. After stirring for 5 min, phases were separated and the aqueous phase was extracted with dichloromethane (2×15 mL). The combined extracts were dried (sodium sulfate) and concentrated in vacuo. The residue was dissolved in dichloromethane (1 mL), MTBE (5 mL) was added and again concentrated in vacuo to give, after drying in vacuo (50° C., 5 mbar), an off white solid as crude product. The crude was purified by chiral preparative HPLC (Chiralpak AD, 250*4.6 mm*5 μm, isocratic, n-heptane/(ethanol+0.1% ammonium acetate) 80/20, flow 1.0 mL/min) to yield the title compound as a white powder (48 mg, 48%). For transfer purpose, the material was dissolved in dichloromethane (1 mL) and MTBE (4 mL) and concentrated and dried in vacuo at 50° C./5 mbar. HPLC (method LCMS_gradient) $t_R$=1.4 min. $^1$H NMR (CDCl$_3$, 400 MHz): δ 1.72-1.94 (m, 3H), 1.84 (s, 3H), 1.92 (2s, 6H), 2.27-2.41 (m, 1H), 3.33-3.41 (m, 1H), 3.53-3.63 (m, 1H), 3.80 (dd, J=3.2, 12.6 Hz, 1H), 4.09 (s, 3H), 7.53 (dd, J=8.9, 10.9 Hz, 1H), 8.22 (d, J=1.1 Hz, 1H), 8.41 (dd, J=3.0, 8.9 Hz, 1H), 9.03 (d, J=1.1 Hz, 1H), 9.96 (br s, 1H). MS (ES+) m/z 476.3 [M+H].

N-(6-((4aS,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide (2AB)

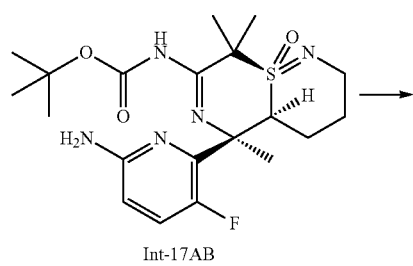

Int-17AB

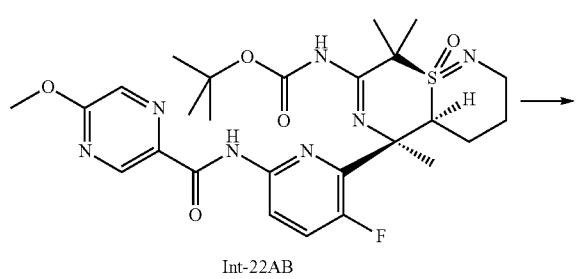

Int-22AB

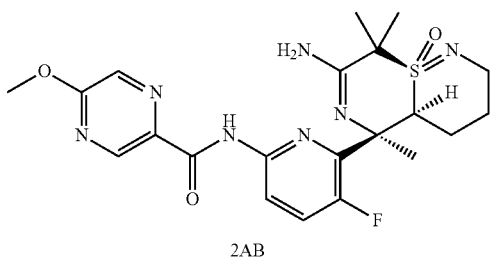

2AB

Step 1: tert-Butyl ((4aS,5R,9R)-5-(3-fluoro-6-(5-methoxypyrazine-2-carboxamido)pyridin-2-yl)-5,8,8-trimethyl-9-oxido-2,3,4,4a,5,8-hexahydro-[1,4]thiazino[2,1-f][1,2]thiazin-7-yl)carbamate (Int-22AB)

5-Methoxypyrazine-2-carboxylic acid (200 mg, 1.3 mmol) was suspended in dichloromethane (5 mL), the suspension was cooled to 0-5° C. (ice bath) and oxalyl chloride (435 mg, 300 μl, 3.43 mmol) as well as a drop of a mixture of dimethylformamide and toluene (1:3, v/v) were added. The mixture was stirred for 2 h at room temperature. Then, it was concentrated in vacuo at 40° C., the residue was treated with n-heptane (2 mL) and again concentrated and dried in vacuo (40° C., 5 mbar) to afford 5-methoxypyrazine-2-carboxylic acid chloride as red oil (229 mg). After that, tert-butyl ((4aS,5R,9R)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-17AB, 70 mg, 159 mol) was dissolved in dichloromethane (4 mL), the solution cooled to 0-5° C. (ice bath) and N,N-diisopropylethylamine (53 mg, 70 μl, 409 μmol) was added, followed by a solution of 5-methoxypyrazine-2-carboxylic acid chloride (vide supra, 100 mg, 579 μmol) in dichloromethane (1.3 mL). The reaction mixture was stirred at room temperature for 4 h. Then, ethanol (200 μl) was added, the mixture was stirred for 30 min at room temperature, poured onto a saturated aqueous solution of sodium hydrogencarbonate (15 mL) and extracted with dichloromethane (1×30 mL, 2×20 mL). The combined extracts were dried (sodium sulfate) and concentrated in vacuo. The crude was purified by column chromatography (silica gel, 50 g, eluting with ethyl acetate/n-heptane, gradient 60:40 to 80:20) to yield, after drying in vacuo (50° C., 5 mbar), the title compound as a white solid (90 mg, 98% yield). HPLC (method LCMS_gradient) $t_R$=2.9 min. $^1$H NMR (CDCl$_3$, 400 MHz): δ 1.62-1.88 (m, 4H), 1.66 (s, 9H), 1.82 (s, 3H), 1.91 (s, 3H), 2.04 (s, 3H), 3.36-3.45 (m, 1H), 3.62-3.71 (m, 2H), 4.09 (s, 3H), 7.59 (dd, J=9.0, 10.1 Hz, 1 H), 8.14 (d, J=1.3 Hz, 1H), 8.48 (dd, J=3.0, 8.9 Hz, 1H), 9.06 (d, J=1.3 Hz, 1H), 10.36 (br s, 1H), 12.49 (br s, 1H). MS (ES+) m/z 576.3 [M+H].

Step 2: N-(6-((4aS,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide (2AB)

tert-Butyl ((4aS,5R,9R)-5-(3-fluoro-6-(5-methoxypyrazine-2-carboxamido)pyridin-2-yl)-5,8,8-trimethyl-9-oxido-2,3,4,4a,5,8-hexahydro-[1,4]thiazino[2,1-f][1,2]thiazin-7-yl)carbamate (Int-22AB, 85 mg, 148 μmol) was dissolved in dichloromethane (4 mL) and trifluoroacetic acid (740 mg, 500 μL, 6.5 mmol) was added. The solution was stirred for 1 h at room temperature. After that, it was concentrated in vacuo (25° C., 5 mbar). The residue, a brown viscous oil, was dissolved in dichloromethane (40 mL), and saturated aqueous sodium hydrogencarbonate solution (15 mL) was added. After stirring for 5 min, phases were separated and the aqueous phase was extracted with dichloromethane (2×15 mL). The combined extracts were dried (sodium sulfate) and concentrated in vacuo. The residue was dissolved in dichloromethane (1 mL), MTBE (5 mL) was added and again concentrated in vacuo to give, after drying in vacuo (50° C., 5 mbar), an off white solid as crude product. The crude was purified by chiral preparative HPLC (Chiralpak IE, 250*4.6 mm*5 μm, isocratic, (isopropanol+0.1% triethylamine)/dichloromethane 90/10, flow 0.7 mL/min) to yield the title compound as a white powder (29 mg, 41%). For transfer purpose, the material was dissolved in dichloromethane (1 mL) and MTBE (4 mL) and concentrated and dried in vacuo at 50° C./5 mbar. HPLC (method LCMS_gradient) $t_R$ 1.3 min $^1$H NMR (CDCl$_3$, 400 MHz): δ 1.64-2.01 (m, 4H), 1.71 (s, 3H), 1.86 (s, 3H), 1.93 (s, 3H), 3.41-3.53 (m, 1H), 3.54-3.63 (m, 1H), 3.64-3.74 (m, 1H), 4.09 (s, 3H), 7.55 (dd, J=9.4, 9.9 Hz, 1H), 8.23 (s, 1H), 8.44 (dd, J=3.0, 8.9 Hz, 1H), 9.03 (s, 1H), 10.19 (br s, 1H). MS (ES+) m/z 476.2 [M+H].

N-(6-((4aR,5R,9S)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide (2BA)

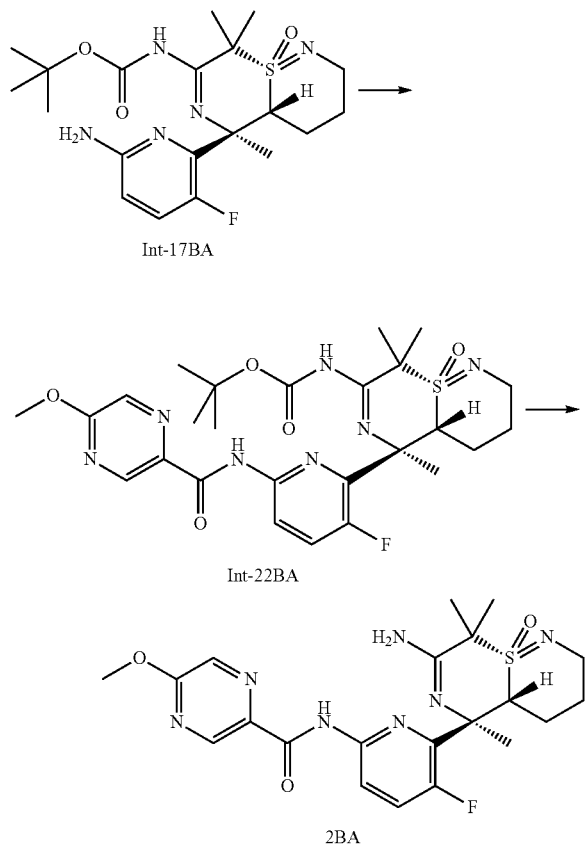

Step 1: tert-Butyl ((4aR,5R,9S)-5-(3-fluoro-6-(5-methoxypyrazine-2-carboxamido)pyridin-2-yl)-5,8,8-trimethyl-9-oxido-2,3,4,4a,5,8-hexahydro-[1,4]thiazino[2,1-f][1,2]thiazin-7-yl)carbamate (Int-22BA)

tert-Butyl ((4aR,5R,9S)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-17BA, 70 mg, 159 μmol) was dissolved in dichloromethane (4 mL), the solution cooled to 0-5° C. (ice bath) and N,N-diisopropylethylamine (53 mg, 70 μl, 409 mol) was added, followed by a solution of 5-methoxypyrazine-2-carboxylic acid chloride (for preparation see example 2AB, 40 mg, 232 μmol) in dichloromethane (1.3 mL). The reaction mixture was stirred at room temperature for 3 h. Then, ethanol (200 μl) was added, the mixture was stirred for 30 min at room temperature, poured onto a saturated aqueous solution of sodium hydrogencarbonate (15 mL) and extracted with dichloromethane (1×30 mL, 2×20 mL). The combined extracts were dried (sodium sulfate) and concentrated in vacuo. The crude was purified by column chromatography (silica gel, 50 g, eluting with ethyl acetate/n-heptane, gradient 80:20 to 100:0) to yield, after drying in vacuo (50° C., 5 mbar), the title compound as a yellow foam (80 mg, 87% yield). HPLC (method LCMS_gradient) $t_R$=2.9 min. $^1$H NMR (CDCl$_3$, 400 MHz): δ 1.34 (s, 3H), 1.57 (s, 9H), 1.79 (s, 3H), 1.82 (s, 3H), 1.86-1.95 (m, 2H), 2.18-2.30 (m, 1H), 2.53-2.62 (m, 1H), 3.51 (ddd, J=5.4, 8.1, 13.4 Hz, 1H), 3.66 (ddd, J=4.6, 4.6, 13.2 Hz, 1H), 3.97 (dd, J=4.7, 10.3 Hz, 1H), 4.08 (s, 3H), 7.48 (dd, J=8.9, 10.5 Hz, 1H), 8.18 (d, J=1.3 Hz, 1H), 8.39 (dd, J=3.1, 9.0 Hz, 1H), 9.02 (d, J=1.3 Hz, 1H), 9.86 (br s, 1H), 10.80 (br s, 1H). MS (ES+) m/z 576.3 [M+H].

Step 2: N-(6-((4aR,5R,9S)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide (2BA)

tert-Butyl ((4aR,5R,9S)-5-(3-fluoro-6-(5-methoxypyrazine-2-carboxamido)pyridin-2-yl)-5,8,8-trimethyl-9-oxido-2,3,4,4a,5,8-hexahydro-[1,4]thiazino[2,1-f][1,2]thiazin-7-yl)carbamate (Int-22BA, 80 mg, 139 μmol) was dissolved in dichloromethane (4 mL) and trifluoroacetic acid (740 mg, 500 μL, 6.5 mmol) was added. The solution was stirred for 1 h at room temperature. After that, it was concentrated in vacuo (25° C., 5 mbar). The residue, a brown viscous oil, was dissolved in dichloromethane (40 mL), and saturated aqueous sodium hydrogencarbonate solution (15 mL) was added. After stirring for 5 min, phases were separated and the aqueous phase was extracted with dichloromethane (2×15 mL). The combined extracts were dried (sodium sulfate) and concentrated in vacuo. The residue was dissolved in dichloromethane (1 mL), MTBE (5 mL) was added and again concentrated in vacuo to give, after drying in vacuo (50° C., 5 mbar), an off white solid as crude product. The crude was purified by chiral preparative HPLC (Reprosil Chiral NR, 250*4.6 mm*8 μm, isocratic, n-heptane/(ethanol+0.1% triethylamine) 50/50, flow 1.0 mL/min) to yield the title compound as a white powder (30 mg, 45%). For transfer purpose, the material was dissolved in dichloromethane (1 mL) and MTBE (5 mL) and concentrated and dried in vacuo at 50° C./5 mbar. HPLC (method LCMS_gradient) $t_R$=1.2 min. $^1$H NMR (CDCl$_3$, 400 MHz): δ 1.39 (s, 3H), 1.74 (s, 3H), 1.79 (s, 3H), 1.81-1.98 (m, 2H), 2.06-2.18 (m, 1H), 2.49-2.59 (m, 1H), 3.48 (ddd, J=4.6, 9.1, 13.5 Hz, 1H), 3.67 (ddd, J=4.7, 4.7, 13.4 Hz, 1H), 3.90 (dd, J=4.7, 10.3 Hz, 1H), 4.07 (s, 3H), 7.45 (dd, J=8.9, 10.8 Hz, 1H), 8.19 (d, J=1.3 Hz, 1H), 8.32 (dd, J=3.0, 8.9 Hz, 1H), 9.01 (d, J=1.1 Hz, 1H), 9.94 (br s, 1H). MS (ES+) m/z 476.3 [M+H].

N-(6-((4aR,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide (3AA)

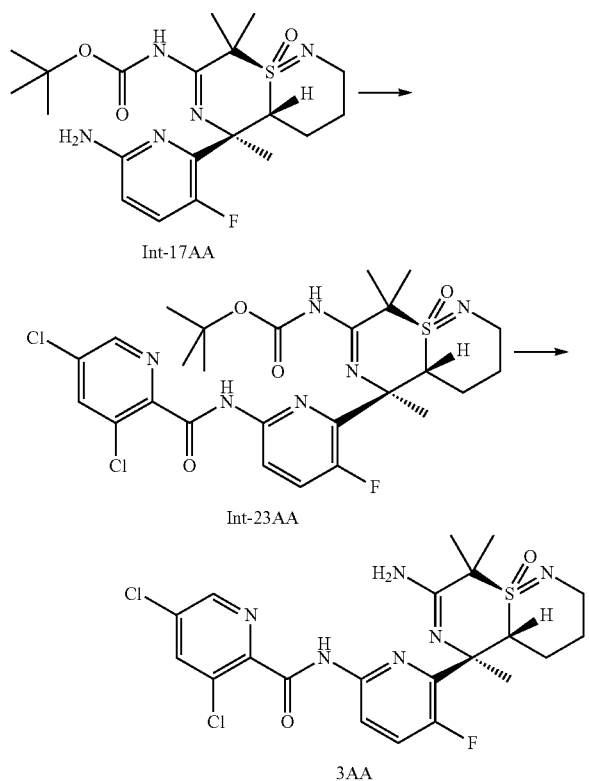

Step 1: tert-Butyl ((4aR,5R,9R)-5-(6-(3,5-dichloropicolinamido)-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-23AA)

3,5-Dichloropicolinic acid (200 mg, 1.04 mmol) was suspended in dichloromethane (4 mL), the suspension was cooled to 0-5° C. (ice bath) and oxalyl chloride (363 mg, 250 µl, 2.86 mmol) as well as a drop of a mixture of dimethylformamide and toluene (1:3, v/v) were added. The mixture was stirred for 1.5 h at room temperature. Then, it was concentrated in vacuo at 40° C., the residue was treated with n-heptane (4 mL) and again concentrated and dried in vacuo (40° C., 5 mbar) to afford 3,5-dichloropicolinoyl chloride as yellow solid (110 mg). After that, tert-butyl ((4aR,5R,9R)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-17AA, 100 mg, 228 µmol) was dissolved in dichloromethane (4 mL), the solution cooled to 0-5° C. (ice bath) and N,N-diisopropylethylamine (75.5 mg, 100 µl, 584 mmol) was added, followed by a solution of 3,5-dichloropicolinoyl chloride (vide supra, 60 mg, 285 µmol) in dichloromethane (1.2 mL). The reaction mixture was stirred at 0-5° C. for 1.5 h. Then, ethanol (100 µl) was added, the mixture was stirred for 45 min at room temperature, poured onto a saturated aqueous solution of sodium hydrogencarbonate (15 mL) and extracted with dichloromethane (1×30 mL, 2×20 mL). The combined extracts were dried (sodium sulfate) and concentrated in vacuo. The crude was purified by column chromatography (silica gel, 50 g, eluting with ethyl acetate/n-heptane, gradient 60:40 to 80:20) to yield, after drying in vacuo (50° C., 5 mbar), the title compound as a light yellow foam (140 mg, 99% yield). HPLC (method LCMS_gradient) $t_R$=3.2 min. $^1$H NMR (CDCl$_3$, 400 MHz): δ 1.48 (s, 9H), 1.79 (s, 3H), 1.81-2.02 (m, 3H), 1.85 (s, 3H), 1.95 (s, 3H), 2.40 (dddd, J=3.8, 12.6, 12.6, 12.6 Hz, 1H), 3.36-3.43 (m, 1H), 3.58-3.66 (m, 1H), 4.08 (dd, J=3.2, 12.4 Hz, 1H), 7.57 (dd, J=8.9, 10.7 Hz, 1H), 7.95 (d, J=2.1 Hz, 1H), 8.44 (dd, J=3.1, 9.0 Hz, 1H), 8.57 (d, J=1.9 Hz, 1H), 10.16 (br s, 1H, exch), 11.23 (br s, 1H, exch). MS (ES+) m/z 613.3, 615.3 & 617.3 [M+H, 2Cl].

Step 2: N-(6-((4aR,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide (3AA)

tert-Butyl ((4aR,5R,9R)-5-(6-(3,5-dichloropicolinamido)-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-23AA, 140 mg, 228 µmol) was dissolved in dichloromethane (6 mL) and trifluoroacetic acid (1.78 g, 1.2 mL, 15.6 mmol) was added. The solution was stirred for 0.5 h at room temperature. After that, it was concentrated in vacuo (25° C., 5 mbar). The residue, a brown viscous oil, was dissolved in dichloromethane (40 mL), and saturated aqueous sodium hydrogencarbonate solution (15 mL) was added. After stirring for 5 min, phases were separated and the aqueous phase was extracted with dichloromethane (2×15 mL). The combined extracts were dried (sodium sulfate) and concentrated in vacuo. The residue was dissolved in dichloromethane (1 mL), MTBE (5 mL) was added and again concentrated in vacuo to give, after drying in vacuo (50° C., 5 mbar), an off white solid as crude product. The crude was purified by chiral preparative HPLC (Chiralpak AD, 250*4.6 mm*5 m, isocratic, n-heptane/(ethanol+ 0.1% ammonium acetate) 80/20, flow 1.0 mL/min) to yield the title compound as a white powder (61 mg, 52%). For transfer purpose, the material was dissolved in dichloromethane (1 mL) and MTBE (4 mL) and concentrated and dried in vacuo at 50° C./5 mbar. HPLC (method LCMS_gradient) $t_R$=1.6 min. $^1$H NMR (CDCl$_3$, 400 MHz): δ 1.73-1.88 (m, 3H), 1.81 (s, 3H), 1.89 (s, 3H), 1.90 (s, 3H), 2.27-2.42 (m, 1H), 3.37 (b d, J=12.6 Hz, 1H), 3.52-3.65 (m, 1H), 3.79 (dd, J=3.1, 12.6 Hz, 1H), 7.51 (dd, J=8.9, 10.7 Hz, 1H), 7.93 (d, J=1.9 Hz, 1H), 8.39 (dd, J=3.0, 8.7 Hz, 1H), 8.56 (d, J=1.9 Hz, 1H), 10.17 (br s, 1H). MS (ES+) m/z 513.2, 515.3 & 517.3 [M+H, 2 Cl].

N-(6-((4aS,5R,9S)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide (1BB)

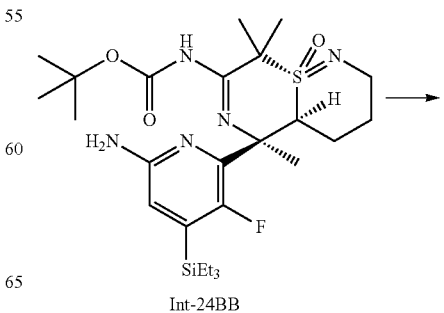

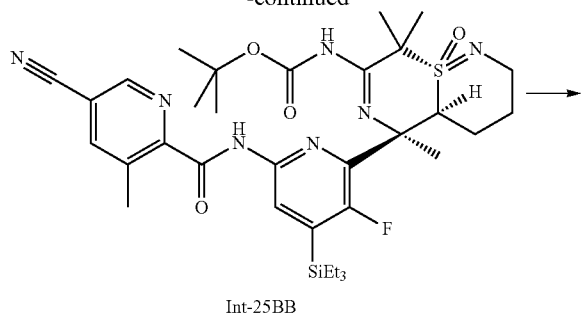

Int-25BB

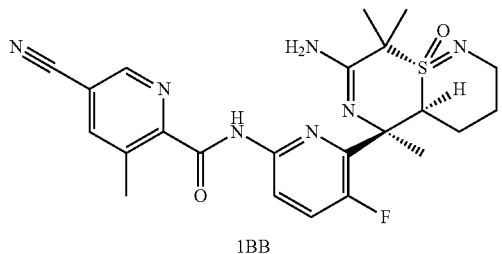

1BB

Step 1: tert-Butyl ((4aS,5R,9S)-5-(6-(5-cyano-3-methylpicolinamido)-3-fluoro-4-(triethyl-silyl)pyridin-2-yl)-5,8,8-trimethyl-9-oxido-2,3,4,4a,5,8-hexahydro-[1,4]thiazino[2,1-f][1,2]thiazin-7-yl)carbamate (Int-25BB)

5-Cyano-3-methylpicolinic acid (100 mg, 617 mol) was suspended in dichloromethane (2 mL), the suspension was cooled to 0-5° C. (ice bath) and oxalyl chloride (145 mg, 100 μL, 1.14 mmol) as well as a drop of a mixture of dimethylformamide and dichloromethane (1:3, v/v) were added. The mixture was stirred for 1.5 h at room temperature. Then, it was concentrated in vacuo, the residue was treated with n-heptane (2 mL) and again concentrated and dried in vacuo (40° C., mbar) to afford 5-cyano-3-methylpicolinoyl chloride as red oil (110 mg). After that, tert-butyl ((4aS,5R,9S)-5-(6-amino-3-fluoro-4-(triethylsilyl)pyridin-2-yl)-5,8,8-trimethyl-9-oxido-2,3,4,4a,5,8-hexahydro-[1,4]thiazino[2,1-f][1,2]thiazin-7-yl)carbamate (Int-24BB, 40 mg, 72 mol) was dissolved in dichloromethane (3 mL), the solution cooled to 0-5° C. (ice bath) and N,N-diisopropylethylamine (37.7 mg, 50 μl, 292 mol) was added, followed by a solution of 5-cyano-3-methylpicolinoyl chloride (vide supra, 21.3 mg, 118 μmol) in dichloromethane (2.5 mL). The reaction mixture was stirred at 0-5° C. for 1.5 h. Then, ethanol (50 μl) was added, the mixture was stirred for 15 min at room temperature, poured onto a saturated aqueous solution of sodium hydrogencarbonate (10 mL) and extracted with dichloromethane (1×30 mL, 2×20 mL). The combined extracts were dried (sodium sulfate) and concentrated in vacuo. The crude (66 mg) was used in the next step without further purification. HPLC (method 7626L05) $t_R$=9.7 min.

Step 2: N-(6-((4aS,5R,9S)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide (1BB)

tert-Butyl ((4aS,5R,9S)-5-(6-(5-cyano-3-methylpicolinamido)-3-fluoro-4-(triethylsilyl)-pyridin-2-yl)-5,8,8-trimethyl-9-oxido-2,3,4,4a,5,8-hexahydro-[1,4]thiazino[2,1-f][1,2]thiazin-7-yl)carbamate (Int-25BB, 66 mg, 72 μmol) was dissolved in dichloromethane (4 mL) and trifluoroacetic acid (740 mg, 0.5 mL, 6.5 mmol) was added. The solution was stirred for 1 h at room temperature. After that, it was concentrated in vacuo (25° C., 5 mbar). The residue, a brown viscous oil, was dissolved in dichloromethane (10 mL), and saturated aqueous sodium hydrogencarbonate solution (5 mL) was added. After stirring for 5 min, phases were separated and the aqueous phase was extracted with dichloromethane (2×5 mL). The combined extracts were dried (sodium sulfate) and concentrated in vacuo. The residue (70 mg) was dissolved in THF (2 mL) and DMF (0.5 mL). Acetic acid (21 mg, 20 μl, 349 μmol) and potassium fluoride (20 mg, 344 μmol) were added at room temperature and the resulting mixture was stirred for 2 h at that temperature, followed by 18 h at 60° C. Then, it was cooled to room temperature and a solution of tetra-n-butylammonium fluoride in tetrahydrofuran (1.0 M, 150 μl, 150 μmol) was added and the mixture was stirred for 4 h at 50° C. After that, it was poured upon a saturated aqueous solution of sodium hydrogencarbonate (10 mL) and extracted with MTBE (1×20 mL, 1×10 mL). The combined extracts were washed with brine (10 mL), dried (sodium sulfate) and concentrated in vacuo to give a brown viscous oil as crude product. The crude was purified by chiral preparative HPLC (Chiralpak AD, 250*4.6 mm*5 m, isocratic, n-heptane/(ethanol+0.1% ammonium acetate) 70/30, flow 1.0 mL/min) to yield the title compound as a off white powder (15 mg, 43% overall yield). For transfer purpose, the material was dissolved in dichloromethane (2 mL) and MTBE (8 mL) and concentrated and dried in vacuo at 50° C./5 mbar. HPLC (method LCMS_gradient) $t_R$=1.4 min. $^1$H NMR (CDCl$_3$, 400 MHz, major rotamer): δ 1.81-1.96 (m, 2H), 1.92 (s, 3H), 2.00 (s, 3H), 2.01 (s, 3H), 2.08-2.21 (m, 1H), 2.55-2.64 (m, 1H), 2.88 (s, 3H), 3.27-3.37 (m, 2H), 3.49 (dd, J=3.4, 12.8 Hz, 1H), 7.50 (dd, J=9.1, 11.0 Hz, 1H), 7.96 (d, J=1.1 Hz, 1H), 8.34 (dd, J=2.8, 9.0 Hz, 1H), 8.80 (d, J=1.3 Hz, 1H), 10.31 (br s, 1H, exch). MS (ES+) m/z 484.3 [M+H].

N-(6-((4aR,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide (4AA)

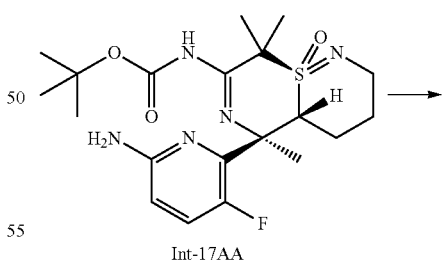

Int-17AA

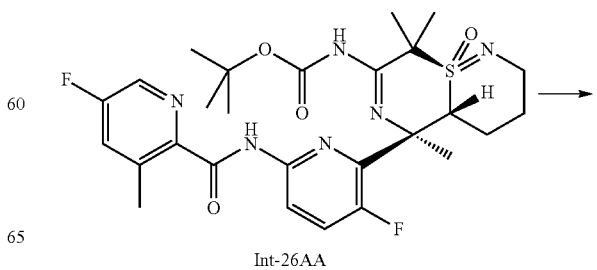

Int-26AA

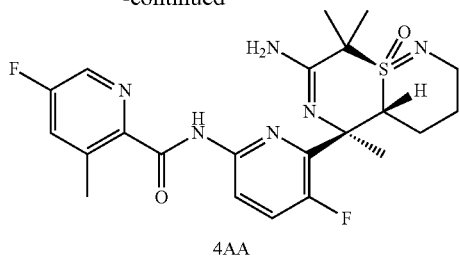

4AA

Step 1: tert-Butyl ((4aR,5R,9R)-5-(3-fluoro-6-(5-fluoro-3-methylpicolinamido)pyridin-2-yl)-5,8,8-trimethyl-9-oxido-2,3,4,4a,5,8-hexahydro-[1,4]thiazino[2,1-f][1,2]thiazin-7-yl)carbamate (Int-26AA)

5-Fluoro-3-methylpicolinic acid (200 mg, 1.29 mmol) was suspended in dichloromethane (4 mL), the suspension was cooled to 0-5° C. (ice bath) and oxalyl chloride (435 mg, 300 µl, 3.43 mmol) as well as a drop of a mixture of dimethylformamide and toluene (1:3, v/v) were added. The mixture was stirred for 1 h at room temperature. Then, it was concentrated in vacuo at 40° C., the residue was treated with n-heptane (4 mL) and again concentrated and dried in vacuo (40° C., 5 mbar) to afford 5-fluoro-3-methylpicolinoyl chloride as dark brown oil (220 mg). After that, tert-butyl ((4aR,5R,9R)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-17AA, 100 mg, 228 mol) was dissolved in dichloromethane (4 mL), the solution cooled to 0-5° C. (ice bath) and N,N-diisopropylethylamine (75.5 mg, 100 µl, 584 mol) was added, followed by a solution of 5-fluoro-3-methylpicolinoyl chloride (vide supra, 50 mg, 288 µmol) in dichloromethane (1 mL). The reaction mixture was stirred at 0-5° C. for 1.5 h. Then, ethanol (100 µl) was added, the mixture was stirred for 45 min at room temperature, poured onto a saturated aqueous solution of sodium hydrogencarbonate (15 mL) and extracted with dichloromethane (1×30 mL, 2×20 mL). The combined extracts were dried (sodium sulfate) and concentrated in vacuo. The crude was purified by column chromatography (silica gel, 50 g, eluting with ethyl acetate/n-heptane, gradient 60:40 to 80:20) to afford, after drying in vacuo (50° C., 5 mbar), the title compound as a white foam (115 mg, 88% yield). HPLC (method LCMS_gradient) $t_R$=3.2 min. $^1$H NMR (CDCl$_3$, 400 MHz): δ 1.48 (s, 9H), 1.79 (s, 3H), 1.80-2.01 (m, 3H), 1.85 (s, 3H), 1.96 (d, J=1.2 Hz, 3H), 2.31-2.48 (m, 1H), 2.83 (s, 3H), 3.35-3.45 (m, 1H), 3.56-3.68 (m, 1H), 4.07-4.14 (m, 1H), 7.40 (ddd, J=0.6, 2.7, 8.8 Hz, 1H), 7.55 (dd, J=8.9, 10.9 Hz, 1H), 8.38 (d, J=2.6 Hz, 1H), 8.41 (dd, J=3.0, 8.9 Hz, 1H), 10.41 (br s, 1H), 11.23 (br s, 1H, exch). MS (ES+) m/z 577.3 [M+H].

Step 2: N-(6-((4aR,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide (4AA)

tert-Butyl ((4aR,5R,9R)-5-(3-fluoro-6-(5-fluoro-3-methylpicolinamido)pyridin-2-yl)-5,8,8-trimethyl-9-oxido-2,3,4,4a,5,8-hexahydro-[1,4]thiazino[2,1-f][1,2]thiazin-7-yl)carbamate (Int-26AA, 110 mg, 191 mol) was dissolved in dichloromethane (5 mL) and trifluoroacetic acid (1.48 g, 1.0 mL, 13.0 mmol) was added. The solution was stirred for 0.5 h at room temperature. After that, it was concentrated in vacuo (25° C., 5 mbar). The residue, a brown viscous oil, was dissolved in dichloromethane (40 mL), and saturated aqueous sodium hydrogencarbonate solution (15 mL) was added. After stirring for 5 min, phases were separated and the aqueous phase was extracted with dichloromethane (2×15 mL). The combined extracts were dried (sodium sulfate) and concentrated in vacuo. The residue was dissolved in dichloromethane (1 mL), MTBE (5 mL) was added and again concentrated in vacuo to give, after drying in vacuo (50° C., 5 mbar), an off white solid as crude product. The crude was purified by chiral preparative HPLC (Chiralpak AD-H, 250*4.6 mm*5 µm, isocratic, n-heptane/(ethanol+0.1% triethylamine) 75/25, flow 1.0 mL/min) to yield the title compound as a white powder (39 mg, 43%). For transfer purpose, the material was dissolved in dichloromethane (1 mL) and MTBE (4 mL) and concentrated and dried in vacuo at 50° C./5 mbar. HPLC (method LCMS_gradient) $t_R$=1.5 min. $^1$H NMR (CDCl$_3$, 400 MHz): δ 1.71-1.90 (m, 3H), 1.75 (s, 3H), 1.85 (s, 3H), 1.87 (s, 3H), 2.26-2.41 (m, 1H), 2.83 (s, 3H), 3.32-3.40 (m, 1H), 3.55-3.64 (m, 1H), 3.81 (dd, J=3.4, 12.8 Hz, 1H), 7.39 (dd, J=2.4, 8.9 Hz, 1H), 7.46 (dd, J=8.9, 11.0 Hz, 1H), 8.33 (dd, J=3.0, 8.9 Hz, 1H), 8.38 (d, J=2.4 Hz, 1H), 10.38 (br s, 1H). MS (ES+) m/z 477.3 [M+H].

N-(6-((4aR,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-6-chloro-3-methylimidazo[1,2-a]pyridine-2-carboxamide (6AA)

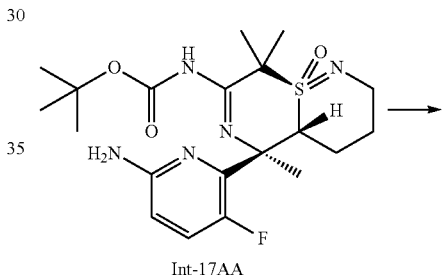

Int-17AA

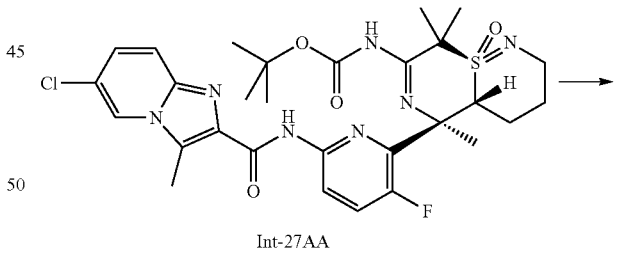

Int-27AA

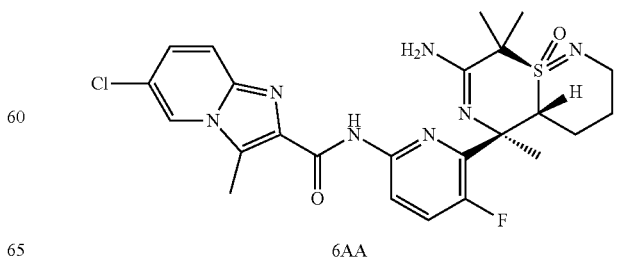

6AA

Step 1: tert-Butyl ((4aR,5R,9R)-5-(6-(6-chloro-3-methylimidazo[1,2-a]pyridine-2-carboxamido)-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-27AA)

6-Chloro-3-methylimidazo[1,2-a]pyridine-2-carboxylic acid (300 mg, 1.42 mmol) was suspended in dichloromethane (4 mL), the suspension was cooled to 0-5° C. (ice bath) and oxalyl chloride (435 mg, 300 µl, 3.43 mmol) as well as a drop of a mixture of dimethylformamide and toluene (1:3, v/v) were added. The mixture was stirred for 1 h at room temperature. Then, it was concentrated in vacuo at 40° C., the residue was treated with n-heptane (4 mL) and again concentrated and dried in vacuo (40° C., 5 mbar) to afford 5-fluoro-3-methylpicolinoyl chloride as brown solid (360 mg). After that, tert-butyl ((4aR,5R,9R)-5-(6-amino-3-fluoropyridin-2-yl)-5,8,8-trimethyl-9-oxido-2,3,4,4a,5,8-hexahydro-[1,4]thiazino[2,1-f][12]thiazin-7-yl)carbamate (Int-17AA, 100 mg, 228 mol) was dissolved in dichloromethane (4 mL), the solution cooled to 0-5° C. (ice bath) and N,N-diisopropylethylamine (113 mg, 150 µl, 876 µmol) was added, followed by a solution of 6-chloro-3-methylimidazo[1,2-a]pyridine-2-carbonyl chloride (vide supra, 80 mg, 349 µmol) in dichloromethane (1 mL). The reaction mixture was stirred at room temperature for 1.5 h. Then, ethanol (200 µl) was added, the mixture was stirred for 30 min at room temperature, poured onto a saturated aqueous solution of sodium hydrogencarbonate (15 mL) and extracted with dichloromethane (1×30 mL, 2×20 mL). The combined extracts were dried (sodium sulfate) and concentrated in vacuo. The crude was purified by column chromatography (silica gel, 50 g, eluting with ethyl acetate/n-heptane, 80:20, v/v) to afford, after drying in vacuo (50° C., 5 mbar), the title compound as white solid (130 mg, 90% yield). HPLC (method LCMS_gradient) $t_R$=3.4 min. $^1$H NMR (CDCl$_3$, 400 MHz): δ 1.48 (s, 9H), 1.75-2.01 (m, 3H), 1.79 (s, 3H), 1.85 (s, 3H), 1.96 (2s, 3H, rotamers), 2.31-2.48 (m, 1H), 2.88 (s, 3H), 3.36-3.45 (m, 1H), 3.57-3.69 (m, 1H), 4.06-4.14 (m, 1H), 7.28 (dd, J=1.8, 9.7 Hz, 1H), 7.54 (dd, J=8.9, 10.9 Hz, 1H), 7.61 (dd, J=0.9, 9.6 Hz, 1H), 7.99-8.02 (m, 1H), 8.43 (dd, J=3.0, 8.9 Hz, 1H), 9.81 (br s, 1H), 11.23 (br s, 1H, exch). MS (ES+) m/z 632.3 [M+H].

Step 2: N-(6-((4aR,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-6-chloro-3-methylimidazo[1,2-a]pyridine-2-carboxamide (6AA)

tert-Butyl ((4aR,5R,9R)-5-(6-(6-chloro-3-methylimidazo[1,2-a]pyridine-2-carboxamido)-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-27AA, 130 mg, 206 µmol) was dissolved in dichloromethane (5 mL) and trifluoroacetic acid (1.48 g, 1.0 mL, 13.0 mmol) was added. The solution was stirred for 1 h at room temperature. After that, it was concentrated in vacuo (25° C., mbar). The residue, a brown viscous oil, was dissolved in dichloromethane (40 mL), and saturated aqueous sodium hydrogencarbonate solution (15 mL) was added. After stirring for 5 min, phases were separated and the aqueous phase was extracted with dichloromethane (2×15 mL). The combined extracts were dried (sodium sulfate) and concentrated in vacuo. The residue was dissolved in dichloromethane (1 mL), MTBE (5 mL) was added and again concentrated in vacuo to give, after drying in vacuo (50° C., 5 mbar), an off white solid as crude product. The crude was purified by chiral preparative HPLC (Chiralpak AD-H, 250*4.6 mm*5 µm, isocratic, n-heptane/(ethanol+0.1% triethylamine) 50/50, flow 1.0 mL/min) to yield the title compound as a white powder (61 mg, 56%). For transfer purpose, the material was dissolved in dichloromethane (1 mL) and MTBE (5 mL) and concentrated and dried in vacuo at 50° C./5 mbar. HPLC (method LCMS_gradient) $t_R$=1.7 min. $^1$H NMR (CDCl$_3$, 400 MHz): δ 1.64-1.89 (m, 3H), 1.73 (s, 3H), 1.83 (s, 3H), 1.86 (s, 3H), 2.26-2.40 (m, 1H), 2.88 (s, 3H), 3.31-3.40 (m, 1H), 3.55-3.66 (m, 1H), 3.81 (dd, J=3.1, 12.7 Hz, 1H), 7.27 (dd, J=1.9, 9.7 Hz, 1H), 7.45 (dd, J=8.9, 11.0 Hz, 1H), 7.60 (d, J=9.7 Hz, 1H), 7.99-8.02 (m, 1H), 8.33 (dd, J=3.0, 8.9 Hz, 1H), 9.79 (br s, 1H). MS (ES+) m/z 532.3 [M+H].

N-(6-((4aR,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide (7AA)

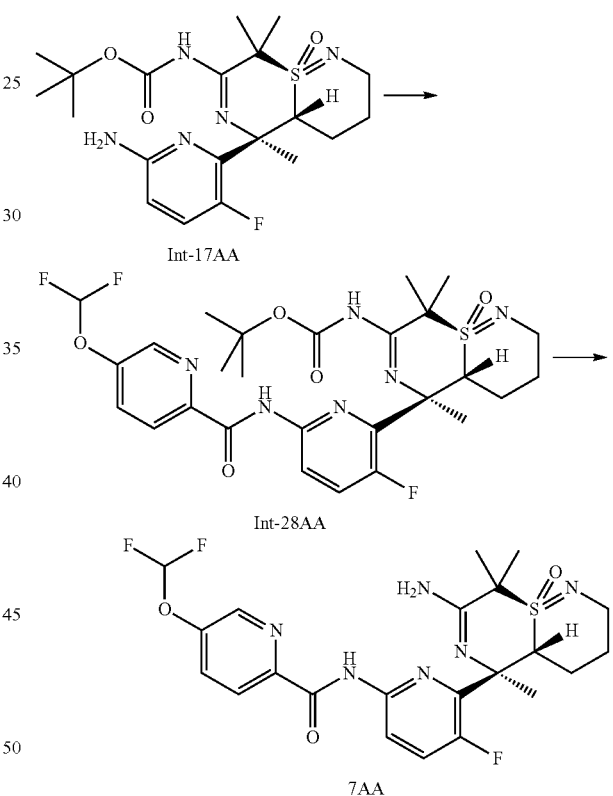

Int-17AA

Int-28AA

7AA

Step 1: tert-Butyl ((4aR,5R,9R)-5-(6-(5-(difluoromethoxy)picolinamido)-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-28AA)

5-(Difluoromethoxy)picolinic acid (300 mg, 1.59 mmol) was suspended in dichloromethane (4 mL), the suspension was cooled to 0-5° C. (ice bath) and oxalyl chloride (508 mg, 350 µl, 4.0 mmol) as well as a drop of a mixture of dimethylformamide and toluene (1:3, v/v) were added. The mixture was stirred for 1 h at room temperature. Then, it was concentrated in vacuo at 40° C., the residue was treated with n-heptane (4 mL) and again concentrated and dried in vacuo (40° C., 5 mbar) to afford 5-(difluoromethoxy)picolinoyl chloride as dark green oil (330 mg). After that, tert-butyl ((4aR,5R,9R)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-17AA, 100 mg, 228 μmol) was dissolved in dichloromethane (4 mL), the solution cooled to 0-5° C. (ice bath) and N,N-diisopropylethylamine (75.5 mg, 100 μl, 584 μmol) was added, followed by a solution of 5-(difluoromethoxy)picolinoyl chloride (vide supra, 65 mg, 313 mol) in dichloromethane (1 mL). The reaction mixture was stirred at room temperature for 1.5 h. Then, ethanol (200 μl) was added, the mixture was stirred for 30 min at room temperature, poured onto a saturated aqueous solution of sodium hydrogencarbonate (15 mL) and extracted with dichloromethane (1×30 mL, 2×20 mL). The combined extracts were dried (sodium sulfate) and concentrated in vacuo. The crude was purified by column chromatography (silica gel, 50 g, eluting with ethyl acetate/n-heptane, gradient 60:40 to 80:20, v/v) to yield, after drying in vacuo (55° C., 5 mbar), the title compound as white solid (135 mg, 97% yield). HPLC (method LCMS_gradient) $t_R$=3.1 min. $^1$H NMR (CDCl$_3$, 400 MHz): δ 1.48 (s, 9H), 1.79 (s, 3H), 1.81-2.04 (m, 3H), 1.85 (s, 3H), 1.96 (br s, 3H), 2.34-2.47 (m, 1H), 3.37-3.44 (m, 1H), 3.58-3.67 (m, 1H), 4.10 (dd, J=3.5, 12.4 Hz, 1H), 6.67 (t, J=71.7 Hz, 1H), 7.58 (dd, J=9.0, 10.9 Hz, 1H), 7.70 (dd, J=2.7, 8.6 Hz, 1H), 8.34 (d, J=8.9 Hz, 1H), 8.45 (dd, J=3.0, 8.9 Hz, 1H), 8.55 (d, J=2.4 Hz, 1H), 10.26 (s, 1H), 11.25 (br s, 1H, exch). MS (ES+) m/z 611.3 [M+H].

Step 2: N-(6-((4aR,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide (7AA)

tert-Butyl ((4aR,5R,9R)-5-(6-(5-(difluoromethoxy)picolinamido)-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-28AA, 130 mg, 213 mol) was dissolved in dichloromethane (5 mL) and trifluoroacetic acid (1.48 g, 1.0 mL, 13.0 mmol) was added. The solution was stirred for 1 h at room temperature. After that, it was concentrated in vacuo (25° C., 5 mbar). The residue, a colorless viscous oil, was dissolved in dichloromethane (40 mL), and saturated aqueous sodium hydrogencarbonate solution (15 mL) was added. After stirring for 5 min, phases were separated and the aqueous phase was extracted with dichloromethane (2×15 mL). The combined extracts were dried (sodium sulfate) and concentrated in vacuo. The residue was dissolved in dichloromethane (1 mL), MTBE (5 mL) was added and again concentrated in vacuo to give, after drying in vacuo (50° C., 5 mbar), an off white solid as crude product. The crude was purified by chiral preparative HPLC (Chiralpak AD-H, 250*4.6 mm*5 μm, isocratic, n-heptane/(ethanol+0.1% triethylamine) 70/30, flow 1.0 mL/min) to yield the title compound as a white powder (73 mg, 67%). For transfer purpose, the material was dissolved in dichloromethane (1 mL) and MTBE (5 mL) and concentrated and dried in vacuo at 50° C./5 mbar. HPLC (method LCMS_gradient) $t_R$=1.5 min. $^1$H NMR (CDCl$_3$, 400 MHz): δ 1.67-1.87 (m, 3H), 1.73 (s, 3H), 1.84 (s, 3H), 1.86 (s, 3H), 2.27-2.41 (m, 1H), 3.32-3.40 (m, 1H), 3.55-3.65 (m, 1H), 3.81 (dd, J=3.2, 12.6 Hz, 1H), 6.66 (t, J=71.7 Hz, 1H), 7.48 (dd, J=8.9, 11.0 Hz, 1H), 7.69 (dd, J=2.7, 8.6 Hz, 1H), 8.31-8.38 (m, 2H), 8.54 (d, J=2.4 Hz, 1H), 10.24 (s, 1H). MS (ES+) m/z 511.3 [M+H].

N-(6-((4aR,5R,9R)-7-Amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide (8AA)

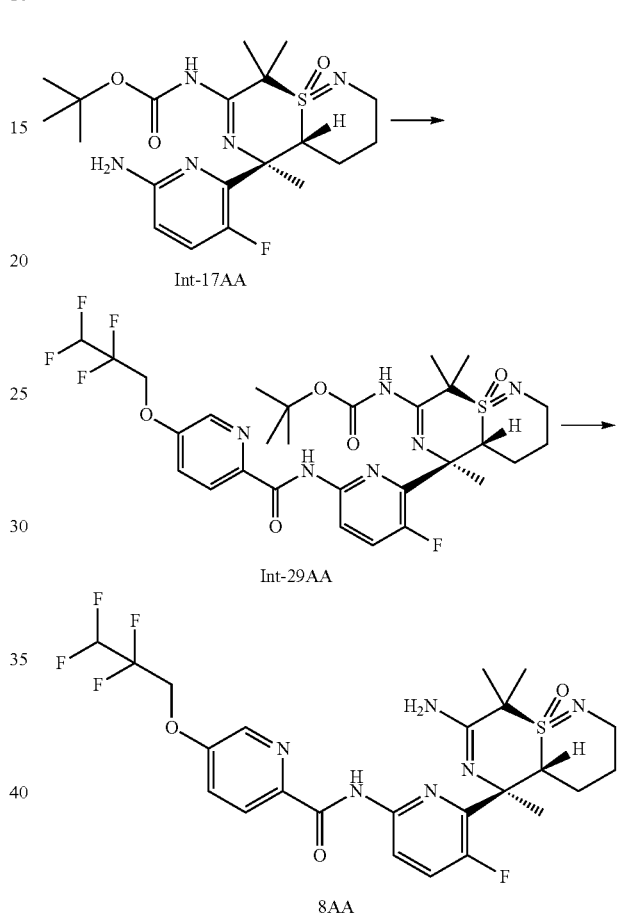

Int-17AA

Int-29AA

8AA

Step 1: tert-Butyl ((4aR,5R,9R)-5-(3-fluoro-6-(5-(2,2,3,3-tetrafluoropropoxy)picolinamido)-pyridin-2-yl)-5,8,8-trimethyl-9-oxido-2,3,4,4a,5,8-hexahydro-[1,4]thiazino[2,1-f][1,2]thiazin-7-yl)carbamate (Int-29AA)

5-(2,2,3,3-Tetrafluoropropoxy)picolinic acid (200 mg, 790 μmol) was suspended in dichloromethane (4 mL), the suspension was cooled to 0-5° C. (ice bath) and oxalyl chloride (290 mg, 200 μl, 2.28 mmol) as well as a drop of a mixture of dimethylformamide and toluene (1:3, v/v) were added. The mixture was stirred for 1 h at room temperature. Then, it was concentrated in vacuo at 40° C., the residue was treated with n-heptane (4 mL) and again concentrated and dried in vacuo (40° C., 5 mbar) to afford 5-(2,2,3,3-tetrafluoropropoxy)picolinoyl chloride as yellow, turbid oil (210 mg). After that, tert-butyl ((4aR,5R,9R)-5-(6-amino-3-fluoropyridin-2-yl)-5,8,8-trimethyl-9-oxido-2,3,4,4a,5,8-hexahydro-[1,4]thiazino[2,1-f][1,2]thiazin-7-yl)carbamate (Int-17AA, 70 mg, 159 μmol) was dissolved in dichloromethane (4 mL), the solution cooled to 0-5° C. (ice bath) and N,N-diisopropylethylamine (52.9 mg, 70 µl, 409 µmol) was added, followed by a solution of 5-(2,2,3,3-tetrafluoropropoxy)picolinoyl chloride (vide supra, 60 mg, 221 µmol) in dichloromethane (1.3 mL). The reaction mixture was stirred at room temperature for 1.5 h. Then, ethanol (200 µl) was added, the mixture was stirred for 30 min at room temperature, poured onto a saturated aqueous solution of sodium hydrogencarbonate (15 mL) and extracted with dichloromethane (1×30 mL, 2×20 mL). The combined extracts were dried (sodium sulfate) and concentrated in vacuo. The crude was purified by column chromatography (silica gel, 50 g, eluting with ethyl acetate/n-heptane, gradient 60:40 to 80:20, v/v) to yield, after drying in vacuo (55° C., 5 mbar), the title compound as white solid (100 mg, 93% yield). HPLC (method LCMS_gradient) $t_R$=3.3 min. $^1$H NMR (CDCl$_3$, 400 MHz): δ 1.48 (s, 9H), 1.79 (s, 3H), 1.80-2.06 (m, 3H), 1.85 (s, 3H), 1.96 (br s, 3H), 2.41 (dddd, J=3.2, 12.1, 12.6, 12.9 Hz, 1H), 3.37-3.44 (m, 1H), 3.63 (ddd, J=3.8, 12.1, 12.9 Hz, 1H), 4.10 (dd, J=3.5, 12.4 Hz, 1H), 4.52 (br t, J=11.8 Hz, 2H), 6.07 (tt, J=4.0, 53.0 Hz, 1H), 7.44 (dd, J=2.8, 8.7 Hz, 1H), 7.57 (dd, J=8.9, 10.8 Hz, 1H), 8.30 (dd, J=0.5, 8.6 Hz, 1H), 8.41 (d, J=2.4 Hz, 1H), 8.45 (dd, J=3.1, 9.0 Hz, 1H), 10.23 (s, 1H), 11.24 (br s, 1H). MS (ES+) m/z 675.4 [M+H].

Step 2: N-(6-((4aR,5R,9R)-7-Amino-5,8,8-trimethyl-9-oxido-2,3,4,4a,5,8-hexahydro-[1,4]thiazino [2,1-f][1,2]thiazin-5-yl)-5-fluoropyridin-2-yl)-5-(2,2,3,3-tetrafluoropropoxy)picolinamide (8AA)

tert-Butyl ((4aR,5R,9R)-5-(3-fluoro-6-(5-(2,2,3,3-tetrafluoropropoxy)picolinamido)pyridin-2-yl)-5,8,8-trimethyl-9-oxido-2,3,4,4a,5,8-hexahydro-[1,4]thiazino[2,1-f][1,2]thiazin-7-yl)carbamate (Int-29AA, 100 mg, 148 µmol) was dissolved in dichloromethane (5 mL) and trifluoroacetic acid (1.48 g, 1.0 mL, 13.0 mmol) was added. The solution was stirred for 1 h at room temperature. After that, it was concentrated in vacuo (25° C., mbar). The residue, a colorless viscous oil, was dissolved in dichloromethane (40 mL), and saturated aqueous sodium hydrogencarbonate solution (15 mL) was added. After stirring for 5 min, phases were separated and the aqueous phase was extracted with dichloromethane (2×15 mL). The combined extracts were dried (sodium sulfate) and concentrated in vacuo. The residue was dissolved in dichloromethane (1 mL), MTBE (5 mL) was added and again concentrated in vacuo to give, after drying in vacuo (40° C., 5 mbar), an off white solid as crude product. The crude was purified by chiral preparative HPLC (Chiralpak AD-H, 250*4.6 mm*5 µm, isocratic, n-heptane/(ethanol+0.1% triethylamine) 70/30, flow 1.0 mL/min) to yield the title compound as a white powder (62 mg, 73%). For transfer purpose, the material was dissolved in dichloromethane (1 mL) and MTBE (5 mL) and concentrated and dried in vacuo at 50° C./5 mbar. HPLC (method LCMS_gradient) $t_R$=1.8 min. $^1$H NMR (CDCl$_3$, 400 MHz): δ 1.71-1.95 (m, 3H), 1.74 (s, 3H), 1.85 (s, 3H), 1.87 (s, 3H), 2.28-2.42 (m, 1H), 3.32-3.41 (m, 1H), 3.54-3.66 (m, 1H), 3.78-3.86 (m, 1H), 4.51 (t, J=11.8 Hz, 2H), 6.07 (tt, J=4.0, 53.0 Hz, 1H), 7.42 (dd, J=2.7, 8.6 Hz, 1H), 7.47 (dd, J=9.1, 11.0 Hz, 1H), 8.29 (d, J=8.6 Hz, 1H), 8.35 (dd, J=3.0, 8.9 Hz, 1H), 8.40 (d, J=2.7 Hz, 1H), 10.21 (s, 1H). MS (ES+) m/z 575.2 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide (9AB)

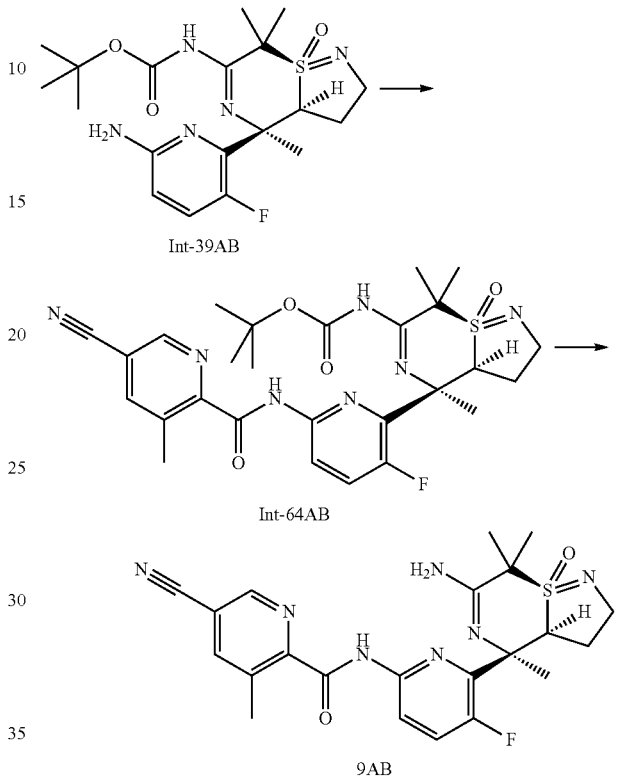

Step 1: tert-Butyl ((3aS,4R,8R)-4-(6-(5-cyano-3-methylpicolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-64AB)

To a solution of tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 100.0 mg, 0.24 mmol) in THF (5.0 mL) was added 5-cyano-3-methylpicolinic acid (76.2 mg, 0.48 mmol), followed by T3P (763.2 mg, 1.2 mmol, 50% in ethyl acetate), and diisopropylethylamine (182.8 mg, 1.44 mmol). The reaction was stirred at 70° C. for 4 h. After that, the reaction mixture was diluted with water (10 mL) and extracted with ethyl acetate (2×10 mL). The combined organic layers were dried over sodium sulfate, filtered and concentrated to give a crude product. The crude was purified by column chromatography (silica gel, eluting with ethyl acetate/petroleum ether 2:1) to yield, after drying in vacuo, the title compound as a yellow solid (100 mg, 75% yield). $^1$H NMR (CDCl$_3$, 400 MHz): δ 1.50-1.65 (m, 1H), 1.67 (s, 9H), 1.87 (s, 3H), 1.99 (s, 3H), 2.06-2.20 (m, 1H), 2.16 (s, 3H), 2.89 (s, 3H), 3.56 (dd, J=7.5, 10.5 Hz, 1H), 3.71 (ddd, J=4.9, 10.5, 10.5 Hz, 1H), 4.26-4.35 (m, 1H), 7.62 (dd, J=8.8, 10.3 Hz, 1H), 8.00 (s, 1H), 8.51 (dd, J=3.0, 8.8 Hz, 1H), 8.72 (s, 1H), 10.78 (s, 1H), 12.53 (s, 1H). MS (ES+) m/z 570.2 [M+H].

Step 2: N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide (9AB)

tert-Butyl ((3aS,4R,8R)-4-(6-(5-cyano-3-methylpicolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-64AB, 100 mg, 0.17 mmol) was dissolved in dichloromethane (4 mL) and trifluoroacetic acid (1.48 g, 1.0 mL, 13.0 mmol) was added. The solution was stirred for 4 h at room temperature. The reaction mixture was basified with saturated aqueous sodium hydrogencarbonate solution to pH=7-8, extracted with dichloromethane (2×10 mL). The combined extracts were dried over sodium sulfate, filtered and concentrated to give a crude product. The crude was purified by preparative TLC (dichloromethane/methanol 10:1, UV) twice to give a product. The product was diluted with water (20.0 mL) and acetonitrile (10 mL), the solution was concentrated to remove organic solvents. The residual aqueous solution was lyophilized to give the title compound as a white solid (38 mg, 46% yield). $^1$H NMR (CDCl$_3$, 400 MHz): δ 1.62-1.75 (m, 1H), 1.87 (s, 3H), 1.97 (s, 3H), 2.06-2.17 (m, 1H), 2.10 (s, 3H), 2.84 (s, 3H), 3.54 (dd, J=7.8, 10.5 Hz, 1H), 3.72 (ddd, J=5.3, 10.5, 10.5 Hz, 1H), 4.24-4.33 (m, 1H), 7.61 (dd, J=9.0, 10.3 Hz, 1H), 7.96 (s, 1H), 8.48 (dd, J=3.3, 9.0 Hz, 1H), 8.79 (s, 1H), 10.86 (s, 1H). MS (ES+) m/z 470.2 [M+H].

N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide (9BA)

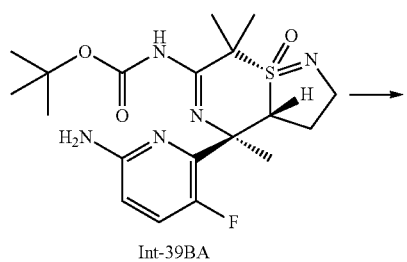

Int-39BA

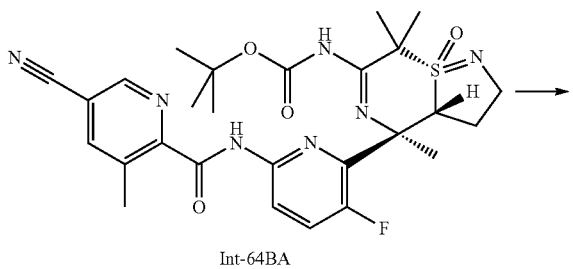

Int-64BA

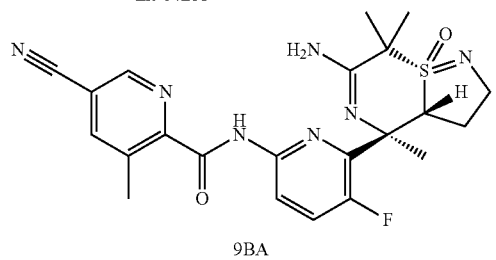

9BA

Step 1: tert-Butyl ((3aR,4R,8S)-4-(6-(5-cyano-3-methylpicolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-64BA)

To a solution of tert-butyl ((3aR,4R,8S)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39BA, 150.0 mg, 0.35 mmol) in THF (20 mL) was added 5-cyano-3-methylpicolinic acid (85.9 mg, 0.53 mmol), followed by T3P (1.1 g, 1.75 mmol, 50% in ethyl acetate), and diisopropylethylamine (266.7 mg, 2.1 mmol). The reaction was stirred at 70° C. for 4 h. After that, the reaction mixture was diluted with aqueous saturated sodium hydrogencarbonate solution (20 mL) and extracted with ethyl acetate (2×10 mL). The combined organic layers were dried over sodium sulfate, filtered and concentrated to give a crude product. The crude was purified by column chromatography (silica gel, eluting with ethyl acetate/petroleum ether 2:1) to yield, after drying in vacuo, the title compound as a yellow solid (120 mg, 60% yield). $^1$H NMR (CDCl$_3$, 400 MHz): δ 0.85 (s, 3H), 1.50-1.57 (m, 9H), 1.68-1.75 (m, 6H), 2.08-2.21 (m, 1H), 2.50-2.63 (m, 1H), 2.80-2.89 (m, 3H), 3.73-3.89 (m, 2H), 5.19 (dd, J=7.1, 11.1 Hz, 1H), 7.55 (dd, J=9.1, 10.2 Hz, 1H), 7.91-8.00 (m, 1H), 8.37-8.49 (m, 1H), 8.78 (d, J=1.4 Hz, 1H), 10.48 (s, 1H), 11.03 (br s, 1H). MS (ES+) m/z 570.2 [M+H].

Step 2: N-(6-((3aR,4R,8S)-6-Amino-4,7,7-trimethyl-8-oxido-3,3a,4,7-tetrahydro-2H-isothiazolo-[1,5-a][1,4]thiazin-4-yl)-5-fluoropyridin-2-yl)-5-cyano-3-methylpicolinamide (9BA)

tert-Butyl ((3aR,4R,8S)-4-(6-(5-cyano-3-methylpicolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-64BA, 120 mg, 0.21 mmol) was dissolved in acetonitrile (20 mL) and dichloromethane (6 mL). Zinc dibromide (142 mg, 0.63 mmol) was added and the reaction solution was stirred for 18 h at 35° C. After that, the reaction mixture was diluted with saturated aqueous sodium hydrogencarbonate solution (20 mL), extracted with dichloromethane (2×20 mL). The combined extracts were dried over sodium sulfate, filtered and concentrated to give a crude product. The crude was purified by preparative TLC (dichloromethane/methanol 10:1, UV) to give the title compound as a white solid (55 mg, 57% yield). $^1$H NMR (CDCl$_3$, 400 MHz): δ 0.99 (s, 3H), 1.85 (2s, 6H), 2.15-2.32 (m, 1H), 2.60-2.71 (m, 1H), 2.86 (s, 3H), 3.73-3.88 (m, 2H), 5.14-5.23 (m, 1H), 7.62 (dd, J=9.4, 9.4 Hz, 1H), 7.97 (s, 1H), 8.48 (dd, J=3.0, 9.0 Hz, 1H), 8.82 (d, J=1.5 Hz, 1H), 10.53 (s, 1H). MS (ES+) m/z 470.2 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide (10AB)

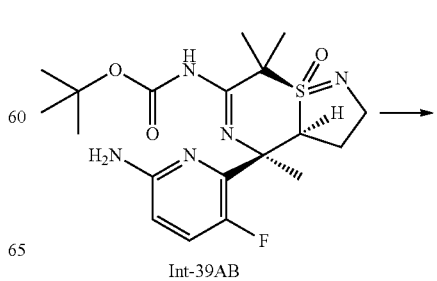

Int-39AB

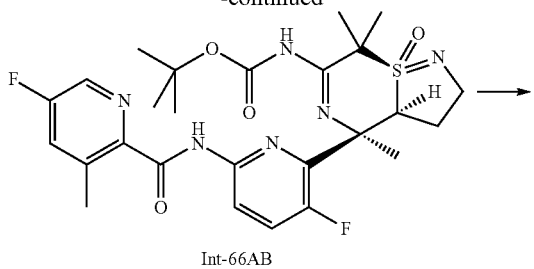

Int-66AB

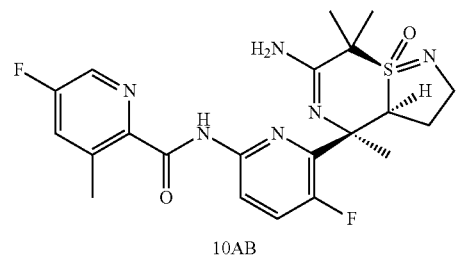

10AB

Step 1: tert-Butyl ((3aS,4R,8R)-4-(3-fluoro-6-(5-fluoro-3-methylpicolinamido)pyridin-2-yl)-4,7,7-trimethyl-8-oxido-3,3a,4,7-tetrahydro-2H-isothiazolo[1,5-a][1,4]thiazin-6-yl)carbamate (Int-66AB)

To a solution of tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 150 mg, 0.35 mmol) in THF (20 mL) was added 5-fluoro-3-methylpicolinic acid (82 mg, 0.53 mmol) followed by T3P (1.1 g, 1.75 mmol, 50% in ethyl acetate), and diisopropylethylamine (267 mg, 2.1 mmol). The reaction was stirred at 70° C. for 4 h. After that, the reaction mixture was diluted with aqueous saturated sodium hydrogencarbonate solution (20 mL) and extracted with ethyl acetate (3×30 mL). The combined organic layers were dried over sodium sulfate, filtered and concentrated to give a crude product. The crude was purified by column chromatography (silica gel, eluting with petroleum ether/ethyl acetate 1:1) to yield, after drying in vacuo, the title compound as a yellow solid (130 mg, 66% yield). $^1$H NMR (CDCl$_3$, 400 MHz): δ 1.50-1.59 (m, 1H), 1.66 (s, 9H), 1.86 (s, 3H), 1.97 (s, 3H), 2.06-2.12 (m, 1H), 2.14 (s, 3H), 2.84 (s, 3H), 3.54 (dd, J=7.7, 10.7 Hz, 1H), 3.69 (ddd, J=4.8, 10.7, 10.7 Hz, 1H), 4.30 (ddd, J=2.1, 7.1, 12.0 Hz, 1H), 7.40 (dd, J=2.1, 8.9 Hz, 1H), 7.58 (dd, J=9.1, 10.0 Hz, 1H), 8.31 (d, J=2.6 Hz, 1H), 8.49 (dd, J=3.1, 8.9 Hz, 1H), 10.78 (s, 1H), 12.54 (s, 1H). MS (ES+) m/z 563.2 [M+H].

Step 2: N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide (10AB)

tert-Butyl ((3aS,4R,8R)-4-(3-fluoro-6-(5-fluoro-3-methylpicolinamido)pyridin-2-yl)-4,7,7-trimethyl-8-oxido-3,3a,4,7-tetrahydro-2H-isothiazolo[1,5-a][1,4]thiazin-6-yl)carbamate (Int-66AB, 130 mg, 0.23 mmol) was dissolved in acetonitrile (20 mL) and zinc dibromide (155 mg, 0.69 mmol) was added. Then, dichloromethane (5 mL) was added and the resulting solution was stirred for 18 h at 40° C. The reaction mixture was diluted with saturated aqueous sodium hydrogencarbonate solution (20 mL), extracted with dichloromethane (2×20 mL). The combined extracts were dried over sodium sulfate, filtered and concentrated to give a crude product. The crude was purified by preparative TLC (dichloromethane/methanol 10:1, UV) to give a product. The product was repurified by preparative HPLC (C18, eluting with 0.05% ammonia*acetonitrile), followed by lyophilization to give the title compound as a white solid (37 mg, 34% yield). $^1$H NMR (CDCl$_3$, 400 MHz): δ 1.65-1.79 (m, 1H), 1.80 (s, 3H), 1.93 (s, 3H), 2.05-2.12 (m, 1H), 2.06 (s, 3H), 2.82 (s, 3H), 3.52 (dd, J=7.6, 10.5 Hz, 1H), 3.71 (ddd, J=5.2, 10.5, 10.5 Hz, 1H), 4.25 (ddd, J=2.0, 7.0, 12.3 Hz, 1H), 7.40 (dd, J=2.3, 8.8 Hz, 1H), 7.56 (dd, J=9.0, 10.3 Hz, 1H), 8.38 (d, J=2.8 Hz, 1H), 8.45 (dd, J=3.1, 8.9 Hz, 1H), 10.62 (s, 1H). MS (ES+) m/z 463.2 [M+H].

N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide (10BA)

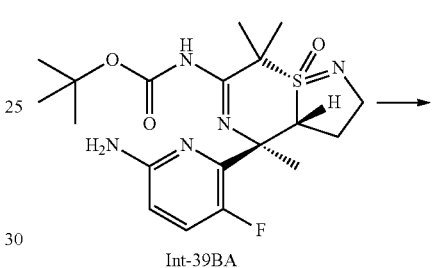

Int-39BA

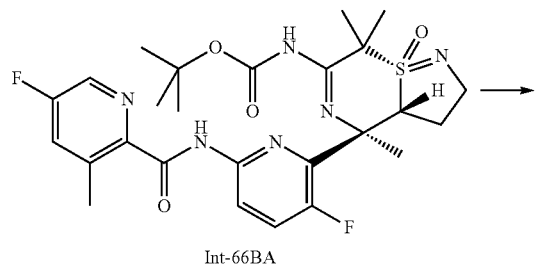

Int-66BA

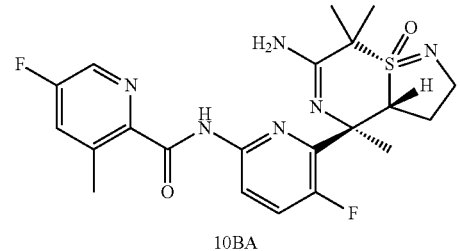

10BA

Step 1: tert-Butyl ((3aR,4R,8S)-4-(3-fluoro-6-(5-fluoro-3-methylpicolinamido)pyridin-2-yl)-4,7,7-trimethyl-8-oxido-3,3a,4,7-tetrahydro-2H-isothiazolo[1,5-a][1,4]thiazin-6-yl)carbamate (Int-66BA)

To a solution of tert-butyl ((3aR,4R,8S)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39BA, 150 mg, 0.35 mmol) in THF (20 mL) was added 5-fluoro-3-methylpicolinic acid (82 mg, 0.53 mmol) followed by T3P (1.1 g, 1.75 mmol, 50% in ethyl acetate), and diisopropylethylamine (267 mg, 2.1 mmol). The reaction was stirred at 70° C. for 4 h. After that, the reaction mixture was diluted with aqueous saturated sodium hydrogencarbonate solution (20 mL) and extracted with ethyl acetate (3×30 mL). The combined organic layers were dried over sodium sulfate, filtered and concentrated to give a crude product. The crude was purified by column chromatography (silica gel, eluting with petroleum ether/ethyl acetate 1:1) to yield, after drying in vacuo, the title compound as a yellow solid (130 mg, 66% yield). $^1$H NMR (CDCl$_3$, 400 MHz): δ 0.81-0.91 (m, 3H), 1.49-1.59 (m, 9H), 1.67-1.76 (m, 6H), 2.08-2.22 (m, 1H), 2.52-2.64 (m, 1H), 2.76-2.87 (m, 3H), 3.71-3.87 (m, 2H), 5.21 (dd, J=7.1, 11.0 Hz, 1H), 7.37 (dd, J=2.3, 8.8 Hz, 1H), 7.48-7.57 (m, 1H), 8.37 (d, J=2.5 Hz, 1H), 8.44 (dd, J=3.0, 8.9 Hz, 1H), 10.46 (s, 1H), 11.00 (br s, 1H). MS (ES+) m/z 563.2 [M+H].

Step 2: N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide (10BA)

tert-Butyl ((3aR,4R,8S)-4-(3-fluoro-6-(5-fluoro-3-methylpicolinamido)pyridin-2-yl)-4,7,7-trimethyl-8-oxido-3,3a,4,7-tetrahydro-2H-isothiazolo[1,5-a][1,4]thiazin-6-yl)carbamate (Int-66BA, 130 mg, 0.23 mmol) was dissolved in acetonitrile (20 mL) and zinc dibromide (155 mg, 0.69 mmol) was added. Then, dichloromethane (5 mL) was added and the resulting solution was stirred for 18 h at 40° C. The reaction mixture was diluted with saturated aqueous sodium hydrogencarbonate solution (20 mL), extracted with dichloromethane (2×20 mL). The combined extracts were dried over sodium sulfate, filtered and concentrated to give a crude product. The crude was purified by preparative TLC (dichloromethane/methanol 10:1, UV) to give the title compound as a white solid (50 mg, 47% yield). $^1$H NMR (d4-MeOH, 400 MHz): δ 0.98 (s, 3H), 1.77 (s, 3H), 1.82 (s, 3H), 2.16-2.28 (m, 1H), 2.72-2.81 (m, 1H), 2.77 (s, 3H), 3.65-3.72 (m, 1H), 3.78 (ddd, J=4.8, 10.5, 10.5 Hz, 1H), 5.37 (dd, J=7.1, 11.4 Hz, 1H), 7.65 (dd, J=2.3, 9.5 Hz, 1H), 7.83 (dd, J=9.0, 10.8 Hz, 1H), 8.43 (d, J=2.3 Hz, 1H), 8.48 (dd, J=3.3, 9.0 Hz, 1H). MS (ES+) m/z 463.2 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide (11AB)

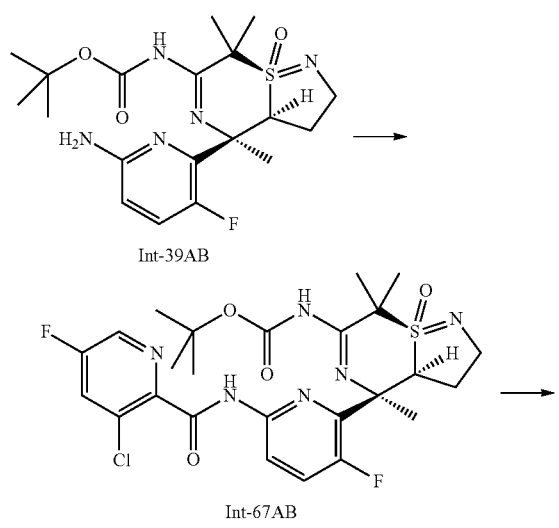

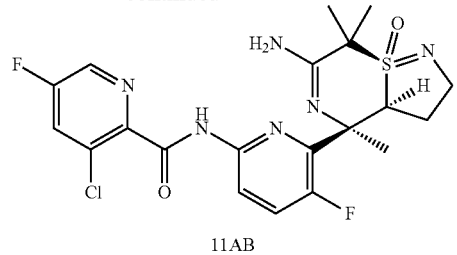

Step 1: tert-Butyl ((3aS,4R,8R)-4-(6-(3-chloro-5-fluoropicolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-67AB)

To a solution of tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 150 mg, 0.35 mmol) in THF (20 mL) was added 3-chloro-5-fluoropicolinic acid (92.8 mg, 0.53 mmol), followed by T3P (1.1 g, 1.75 mmol, 50% in ethyl acetate), and diisopropylethylamine (267 mg, 2.1 mmol). The reaction was stirred at 60° C. for 16 h. After that, the reaction mixture was diluted with aqueous saturated sodium hydrogencarbonate solution (20 mL) and extracted with ethyl acetate (2×30 mL). The combined organic layers were dried over sodium sulfate, filtered and concentrated to give a crude product. The crude was purified by column chromatography (silica gel, eluting with petroleum ether/ethyl acetate 1:1) to yield, after drying in vacuo, the title compound as a yellow solid (120 mg, 58% yield). $^1$H NMR (CDCl$_3$, 400 MHz): δ 1.53-1.59 (m, 1H), 1.64 (s, 9H), 1.86 (s, 3H), 1.97 (s, 3H), 2.06-2.12 (m, 1H), 2.14 (s, 3H), 3.50-3.58 (m, 1H), 3.64-3.76 (m, 1H), 4.29 (ddd, J=2.0, 7.2, 12.0 Hz, 1H), 7.60 (dd, J=9.1, 10.0 Hz, 1H), 7.70 (dd, J=2.5, 7.7 Hz, 1H), 8.41 (d, J=2.0 Hz, 1H), 8.52 (dd, J=3.0, 8.9 Hz, 1H), 10.43-10.63 (m, 1H), 12.53 (s, 1H). MS (ES+) m/z 583.1 [M+H].

Step 2: N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide (11AB)

tert-Butyl ((3aS,4R,8R)-4-(6-(3-chloro-5-fluoropicolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-67AB, 120 mg, 0.20 mmol) was dissolved in acetonitrile (20 mL) and dichloromethane (5 mL). Then, zinc dibromide (135 mg, 0.60 mmol) was added and the resulting solution was stirred for 18 h at 40° C. The reaction mixture was diluted with saturated aqueous sodium hydrogencarbonate solution (20 mL), extracted with dichloromethane (2×20 mL). The combined extracts were dried over sodium sulfate, filtered and concentrated to give a crude product. The crude was purified by preparative TLC (dichloromethane/methanol 10:1, UV) to give a product. The product was repurified by preparative HPLC (C18, eluting with 0.05% ammonia/acetonitrile), followed by lyophilization to give the title compound as a white solid (24 mg, 24% yield). $^1$H NMR (CDCl$_3$, 400 MHz): δ 1.63-1.79 (m, 1H), 1.80 (s, 3H), 1.93 (s, 3H), 2.06-2.12 (m, 1H), 2.06 (s, 3H), 3.52 (dd, J=7.8, 10.5 Hz, 1H), 3.71 (ddd, J=5.1, 10.5, 10.5 Hz, 1H), 4.25 (ddd, J=2.0, 7.1, 12.4 Hz, 1H), 7.58 (dd, J=9.0, 10.3 Hz, 1H), 7.69 (dd, J=2.4, 7.7 Hz, 1H), 8.46-8.52 (m, 2H), 10.38 (s, 1H). MS (ES+) m/z 483.1 [M+H].

N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide (11BA)

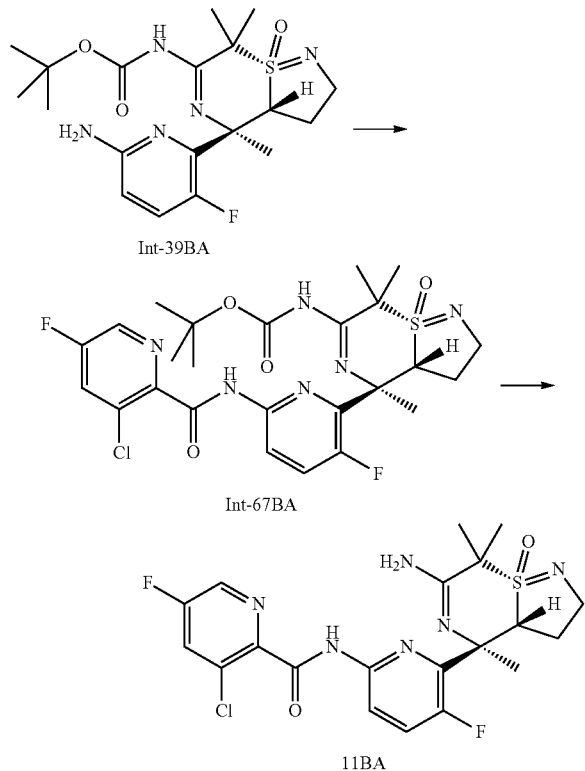

Step 1: tert-Butyl ((3aR,4R,8S)-4-(6-(3-chloro-5-fluoropicolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-67BA)

To a solution of tert-butyl ((3aR,4R,8S)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39BA, 150 mg, 0.35 mmol) in THF (20 mL) was added 3-chloro-5-fluoropicolinic acid (92.8 mg, 0.53 mmol) followed by T3P (1.1 g, 1.75 mmol, 50% in ethyl acetate), and diisopropylethylamine (267 mg, 2.1 mmol). The reaction was stirred at 60° C. for 16 h. After that, the reaction mixture was diluted with aqueous saturated sodium hydrogencarbonate solution (20 mL) and extracted with ethyl acetate (2×30 mL). The combined organic layers were dried over sodium sulfate, filtered and concentrated to give a crude product. The crude was purified by column chromatography (silica gel, eluting with petroleum ether/ethyl acetate 1:1) to yield, after drying in vacuo, the title compound as a yellow solid (120 mg, 58% yield). $^1$H NMR (CDCl$_3$, 400 MHz): δ 0.85 (s, 3H), 1.54 (s, 9H), 1.73 (s, 6H), 2.08-2.22 (m, 1H), 2.52-2.63 (m, 1H), 3.70-3.87 (m, 2H), 5.19 (dd, J=7.1, 11.1 Hz, 1H), 7.54 (dd, J=9.1, 10.2 Hz, 1H), 7.67 (dd, J=2.4, 7.7 Hz, 1H), 8.42-8.51 (m, 2H), 10.21 (s, 1H), 11.03 (br s, 1H). MS (ES+) m/z 583.1 [M+H].

Step 2: N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide (11BA)

tert-Butyl ((3aR,4R,8S)-4-(6-(3-chloro-5-fluoropicolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-67BA, 120 mg, 0.20 mmol) was dissolved in acetonitrile (20 mL) and dichloromethane (5 mL). Then, zinc dibromide (135 mg, 0.60 mmol) was added and the resulting solution was stirred for 18 h at 40° C. The reaction mixture was diluted with saturated aqueous sodium hydrogencarbonate solution (20 mL), extracted with dichloromethane (2×20 mL). The combined extracts were dried over sodium sulfate, filtered and concentrated to give a crude product. The crude was purified by preparative TLC (dichloromethane/methanol 10:1, UV) to give the title compound as a white solid (25.0 mg, 24% yield). $^1$H NMR (d4-MeOH, 400 MHz): δ 1.07 (s, 3H), 1.91 (s, 3H), 1.92 (s, 3H), 2.40-2.52 (m, 1H), 2.85-2.93 (m, 1H), 3.78-3.86 (m, 1H), 3.87-3.96 (m, 1H), 5.81 (dd, J=7.5, 11.5 Hz, 1H), 7.92 (dd, J=9.0, 10.5 Hz, 1H), 8.03 (dd, J=2.5, 8.3 Hz, 1H), 8.49 (dd, J=2.9, 8.9 Hz, 1H), 8.58 (d, J=2.5 Hz, 1H). MS (ES+) m/z 483.2 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide (12AB)

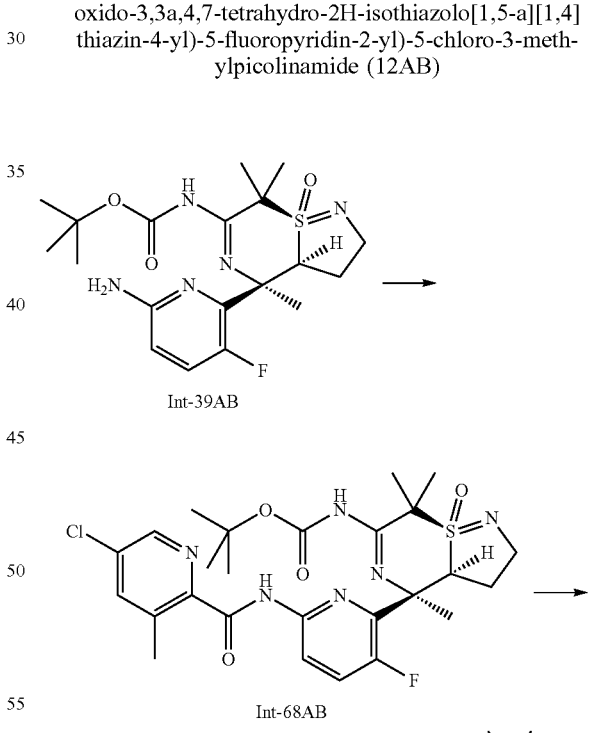

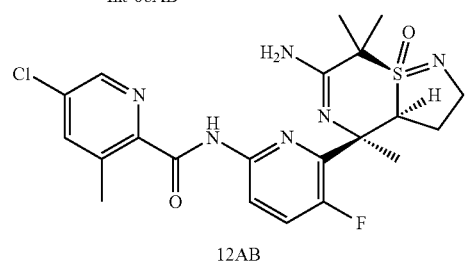

Step 1: tert-Butyl ((3aS,4R,8R)-4-(3-fluoro-6-(5-chloro-3-methylpicolinamido)pyridin-2-yl)-4,7,7-trimethyl-8-oxido-3,3a,4,7-tetrahydro-2H-isothiazolo[1,5-a][1,4]thiazin-6-yl)carbamate (Int-68AB)

To a solution of tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 150 mg, 0.35 mmol) in THF (20 mL) was added 5-chloro-3-methylpicolinic acid (92.8 mg, 0.53 mmol), followed by T3P (1.1 g, 1.75 mmol, 50% in ethyl acetate), and diisopropylethylamine (267 mg, 2.1 mmol). The reaction was stirred at 70° C. for 4 h. After that, the reaction mixture was diluted with aqueous saturated sodium hydrogencarbonate solution (20 mL) and extracted with ethyl acetate (3×30 mL). The combined organic layers were dried over sodium sulfate, filtered and concentrated to give a crude product. The crude was purified by preparative TLC (silica gel, dichloromethane/ethyl acetate 1:1, UV) to yield, after drying in vacuo, the title compound as a yellow solid (100 mg, 50% yield). MS (ES+) m/z 579.2 [M+H].

Step 2: N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide (12AB)

tert-Butyl ((3aS,4R,8R)-4-(3-fluoro-6-(5-chloro-3-methylpicolinamido)pyridin-2-yl)-4,7,7-trimethyl-8-oxido-3,3a,4,7-tetrahydro-2H-isothiazolo[1,5-a][1,4]thiazin-6-yl)carbamate (Int-68AB, 100 mg, 0.17 mmol) was dissolved in acetonitrile (20 mL) and dichloromethane (1 mL). Then, zinc dibromide (100 mg, 0.45 mmol) was added and the resulting solution was stirred for 16 h at 40° C. The reaction mixture was diluted with saturated aqueous sodium hydrogencarbonate solution (20 mL), extracted with ethyl acetate (3×30 mL). The combined extracts were dried over sodium sulfate, filtered and concentrated to give a crude product. The crude was purified by preparative TLC (dichloromethane/methanol 10:1, UV) to give a product. The product was repurified by preparative HPLC (C18, eluting with 0.05% ammonia/acetonitrile), followed by lyophilization to give the title compound as a white solid (32 mg, 40% yield). ¹H NMR (CDCl₃, 400 MHz): δ 1.66-1.79 (m, 1H), 1.81 (s, 3H), 1.94 (s, 3H), 2.04-2.13 (m, 1H), 2.06 (s, 3H), 2.80 (s, 3H), 3.53 (dd, J=7.5, 10.5 Hz, 1H), 3.72 (ddd, J=5.0, 10.5, 10.5 Hz, 1H), 4.26 (ddd, J=2.2, 7.2, 12.4 Hz, 1H), 7.57 (dd, J=9.0, 10.3 Hz, 1H), 7.68-7.70 (m, 1H), 8.44-8.50 (m, 2H), 10.64 (s, 1H). MS (ES+) m/z 479.2 [M+H].

N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide (12BA)

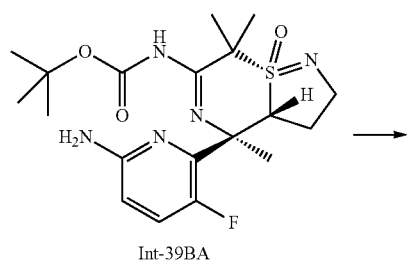

Int-39BA

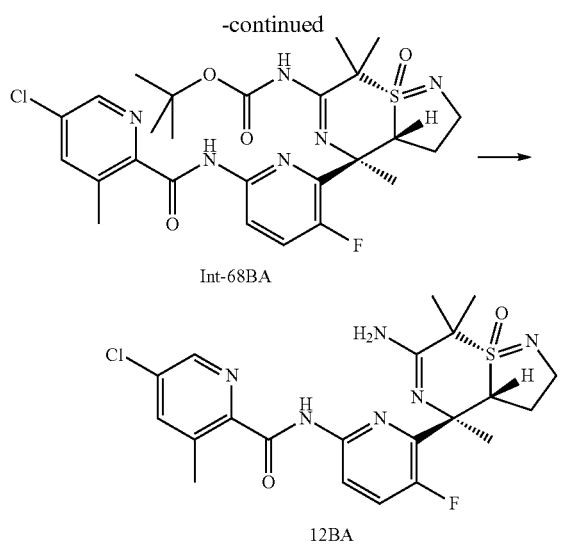

Int-68BA

12BA

Step 1: tert-Butyl ((3aR,4R,8S)-4-(3-fluoro-6-(5-chloro-3-methylpicolinamido)pyridin-2-yl)-4,7,7-trimethyl-8-oxido-3,3a,4,7-tetrahydro-2H-isothiazolo[1,5-a][1,4]thiazin-6-yl)carbamate (Int-68BA)

To a solution of tert-butyl ((3aR,4R,8S)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39BA, 150 mg, 0.35 mmol) in THF (20 mL) was added 5-chloro-3-methylpicolinic acid (92.4 mg, 0.53 mmol) followed by T3P (1.1 g, 1.75 mmol, 50% in ethyl acetate), and diisopropylethylamine (267 mg, 2.1 mmol). The reaction was stirred at 70° C. for 4 h. After that, the reaction mixture was diluted with aqueous saturated sodium hydrogencarbonate solution (20 mL) and extracted with ethyl acetate (3×30 mL). The combined organic layers were dried over sodium sulfate, filtered and concentrated to give a crude product. The crude was purified by preparative TLC (silica gel, dichloromethane/ethyl acetate 1:1, UV) to yield, after drying in vacuo, the title compound as a yellow solid (100 mg, 50% yield). MS (ES+) m/z 579.2 [M+H].

Step 2: N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide (12BA)

tert-Butyl ((3aR,4R,8S)-4-(3-fluoro-6-(5-chloro-3-methylpicolinamido)pyridin-2-yl)-4,7,7-trimethyl-8-oxido-3,3a,4,7-tetrahydro-2H-isothiazolo[1,5-a][1,4]thiazin-6-yl)carbamate (Int-68BA, 100 mg, 0.23 mmol) was dissolved in acetonitrile (20 mL) and dichloromethane (1 mL). Then, zinc dibromide (100 mg, 0.45 mmol) was added and the resulting solution was stirred for 16 h at 40° C. The reaction mixture was diluted with saturated aqueous sodium hydrogencarbonate solution (20 mL), extracted with ethyl acetate (3×30 mL). The combined extracts were dried over sodium sulfate, filtered and concentrated to give a crude product. The crude was purified by preparative TLC (dichloromethane/methanol 10:1, UV) to give a product. The product was repurified by preparative HPLC (C18, eluting with 0.05% ammonia/acetonitrile), followed by lyophilization to give the title compound as a white solid (21.3 mg, 26% yield). ¹H NMR (CDCl₃, 400 MHz): δ 0.82 (s, 3H), 1.67 (s, 3H), 1.69

(s, 3H), 2.11-2.24 (m, 1H), 2.51-2.60 (m, 1H), 2.79 (s, 3H), 3.66-3.73 (m, 1H), 3.76-3.84 (m, 1H), 5.13 (dd, J=7.0, 10.8 Hz, 1H), 7.49 (dd, J=9.4, 9.4 Hz, 1H), 7.66 (d, J=2.0 Hz, 1H), 8.37 (dd, J=2.3, 8.8 Hz, 1H), 8.49 (d, J=2.3 Hz, 1H), 10.48 (s, 1H). MS (ES+) m/z 479.2 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide (13AB)

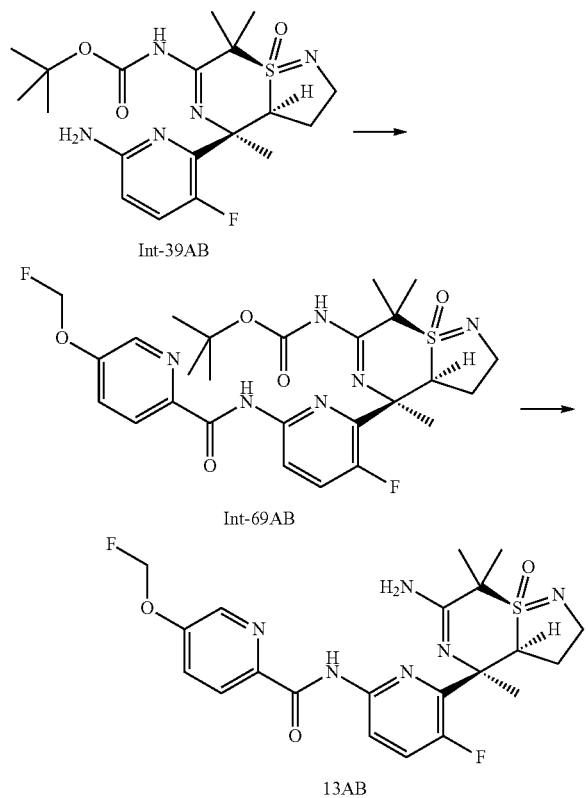

Step 1: tert-Butyl ((3aS,4R,8R)-4-(3-fluoro-6-(5-(fluoromethoxy)picolinamido)pyridin-2-yl)-4,7,7-trimethyl-8-oxido-3,3a,4,7-tetrahydro-2H-isothiazolo[1,5-a][1,4]thiazin-6-yl)carbamate (Int-69AB)

To a solution of tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 150 mg, 0.35 mmol) in THF (20 mL) was added 5-(fluoromethoxy)picolinic acid (90.6 mg, 0.53 mmol), followed by T3P (1.1 g, 1.75 mmol, 50% in ethyl acetate), and diisopropylethylamine (267 mg, 2.1 mmol). The reaction was stirred at 70° C. for 4 h. After that, the reaction mixture was diluted with aqueous saturated sodium hydrogencarbonate solution (20 mL) and extracted with ethyl acetate (3×30 mL). The combined organic layers were dried over sodium sulfate, filtered and concentrated to give a crude product. The crude was purified by preparative TLC (silica gel, dichloromethane/ethyl acetate 1:1, UV) to yield, after drying in vacuo, the title compound as a yellow solid (0.1 g, 50% yield). MS (ES+) m/z 579.2 [M+H].

Step 2: N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide (13AB)

tert-Butyl ((3aS,4R,8R)-4-(3-fluoro-6-(5-(fluoromethoxy)picolinamido)pyridin-2-yl)-4,7,7-trimethyl-8-oxido-3,3a,4,7-tetrahydro-2H-isothiazolo[1,5-a][1,4]thiazin-6-yl)carbamate (Int-69AB, 100 mg, 0.17 mmol) was dissolved in acetonitrile (20 mL) and dichloromethane (1 mL). Then, zinc dibromide (100 mg, 0.45 mmol) was added and the resulting solution was stirred for 16 h at 40° C. The reaction mixture was diluted with saturated aqueous sodium hydrogencarbonate solution (20 mL), extracted with ethyl acetate (3×30 mL). The combined extracts were dried over sodium sulfate, filtered and concentrated to give a crude product. The crude was purified by preparative TLC (dichloromethane/methanol 10:1, UV) to give a product. The product was repurified by preparative HPLC (C18, eluting with 0.05% ammonia/acetonitrile), followed by lyophilization to give the title compound as a white solid (20 mg, 25% yield). $^1$H NMR (d6-DMSO, 400 MHz): δ 1.67-1.81 (m, 1H), 1.95 (s, 3H), 1.97 (s, 3H), 2.03 (s, 3H), 2.12-2.21 (m, 1H), 3.36-3.44 (m, 1H), 3.58-3.67 (m, 1H), 4.89-5.00 (m, 1H), 6.06 (d, J=53.2 Hz, 2H), 7.82 (dd, J=2.8, 8.8 Hz, 1H), 8.06 (dd, J=9.3, 10.3 Hz, 1H), 8.23 (d, J=8.8 Hz, 1H), 8.44 (dd, J=2.8, 9.0 Hz, 1H), 8.50 (d, J=2.8 Hz, 1H), 10.17 (s, 1H), 11.04 (s, 1H), 11.10 (s, 1H), 11.43 (s, 1H). MS (ES+) m/z 479.2 [M+H].

N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide (13BA)

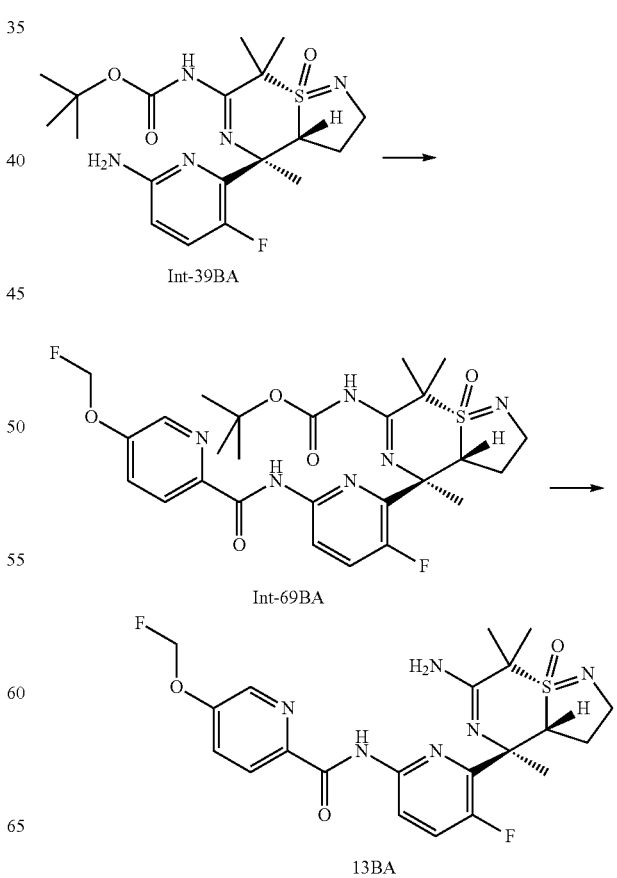

Step 1: tert-Butyl ((3aR,4R,8S)-4-(3-fluoro-6-(5-(fluoromethoxy)picolinamido)pyridin-2-yl)-4,7,7-trimethyl-8-oxido-3,3a,4,7-tetrahydro-2H-isothiazolo[1,5-a][1,4]thiazin-6-yl)carbamate (Int-69BA)

To a solution of tert-butyl ((3aR,4R,8S)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39BA, 150 mg, 0.35 mmol) in THF (20 mL) was added 5-(fluoromethoxy)picolinic acid (90.6 mg, 0.53 mmol) followed by T3P (1.1 g, 1.75 mmol, 50% in ethyl acetate), and diisopropylethylamine (267 mg, 2.1 mmol). The reaction was stirred at 70° C. for 4 h. After that, the reaction mixture was diluted with aqueous saturated sodium hydrogencarbonate solution (20 mL) and extracted with ethyl acetate (3×30 mL). The combined organic layers were dried over sodium sulfate, filtered and concentrated to give a crude product. The crude was purified by preparative TLC (silica gel, dichloromethane/ethyl acetate 1:1, UV) to yield, after drying in vacuo, the title compound as a yellow solid (0.1 g, 50% yield). $^1$H NMR (CDCl$_3$, 400 MHz): δ 1.51-1.60 (m, 12H), 1.73 (2s, 6H), 2.06-2.23 (m, 1H), 2.59 (ddd, J=5.7, 11.3, 11.3 Hz, 1H), 3.67-3.89 (m, 2H), 5.21 (dd, J=7.2, 10.8 Hz, 1H), 5.82 (d, J=52.0 Hz, 2H), 7.46-7.66 (m, 2H), 8.28 (d, J=8.5 Hz, 1H), 8.43-8.53 (m, 2H), 10.36 (s, 1H), 11.02 (s, 1H). MS (ES+) m/z 579.2 [M+H].

Step 2: N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide (13BA)

tert-Butyl ((3aR,4R,8S)-4-(3-fluoro-6-(5-(fluoromethoxy)picolinamido)pyridin-2-yl)-4,7,7-trimethyl-8-oxido-3,3a,4,7-tetrahydro-2H-isothiazolo[1,5-a][1,4]thiazin-6-yl)carbamate (Int-69BA, 100 mg, 0.17 mmol) was dissolved in acetonitrile (20 mL) and dichloromethane (1 mL). Then, zinc dibromide (100 mg, 0.45 mmol) was added and the resulting solution was stirred for 16 h at 40° C. The reaction mixture was diluted with saturated aqueous sodium hydrogencarbonate solution (20 mL), extracted with ethyl acetate (3×30 mL). The combined extracts were dried over sodium sulfate, filtered and concentrated to give the title compound as a white solid (56.0 mg, 69% yield). $^1$H NMR (CDCl$_3$, 400 MHz): δ 0.90 (s, 3H), 1.75 (s, 3H), 1.76 (s, 3H), 2.13-2.26 (m, 1H), 2.56-2.64 (m, 1H), 3.69-3.77 (m, 1H), 3.82 (ddd, J=4.9, 10.5, 10.5 Hz, 1H), 5.17 (dd, J=7.3, 11.3 Hz, 1H), 5.82 (d, J=53.2 Hz, 2H), 7.51-7.61 (m, 1H), 8.29 (d, J=8.5 Hz, 1H), 8.45 (dd, J=3.0, 9.0 Hz, 1H), 8.50 (d, J=2.5 Hz, 1H), 10.37 (s, 1H). MS (ES+) m/z 479.2 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide (14AB)

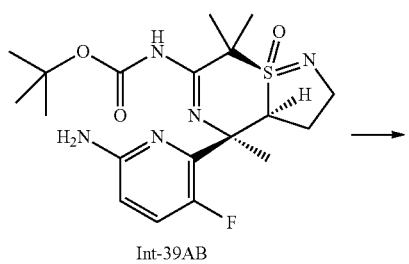

Int-39AB

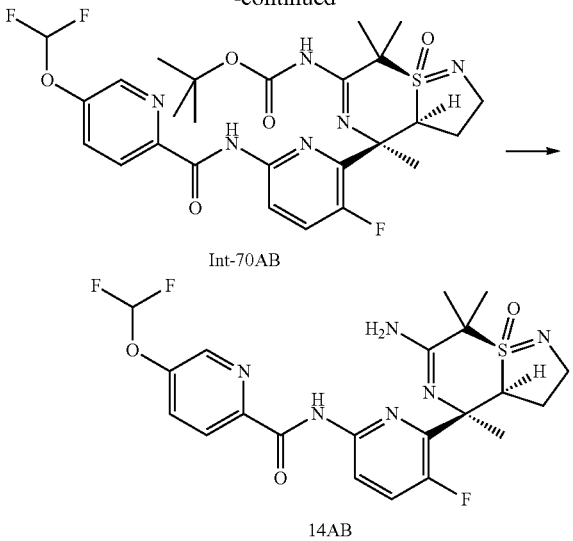

Int-70AB

14AB

Step 1: tert-Butyl ((3aS,4R,8R)-4-(6-(5-(difluoromethoxy)picolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-70AB)

To a solution of tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 150 mg, 0.35 mmol) in THF (20 mL) was added 5-(difluoromethoxy)picolinic acid (100 mg, 0.53 mmol), followed by T3P (1.1 g, 1.75 mmol, 50% in ethyl acetate), and diisopropylethylamine (267 mg, 2.1 mmol). The reaction was stirred at 60° C. for 16 h. After that, the reaction mixture was diluted with aqueous saturated sodium hydrogencarbonate solution (20 mL) and extracted with ethyl acetate (2×30 mL). The combined organic layers were dried over sodium sulfate, filtered and concentrated to give a crude product. The crude was purified by column chromatography (silica gel, eluting with petroleum ether/ethyl acetate 1:1) to yield, after drying in vacuo, the title compound as a yellow solid (120 mg, 57% yield). MS (ES+) m/z 597.2 [M+H].

Step 2: N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide (14AB)

tert-Butyl ((3aS,4R,8R)-4-(6-(5-(difluoromethoxy)picolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-70AB, 120 mg, 0.20 mmol) was dissolved in acetonitrile (20 mL) and dichloromethane (5 mL). Then, zinc dibromide (135 mg, 0.60 mmol) was added and the resulting solution was stirred for 18 h at 40° C. The reaction mixture was diluted with saturated aqueous sodium hydrogencarbonate solution (20 mL), extracted with ethyl acetate (2×20 mL). The combined extracts were dried over sodium sulfate, filtered and concentrated to give a crude product. The crude was purified by preparative TLC (dichloromethane/methanol 10:1, UV) to give a product. The product was repurified by preparative HPLC (C18, eluting with 0.05% ammonia/acetonitrile), followed by lyophilization to give the title compound as a white solid (19 mg, 19% yield). $^1$H NMR (d6-DMSO, 400 MHz): δ 1.58-1.68 (m, 1H), 1.62 (s, 3H), 1.73 (s, 3H), 1.91 (s, 3H), 2.04-2.13 (m, 1H), 3.24-3.31 (m, 1H), 3.45-3.54 (m, 1H), 3.92-4.04 (m, 1H), 7.53 (t, J=72.8 Hz, 1H), 7.86-7.94 (m, 1H), 7.95 (dd, J=2.8, 8.5 Hz, 1H), 8.26-8.32 (m, 2H), 8.30 (d, J=8.5 Hz, 1H), 8.66-8.68 (m, 1H), 10.84 (s, 1H). MS (ES+) m/z 497.2 [M+H].

N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide (14BA)

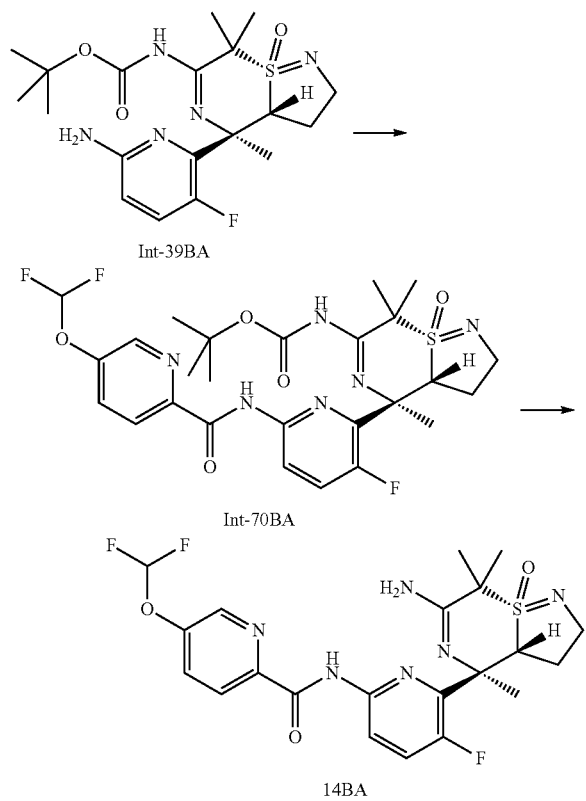

Step 1: tert-Butyl ((3aR,4R,8S)-4-(6-(5-(difluoromethoxy)picolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-70BA)

To a solution of tert-butyl ((3aR,4R,8S)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39BA, 150 mg, 0.35 mmol) in THF (20 mL) was added 5-(difluoromethoxy)picolinic acid (100 mg, 0.53 mmol) followed by T3P (1.1 g, 1.75 mmol, 50% in ethyl acetate), and diisopropylethylamine (267 mg, 2.1 mmol). The reaction was stirred at 60° C. for 16 h. After that, the reaction mixture was diluted with aqueous saturated sodium hydrogencarbonate solution (20 mL) and extracted with ethyl acetate (2×30 mL). The combined organic layers were dried over sodium sulfate, filtered and concentrated to give a crude product. The crude was purified by column chromatography (silica gel, eluting with petroleum ether/ethyl acetate 1:1) to yield, after drying in vacuo, the title compound as a yellow solid (120 mg, 57% yield). ¹H NMR (CDCl₃, 400 MHz): δ 1.68 (s, 9H), 1.86 (s, 3H), 1.98 (s, 3H), 2.15 (s, 3H), 3.55 (dd, J=7.5, 10.7 Hz, 1H), 3.70 (ddd, J=4.7, 10.7, 10.7 Hz, 1H), 4.25-4.33 (m, 1H), 6.46-6.86 (m, 1H), 7.61 (dd, J=9.0, 10.0 Hz, 1H), 7.70 (dd, J=2.6, 8.7 Hz, 1H), 8.35 (d, J=8.7 Hz, 1H), 8.46-8.52 (m, 2H), 10.69 (s, 1H), 12.63 (s, 1H). MS (ES+) m/z 597.1 [M+H].

Step 2: N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide (14BA)

tert-Butyl ((3aR,4R,8S)-4-(6-(5-(difluoromethoxy)picolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-70BA, 120 mg, 0.20 mmol) was dissolved in acetonitrile (20 mL) and dichloromethane (5 mL). Then, zinc dibromide (135 mg, 0.60 mmol) was added and the resulting solution was stirred for 18 h at 40° C. The reaction mixture was diluted with saturated aqueous sodium hydrogencarbonate solution (20 mL), extracted with ethyl acetate (2×20 mL). The combined extracts were dried over sodium sulfate, filtered and concentrated to give a crude product. The crude was purified by preparative TLC (dichloromethane/methanol 10:1, UV) to give the title compound as a white solid (55.0 mg, 55% yield). ¹H NMR (CDCl₃, 400 MHz): δ 0.95 (s, 3H), 1.80 (s, 3H), 1.83 (s, 3H), 2.13-2.28 (m, 1H), 2.57-2.67 (m, 1H), 3.70-3.88 (m, 2H), 5.19 (dd, J=7.2, 11.4 Hz, 1H), 6.67 (t, J=71.9 Hz, 1H), 7.59 (dd, J=9.5, 9.5 Hz, 1H), 7.68 (dd, J=2.5, 8.5 Hz, 1H), 8.32 (d, J=8.8 Hz, 1H), 8.48 (dd, J=2.9, 8.9 Hz, 1H), 8.55 (d, J=2.5 Hz, 1H), 10.37 (s, 1H). MS (ES+) m/z 497.1 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide (15AB)

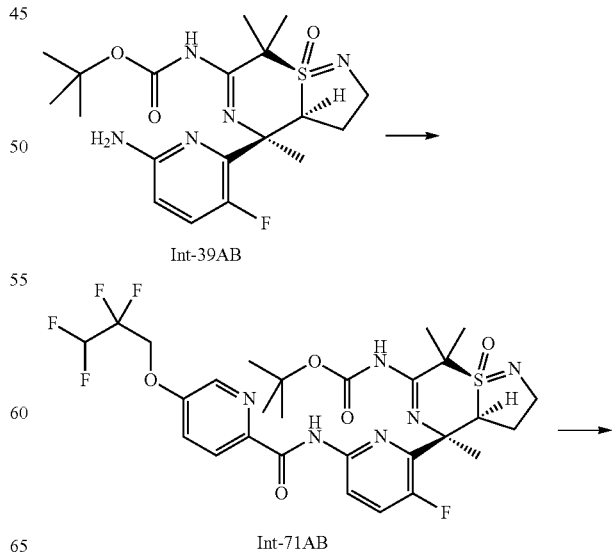

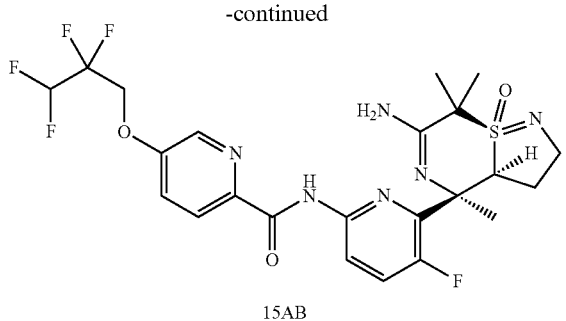

15AB

Step 1: tert-Butyl ((3aS,4R,8R)-4-(3-fluoro-6-(5-(2,2,3,3-tetrafluoropropoxy)picolinamido)-pyridin-2-yl)-4,7,7-trimethyl-8-oxido-3,3a,4,7-tetrahydro-2H-isothiazolo[1,5-a][1,4]thiazin-6-yl)carbamate (Int-71AB)

To a solution of tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 150 mg, 0.35 mmol) in THF (20 mL) was added 5-(2,2,3,3-tetrafluoropropoxy)picolinic acid (134 mg, 0.53 mmol), followed by T3P (1.1 g, 1.75 mmol, 50% in ethyl acetate), and diisopropylethylamine (267 mg, 2.1 mmol). The reaction was stirred at 70° C. for 18 h. After that, the reaction mixture was diluted with aqueous saturated sodium hydrogencarbonate solution (20 mL) and extracted with ethyl acetate (2×10 mL). The combined organic layers were dried over sodium sulfate, filtered and concentrated to give a crude product. The crude was purified by column chromatography (silica gel, eluting with petroleum ether/ethyl acetate 1:2) to yield, after drying in vacuo, the purified product. The pure title compound was obtained by stirring this material in petroleum ether (10 mL) and dichloromethane (2 mL) at 15° C. for 1 h. The suspension was filtered, and dried in vacuo to give the title compound as white solid (80 mg, 34% yield). $^1$H NMR (CDCl$_3$, 400 MHz): δ 1.51-1.57 (m, 1H), 1.69 (s, 9H), 1.86 (s, 3H), 1.98 (s, 3H), 2.09 (d, J=7.2 Hz, 1H), 2.15 (s, 3H), 3.49-3.59 (m, 1H), 3.64-3.75 (m, 1H), 4.31 (d, J=6.8 Hz, 1H), 4.50 (t, J=11.8 Hz, 2H), 5.89-6.26 (m, 1H), 7.43 (d, J=8.3 Hz, 1H), 7.60 (dd, J=9.5 Hz, 1H), 8.32 (d, J=2.6 Hz, 2H), 8.44-8.59 (m, 1H), 10.38-10.71 (m, 1H), 12.38-12.74 (m, 1H). MS (ES+) m/z 661.2 [M+H].

Step 2: N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide (15AB)

tert-Butyl ((3aS,4R,8R)-4-(3-fluoro-6-(5-(2,2,3,3-tetrafluoropropoxy)picolinamido)pyridin-2-yl)-4,7,7-trimethyl-8-oxido-3,3a,4,7-tetrahydro-2H-isothiazolo[1,5-a][1,4]thiazin-6-yl)carbamate (Int-71AB, 70 mg, 01 mmol) was dissolved in acetonitrile (10 mL) and dichloromethane (5 mL). Then, zinc dibromide (67.5 mg, 0.3 mmol) was added and the resulting solution was stirred for 16 h at 35° C. The reaction mixture was diluted with saturated aqueous sodium hydrogencarbonate solution (20 mL), extracted with dichloromethane (2×20 mL). The combined extracts were dried over sodium sulfate, filtered and concentrated to give a crude product. The crude was purified by preparative HPLC (C18, eluting with 0.05% ammonia/acetonitrile), followed by lyophilization to give the title compound as a white solid (17 mg, 29% yield). $^1$H NMR (CDCl$_3$, 400 MHz): δ 1.65-1.81 (m, 1H), 1.81 (s, 3H), 1.94 (s, 3H), 2.05-2.14 (m, 1H), 2.07 (s, 3H), 3.49-3.57 (m, 1H), 3.67-3.77 (m, 1H), 4.21-4.30 (m, 1H), 4.52 (t, J=11.8 Hz, 2H), 6.09 (tt, J=4.0, 52.8 Hz, 1H), 7.40-7.47 (m, 1H), 7.58 (dd, J=9.5, 10.0 Hz, 1H), 8.29 (d, J=8.5 Hz, 1H), 8.40 (s, 1H), 8.49 (dd, J=2.8, 8.8 Hz, 1H), 10.45 (s, 1H). MS (ES+) m/z 561.1 [M+H].

N-(6-43aR,4R,8S)-6-Amino-4,7,7-trimethyl-8-oxido-3,3a,4,7-tetrahydro-2H-isothiazolo[1,5-a][1,4]-thiazin-4-yl)-5-fluoropyridin-2-yl)-5-(2,2,3,3-tetrafluoropropoxy)picolinamide (15BA)

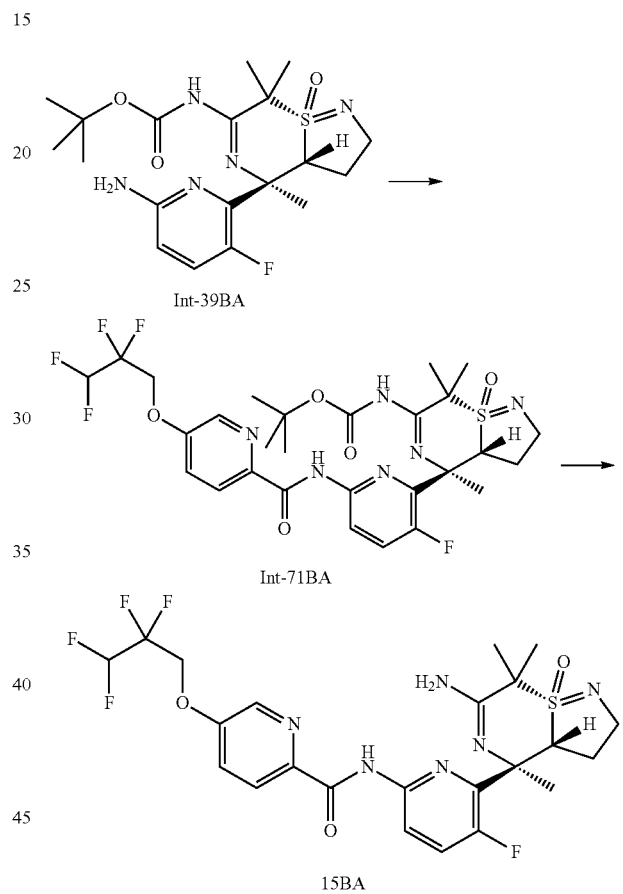

Step 1: tert-Butyl ((3aR,4R,8S)-4-(3-fluoro-6-(5-(2,2,3,3-tetrafluoropropoxy)picolinamido)-pyridin-2-yl)-4,7,7-trimethyl-8-oxido-3,3a,4,7-tetrahydro-2H-isothiazolo[1,5-a][1,4]thiazin-6-yl)carbamate (Int-71BA)

To a solution of tert-butyl ((3aR,4R,8S)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39BA, 150 mg, 0.35 mmol) in THF (20 mL) was added 5-(2,2,3,3-tetrafluoropropoxy)picolinic acid (134 mg, 0.53 mmol) followed by T3P (1.1 g, 1.75 mmol, 50% in ethyl acetate), and diisopropylethylamine (267 mg, 2.1 mmol). The reaction was stirred at 70° C. for 16 h. After that, the reaction mixture was diluted with aqueous saturated sodium hydrogencarbonate solution (20 mL) and extracted with ethyl acetate (2×10 mL). The combined organic layers were dried over sodium sulfate, filtered and concentrated to give a crude product. The crude was purified by column chromatography (silica gel, eluting with petroleum ether/ethyl acetate 1:1) to yield, after drying in vacuo, the title compound as a yellow solid (100 mg, 43% yield). MS (ES+) m/z 661.2 [M+H].

Step 2: N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide (15BA)

tert-Butyl ((3aR,4R,8S)-4-(3-fluoro-6-(5-(2,2,3,3-tetrafluoropropoxy)picolinamido)pyridin-2-yl)-4,7,7-trimethyl-8-oxido-3,3a,4,7-tetrahydro-2H-isothiazolo[1,5-a][1,4]thiazin-6-yl)carbamate (Int-71BA, 100 mg, 0.16 mmol) was dissolved in acetonitrile (15 mL) and dichloromethane (8 mL). Then, zinc dibromide (111 mg, 0.5 mmol) was added and the resulting solution was stirred for 18 h at 35° C. The reaction mixture was diluted with saturated aqueous sodium hydrogencarbonate solution (20 mL), extracted with dichloromethane (2×20 mL). The combined extracts were dried over sodium sulfate, filtered and concentrated to give a crude product. The crude was purified by preparative HPLC (C18, eluting with 0.05% ammonia/acetonitrile), followed by preparative TLC (dichloromethane/methanol 10:1, UV) to give the title compound as a white solid (19.6 mg, 23% yield). $^1$H NMR (CDCl$_3$, 400 MHz): δ 1.00 (s, 3H), 1.85 (2s, 6H), 2.17-2.30 (m, 1H), 2.60-2.71 (m, 1H), 3.74-3.89 (m, 2H), 4.52 (t, J=11.8 Hz, 2H), 5.23 (dd, J=7.2, 11.4 Hz, 1H), 6.08 (tt, J=4.3, 52.9 Hz, 1H), 7.43 (dd, J=2.8, 8.8 Hz, 1H), 7.60 (dd, J=9.3, 9.8 Hz, 1H), 8.29 (d, J=8.8 Hz, 1H), 8.41 (d, J=2.8 Hz, 1H), 8.51 (dd, J=2.7, 8.9 Hz, 1H), 10.36 (s, 1H). MS (ES+) m/z 561.1 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide (16AB)

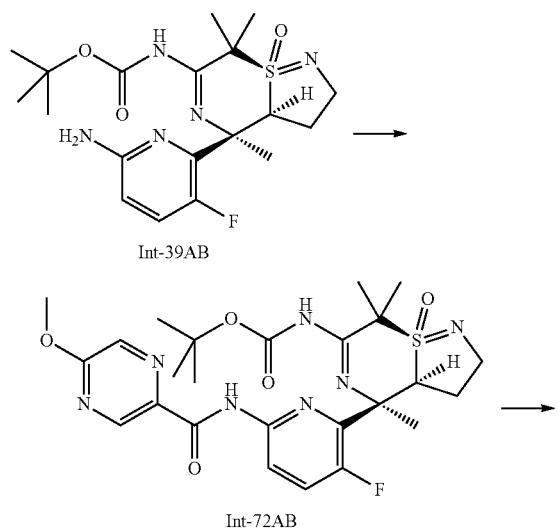

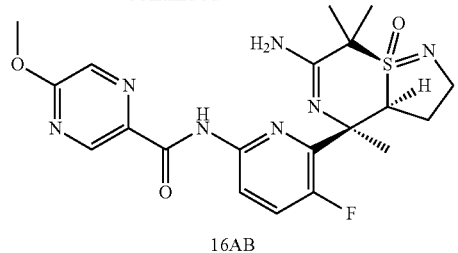

16AB

Step 1: tert-Butyl ((3aS,4R,8R)-4-(3-fluoro-6-(5-methoxypyrazine-2-carboxamido)pyridin-2-yl)-4,7,7-trimethyl-8-oxido-3,3a,4,7-tetrahydro-2H-isothiazolo[1,5-a][1,4]thiazin-6-yl)carbamate (Int-72AB)

To a solution of tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 150 mg, 0.35 mmol) in THF (20 mL) was added 5-methoxypyrazine-2-carboxylic acid (90 mg, 0.53 mmol) followed by T3P (1.1 g, 1.75 mmol, 50% in ethyl acetate), and diisopropylethylamine (267 mg, 2.1 mmol). The reaction was stirred at 70° C. for 4 h. After that, the reaction mixture was diluted with aqueous saturated sodium hydrogencarbonate solution (20 mL) and extracted with ethyl acetate (3×30 mL). The combined organic layers were dried over sodium sulfate, filtered and concentrated to give a crude product. The crude was purified by preparative TLC (silica gel, dichloromethane/ethyl acetate 1:1, UV) to yield, after drying in vacuo, the title compound as a yellow solid (100 mg, 50% yield). $^1$H NMR (CDCl$_3$, 400 MHz): δ 1.62-2.20 (m, 24H), 4.05-4.14 (m, 4H), 4.28 (dd, J=6.8, 10.4 Hz, 1H), 7.54-7.65 (m, 1H), 8.12 (s, 1H), 8.48 (dd, J=2.9, 8.9 Hz, 1H), 9.03 (s, 1H), 10.37 (s, 1H), 12.60 (s, 1H). MS (ES+) m/z 562.2 [M+H].

Step 2: N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide (16AB)

tert-Butyl ((3aS,4R,8R)-4-(3-fluoro-6-(5-methoxypyrazine-2-carboxamido)pyridin-2-yl)-4,7,7-trimethyl-8-oxido-3,3a,4,7-tetrahydro-2H-isothiazolo[1,5-a][1,4]thiazin-6-yl)carbamate (Int-72AB, 100 mg, 0.17 mmol) was dissolved in acetonitrile (20 mL) and dichloromethane (1 mL). Zinc dibromide (100 mg, 0.45 mmol) was added and the solution was stirred for 16 h at 40° C. After that, the reaction mixture was diluted with saturated aqueous sodium hydrogencarbonate solution (20 mL), extracted with ethyl acetate (3×30 mL). The combined extracts were dried over sodium sulfate, filtered and concentrated to give a crude product. The crude was purified by preparative TLC (dichloromethane/methanol 10:1, UV) to give a yellow solid as product. The product was repurified by preparative HPLC (C18, eluting with 0.05% ammonia/acetonitrile), followed by lyophilization to give the title compound as a white solid (23 mg, 28% yield). $^1$H NMR (CDCl$_3$, 400 MHz): δ 1.65-1.78 (m, 1H), 1.81 (s, 3H), 1.93 (s, 3H), 2.04-2.13 (m, 1H), 2.06 (s, 3H), 3.52 (dd, J=7.7, 10.7 Hz, 1H), 3.71 (ddd, J=5.0, 10.5, 10.5 Hz, 1H), 4.09 (s, 3H), 4.25 (ddd, J=2.0, 6.8, 12.1 Hz, 1H), 7.59 (dd, J=8.9, 10.4 Hz, 1H), 8.23 (d, J=1.3 Hz, 1H), 8.48 (dd, J=3.1, 8.9 Hz, 1H), 9.03 (d, J=1.2 Hz, 1H), 10.19 (s, 1H). MS (ES+) m/z 462.2 [M+H].

N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide (16BA)

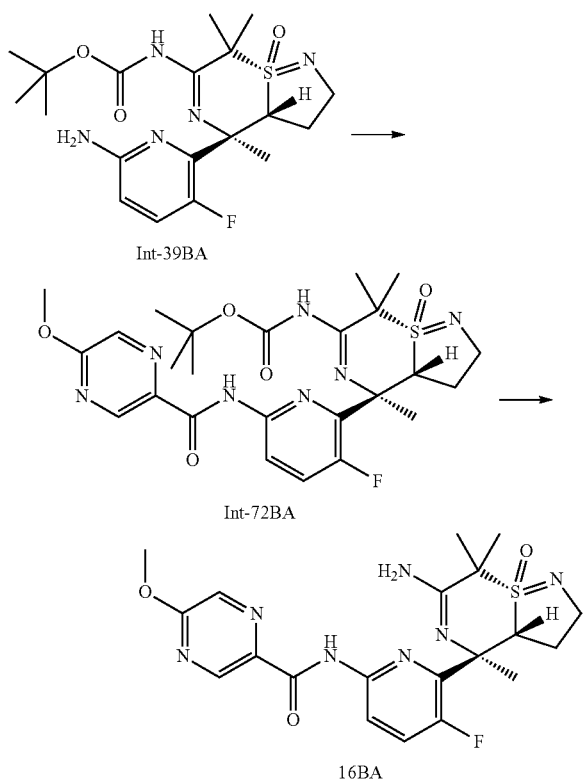

Step 1: tert-Butyl ((3aR,4R,8S)-4-(3-fluoro-6-(5-methoxypyrazine-2-carboxamido)pyridin-2-yl)-4,7,7-trimethyl-8-oxido-3,3a,4,7-tetrahydro-2H-isothiazolo[1,5-a][1,4]thiazin-6-yl)carbamate (Int-72BA)

To a solution of tert-butyl ((3aR,4R,8S)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39BA, 150 mg, 0.35 mmol) in THF (20 mL) was added 5-methoxypyrazine-2-carboxylic acid (90 mg, 0.53 mmol) followed by T3P (1.1 g, 1.75 mmol, 50% in ethyl acetate), and diisopropylethylamine (267 mg, 2.1 mmol). The reaction was stirred at 70° C. for 4 h. After that, the reaction mixture was diluted with aqueous saturated sodium hydrogencarbonate solution (20 mL) and extracted with ethyl acetate (3×30 mL). The combined organic layers were dried over sodium sulfate, filtered and concentrated to give a crude product. The crude was purified by preparative TLC (silica gel, dichloromethane/ethyl acetate 1:1, UV) to yield, after drying in vacuo, the title compound as a yellow solid (100 mg, 50% yield). $^1$H NMR (CDCl$_3$, 400 MHz): δ 0.87 (s, 3H), 1.52-1.60 (m, 9H), 1.73 (2s, 6H), 2.09-2.21 (m, 1H), 2.54-2.62 (m, 1H), 3.72-3.87 (m, 2H), 4.08 (s, 3H), 5.19 (dd, J=7.2, 10.9 Hz, 1H), 7.48-7.60 (m, 1H), 8.21 (d, J=1.4 Hz, 1H), 8.47 (dd, J=3.0, 8.9 Hz, 1H), 9.02 (d, J=1.3 Hz, 1H), 10.04 (s, 1H), 11.02 (s, 1H). MS (ES+) m/z 562.2 [M+H].

Step 2: N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide (16BA)

tert-Butyl ((3aR,4R,8S)-4-(3-fluoro-6-(5-methoxypyrazine-2-carboxamido)pyridin-2-yl)-4,7,7-trimethyl-8-oxido-3,3a,4,7-tetrahydro-2H-isothiazolo[1,5-a][1,4]thiazin-6-yl)carbamate (Int-72BA, 100 mg, 0.17 mmol) was dissolved in acetonitrile (20 mL) and dichloromethane (1 mL). Zinc dibromide (100 mg, 0.45 mmol) was added and the solution was stirred for 16 h at 40° C. After that, the reaction mixture was diluted with saturated aqueous sodium hydrogencarbonate solution (20 mL), extracted with ethyl acetate (3×30 mL). The combined extracts were dried over sodium sulfate, filtered and concentrated to give a crude product. The crude was purified by preparative TLC (dichloromethane/methanol 10:1, UV) to give a yellow solid as product. The product was repurified by preparative HPLC (C18, eluting with 0.05% ammonia/acetonitrile), followed by lyophilization to give the title compound as a white solid (15 mg, 18% yield). $^1$H NMR (CDCl$_3$, 400 MHz): δ 0.82 (s, 3H), 1.68 (s, 3H), 1.70 (s, 3H), 2.11-2.24 (m, 1H), 2.52-2.60 (m, 1H), 3.67-3.74 (m, 1H), 3.80 (ddd, J=4.7, 10.5, 10.5 Hz, 1H), 4.08 (s, 3H), 5.11 (dd, J=7.3, 11.3 Hz, 1H), 7.51 (dd, J=9.0, 10.3 Hz, 1H), 8.23 (d, J=1.0 Hz, 1H), 8.40 (dd, J=2.9, 8.9 Hz, 1H), 9.02 (d, J=1.3 Hz, 1H), 10.06 (br s, 1H). MS (ES+) m/z 462.2 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide (25AB)

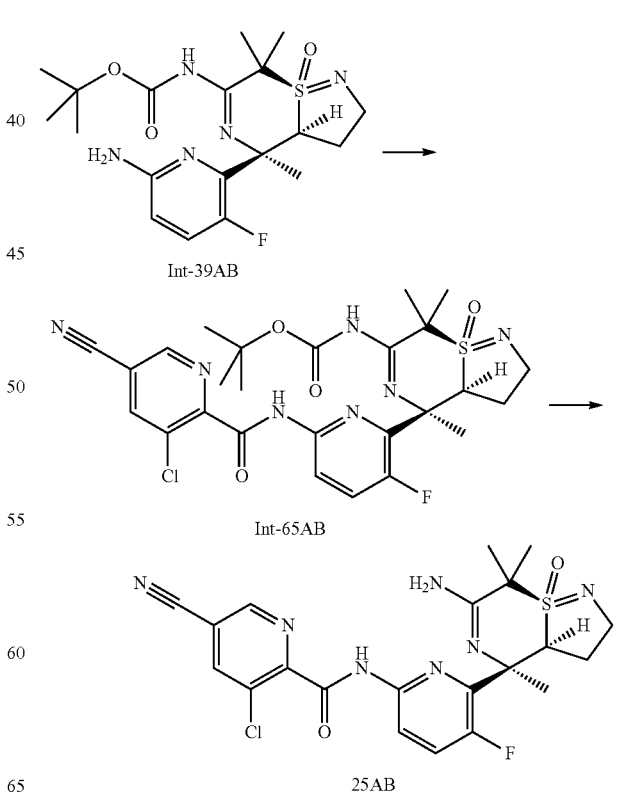

Step 1: tert-Butyl ((3aS,4R,8R)-4-(6-(3-chloro-5-cyanopicolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-65AB)

To a solution of tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 150.0 mg, 0.35 mmol) in THF (15 mL) was added 5-cyano-3-chloropicolinic acid (96.5 mg, 0.53 mmol), followed by T3P (1.1 g, 1.75 mmol, 50% in ethyl acetate), and diisopropylethylamine (266.7 mg, 2.1 mmol). The reaction was stirred at 70° C. for 16 h. After that, the reaction mixture was diluted with aqueous saturated sodium hydrogencarbonate solution (20 mL) and extracted with ethyl acetate (2×10 mL). The combined organic layers were dried over sodium sulfate, filtered and concentrated to give a crude product. The crude was purified by column chromatography (silica gel, eluting with ethyl acetate/petroleum ether 1:1) to yield, after drying in vacuo, the title compound as a yellow solid (105 mg, 50% yield). $^1$H NMR (CDCl$_3$, 400 MHz): δ 1.61-1.70 (m, 10H), 1.87 (s, 3H), 1.98 (s, 3H), 2.10-2.31 (m, 1H), 2.15 (s, 3H), 3.50-3.60 (m, 1H), 3.66-3.76 (m, 1H), 4.28-4.35 (m, 1H), 7.59-7.68 (m, 1H), 8.23 (s, 1H), 8.49-8.56 (m, 1H), 8.73-8.78 (m, 1H), 10.40-10.57 (m, 1H), 12.41-12.62 (m, 1H). MS (ES+) m/z 590.2 [M+H].

Step 2: N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide (25AB)

tert-Butyl ((3aS,4R,8R)-4-(6-(3-chloro-5-cyanopicolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-65AB, 100 mg, 0.17 mmol) was dissolved in dichloromethane (10 mL) and trifluoroacetic acid (194 mg, 1.7 mmol) was added. The solution was stirred for 4 h at room temperature. The reaction mixture was basified with saturated aqueous sodium hydrogencarbonate solution to pH=7-8, extracted with dichloromethane (2×10 mL). The combined extracts were dried over sodium sulfate, filtered and concentrated to give a crude product. The crude was purified by preparative TLC (dichloromethane/methanol 10:1, UV) to give a product. The product was repurified by preparative HPLC (C18, eluting with 0.05% ammonia/acetonitrile), followed by lyophilization to give the title compound as a white solid (18 mg, 22% yield). $^1$H NMR (CDCl$_3$, 400 MHz): δ 1.51-1.67 (m, 1H), 1.79 (s, 3H), 2.07 (s, 3H), 2.17-2.26 (m, 1H), 2.19 (s, 3H), 3.56-3.64 (m, 1H), 3.67-3.77 (m, 1H), 4.31-4.40 (m, 1H), 7.68 (dd, J=9.5, 9.5 Hz, 1H), 8.13 (s, 1H), 8.57 (dd, J=2.8, 9.0 Hz, 1H), 8.87 (d, J=1.3 Hz, 1H), 11.46 (s, 1H). MS (ES+) m/z 490.2 [M+H].

N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide (25BA)

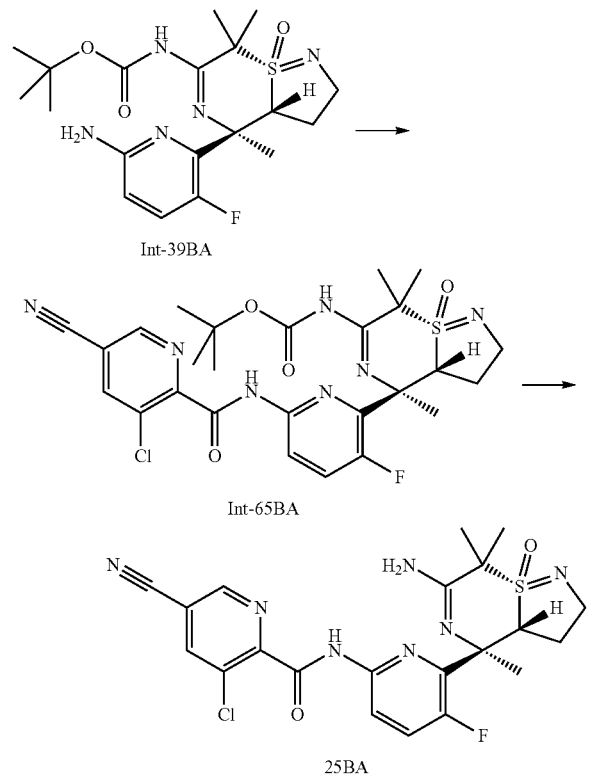

Step 1: tert-Butyl ((3aR,4R,8S)-4-(6-(3-chloro-5-cyanopicolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-65BA)

To a solution of tert-butyl ((3aR,4R,8S)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39BA, 150.0 mg, 0.35 mmol) in THF (20 mL) was added 5-cyano-3-chloropicolinic acid (96.5 mg, 0.53 mmol), followed by T3P (1.1 g, 1.75 mmol, 50% in ethyl acetate), and diisopropylethylamine (222.2 mg, 1.75 mmol). The reaction was stirred at 70° C. for 16 h. After that, the reaction mixture was diluted with aqueous saturated sodium hydrogencarbonate solution (20 mL) and extracted with ethyl acetate (2×10 mL). The combined organic layers were dried over sodium sulfate, filtered and concentrated to give a crude product. The crude was purified by column chromatography (silica gel, eluting with ethyl acetate/petroleum ether 1:1) to yield, after drying in vacuo, the title compound as a yellow solid (100 mg, 50% yield). $^1$H NMR (CDCl$_3$, 400 MHz): δ 0.84 (s, 3H), 1.54 (s, 9H), 1.73 (2s, 6H), 2.09-2.22 (m, 1H), 2.48-2.64 (m, 1H), 3.70-3.88 (m, 2H), 5.11-5.21 (m, 1H), 7.52-7.64 (m, 1H), 8.11-8.23 (m, 1H), 8.37-8.52 (m, 1H), 8.72-8.91 (m, 1H), 10.03-10.26 (m, 1H), 10.88-11.12 (m, 1H). MS (ES+) m/z 590.2 [M+H].

Step 2: N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide (25BA)

tert-Butyl ((3aR,4R,8S)-4-(6-(3-chloro-5-cyanopicolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-65BA, 100 mg, 0.17 mmol) was dissolved in acetonitrile (20 mL) and zinc dibromide (115 mg, 0.51 mmol) was added. Then, dichloromethane (6 mL) was added and the resulting solution was stirred for 18 h at 35° C. The reaction mixture was diluted with saturated aqueous sodium hydrogencarbonate solution (20 mL), extracted with dichloromethane (2×20 mL). The combined extracts were dried over sodium sulfate, filtered and concentrated to give a crude product. The crude was purified by preparative TLC (dichloromethane/methanol 10:1, UV) to give a product. The product was repurified by preparative HPLC (C18, eluting with 0.05% ammonia/acetonitrile), followed by lyophilization to give the title compound as a white solid (16 mg, 19% yield). $^1$H NMR (CDCl$_3$, 400 MHz): δ 0.96 (s, 3H), 1.83 (s, 3H), 1.84 (s, 3H), 2.17-2.29 (m, 1H), 2.59-2.69 (m, 1H), 3.73-3.86 (m, 2H), 5.10 (dd, J=7.1, 11.2 Hz, 1H), 7.63 (dd, J=9.4, 9.4 Hz, 1H), 8.20 (d, J=1.8 Hz, 1H), 8.49 (dd, J=2.9, 8.9 Hz, 1H), 8.88 (d, J=1.5 Hz, 1H), 10.25 (br s, 1H). MS (ES+) m/z 490.2 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide (26AB)

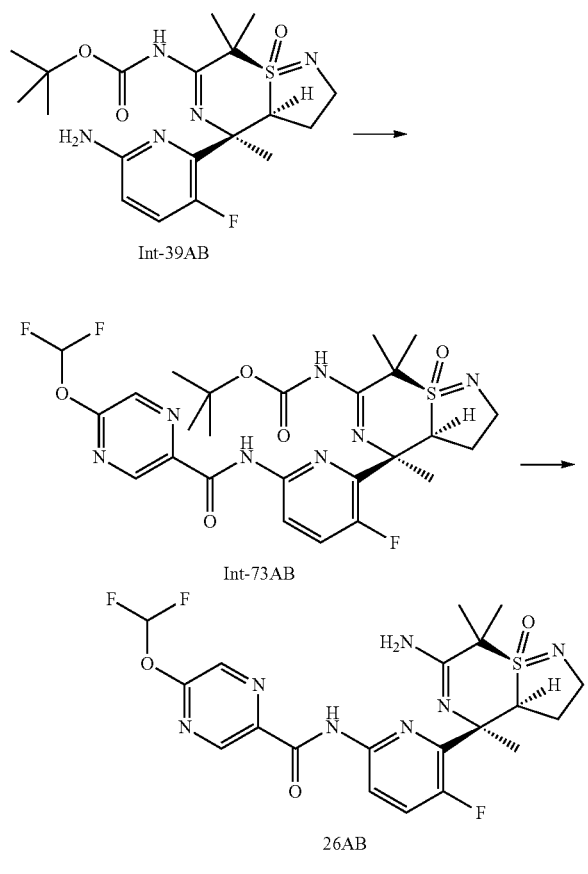

Int-39AB

Int-73AB

26AB

Step 1: tert-Butyl ((3aS,4R,8R)-4-(6-(5-(difluoromethoxy)pyrazine-2-carboxamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-73AB)

To a solution of tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 150 mg, 0.35 mmol) in THF (20 mL) was added 5-(difluoromethoxy)pyrazine-2-carboxylic acid (150 mg, 0.78 mmol), followed by T3P (1.1 g, 1.75 mmol, 50% in ethyl acetate), and diisopropylethylamine (267 mg, 2.1 mmol). The reaction was stirred at 70° C. for 4 h. After that, the reaction mixture was diluted with aqueous saturated sodium hydrogencarbonate solution (20 mL) and extracted with ethyl acetate (3×30 mL). The combined organic layers were dried over sodium sulfate, filtered and concentrated to give a crude product. The crude was purified by preparative TLC (silica gel, dichloromethane/ethyl acetate 1:1, UV) to yield, after drying in vacuo, the title compound as a yellow solid (0.1 g, 50% yield). MS (ES+) m/z 598.2 [M+H].

Step 2: N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide (26AB)

tert-Butyl ((3aS,4R,8R)-4-(6-(5-(difluoromethoxy)pyrazine-2-carboxamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-73AB, 100 mg, 0.18 mmol) was dissolved in acetonitrile (20 mL) and dichloromethane (1 mL). Then, zinc dibromide (100 mg, 0.45 mmol) was added and the resulting solution was stirred for 16 h at 40° C. The reaction mixture was diluted with saturated aqueous sodium hydrogencarbonate solution (20 mL), extracted with ethyl acetate (3×30 mL). The combined extracts were dried over sodium sulfate, filtered and concentrated to give a crude product. The crude was purified by preparative TLC (dichloromethane/methanol 10:1, UV) to give a product. The product was repurified by preparative HPLC (C18, eluting with 0.05% ammonia/acetonitrile), followed by lyophilization to give the title compound as a white solid (32 mg, 38% yield). $^1$H NMR (d6-DMSO, 400 MHz): δ 1.54-1.67 (m, 1H), 1.62 (s, 3H), 1.73 (s, 3H), 1.91 (s, 3H), 2.05-2.14 (m, 1H), 3.23-3.31 (m, 1H), 3.44-3.53 (m, 1H), 3.90-4.06 (m, 1H), 7.82 (t, J=71.3 Hz, 1H), 7.86-7.95 (m, 1H), 8.21-8.32 (m, 2H), 8.71-8.75 (m, 1H), 9.04 (d, J=1.3 Hz, 1H), 10.87 (br s, 1H). MS (ES+) m/z 498.2 [M+H].

N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide (26BA)

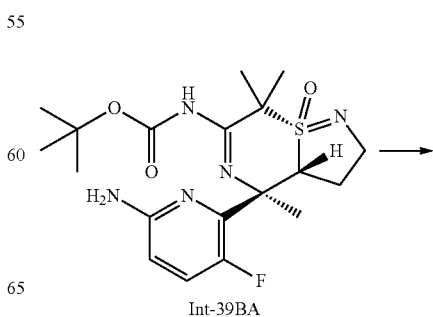

Int-39BA

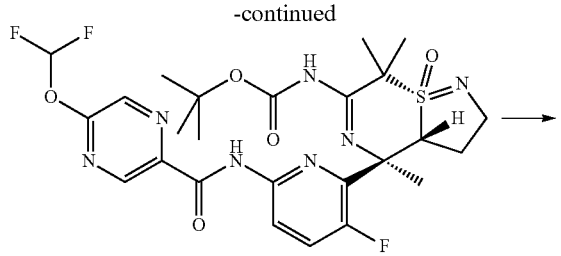

Int-73BA

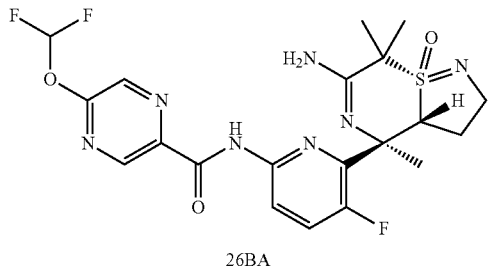

26BA

Step 1: tert-Butyl ((3aR,4R,8S)-4-(6-(5-(difluoromethoxy)pyrazine-2-carboxamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-73BA)

To a solution of tert-butyl ((3aR,4R,8S)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39BA, 150 mg, 0.35 mmol) in THF (20 mL) was added 5-(difluoromethoxy)pyrazine-2-carboxylic acid (150 mg, 0.53 mmol) followed by T3P (1.1 g, 1.75 mmol, 50% in ethyl acetate), and diisopropylethylamine (267 mg, 2.1 mmol). The reaction was stirred at 70° C. for 4 h. After that, the reaction mixture was diluted with aqueous saturated sodium hydrogencarbonate solution (20 mL) and extracted with ethyl acetate (3×30 mL). The combined organic layers were dried over sodium sulfate, filtered and concentrated to give a crude product. The crude was purified by preparative TLC (silica gel, dichloromethane/ethyl acetate 1:1, UV) to yield, after drying in vacuo, the title compound as a yellow solid (0.1 g, 50% yield). $^1$H NMR (CDCl$_3$, 400 MHz): δ 0.86 (s, 3H), 1.54 (s, 9H), 1.70-1.77 (m, 6H), 2.06-2.22 (m, 1H), 2.58 (ddd, J=5.7, 11.1, 11.1 Hz, 1H), 3.70-3.89 (m, 2H), 5.17 (dd, J=7.2, 11.2 Hz, 1H), 7.32-7.70 (m, 2H), 8.39 (d, J=1.3 Hz, 1H), 8.46 (dd, J=3.0, 8.9 Hz, 1H), 9.03-9.10 (m, 1H), 10.01 (s, 1H), 11.04 (br s, 1H). MS (ES+) m/z 598.2 [M+H].

Step 2: N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide (26BA)

tert-Butyl ((3aR,4R,8S)-4-(6-(5-(difluoromethoxy)pyrazine-2-carboxamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-73BA, 100 mg, 0.18 mmol) was dissolved in acetonitrile (20 mL) and dichloromethane (1 mL). Then, zinc dibromide (100 mg, 0.45 mmol) was added and the resulting solution was stirred for 16 h at 40° C. The reaction mixture was diluted with saturated aqueous sodium hydrogencarbonate solution (20 mL), extracted with ethyl acetate (3×30 mL). The combined extracts were dried over sodium sulfate, filtered and concentrated to give a crude product. The crude was purified by preparative TLC (dichloromethane/methanol 10:1, UV) to give the title compound as a white solid (33.0 mg, 38% yield). $^1$H NMR (CDCl$_3$, 400 MHz): δ 1.01 (s, 3H), 1.88 (2s, 6H), 2.17-2.31 (m, 1H), 2.60-2.71 (m, 1H), 3.74-3.89 (m, 2H), 5.19 (dd, J=7.2, 11.3 Hz, 1H), 7.52 (t, J=71.3 Hz, 1H), 7.66 (dd, J=9.4, 9.4 Hz, 1H), 8.42 (s, 1H), 8.49-8.55 (m, 1H), 9.09 (s, 1H), 10.06 (s, 1H). MS (ES+) m/z 498.3 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-fluoropicolinamide (27AB)

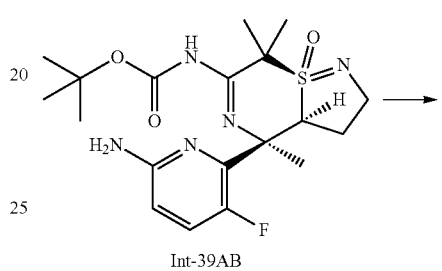

Int-39AB

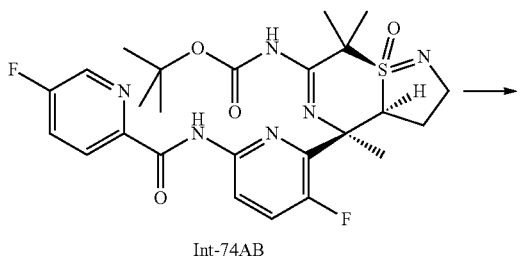

Int-74AB

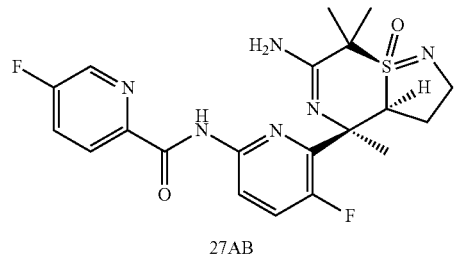

27AB

Step 1: tert-Butyl ((3aS,4R,8R)-4-(3-fluoro-6-(5-fluoropicolinamido)pyridin-2-yl)-4,7,7-trimethyl-8-oxido-3,3a,4,7-tetrahydro-2H-isothiazolo[1,5-a][1,4]thiazin-6-yl)carbamate (Int-74AB)

To a solution of tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 150.0 mg, 0.35 mmol) in THF (20 mL) was added 5-fluoropicolinic acid (80 mg, 0.53 mmol) followed by T3P (1.1 g, 1.75 mmol, 50% in ethyl acetate), and diisopropylethylamine (267 mg, 2.1 mmol). The reaction was stirred at 70° C. for 4 h. After that, the reaction mixture was diluted with aqueous saturated sodium hydrogencarbonate solution (20 mL) and extracted with ethyl acetate (3×30 mL). The combined organic layers were dried over sodium sulfate, filtered and concentrated to give a crude product. The crude was purified by preparative TLC (silica gel, dichloromethane/ethyl acetate 1:1, UV) to yield, after drying in vacuo, the title compound as a yellow solid (100 mg, 50% yield). ¹H NMR (CDCl₃, 400 MHz): δ 1.68 (s, 9H), 1.87 (s, 3H), 1.98 (s, 3H), 2.06-2.19 (m, 4H), 3.44-3.59 (m, 11H), 3.68 (d, J=13.2 Hz, 1H), 4.24-4.36 (m, 1H), 7.58-7.66 (m, 2H), 8.37 (dd, J=4.5, 8.7 Hz, 1H), 8.45 (d, J=2.6 Hz, 1H), 8.51 (dd, J=3.0, 8.9 Hz, 1H), 10.64 (s, 1H), 12.48-12.70 (m, 1H). MS (ES+) m/z 549.1 [M+H].

Step 2: N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-fluoropicolinamide (27AB)

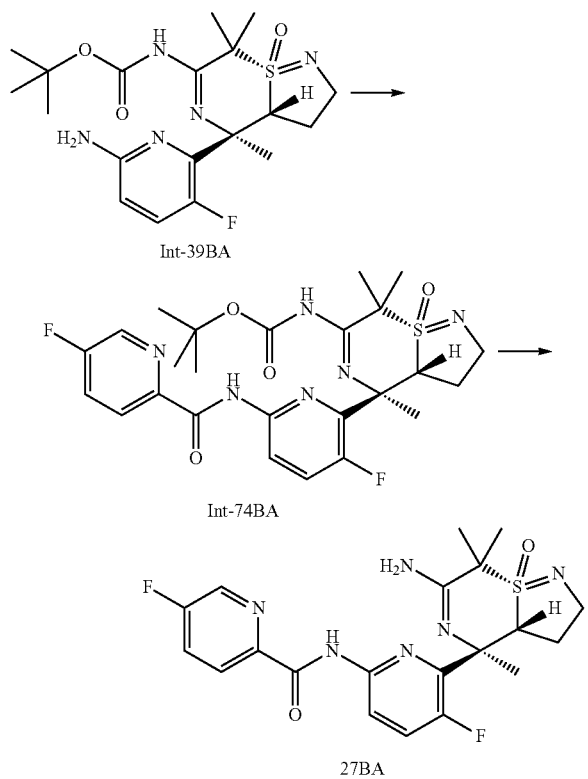

Step 1: tert-Butyl ((3aR,4R,8S)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-74BA)

To a solution of tert-butyl ((3aR,4R,8S)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39BA, 150 mg, 0.35 mmol) in THF (20 mL) was added 5-fluoropicolinic acid (80 mg, 0.53 mmol) followed by T3P (1.1 g, 1.75 mmol, 50% in ethyl acetate), and diisopropylethylamine (267 mg, 2.1 mmol). The reaction was stirred at 70° C. for 4 h. After that, the reaction mixture was diluted with aqueous saturated sodium hydrogencarbonate solution (20 mL) and extracted with ethyl acetate (3×30 mL). The combined organic layers were dried over sodium sulfate, filtered and concentrated to give a crude product. The crude was purified by preparative TLC (silica gel, dichloromethane/ethyl acetate 1:1, UV) to yield, after drying in vacuo, the title compound as a yellow solid (100 mg, 50% yield). ¹H NMR (CDCl₃, 400 MHz): δ 0.75-0.93 (m, 3H), 1.49-1.63 (m, 9H), 1.70-1.83 (m, 6H), 2.06-2.23 (m, 1H), 2.52-2.66 (m, 1H), 3.74-3.91 (m, 2H), 5.23 (dd, J=7.3, 11.2 Hz, 1H), 7.51-7.69 (m, 2H), 8.35 (dd, J=4.5, 8.7 Hz, 1H), 8.44-8.58 (m, 2H), 10.35 (s, 1H), 11.05 (s, 1H). MS (ES+) m/z 549.1 [M+H].

Step 2: N-(6-((3aR,4R,8S)-6-Amino-4,7,7-trimethyl-8-oxido-3,3a,4,7-tetrahydro-2H-isothiazolo[1,5-a][1,4]thiazin-4-yl)-5-fluoropyridin-2-yl)-5-fluoropicolinamide (27BA)

tert-Butyl ((3aR,4R,8S)-4-(3-fluoro-6-(5-fluoropicolinamido)pyridin-2-yl)-4,7,7-trimethyl-8-oxido-3,3a,4,7-tetrahydro-2H-isothiazolo[1,5-a][1,4]thiazin-6-yl)carbamate (Int-74BA, 100 mg, 0.18 mmol) was dissolved in acetonitrile (20 mL) and dichloromethane (1 mL). Zinc dibromide (100 mg, 0.45 mmol) was added and the solution was stirred for 16 h at 40° C. After that, the reaction mixture was diluted with saturated aqueous sodium hydrogencarbonate solution (20 mL), extracted with ethyl acetate (3×30 mL). The combined extracts were dried over sodium sulfate, filtered and concentrated to give a crude product. The crude was purified by preparative TLC (dichloromethane/methanol 10:1, UV) to give a yellow solid as product. The product was repurified by preparative HPLC (C18, eluting with 0.05% ammonia/acetonitrile), followed by lyophilization to give the title compound as a white solid (24 mg, 30% yield). ¹H NMR (CDCl₃, 400 MHz): δ 0.82 (s, 3H), 1.67 (s, 3H), 1.70 (s, 3H), 2.10-2.24 (m, 1H), 2.51-2.60 (m, 1H), 3.67-3.74 (m, 1H), 3.81 (ddd, J=4.8, 10.5, 10.5 Hz, 1H), 5.12 (dd, J=7.3, 11.3 Hz, 1H), 7.51 (dd, J=9.0, 10.3 Hz, 1H), 7.61 (ddd, J=2.8, 8.2, 8.2 Hz, 1H), 8.33 (dd, J=4.5, 8.8 Hz, 1H), 8.40 (dd, J=2.9, 8.9 Hz, 1H), 8.53 (d, J=2.5 Hz, 1H), 10.33 (s, 1H). MS (ES+) m/z 449.1 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-(difluoromethoxy)picolinamide (28AB)

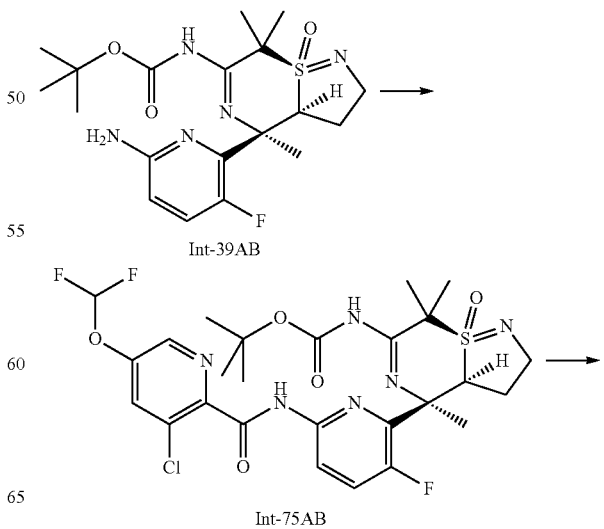

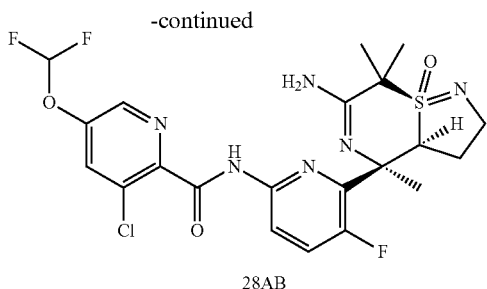

28AB

Step 1: tert-Butyl ((3aS,4R,8R)-4-(6-(3-chloro-5-(difluoromethoxy)picolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-75AB)

3-Chloro-5-(difluoromethoxy)picolinic acid (78 mg, 353 mol) was suspended in dichloromethane (3 mL), the suspension was cooled to 0-5° C. (ice bath) and oxalyl chloride (62 mg, 494 μmol) as well as dimethylformamide (0.242 M in toluene, 36 μL, 9 μmol) were added. The mixture was stirred for 2 h at room temperature. Then, it was concentrated in vacuo (40° C., 5 mbar) to afford 3-chloro-5-(difluoromethoxy)picolinoyl chloride as yellow oil (85 mg, quant.). After that, tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 100 mg, 235 μmol) was dissolved in dichloromethane (5 mL), the solution cooled to 0-5° C. (ice bath) and N,N-diisopropylethylamine (60.7 mg, 82.1 μL, 470 μmol) was added, followed by a solution of 3-chloro-5-(difluoromethoxy)picolinoyl chloride (vide supra, 85 mg, 353 μmol) in dichloromethane (3 mL). The reaction mixture was stirred for 15 min at 0-5° C., followed by 45 min at room temperature. Then, methanol (5 mL) was added, the mixture was stirred for 15 min at room temperature, and concentrated in vacuo. The crude was purified by column chromatography (silica gel, 12 g, eluting with ethyl acetate/n-heptane, gradient 20:80 to 100:0) to yield, after drying in vacuo (40° C., 5 mbar), the title compound as a light orange solid (90 mg, 61% yield). HPLC (method LCMS_fglm) $t_R$=1.36 min. MS (ES+) m/z 631.3 [M+H].

Step 2: N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-(difluoromethoxy)picolinamide (28AB)

tert-Butyl ((3aS,4R,8R)-4-(6-(3-chloro-5-(difluoromethoxy)picolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-75AB, 90 mg, 143 μmol) was dissolved in dichloromethane (10 mL) and trifluoroacetic acid (268 mg, 181 μL, 2.35 mmol) was added. The solution was stirred for 16 h at room temperature. After that, the mixture was cooled to 0-5° C. (ice bath), water (20 mL) and aqueous ammonia (2 M, 8 mL) was added cautiously upon stirring, until the pH of the aqueous layer was 11-12. After phase separation, the aqueous layer was extracted with dichloromethane (2×50 mL), the combined extracts were dried (sodium sulfate) and concentrated in vacuo. The residue was purified by column chromatography (silica gel, 24 g, eluting with 2 M ammonia in methanol/dichlormethane, gradient 2:98 to 6:94) to yield, after drying in vacuo (40° C., 5 mbar), the title compound as an off-white foam (70 mg). Enantiomeric purification was performed by chiral preparative HPLC (Chiralpak AD, 250*4.6 mm*5 μm, isocratic, n-heptane/(ethanol+0.01% ammonium acetate) 60/40, flow 1.0 mL/min) to yield the desired second eluting enantiomer as an off-white powder (48 mg, 62%), and the opposite first eluting enantiomer as an off white powder (12 mg, 15%). HPLC (method LCMS_gradient) $t_R$=1.4 min. ¹H NMR (CDCl₃, 300 MHz): δ 1.59-1.76 (m, 1H), 1.91 (s, 3H), 2.01 (s, 3H), 2.10-2.20 (m, 1H), 2.14 (s, 3H), 3.55 (dd, J=7.7, 10.7 Hz, 1H), 3.72 (ddd, J=5.1, 10.7, 10.7 Hz, 1H), 4.30 (ddd, J=1.9, 7.2, 12.2 Hz, 1H), 6.68 (t, J=71.3 Hz, 1H), 7.60 (dd, J=8.9, 10.3 Hz, 1 H), 7.69 (d, J=2.4 Hz, 1H), 8.11 (br s, 2H), 8.50 (d, J=2.4 Hz, 1H), 8.54 (dd, J=3.0, 8.9 Hz, 1H), 11.21 (s, 1H). MS (ES+) m/z 531.3 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-3,5-dichloropicolinamide (29AB)

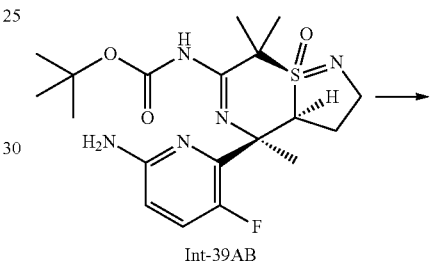

Int-39AB

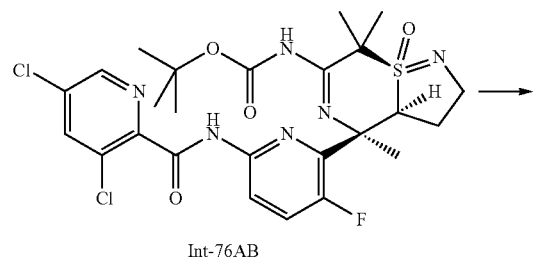

Int-76AB

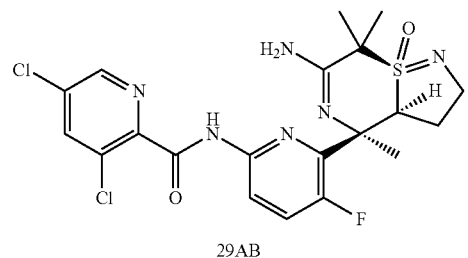

29AB

Step 1: tert-Butyl ((3aS,4R,8R)-4-(6-(3,5-dichloropicolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-76AB)

3,5-Dichloropicolinic acid (68 mg, 353 μmol) was suspended in dichloromethane (3 mL), the suspension was cooled to 0-5° C. (ice bath) and oxalyl chloride (62 mg, 494 μmol) as well as dimethylformamide (0.242 M in toluene, 36 pt, 9 μmol) were added. The mixture was stirred for 2 h at room temperature. Then, it was concentrated in vacuo (40° C., 5 mbar) to afford 3,5-dichloropicolinoyl chloride as light yellow oil (74 mg, quant.). After that, tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 100 mg, 235 μmol) was dissolved in dichloromethane (5 the solution cooled to 0-5° C. (ice bath) and N,N-diisopropylethylamine (61 mg, 82 μL, 470 μmol) was added, followed by a solution of 3,5-dichloropicolinoyl chloride (vide supra, 74 mg, 353 μmol) in dichloromethane (3 mL). The reaction mixture was stirred for 60 min at 0-5° C. Then, methanol (5 mL) was added, the mixture was stirred for 15 min at room temperature, and concentrated in vacuo. The crude was purified by column chromatography (silica gel, 24 g, eluting with ethyl acetate/n-heptane, gradient 20:80 to 100:0) to yield, after drying in vacuo (40° C., 5 mbar), the title compound as a light purple solid (75 mg, 53% yield). HPLC (method LCMS_fglm) $t_R$=1.41 min. MS (ES+) m/z 599.2 [M+H].

Step 2: N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-3,5-dichloropicolinamide (29AB)

tert-Butyl ((3aS,4R,8R)-4-(6-(3,5-dichloropicolinamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-76AB, 75 mg, 125 mol) was dissolved in dichloromethane (10 mL) and trifluoroacetic acid (268 mg, 181 μL, 2.35 mmol) was added. The solution was stirred for 16 h at room temperature. After that, the mixture was cooled to 0-5° C. (ice bath), water (20 mL) and aqueous ammonia (2 M, 8 mL) was added cautiously upon stirring, until the pH of the aqueous layer was 11-12. After phase separation, the aqueous layer was extracted with dichloromethane (2×50 mL), the combined extracts were dried (sodium sulfate) and concentrated in vacuo. The residue was purified by column chromatography (silica gel, 12 g, eluting with 2 M ammonia in methanol/dichlormethane, gradient 2:98 to 6:94) to yield, after drying in vacuo (40° C., 5 mbar), the title compound as an off-white foam (67 mg). Enantiomeric purification was performed by chiral preparative HPLC (Chiralpak AD, 250*4.6 mm*5 μm, isocratic, n-heptane/(ethanol+0.01% ammonium acetate) 70/30, flow 1.0 mL/min) to yield the desired second eluting enantiomer as an off-white powder (49 mg, 79%), and the opposite first eluting enantiomer as an off white powder (12 mg, 19%). HPLC (method LCMS_gradient) $t_R$=1.4 min. ¹H NMR (CDCl₃, 300 MHz): δ 1.59-1.78 (m, 1H), 1.89 (s, 3H), 1.99 (s, 3H), 2.08-2.19 (m, 1H), 2.12 (s, 3H), 3.54 (dd, J=7.8, 10.6 Hz, 1H), 3.72 (ddd, J=5.0, 10.6, 10.6 Hz, 1H), 4.29 (ddd, J=1.9, 7.2, 12.2 Hz, 1H), 5.83 (br s, 2H), 7.60 (dd, J=9.0, 10.2 Hz, 1H), 7.91 (d, J=2.0 Hz, 1H), 8.52 (dd, J=2.9, 9.0 Hz, 1H), 8.56 (d, J=2.0 Hz, 1H), 11.00 (s, 1H). MS (ES+) m/z 499.2 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-4-cyanobenzamide (30AB)

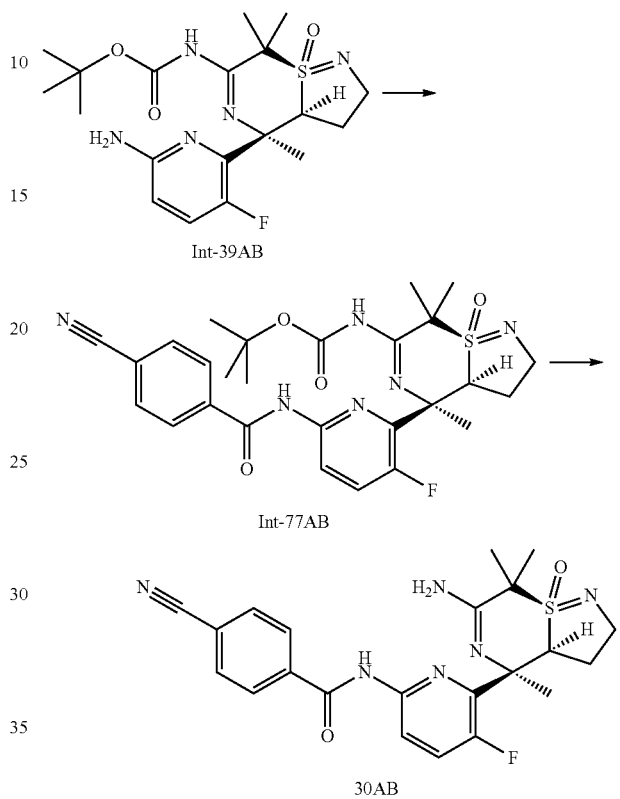

Step 1: tert-Butyl ((3aS,4R,8R)-4-(6-(4-cyanobenzamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-77AB)

To a solution of tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 100 mg, 0.23 mmol) in dichloromethane (2.3 mL) was added 4-cyanobenzoic acid (86.4 mg, 0.59 mmol), followed by T3P (0.70 mL, 1.2 mmol, 50% in ethyl acetate), and diisopropylethylamine (0.25 mL, 1.4 mmol). The reaction was stirred in a sealed vial at 60° C. for 20 h. After that, the reaction was stopped by addition of aqueous ammonia solution (25% m/m, 0.2 mL), and stirred for 1 h at room temperature. The mixture was diluted with aqueous sodium hydrogencarbonate solution (1 M, 20 mL) and extracted with dichloromethane (2×30 mL). The combined organic layers were dried over sodium sulfate, filtered and concentrated in vacuo to give a crude product. The crude was purified by column chromatography (silica gel, 12 g, eluting with ethyl acetate/n-heptane, gradient 20:80 to 100:0) to yield, after drying in vacuo (40° C., 5 mbar), the title compound as a yellow solid (0.033 g, 25% yield). MS (ES+) m/z 555 [M+H].

Step 2: N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-4-cyanobenzamide (30AB)

To a solution of tert-butyl ((3aS,4R,8R)-4-(6-(4-cyanobenzamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-77AB, 0.033 g, 0.060 mmol) in dichloromethane (0.6 mL) was added trifluoroacetic acid (0.092 mL, 1.19 mmol) at room temperature. The mixture was stirred for 15 h at room temperature. Then, it was concentrated in vacuo and the residue was purified by preparative HPLC (C18, eluting with water/acetonitrile/triethylamine) to give the title compound as an off-white solid (3 mg, 11% yield). $^1$H NMR (CDCl$_3$, 300 MHz): δ 1.55-1.73 (m, 1H), 1.99 (s, 3H), 2.09 (s, 3H), 2.15-2.28 (m, 1H), 2.20 (s, 3H), 3.55-3.65 (m, 1H), 3.67-3.79 (m, 1H), 4.34-4.44 (m, 1H), 7.66 (dd, J=9.2, 10.2 Hz, 1H), 7.77 (d, J=8.5 Hz, 2H), 8.23 (d, J=8.3 Hz, 2H), 8.57 (dd, J=3.2, 9.1 Hz, 1H), 11.10 (s, 1H). MS (ES+) m/z 455 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-2-chloro-4-cyanobenzamide (31AB)

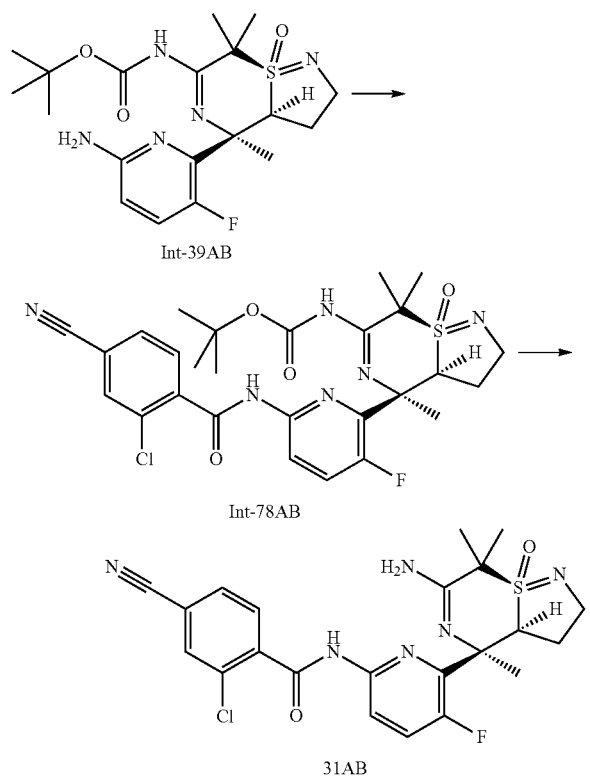

Int-39AB

Int-78AB

31AB

Step 1: tert-Butyl ((3aS,4R,8R)-4-(6-(2-chloro-4-cyanobenzamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-78AB)

To a solution of tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 100 mg, 0.23 mmol) in tetrahydrofuran (2.4 mL) was added 2-chloro-4-cyanobenzoic acid (107 mg, 0.59 mmol), followed by T3P (0.70 mL, 1.2 mmol, 50% in ethyl acetate), and diisopropylethylamine (0.25 mL, 1.4 mmol). The reaction was stirred in a sealed vial at 60° C. for 20 h. After that, the reaction was stopped by addition of aqueous ammonia solution (25% m/m, 0.2 mL), and stirred for 1 h at room temperature. The mixture was diluted with aqueous sodium hydrogencarbonate solution (1 M, 20 mL) and extracted with dichloromethane (2×30 mL). The combined organic layers were dried over sodium sulfate, filtered and concentrated in vacuo to give a crude product. The crude was purified by column chromatography (silica gel, 12 g, eluting with ethyl acetate/n-heptane, gradient 20:80 to 100:0) to yield, after drying in vacuo (40° C., 5 mbar), the title compound as a yellow solid (0.035 g, 25% yield). MS (ES+) m/z 589 [M+H].

Step 2: N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-2-chloro-4-cyanobenzamide (31AB)

To a solution tert-butyl ((3aS,4R,8R)-4-(6-(2-chloro-4-cyanobenzamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-78AB, 0.035 g, 0.059 mmol) in dichloromethane (0.6 mL) was added trifluoroacetic acid (0.092 mL, 1.19 mmol) at room temperature. The mixture was stirred for 15 h at room temperature. Then, it was concentrated in vacuo and the residue was purified by preparative HPLC (C18, eluting with water/acetonitrile/triethylamine) to give the title compound as an off-white solid (9 mg, 31% yield). $^1$H NMR (CDCl$_3$, 300 MHz): δ 1.52-1.70 (m, 1H), 1.94 (s, 3H), 2.05 (s, 3H), 2.17-2.29 (m, 1H), 2.19 (s, 3H), 3.60 (dd, J=7.7, 10.9 Hz, 1H), 3.74 (ddd, J=5.0, 10.7, 10.7 Hz, 1H), 4.40 (ddd, J=1.5, 7.2, 11.8 Hz, 1H), 7.60-7.71 (m, 3H), 7.74-7.77 (m, 1H), 8.58 (dd, J=3.2, 9.0 Hz, 1H), 10.78 (s, 1H), 11.17 (s, 1H), 11.88 (br s, 1H). MS (ES+) m/z 489 [M+H].

N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide (32AA)

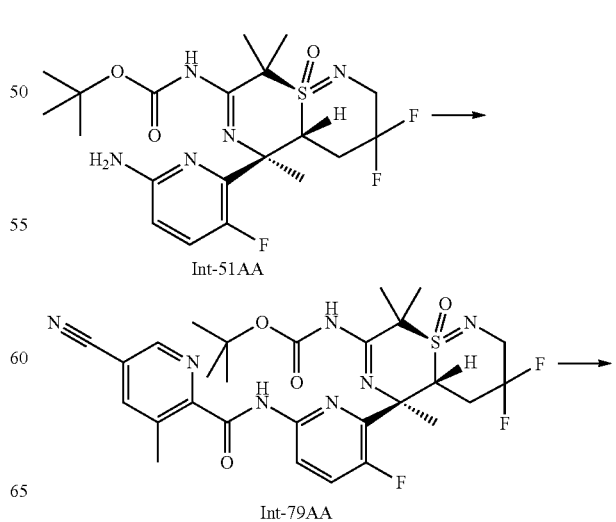

Int-51AA

Int-79AA

205

-continued

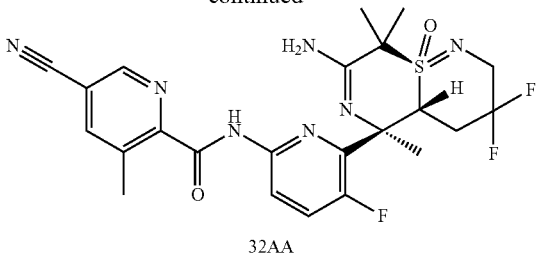

32AA

Step 1: tert-Butyl ((4aR,5R,9R)-5-(6-(5-cyano-3-methylpicolinamido)-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-79AA)

5-Cyano-3-methylpicolinic acid (195 mg, 1.2 mmol) was suspended in dichloromethane (4 mL), the suspension was cooled to 0-5° C. (ice bath) and oxalyl chloride (203 mg, 140 µL, 1.6 mmol) as well as a drop of a mixture of dimethylformamide and toluene (1:3, v/v) were added. The mixture was stirred for 1.75 h at room temperature. Then, it was concentrated in vacuo, the residue was treated with n-heptane (3 mL) and again concentrated and dried in vacuo (40° C., 5 mbar) to afford 5-cyano-3-methylpicolinoyl chloride as red oil (220 mg, 99%). After that, tert-butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AA, 70 mg, 147 µmol) was dissolved in dichloromethane (3 mL), the solution cooled to 0-5° C. (ice bath) and N,N-diisopropylethylamine (37.7 mg, 50 µL, 292 µmol) was added, followed by a solution of 5-cyano-3-methylpicolinoyl chloride (vide supra, 35 mg, 194 µmol) in dichloromethane (650 µL). The reaction mixture was stirred at 0-5° C. for 1.5 h. Then, ethanol (100 µL) was added, the mixture was stirred for 30 min at room temperature, and the mixture was poured into a saturated aqueous solution of sodium hydrogencarbonate (10 mL) and extracted with dichloromethane (1×40 mL, 2×20 mL). The combined extracts were dried (sodium sulfate) and concentrated in vacuo. The crude was purified by column chromatography (silica gel, 80 g, eluting with ethyl acetate/n-heptane, gradient 20:80 to 40:60) to yield, after drying in vacuo (50° C., 5 mbar), the title compound as a white solid (90 mg, 99%). HPLC (method LCMS_gradient) $t_R$=3.4 min. $^1$H NMR (CDCl$_3$, 400 MHz): δ 1.49 (s, 9H), 1.81 (s, 3H), 1.83 (s, 3H), 1.95 (s, 3H), 2.52-2.82 (m, 2H), 2.87 (s, 3H), 3.64-3.88 (m, 2H), 4.56-4.62 (m, 1H), 7.62 (dd, J=9.0, 10.6 Hz, 1H), 7.97-7.99 (m, 1H), 8.45 (dd, J=3.1, 9.0 Hz, 1H), 8.79-8.81 (m, 1H), 10.50 (s, 1H), 11.36 (s, 1H). MS (ES+) m/z 620.2 [M+H].

Step 2: N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide (32AA)

tert-Butyl ((4aR,5R,9R)-5-(6-(5-cyano-3-methylpicolinamido)-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)-carbamate (Int-79AA, 90 mg, 145 mol) was dissolved in dichloromethane (5 mL) and trifluoroacetic acid (1.33 g, 900 µL, 11.7 mmol) was added. The solution was stirred for 0.5 h at room temperature. After that, it was concentrated in vacuo (25° C., 5 mbar). The residue, a brown viscous oil, was dissolved in dichloromethane (40 mL), and saturated aqueous sodium hydrogencarbonate solution (15 mL) was added. After stirring for 5 min, phases were separated and the aqueous phase was extracted with dichloromethane (2×15 mL). The combined extracts were dried (sodium sulfate) and concentrated in vacuo. The residue was dissolved in dichloromethane (1 mL), MTBE (5 mL) was added and again concentrated in vacuo to give, after drying in vacuo (50° C., 5 mbar), an off white solid as crude product. The crude was purified by chiral preparative HPLC (Chiralpak AD, 250*4.6 mm*5 rpm, isocratic, n-heptane/(ethanol+0.01% ammonium acetate) 70/30, flow 1.0 mL/min) to yield the desired (−)-rotating enantiomer as a white solid (49.8 mg, 66%), and the opposite (+)-rotating enantiomer as a white solid (24.2 mg, 32%). For transfer purpose, the material was dissolved in dichloromethane (1 mL) and tert-butylmethyl ether (3 mL) and concentrated and dried in vacuo at 50° C./5 mbar. HPLC (method LCMS_gradient) $t_R$=1.7 min. $^1$H NMR (CDCl$_3$, 400 MHz): δ 1.89 (s, 3H), 1.91 (s, 3H), 1.96 (s, 3H), 2.22-2.39 (m, 1H), 2.57-2.79 (m, 1H), 2.87 (s, 3H), 3.57-3.85 (m, 2H), 4.07-4.15 (m, 1H), 7.09 (br s, 2H, exch), 7.56 (dd, J=9.0, 10.8 Hz, 1H), 7.97-8.00 (m, 1H), 8.43 (dd, J=3.0, 8.9 Hz, 1H), 8.79 (d, J=1.6 Hz, 1H), 10.46 (s, 1H). MS (ES+) m/z 520.1 [M+H].

N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoropicolinamide (33AA)

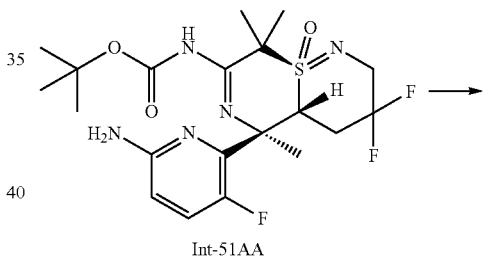

Int-51AA

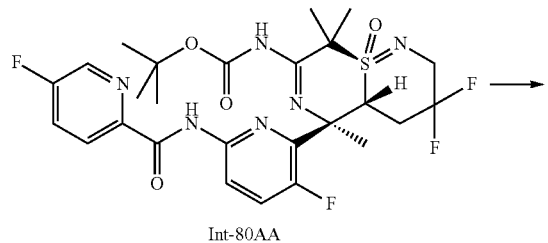

Int-80AA

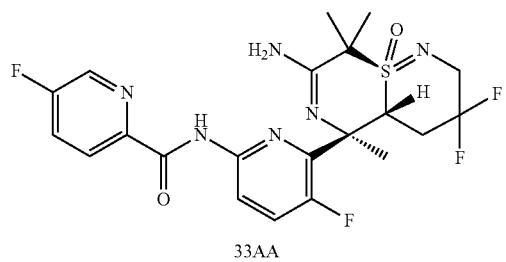

33AA

Step 1: tert-Butyl ((4aR,5R,9R)-3,3-difluoro-5-(3-fluoro-6-(5-fluoropicolinamido)pyridin-2-yl)-5,8,8-trimethyl-9-oxido-2,3,4,4a,5,8-hexahydro-[1,4]thiazino[2,1-f][1,2]thiazin-7-yl)carbamate (Int-80AA)

5-Fluoropicolinic acid (47.6 mg, 337 μmol) was suspended in dichloromethane (3 mL), the suspension was cooled to 0-5° C. (ice bath) and oxalyl chloride (56.9 mg, 39.3 μL, 449 gμmol) as well as a drop of a mixture of dimethylformamide and toluene (1:3, v/v) were added. The mixture was stirred for 2 h at room temperature. A second portion of oxalyl chloride (28.7 mg, 19.8 μL, 226 μmol) was added and the mixture was stirred for additional 1 h at room temperature to drive the reaction to completion. Then, it was concentrated in vacuo, the residue was treated with toluene (5 mL) and again concentrated and dried in vacuo (40° C., 5 mbar) to afford 5-fluoropicolinoyl chloride as red oil (52.1 mg, 97%). After that, tert-butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AA, 115 mg, 242 mol) was dissolved in dichloromethane (6 mL), the solution cooled to 0-5° C. (ice bath) and N,N-diisopropylethylamine (61.9 mg, 83.6 μL, 479 μmol) was added, followed by a solution of 5-fluoropicolinoyl chloride (vide supra, 52.1 mg, 326 μmol) in dichloromethane (5 mL). The reaction mixture was stirred for 15 min at 0-5° C., followed by 14 h at room temperature. Then, methanol (2 mL) was added, the mixture was stirred for 15 min at room temperature, and concentrated in vacuo. The crude was purified by column chromatography (silica gel, 12 g, eluting with ethyl acetate/n-heptane, gradient 20:80 to 35:65) to yield, after drying in vacuo (40° C., 5 mbar), the title compound as a white solid (100 mg, 69%). HPLC (method LCMS_gradient) $t_R$=3.4 min. MS (ES+) m/z 599.2 [M+H].

Step 2: N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoropicolinamide (33AA)

tert-Butyl ((4aR,5R,9R)-3,3-difluoro-5-(3-fluoro-6-(5-fluoropicolinamido)pyridin-2-yl)-5,8,8-trimethyl-9-oxido-2,3,4,4a,5,8-hexahydro-[1,4]thiazino[2,1-f][1,2]thiazin-7-yl)carbamate (Int-80AA, 99 mg, 165 μmol) was dissolved in dichloromethane (5 mL) and trifluoroacetic acid (378 mg, 254 μL, 3.30 mmol) was added. The solution was stirred for 4 h at room temperature. After that, the mixture was cooled to 0-5° C. (ice bath), and aqueous ammonia (8% m/m, 6 mL) was added cautiously upon stirring, until the pH of the aqueous layer was 11-12. After phase separation, the aqueous layer was extracted with dichloromethane (2×5 mL), the combined extracts were dried (sodium sulfate) and concentrated in vacuo. The residue was purified by column chromatography (silica gel, 20 g, eluting with 2 M ammonia in methanol/dichlormethane, gradient 0:100 to 10:90) to yield, after drying in vacuo (40° C., 5 mbar), the title compound as a white foam (80 mg, 96%). Enantiomeric purification was performed by chiral preparative HPLC (Chiralpak AD, 250*4.6 mm*5 μm, isocratic, n-heptane/(ethanol+0.01% ammonium acetate) 80/20, flow 1.0 mL/min) to yield the desired (−)-rotating enantiomer as a white solid (51 mg, 61%), and the opposite (+)-rotating enantiomer as a white solid (18.3 mg, 22%). For transfer purpose, the material was dissolved in dichloromethane (1 mL) and tert-butylmethyl ether (3 mL) and concentrated and dried in vacuo at 40° C./5 mbar. HPLC (method LCMS_gradient) $t_R$=1.7 min. $^1$H NMR (CDCl$_3$, 300 MHz): δ 1.80 (s, 3H), 1.85 (2s, 6H), 2.29-2.44 (m, 1H), 2.57-2.79 (m, 1H), 3.58-3.88 (m, 2H), 4.16-4.27 (m, 1H), 7.52 (dd, J=9.0, 10.8 Hz, 1H), 7.63 (ddd, J=2.6, 8.3, 8.3 Hz, 1H), 8.31-8.46 (m, 2H), 8.54 (d, J=2.6 Hz, 1H), 10.26 (s, 1H). MS (ES+) m/z 499.1 [M+H].

N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-cyanopicolinamide (34AA)

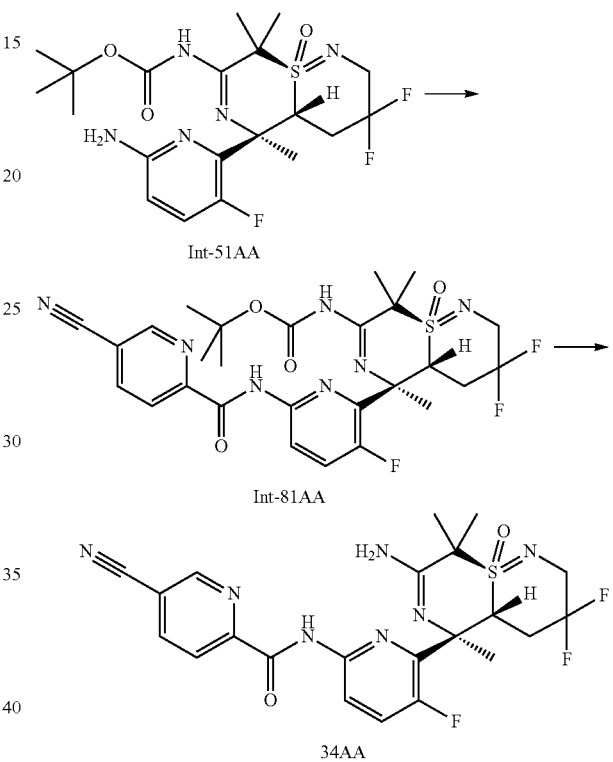

Step 1: tert-Butyl ((4aR,5R,9R)-5-(6-(5-cyanopicolinamido)-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-81AA)

5-Cyanopicolinic acid (60 mg, 405 μmol) was suspended in dichloromethane (3 mL), the suspension was cooled to 0-5° C. (ice bath) and oxalyl chloride (86.1 mg, 59.4 μL, 679 mol) as well as a drop of a mixture of dimethylformamide and toluene (1:3, v/v) were added. The mixture was stirred for 18 h at room temperature. Then, it was concentrated in vacuo, the residue was treated with toluene (5 mL) and again concentrated and dried in vacuo (40° C., 5 mbar) to afford 5-cyanopicolinoyl chloride as red oil (52 mg, 77%). After that, tert-butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AA, 110 mg, 231 μmol) was dissolved in dichloromethane (6 mL), the solution cooled to 0-5° C. (ice bath) and N,N-diisopropylethylamine (59.2 mg, 80 μL, 458 μmol) was added, followed by a solution of 5-fluoropicolinoyl chloride (vide supra, 52 mg, 312 μmol) in dichloromethane (5 mL).

The reaction mixture was stirred for 45 min at 0-5° C. Then, methanol (2 mL) was added, the mixture was stirred for 15 min at room temperature, and the mixture was concentrated in vacuo. The crude was purified by column chromatography (silica gel, 12 g, eluting with ethyl acetate/n-heptane, gradient 20:80 to 40:60) to yield, after drying in vacuo (40° C., 5 mbar), the title compound as a white solid (140 mg, 96%). HPLC (method LCMS_gradient) $t_R$=3.2 min. $^1$H NMR (CDCl$_3$, 300 MHz): δ 1.50 (s, 9H), 1.82 (s, 3H), 1.84 (s, 3H), 1.97 (s, 3H), 2.52-2.85 (m, 2H), 3.64-3.92 (m, 2H), 4.54-4.65 (m, 1H), 7.66 (dd, J=9.0, 10.6 Hz, 1H), 8.25 (dd, J=2.0, 8.3 Hz, 1H), 8.46 (dd, J=0.7, 8.2 Hz, 1H), 8.50 (dd, J=3.1, 9.0 Hz, 1H), 8.97-9.00 (m, 1H), 10.33 (s, 1H), 11.38 (s, 1H). MS (ES+) m/z 606.2 [M+H].

Step 2: N-(6-((4aR,5R,9R)-7-Amino-3,3-difluoro-5, 8,8-trimethyl-9-oxido-2,3,4,4a,5,8-hexahydro-[1,4] thiazino[2,1-f][1,2]thiazin-5-yl)-5-fluoropyridin-2-yl)-5-cyanopicolinamide (34AA)

tert-Butyl ((4aR,5R,9R)-5-(6-(5-cyanopicolinamido)-3-fluoropyridin-2-yl)-3,3-difluoro-5,8,8-trimethyl-9-oxido-2, 3,4,4a,5,8-hexahydro-[1,4]thiazino[2,1-f][1,2]thiazin-7-yl) carbamate (Int-81AA, 137 mg, 226 μmol) was dissolved in dichloromethane (5 mL) and trifluoroacetic acid (516 mg, 349 μL, 4.52 mmol) was added. The solution was stirred for 90 min at room temperature. After that, the mixture was cooled to 0-5° C. (ice bath), and aqueous ammonia (8% m/m, 8 mL) was added cautiously upon stirring, until the pH of the aqueous layer was 11-12. After phase separation, the aqueous layer was extracted with dichloromethane (2×5 mL), the combined extracts were dried (sodium sulfate) and concentrated in vacuo. The residue was purified by column chromatography (silica gel, 20 g, eluting with 2 M ammonia in methanol/dichlormethane, gradient 0:100 to 10:90) to yield, after drying in vacuo (40° C., 5 mbar), the title compound as a white solid (100 mg, 94%). Enantiomeric purification was performed by chiral preparative HPLC (Chiralpak AD, 250*4.6 mm*5 μm, isocratic, n-heptane/ (ethanol+0.01% ammonium acetate) 70/30, flow 1.0 mL/min) to yield the desired (–)-rotating enantiomer as a white solid (68 mg, 59%), and the opposite (+)-rotating enantiomer as a white solid (15 mg, 13%). For transfer purpose, the material was dissolved in dichloromethane (1 mL) and tert-butylmethyl ether (3 mL) and concentrated and dried in vacuo at 40° C./5 mbar. HPLC (method LCMS_gradient) $t_R$=1.7 min. $^1$H NMR (CDCl$_3$, 300 MHz): δ 1.83 (s, 3H), 1.88 (s, 3H), 1.89 (s, 3H), 2.26-2.41 (m, 1H), 2.57-2.80 (m, 1H), 3.58-3.78 (m, 2H), 4.11-4.21 (m, 1H), 5.55 (br s, 2H, exch), 7.56 (dd, J=8.9, 10.9 Hz, 1H), 8.24 (dd, J=2.0, 8.1 Hz, 1H), 8.40-8.48 (m, 2H), 8.95-9.00 (m, 1H), 10.29 (s, 1H). MS (ES+) m/z 506.1 [M+H].

N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide (35AA)

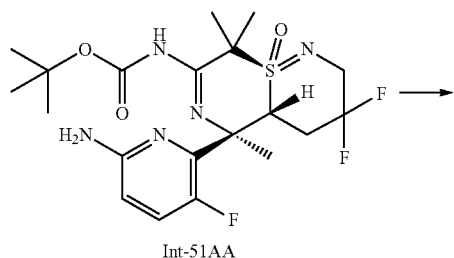

Int-51AA

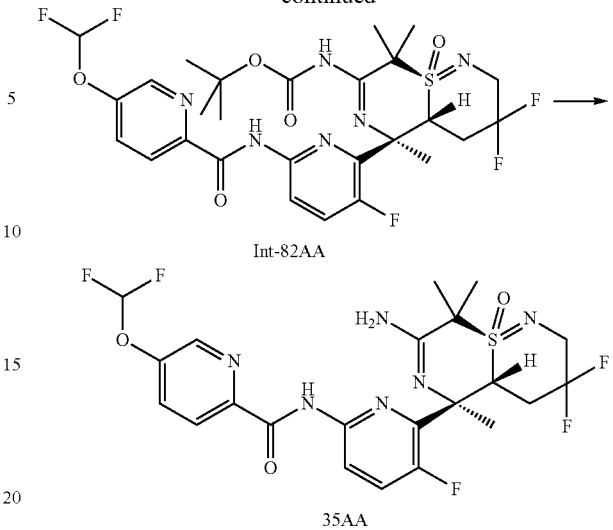

Int-82AA

35AA

Step 1: tert-Butyl ((4aR,5R,9R)-5-(6-(5-(difluoromethoxy)picolinamido)-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl) carbamate (Int-82AA)

5-(Difluoromethoxy)picolinic acid (76.6 mg, 405 mol) was suspended in dichloromethane (3 mL), the suspension was cooled to 0-5° C. (ice bath) and oxalyl chloride (68.4 mg, 47.2 μL, 539 mol) as well as dimethylformamide (0.25 M in toluene, 40.5 μL, 10 μmol) were added. The mixture was stirred for 17 h at room temperature. Then, it was concentrated in vacuo, the residue was treated with toluene (5 mL) and again concentrated and dried in vacuo (40° C., 5 mbar) to afford 5-(difluoromethoxy)picolinoyl chloride as green oil (72 mg, 86%). After that, tert-butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AA, 110 mg, 231 mol) was dissolved in dichloromethane (5 mL), the solution cooled to 0-5° C. (ice bath) and N,N-diisopropylethylamine (59.8 mg, 80.8 μL, 463 μmol) was added, followed by a solution of 5-(difluoromethoxy)picolinoyl chloride (vide supra, 72 mg, 347 μmol) in dichloromethane (3 mL). The reaction mixture was stirred for 45 min at 0-5° C. Then, methanol (5 mL) was added, the mixture was stirred for 15 min at room temperature, and concentrated in vacuo. The crude was purified by column chromatography (silica gel, 20 g, eluting with ethyl acetate/n-heptane, gradient 5:95 to 70:30) to yield, after drying in vacuo (40° C., 5 mbar), the title compound as a waxy solid (173 mg), which was used in the next step without further purification. HPLC (method LCMS_fglm) $t_R$=1.50 min. MS (ES+) m/z 647.5 [M+H].

Step 2: N-(6-((4aR,5R,9R)-7-Amino-3,3-difluoro-5, 8,8-trimethyl-9-oxido-2,3,4,4a,5,8-hexahydro-[1,4] thiazino[2,1-f][1,2]thiazin-5-yl)-5-fluoropyridin-2-yl)-5-(difluoromethoxy)-picolinamide (35AA)

tert-Butyl ((4aR,5R,9R)-5-(6-(5-(difluoromethoxy)picolinamido)-3-fluoropyridin-2-yl)-3,3-difluoro-5,8,8-trimethyl-9-oxido-2,3,4,4a,5,8-hexahydro-[1,4]thiazino[2,1-f] [1,2]thiazin-7-yl)carbamate (Int-82AA, 173 mg, see preceeding step, 231 μmol) was dissolved in dichloromethane (5 mL) and trifluoroacetic acid (528 mg, 356 μL, 4.63 mmol) was added. The solution was stirred for 17 h at room temperature. After that, the mixture was cooled to 0-5° C. (ice bath), and aqueous ammonia (8% m/m, 6 mL) was added cautiously upon stirring, until the pH of the aqueous layer was 11-12. After phase separation, the aqueous layer was extracted with dichloromethane (2×5 mL), the combined extracts were dried (sodium sulfate) and concentrated in vacuo. The residue was purified by column chromatography (silica gel, 12 g, eluting with 2 M ammonia in methanol/dichlormethane, gradient 0:100 to 10:90) to yield, after drying in vacuo (40° C., 5 mbar), the title compound as a white solid (121 mg). Enantiomeric purification was performed by chiral preparative HPLC (Chiralpak AD, 250*4.6 mm*5 m, isocratic, n-heptane/(ethanol+0.01% ammonium acetate) 80/20, flow 1.0 mL/min) to yield the desired (−)-rotating first eluting enantiomer as a white solid (66 mg, 52% over 2 steps), and the opposite (+)-rotating enantiomer as a white solid (22 mg, 17%). For transfer purpose, the material was dissolved in dichloromethane (1 mL) and tert-butylmethyl ether (3 mL) and concentrated and dried in vacuo at 40° C./5 mbar. HPLC (method LCMS_gradient) $t_R$=1.8 min. $^1$H NMR (CDCl$_3$, 300 MHz): δ 1.86 (s, 3H), 1.90 (2s, 6H), 2.27-2.42 (m, 1H), 2.56-2.80 (m, 1H), 3.58-3.86 (m, 2H), 4.11-4.21 (m, 1H), 5.41 (br s, 2H, exch), 6.67 (t, J=71.8 Hz, 1H), 7.54 (dd, J=9.1, 10.7 Hz, 1H), 7.70 (dd, J=2.5, 8.6 Hz, 1H), 8.34 (d, J=8.7 Hz, 1H), 8.43 (dd, J=3.0, 8.9 Hz, 1H), 8.55 (d, J=2.4 Hz, 1H), 10.29 (s, 1H). MS (ES+) m/z 547.1 [M+H].

N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide (36AA)

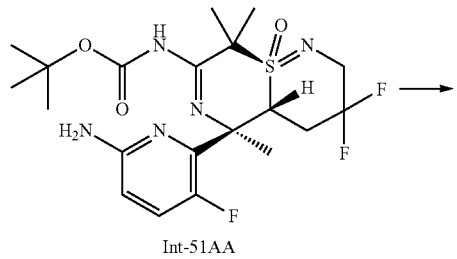
Int-51AA

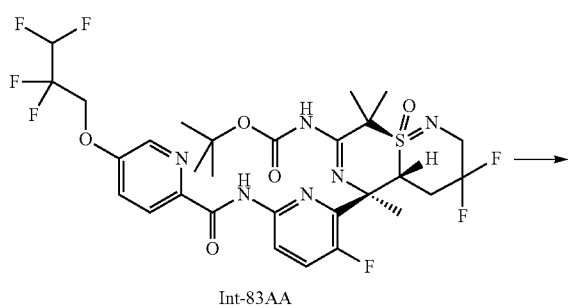
Int-83AA

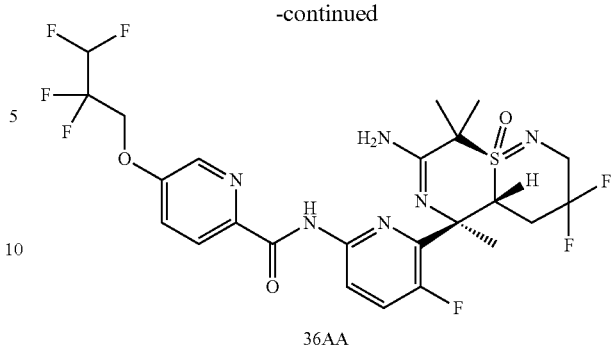
36AA

Step 1: tert-Butyl ((4aR,5R,9R)-3,3-difluoro-5-(3-fluoro-6-(5-(2,2,3,3-tetrafluoropropoxy)-picolinamido)pyridin-2-yl)-5,8,8-trimethyl-9-oxido-2,3,4,4a, 5,8-hexahydro-[1,4]thiazino[2,1-f][1,2]thiazin-7-yl) carbamate (Int-83AA)

5-(2,2,3,3-Tetrafluoropropoxy)picolinic acid (103 mg, 405 μmol) was suspended in dichloromethane (3 mL), the suspension was cooled to 0-5° C. (ice bath) and oxalyl chloride (68.4 mg, 47.2 μL, 539 μmol) as well as dimethylformamide (0.25 M in toluene, 40.5 μL, 10 mol) were added. The mixture was stirred for 15 h at room temperature. Then, it was concentrated in vacuo, the residue was treated with toluene (5 mL) and again concentrated and dried in vacuo (40° C., 5 mbar) to afford 5-(2,2,3,3-tetrafluoropropoxy)picolinoyl chloride as orange oil (94.2 mg, 86%). After that, tert-butyl ((4aR,5R,9R)-5-(6-amino-3-fluoropyridin-2-yl)-3,3-difluoro-5,8,8-trimethyl-9-oxido-2,3,4,4a, 5,8-hexahydro-[1,4]thiazino[2,1-f][1,2]thiazin-7-yl)carbamate (Int-51AA, 110 mg, 231 mol) was dissolved in dichloromethane (5 mL), the solution cooled to 0-5° C. (ice bath) and N,N-diisopropylethylamine (59.8 mg, 80.8 μL, 463 μmol) was added, followed by a solution of 5-(2,2,3,3-tetrafluoropropoxy)picolinoyl chloride (vide supra, 94.2 mg, 347 μmol) in dichloromethane (3 mL). The reaction mixture was stirred for 15 min at 0-5° C., followed by 90 min at room temperature. Then, methanol (5 mL) was added, the mixture was stirred for 15 min at room temperature, and concentrated in vacuo. The crude was purified by column chromatography (silica gel, 20 g, eluting with ethyl acetate/n-heptane, gradient 5:95 to 70:30) to yield, after drying in vacuo (40° C., 5 mbar), the title compound as a white foam (173 mg), which was used in the next step without further purification. HPLC (method LCMS_fglm) $t_R$=1.53 min. MS (ES+) m/z 711.3 [M+H].

Step 2: N-(6-((4aR,5R,9R)-7-Amino-3,3-difluoro-5, 8,8-trimethyl-9-oxido-2,3,4,4a,5,8-hexahydro-[1,4] thiazino[2,1-f][1,2]thiazin-5-yl)-5-fluoropyridin-2-yl)-5-(2,2,3,3-tetrafluoro-propoxy)picolinamide (36AA)

tert-Butyl ((4aR,5R,9R)-3,3-difluoro-5-(3-fluoro-6-(5-(2, 2,3,3-tetrafluoropropoxy)-picolinamido)pyridin-2-yl)-5,8,8-trimethyl-9-oxido-2,3,4,4a,5,8-hexahydro-[1,4]thiazino[2, 1-f][1,2]thiazin-7-yl)carbamate (Int-83AA, 173 mg, see preceeding step, 231 μmol) was dissolved in dichloromethane (5 mL) and trifluoroacetic acid (528 mg, 356 μL, 4.63 mmol) was added. The solution was stirred for 17 h at room temperature. After that, the mixture was cooled to 0-5° C. (ice bath), and aqueous ammonia (8% m/m, 6 mL) was added cautiously upon stirring, until the pH of the aqueous layer was 11-12. After phase separation, the aqueous layer was extracted with dichloromethane (2×5 mL), the combined extracts were dried (sodium sulfate) and concentrated in vacuo. The residue was purified by column chromatography (silica gel, 12 g, eluting with 2 M ammonia in methanol/dichlormethane, gradient 0:100 to 10:90) to yield, after drying in vacuo (40° C., 5 mbar) the title compound as a white solid (127 mg). Enantiomeric purification was performed by chiral preparative HPLC (Chiralpak AD, 250*4.6 mm*5 µm, isocratic, n-heptane/(ethanol+0.01% ammonium acetate) 80/20, flow 1.0 mL/min) to yield the desired (−)-rotating first eluting enantiomer as a white solid (85 mg, 60% over 2 steps), and the opposite (+)-rotating enantiomer as a white solid (26 mg, 18%). For transfer purpose, the material was dissolved in dichloromethane (1 mL) and tert-butylmethyl ether (3 mL) and concentrated and dried in vacuo at 40° C./5 mbar. HPLC (method LCMS_gradient) $t_R$=2.1 min. $^1$H NMR (CDCl$_3$, 300 MHz): δ 1.82 (s, 3H), 1.87 (2s, 6H), 2.28-2.44 (m, 1H), 2.56-2.80 (m, 1H), 3.57-3.88 (m, 2H), 4.02 (br s, 2H), 4.14-4.25 (m, 1H), 4.52 (t, J=11.8 Hz, 1H), 6.08 (tt, J=4.2, 53.1 Hz, 1H), 7.44 (dd, J=2.8, 8.7 Hz, 1H), 7.52 (dd, J=9.0, 10.8 Hz, 1H), 8.30 (d, J=8.7 Hz, 1H), 8.37-8.44 (m, 2H), 10.26 (s, 1H). MS (ES+) m/z 611.1 [M+H].

N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide (37AA)

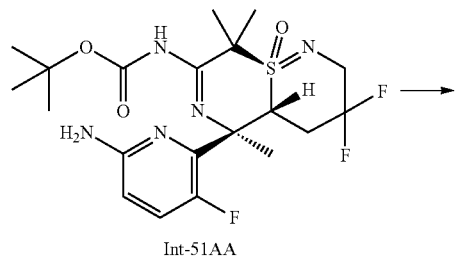

Int-51AA

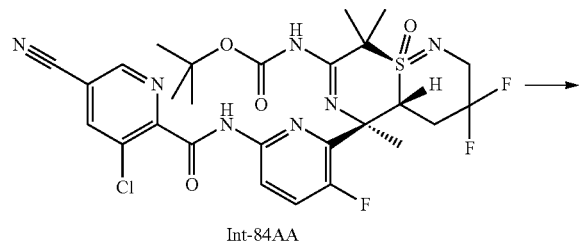

Int-84AA

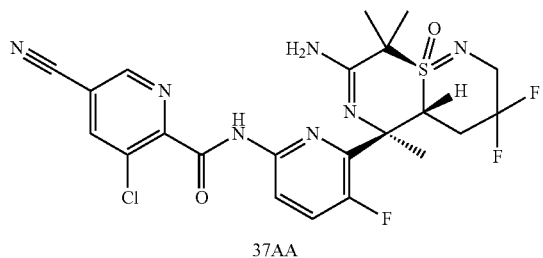

37AA

Step 1: tert-Butyl ((4aR,5R,9R)-5-(6-(3-chloro-5-cyanopicolinamido)-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-84AA)

3-Chloro-5-cyanopicolinic acid (73.9 mg, 405 µmol) was suspended in dichloromethane (3 mL), the suspension was cooled to 0-5° C. (ice bath) and oxalyl chloride (68.4 mg, 47.2 µL, 539 µmol) as well as dimethylformamide (0.25 M in toluene, 40.5 tµL, 10 µmol) were added. The mixture was stirred for 17 h at room temperature. Then, it was concentrated in vacuo, the residue was treated with toluene (5 mL) and again concentrated and dried in vacuo (40° C., 5 mbar) to afford 3-chloro-5-cyanopicolinoyl chloride as brown oil (69.7 mg, 86%). After that, tert-butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AA, 110 mg, 231 µmol) was dissolved in dichloromethane (5 mL), the solution cooled to 0-5° C. (ice bath) and N,N-diisopropylethylamine (59.8 mg, 80.8 µL, 463 mol) was added, followed by a solution of 3-chloro-5-cyanopicolinoyl chloride (vide supra, 69.7 mg, 347 gµmol) in dichloromethane (3 mL). The reaction mixture was stirred for 15 min at 0-5° C., followed by 90 min at room temperature. Then, methanol (5 mL) was added, the mixture was stirred for 15 min at room temperature, and concentrated in vacuo. The crude was purified by column chromatography (silica gel, 12 g, eluting with ethyl acetate/n-heptane, gradient 10:90 to 60:40) to yield, after drying in vacuo (40° C., 5 mbar), the title compound as a white solid (141 mg, 95%). HPLC (method LCMS_fglm) $t_R$=1.44 min. MS (ES+) m/z 640.1 [M+H].

Step 2: N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide (37AA)

tert-Butyl ((4aR,5R,9R)-5-(6-(3-chloro-5-cyanopicolinamido)-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-84AA, 141 mg, 220 µmol) was dissolved in dichloromethane (5 mL) and trifluoroacetic acid (528 mg, 356 µL, 4.63 mmol) was added. The solution was stirred for 17 h at room temperature. After that, the mixture was cooled to 0-5° C. (ice bath), and aqueous ammonia (8% m/m, 6 mL) was added cautiously upon stirring, until the pH of the aqueous layer was 11-12. After phase separation, the aqueous layer was extracted with dichloromethane (2×5 mL), the combined extracts were dried (sodium sulfate) and concentrated in vacuo. The residue was purified by column chromatography (silica gel, 12 g, eluting with 2 M ammonia in methanol/dichlormethane, gradient 0:100 to 10:90) to yield, after drying in vacuo (40° C., 5 mbar), the title compound as a white solid (110 mg). Enantiomeric purification was performed by chiral preparative HPLC (Chiralpak AD, 250*4.6 mm*5 µm, isocratic, n-heptane/(ethanol+0.01% ammonium acetate) 70/30, flow 1.0 mL/min) to yield the desired (−)-rotating first eluting enantiomer as a white solid (66 mg, 56%), and the opposite (+)-rotating enantiomer as a white solid (22 mg, 19%). For transfer purpose, the material was dissolved in dichloromethane (1 mL) and tert-butylmethyl ether (3 mL) and concentrated and dried in vacuo at 40° C./5 mbar. HPLC (method LCMS_gradient) $t_R$=1.7 min. $^1$H NMR (CDCl$_3$, 300 MHz): δ 1.83 (s, 3H), 1.86 (s, 3H), 1.87 (s, 3H), 2.27-2.42 (m, 1H), 2.56-2.79 (m, 1H), 3.58-3.87 (m, 2H), 4.12-4.22 (m, 1H), 4.67 (br s, 2H), 7.55 (dd, J=8.9, 10.7 Hz, 1H), 8.21 (d, J=1.6 Hz, 1H), 8.41 (dd, J=3.0, 8.9 Hz, 1H), 8.86 (d, J=1.8 Hz, 1H), 10.15 (s, 1H). MS (ES+) m/z 540.1 [M+H].

N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide (38AA)

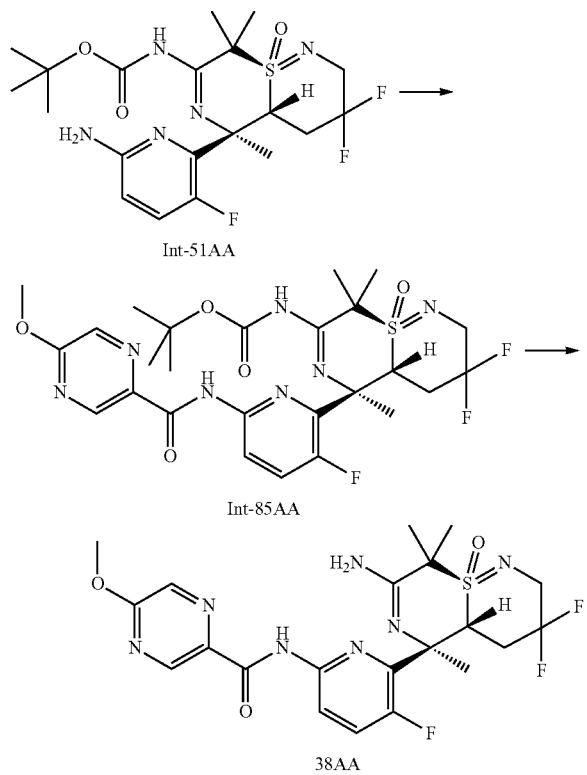

Step 1: tert-Butyl ((4aR,5R,9R)-3,3-difluoro-5-(3-fluoro-6-(5-methoxypyrazine-2-carboxamido)pyridin-2-yl)-5,8,8-trimethyl-9-oxido-2,3,4,4a,5,8-hexahydro-[1,4]thiazino[2,1-f][1,2]thiazin-7-yl)carbamate (Int-85AA)

5-Methoxypyrazine-2-carboxylic acid (62.4 mg, 405 µmol) was suspended in dichloromethane (3 mL), the suspension was cooled to 0-5° C. (ice bath) and oxalyl chloride (68.4 mg, 47.2 µL, 539 µmol) as well as dimethylformamide (0.25 M in toluene, 40.5 µL, 10 µmol) were added. The mixture was stirred for 17 h at room temperature. Then, it was concentrated in vacuo, the residue was treated with toluene (5 mL) and again concentrated and dried in vacuo (40° C., 5 mbar) to afford 5-methoxypyrazine-2-carbonyl chloride as brown oil (59.9 mg, 86%). After that, tert-butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AA, 110 mg, 231 µmol) was dissolved in dichloromethane (5 mL), the solution cooled to 0-5° C. (ice bath) and N,N-diisopropylethylamine (59.8 mg, 80.8 µL, 463 µmol) was added, followed by a solution of 5-methoxypyrazine-2-carbonyl chloride (vide supra, 59.9 mg, 347 µmol) in dichloromethane (3 mL). The reaction mixture was stirred for 15 min at 0-5° C., followed by 90 min at room temperature. Then, methanol (5 mL) was added, the mixture was stirred for 15 min at room temperature, and concentrated in vacuo. The crude was purified by column chromatography (silica gel, 12 g, eluting with ethyl acetate/n-heptane, gradient 10:90 to 70:30) to yield, after drying in vacuo (40° C., 5 mbar), the title compound as a white foam (131 mg, 93%). HPLC (method LCMS_fglm) t$_R$=1.49 min. MS (ES+) m/z 612.2 [M+H].

Step 2: N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide (38AA)

tert-Butyl ((4aR,5R,9R)-3,3-difluoro-5-(3-fluoro-6-(5-methoxypyrazine-2-carboxamido)pyridin-2-yl)-5,8,8-trimethyl-9-oxido-2,3,4,4a,5,8-hexahydro-[1,4]thiazino[2,1-f][1,2]thiazin-7-yl)carbamate (Int-85AA, 131 mg, 214 µmol) was dissolved in dichloromethane (5 mL) and trifluoroacetic acid (528 mg, 356 µL, 4.63 mmol) was added. The solution was stirred for 17 h at room temperature. After that, the mixture was cooled to 0-5° C. (ice bath), and aqueous ammonia (8% m/m, 6 mL) was added cautiously upon stirring, until the pH of the aqueous layer was 11-12. After phase separation, the aqueous layer was extracted with dichloromethane (2×5 mL), the combined extracts were dried (sodium sulfate) and concentrated in vacuo. The residue was purified by column chromatography (silica gel, 12 g, eluting with 2 M ammonia in methanol/dichlormethane, gradient 0:100 to 10:90) to yield, after drying in vacuo (40° C., 5 mbar), the title compound as a white solid (110 mg). Enantiomeric purification was performed by chiral preparative HPLC (Chiralpak AD, 250*4.6 mm*5 µm, isocratic, n-heptane/(ethanol+0.01% ammonium acetate) 80/20, flow 1.0 mL/min) to yield the desired (−)-rotating first eluting enantiomer as a white solid (75 mg, 68%), and the opposite (+)-rotating enantiomer as a white solid (20 mg, 18%). For transfer purpose, the material was dissolved in dichloromethane (1 mL) and tert-butylmethyl ether (3 mL) and concentrated and dried in vacuo at 50° C./5 mbar. HPLC (method LCMS_gradient) t$_R$=1.6 min. $^1$H NMR (CDCl$_3$, 300 MHz): δ 1.80 (s, 3H), 1.85 (2s, 6H), 2.28-2.43 (m, 1H), 2.55-2.79 (m, 1H), 3.57-3.87 (m, 2H), 4.09 (s, 3H), 4.11 (br s, 2H), 4.15-4.25 (m, 1H), 7.51 (dd, J=9.1, 10.9 Hz, 1H), 8.23 (d, J=1.2 Hz, 1H), 8.40 (dd, J=3.0, 8.9 Hz, 1H), 9.04 (d, J=1.2 Hz, 1H), 9.97 (s, 1H). MS (ES+) m/z 512.2 [M+H].

N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide (39AA)

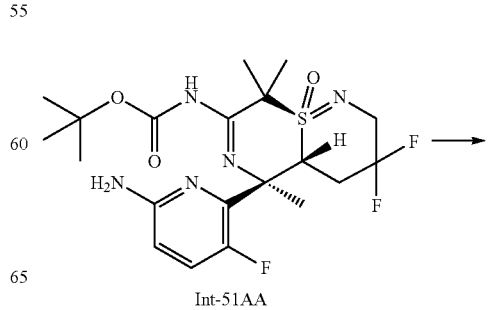

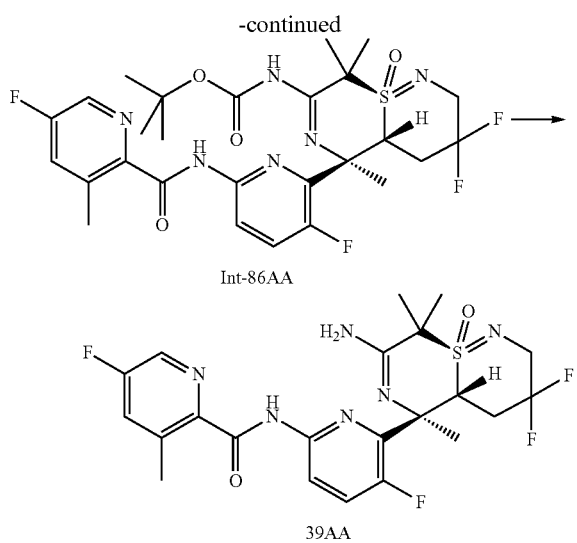

Step 1: tert-Butyl ((4aR,5R,9R)-3,3-difluoro-5-(3-fluoro-6-(5-fluoro-3-methylpicolinamido)-pyridin-2-yl)-5,8,8-trimethyl-9-oxido-2,3,4,4a,5,8-hexahydro-[1,4]thiazino[2,1-f][1,2]thiazin-7-yl)carbamate (Int-86AA)

5-Fluoro-3-methylpicolinic acid (57.4 mg, 370 μmol) was suspended in dichloromethane (3 mL), the suspension was cooled to 0-5° C. (ice bath) and oxalyl chloride (62.5 mg, 43.1 μL, 492 μmol) as well as dimethylformamide (0.25 M in toluene, 37 μL, 9.2 μmol) were added. The mixture was stirred for 2 h at room temperature. Then, it was concentrated in vacuo (40° C., 5 mbar) to afford 5-fluoro-3-methylpicolinoyl chloride as brown oil (50.4 mg, 78%). After that, tert-butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AA, 92 mg, 193 μmol) was dissolved in dichloromethane (5 mL), the solution cooled to 0-5° C. (ice bath) and N,N-diisopropylethylamine (50 mg, 67.6 μL, 387 μmol) was added, followed by a solution of 5-fluoro-3-methylpicolinoyl chloride (vide supra, 50.4 mg, 290 gμmol) in dichloromethane (3 mL). The reaction mixture was stirred for 15 min at 0-5° C., followed by 90 min at room temperature. Then, methanol (5 mL) was added, the mixture was stirred for 15 min at room temperature, and concentrated in vacuo. The crude was purified by column chromatography (silica gel, 12 g, eluting with ethyl acetate/n-heptane, gradient 10:90 to 40:60) to yield, after drying in vacuo (40° C., 5 mbar), the title compound as a white solid (118 mg, quant.). HPLC (method LCMS_fglm) $t_R$=1.56 min. MS (ES+) m/z 613.2 [M+H].

Step 2: N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide (39AA)

tert-Butyl ((4aR,5R,9R)-3,3-difluoro-5-(3-fluoro-6-(5-fluoro-3-methylpicolinamido)-pyridin-2-yl)-5,8,8-trimethyl-9-oxido-2,3,4,4a,5,8-hexahydro-[1,4]thiazino[2,1-f][1,2]thiazin-7-yl)carbamate (Int-86AA, 118 mg, 193 μmol) was dissolved in dichloromethane (5 mL) and trifluoroacetic acid (441 mg, 298 μL, 3.87 mmol) was added. The solution was stirred for 17 h at room temperature. After that, the mixture was cooled to 0-5° C. (ice bath), and aqueous ammonia (8% m/m, 6 mL) was added cautiously upon stirring, until the pH of the aqueous layer was 11-12. After phase separation, the aqueous layer was extracted with ethyl acetate (2×50 mL), the combined extracts were dried (sodium sulfate) and concentrated in vacuo. The residue was purified by column chromatography (silica gel, 12 g, eluting with 2 M ammonia in methanol/dichlormethane, gradient 0:100 to 10:90) to yield, after drying in vacuo (40° C., 5 mbar), the title compound as a white solid (60 mg). Enantiomeric purification was performed by chiral preparative HPLC (Reprosil Chiral NR, 250*4.6 mm*5 μm, isocratic, n-heptane/(ethanol+0.01% ammonium acetate) 80/20, flow 1.0 mL/min) to yield the desired (−)-rotating first eluting enantiomer as a white solid (32 mg, 32%), and the opposite (+)-rotating enantiomer as a white solid (7 mg, 7%). For transfer purpose, the material was dissolved in dichloromethane (1 mL) and tert-butylmethyl ether (3 mL) and concentrated and dried in vacuo at 40° C./5 mbar. HPLC (method LCMS_gradient) $t_R$=1.7 min. $^1$H NMR (CDCl$_3$, 300 MHz): δ 1.80 (s, 3H), 1.86 (2s, 6H), 2.29-2.44 (m, 1H), 2.56-2.78 (m, 1H), 2.84 (s, 3H), 3.58-3.87 (m, 2H), 4.15-4.24 (m, 1H), 4.42 (br s, 2H), 7.36-7.43 (m, 1H), 7.50 (dd, J=9.1, 10.9 Hz, 1H), 8.34-8.41 (m, 2H), 10.43 (s, 1H). MS (ES+) m/z 513.2 [M+H].

N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide (40AA)

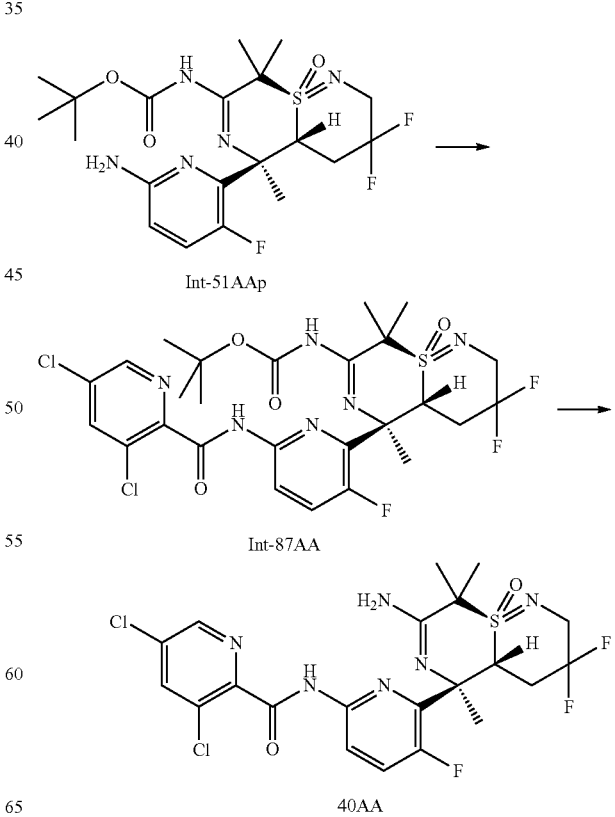

Step 1: tert-Butyl ((4aR,5R,9R)-5-(6-(3,5-dichloropicolinamido)-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-87AA)

3,5-Dichloropicolinic acid (46.1 mg, 240 μmol) was suspended in dichloromethane (3 mL), the suspension was cooled to 0-5° C. (ice bath) and oxalyl chloride (42.6 mg, 29.4 μL, 336 μmol) as well as dimethylformamide (0.137 M in toluene, 43.8 μL, 6 μmol) were added. The mixture was stirred for 17 h at room temperature. Then, it was concentrated in vacuo (40° C., 5 mbar) to afford 3,5-dichloropicolinoyl chloride as yellow oil (50.6 mg, quant.). After that, tert-butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AAp, 80 mg, 168 μmol) was dissolved in dichloromethane (5 mL), the solution cooled to 0-5° C. (ice bath) and N,N-diisopropylethylamine (41.3 mg, 55.8 μL, 320 μmol) was added, followed by a solution of 3,5-dichloropicolinoyl chloride (vide supra, 50.6 mg, 240 mol) in dichloromethane (3 mL). The reaction mixture was stirred for 15 min at 0-5° C., followed by 90 min at room temperature. Then, methanol (5 mL) was added, the mixture was stirred for 15 min at room temperature, and concentrated in vacuo. The crude was purified by column chromatography (silica gel, 12 g, eluting with ethyl acetate/n-heptane, gradient 10:90 to 40:60) to yield, after drying in vacuo (40° C., 5 mbar), the title compound as an off-white solid (115 mg), which was used in the next step without further purification. HPLC (method LCMS_fglm) $t_R$=1.56 min. MS (ES+) m/z 649.1 [M+H].

Step 2: N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide (40AA)

tert-Butyl ((4aR,5R,9R)-5-(6-(3,5-dichloropicolinamido)-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-87AA, 115 mg, see preceeding step, 168.4 mol) was dissolved in dichloromethane (5 mL) and trifluoroacetic acid (384 mg, 259 μL, 3.36 mmol) was added. The solution was stirred for 17 h at room temperature. After that, the mixture was cooled to 0-5° C. (ice bath), and aqueous ammonia (8% m/m, 6 mL) was added cautiously upon stirring, until the pH of the aqueous layer was 11-12. After phase separation, the aqueous layer was extracted with dichloromethane (2×5 mL), the combined extracts were dried (sodium sulfate) and concentrated in vacuo. The residue was purified by column chromatography (silica gel, 12 g, eluting with 2 M ammonia in methanol/dichlormethane, gradient 0:100 to 10:90) to yield, after drying in vacuo (40° C., 5 mbar), the title compound as a white powder (85 mg, 92% over 2 steps). For transfer purpose, the material was dissolved in dichloromethane (1 mL) and tert-butylmethyl ether (3 mL) and concentrated and dried in vacuo at 40° C./5 mbar. HPLC (method LCMS_gradient) $t_R$=1.7 min. $^1$H NMR (CDCl$_3$, 300 MHz): δ 1.78 (s, 3H), 1.83 (2s, 6H), 2.30-2.47 (m, 1H), 2.54-2.79 (m, 1H), 3.57-3.88 (m, 2H), 4.17-4.30 (m, 1H), 4.41 (br s, 2H), 7.50 (dd, J=9.3, 10.3 Hz, 1H), 7.94 (s, 1H), 8.34-8.43 (m, 1H), 8.57 (d, J=1.0 Hz, 1H), 10.17 (s, 1H). MS (ES+) m/z 549.0 [M+H].

N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-fluoropicolinamide (41AA)

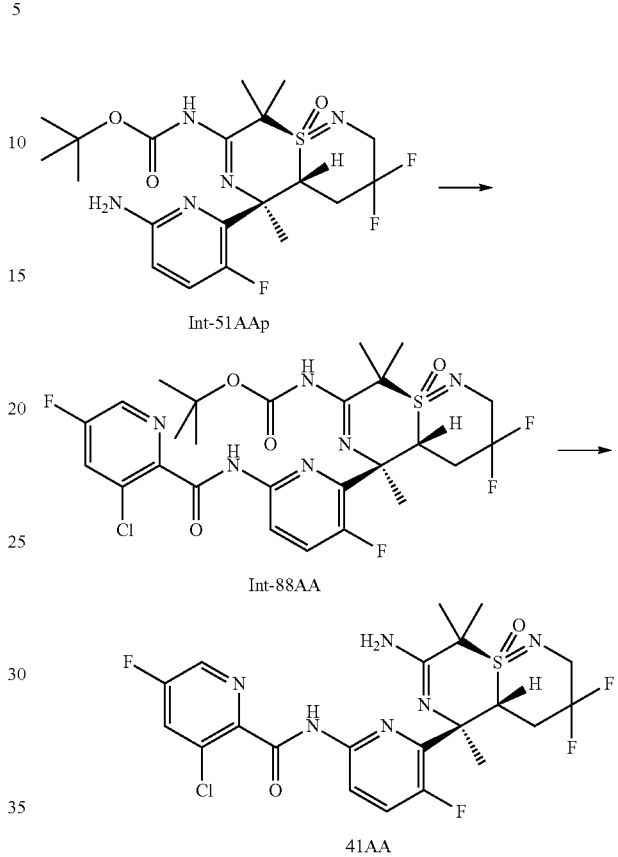

Int-51AAp

Int-88AA

41AA

Step 1: tert-Butyl ((4aR,5R,9R)-5-(6-(3-chloro-5-fluoropicolinamido)-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-88AA)

3-Chloro-5-fluoropicolinic acid (42.1 mg, 240 mol) was suspended in dichloromethane (3 mL), the suspension was cooled to 0-5° C. (ice bath) and oxalyl chloride (42.6 mg, 29.4 μL, 336 mol) as well as dimethylformamide (0.137 M in toluene, 43.8 μL, 6 mol) were added. The mixture was stirred for 17 h at room temperature. Then, it was concentrated in vacuo (40° C., mbar) to afford 3-chloro-5-fluoropicolinoyl chloride as brown oil (49 mg). After that, tert-butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AAp, 80 mg, 168 μmol) was dissolved in dichloromethane (5 mL), the solution cooled to 0-5° C. (ice bath) and N,N-diisopropylethylamine (41.3 mg, 55.8 μL, 320 mol) was added, followed by a solution of 3-chloro-5-fluoropicolinoyl chloride (vide supra, 49 mg, 240 μmol) in dichloromethane (3 mL). The reaction mixture was stirred for 15 min at 0-5° C., followed by 90 min at room temperature. Then, methanol (5 mL) was added, the mixture was stirred for 15 min at room temperature, and concentrated in vacuo. The crude was purified by column chromatography (silica gel, 12 g, eluting with ethyl acetate/n-heptane, gradient 10:90 to 40:60) to yield, after drying in vacuo (40° C., 5 mbar), the title compound as an off-white solid (110 mg), which was used in the next step without further purification. HPLC (method LCMS_gradient) $t_R$=3.4 min. MS (ES+) m/z 633.1 [M+H].

Step 2: N-(6-((4aR,5R,9R)-7-Amino-3,3-difluoro-5, 8,8-trimethyl-9-oxido-2,3,4,4a,5,8-hexahydro-[1,4] thiazino[2,1-f][1,2]thiazin-5-yl)-5-fluoropyridin-2-yl)-3-chloro-5-fluoropicolinamide (41AA)

tert-Butyl ((4aR,5R,9R)-5-(6-(3-chloro-5-fluoropicolinamido)-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-88AA, 110 mg, see preceeding step, 168 mol) was dissolved in dichloromethane (5 mL) and trifluoroacetic acid (384 mg, 259 μL, 3.36 mmol) was added. The solution was stirred for 2 h at room temperature. After that, the mixture was cooled to 0-5° C. (ice bath), and aqueous ammonia (8% m/m, 6 mL) was added cautiously upon stirring, until the pH of the aqueous layer was 11-12. After phase separation, the aqueous layer was extracted with dichloromethane (2×5 mL), the combined extracts were dried (sodium sulfate) and concentrated in vacuo. The residue was purified by column chromatography (silica gel, 12 g, eluting with 2 M ammonia in methanol/dichlormethane, gradient 0:100 to 10:90) to yield, after drying in vacuo (40° C., 5 mbar), the title compound as off-white powder (85 mg, 95% over 2 steps). For transfer purpose, the material was dissolved in dichloromethane (1 mL) and tert-butylmethyl ether (3 mL) and concentrated and dried in vacuo at 40° C./5 mbar. HPLC (method LCMS_gradient) $t_R$=1.5 min. $^1$H NMR (CDCl$_3$, 300 MHz): δ 1.78 (s, 3H), 1.83 (2s, 6H), 2.31-2.46 (m, 1H), 2.55-2.78 (m, 1H), 3.58-3.88 (m, 2H), 4.18-4.29 (m, 1H), 4.41 (br s, 2H), 7.50 (dd, J=8.9, 10.9 Hz, 1H), 7.68 (dd, J=2.4, 7.9 Hz, 1H), 8.38 (dd, J=3.0, 8.9 Hz, 1H), 8.50 (d, J=1.8 Hz, 1H), 10.15 (s, 1H). MS (ES+) m/z 533.1 [M+H].

N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-chloro-3-methylpicolinamide (42AA)

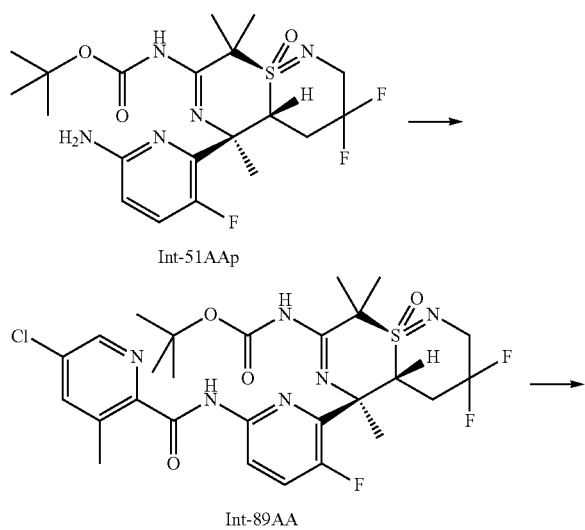

Int-51AAp

Int-89AA

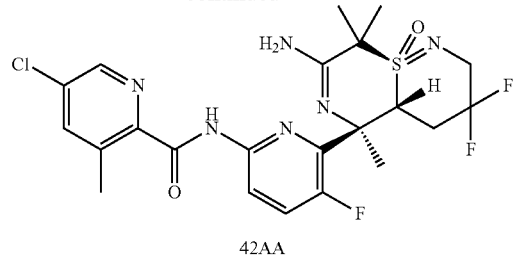

42AA

Step 1: tert-Butyl ((4aR,5R,9R)-5-(6-(5-chloro-3-methylpicolinamido)-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl) carbamate (Int-89AA)

5-Chloro-3-methylpicolinic acid (42.1 mg, 240 μmol) was suspended in dichloromethane (3 mL), the suspension was cooled to 0-5° C. (ice bath) and oxalyl chloride (42.6 mg, 29.4 μL, 336 mol) as well as dimethylformamide (0.137 M in toluene, 43.8 μL, 6 μmol) were added. The mixture was stirred for 17 h at room temperature. Then, it was concentrated in vacuo (40° C., mbar) to afford 5-chloro-3-methylpicolinoyl chloride as brown oil (48 mg, quant.). After that, tert-butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AAp, 80 mg, 168 mol) was dissolved in dichloromethane (5 mL), the solution cooled to 0-5° C. (ice bath) and N,N-diisopropylethylamine (41.3 mg, 55.8 μL, 320 mol) was added, followed by a solution of 5-chloro-3-methylpicolinoyl chloride (vide supra, 50.6 mg, 240 gμmol) in dichloromethane (3 mL). The reaction mixture was stirred for 15 min at 0-5° C., followed by 90 min at room temperature. Then, an aqueous solution of sodium carbonate (10%, 15 mL) was added, the mixture was stirred for 10 min at room temperature. After phase separation, the aqueous layer was extracted the dichloromethane (2×10 mL), the combined organics were dried (sodium sulfate) and concentrated in vacuo. The crude was purified by column chromatography (silica gel, 12 g, eluting with ethyl acetate/n-heptane, gradient 10:90 to 40:60) to yield, after drying in vacuo (40° C., 5 mbar), the title compound as an off-white solid (61 mg, 58%). HPLC (method LCMS_gradient) $t_R$=3.86 min. MS (ES+) m/z 629.2 [M+H].

Step 2: N-(6-((4aR,5R,9R)-7-Amino-3,3-difluoro-5, 8,8-trimethyl-9-oxido-2,3,4,4a,5,8-hexahydro-[1,4] thiazino[2,1-f][1,2]thiazin-5-yl)-5-fluoropyridin-2-yl)-5-chloro-3-methylpicolinamide (42AA)

tert-Butyl ((4aR,5R,9R)-5-(6-(5-chloro-3-methylpicolinamido)-3-fluoropyridin-2-yl)-3,3-difluoro-5,8,8-trimethyl-9-oxido-2,3,4,4a,5,8-hexahydro-[1,4]thiazino[2,1-f] [1,2]thiazin-7-yl)carbamate (Int-89AA, 61 mg, 97 μmol) was dissolved in dichloromethane (5 mL) and trifluoroacetic acid (192 mg, 130 μL, 1.68 mmol) was added. The solution was stirred for 17 h at room temperature. After that, the mixture was cooled to 0-5° C. (ice bath), and aqueous ammonia (8% m/m, 6 mL) was added cautiously upon stirring, until the pH of the aqueous layer was 11-12. After phase separation, the aqueous layer was extracted with dichloromethane (2×5 mL), the combined extracts were dried (sodium sulfate) and concentrated in vacuo. The residue was purified by column chromatography (silica gel, 12 g, eluting with 2 M ammonia in methanol/dichlormethane, gradient 0:100 to 10:90) to yield, after drying in vacuo (40° C., 5 mbar), the title compound as a white powder (49 mg, 95%). For transfer purpose, the material was dissolved in dichloromethane (1 mL) and tert-butylmethyl ether (3 mL) and concentrated and dried in vacuo at 40° C./5 mbar. HPLC (method LCMS_gradient) $t_R$=1.95 min. $^1$H NMR (CDCl$_3$, 300 MHz): δ 1.79 (s, 3H), 1.84 (2s, 6H), 2.31-2.46 (m, 1H), 2.56-2.78 (m, 1H), 2.81 (s, 3H), 3.58-3.87 (m, 2H), 4.18-4.28 (m, 1H), 4.44 (br s, 2H), 7.48 (dd, J=8.9, 10.9 Hz, 1H), 7.65-7.70 (m, 1H), 8.35 (dd, J=3.0, 8.9 Hz, 1H), 8.49 (d, J=1.8 Hz, 1H), 10.44 (s, 1H). MS (ES+) m/z 529.1 [M+H].

N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-chloropicolinamide (43AA)

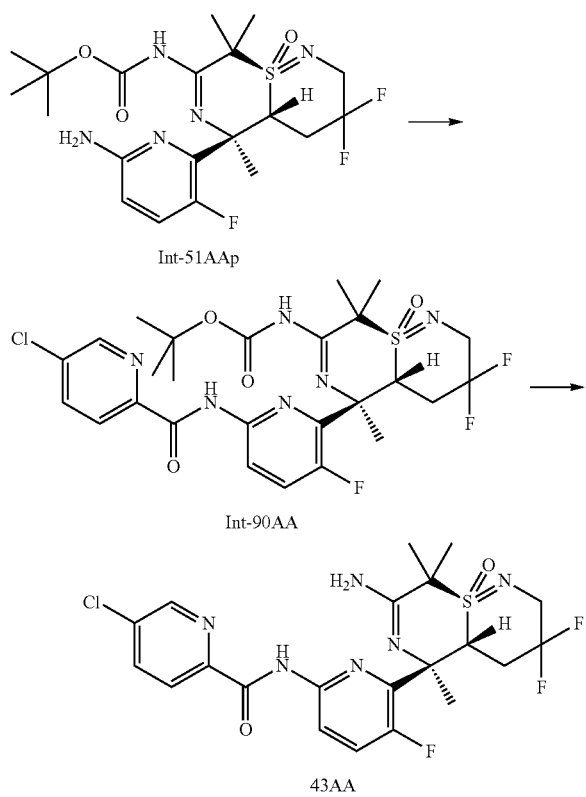

Step 1: tert-Butyl ((4aR,5R,9R)-5-(6-(5-chloropicolinamido)-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-90AA)

5-Chloropicolinic acid (75.6 mg, 480 μmol) was suspended in dichloromethane (6 mL), the suspension was cooled to 0-5° C. (ice bath) and oxalyl chloride (85.2 mg, 58.8 μL, 672 mol) as well as dimethylformamide (0.137 M in toluene, 87.6 μL, 12 mol) were added. The mixture was stirred for 17 h at room temperature. Then, it was concentrated in vacuo (40° C., 5 mbar) to afford 5-chloropicolinoyl chloride as yellow oil (88.8 mg, quant.). After that, tert-butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AAp, 80 mg, 168 μmol) was dissolved in dichloromethane (5 mL), the solution cooled to 0-5° C. (ice bath) and N,N-diisopropylethylamine (82.6 mg, 111.6 μL, 640 μmol) was added, followed by a solution of 5-chloropicolinoyl chloride (vide supra, 88.8 mg, 480 mol) in dichloromethane (6 mL). The reaction mixture was stirred for 15 min at 0-5° C., followed by 3 h at room temperature. Then, an aqueous solution of sodium carbonate (10%, 15 mL) was added, the mixture was stirred for 10 min at room temperature. After phase separation, the aqueous layer was extracted the dichloromethane (2×10 mL), the combined organics were dried (sodium sulfate) and concentrated in vacuo. The crude was purified by column chromatography (silica gel, 12 g, eluting with ethyl acetate/n-heptane, gradient 10:90 to 40:60) to yield, after drying in vacuo (40° C., 5 mbar), the title compound as an off-white solid (110 mg), that was used in the next step without further purification. HPLC (method LCMS_gradient) $t_R$=3.6 min. MS (ES+) m/z 615.1 [M+H].

Step 2: N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-chloropicolinamide (43AA)

tert-Butyl ((4aR,5R,9R)-5-(6-(5-chloropicolinamido)-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-90AA, 110 mg, see preceeding step, 168 mol) was dissolved in dichloromethane (5 mL) and trifluoroacetic acid (384 mg, 259 jμL, 3.36 mmol) was added. The solution was stirred for 17 h at room temperature. After that, the mixture was cooled to 0-5° C. (ice bath), and aqueous ammonia (8% m/m, 6 mL) was added cautiously upon stirring, until the pH of the aqueous layer was 11-12. After phase separation, the aqueous layer was extracted with dichloromethane (2×5 mL), the combined extracts were dried (sodium sulfate) and concentrated in vacuo. The residue was purified by column chromatography (silica gel, 12 g, eluting with 2 M ammonia in methanol/dichlormethane, gradient 0:100 to 10:90) to yield, after drying in vacuo (40° C., 5 mbar), the title compound as a white powder (75 mg, 87% over 2 steps). For transfer purpose, the material was dissolved in dichloromethane (1 mL) and tert-butylmethyl ether (3 mL) and concentrated and dried in vacuo at 40° C./5 mbar. HPLC (method LCMS_gradient) $t_R$=1.8 min. $^1$H NMR (CDCl$_3$, 300 MHz): δ 1.79 (s, 3H), 1.84 (2s, 6H), 2.30-2.45 (m, 1H), 2.56-2.79 (m, 1H), 3.58-3.88 (m, 2H), 4.17-4.28 (m, 1H), 4.43 (br s, 2H), 7.51 (dd, J=8.9, 10.9 Hz, 1H), 7.91 (dd, J=2.3, 8.4 Hz, 1H), 8.27 (dd, J=0.6, 8.5 Hz, 1H), 8.39 (dd, J=3.0, 8.9 Hz, 1H), 8.65 (dd, J=0.6, 2.4 Hz, 1H), 10.26 (s, 1H). MS (ES+) m/z 515.1 [M+H].

6-((6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)carbamoyl)nicotinic acid (44AA)

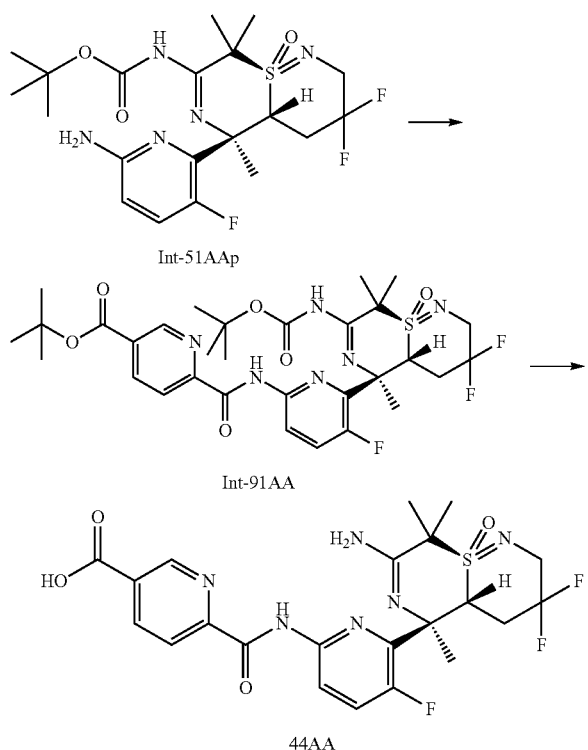

Step 1: tert-Butyl 6-((6-((4aR,5R,9R)-7-((tert-butoxycarbonyl)amino)-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)carbamoyl)nicotinate (Int-91AA)

5-(tert-Butoxycarbonyl)picolinic acid (70.4 mg, 315 µmol) was suspended in dichloromethane (5 mL), the suspension cooled to −10-0° C. (ethanol/ice bath) and 1-chloro-N,N,2-trimethylpropenylamine (98.3 mg, 736 µmol) was added. After 60 min stirring at −10-0° C., a solution of tert-butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AAp, 100 mg, 210 µmol) and N,N-diisopropylethylamine (136 mg, 184 µL, 1.05 mmol) in dichloromethane (3 mL) was added over 5 min at −4° C. The reaction mixture was stirred at 0-5° C. for 30 min and allowed to warm to room temperature. Then, an aqueous solution of sodium carbonate (10%, 15 mL) was added, the mixture was stirred for 10 min at room temperature. After phase separation, the aqueous layer was extracted the dichloromethane (2×20 mL), the combined organics were dried (sodium sulfate) and concentrated in vacuo. The crude was purified by column chromatography (silica gel, 12 g, eluting with ethyl acetate/n-heptane, gradient 10:90 to 30:70) to yield, after drying in vacuo (40° C., 5 mbar), the title compound as an off-white solid (140 mg, 98%). HPLC (method LCMS_gradient) $t_R$=4.0 min. $^1$H NMR (CDCl$_3$, 300 MHz): δ 1.50 (s, 9H), 1.65 (s, 9H), 1.83 (s, 3H), 1.84 (s, 3H), 1.97 (s, 3H), 2.53-2.85 (m, 2H), 3.65-3.92 (m, 2H), 4.56-4.65 (m, 1H), 7.64 (dd, J=9.0, 10.7 Hz, 1H), 8.36 (d, J=8.1 Hz, 1H), 8.45-8.55 (m, 2H), 9.20-9.24 (m, 1H), 10.51 (s, 1H), 11.37 (s, 1H). MS (ES+) m/z 681.3 [M+H].

Step 2: 6-((6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)carbamoyl)nicotinic acid (44AA)

tert-Butyl 6-((6-((4aR,5R,9R)-7-((tert-butoxycarbonyl)amino)-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)carbamoyl)nicotinate (Int-91AA, 140 mg, 206 mol) was dissolved in dichloromethane (7 mL) and trifluoroacetic acid (703 mg, 475 µL, 6.17 mmol) was added. The solution was stirred for 42 h at room temperature. After that, the mixture was concentrated in water, the foamy residue was redissolved in water (5 mL). Aqueous sodium hydroxide solution (1M) was added until the pH was adjusted to 11. Then, acetic acid was added until the pH was 5. The formed precipitate was filtered off and washed thoroughly and subsequently with water, acetonitrile, and diethyl ether to yield, after drying in vacuo (40° C., 5 mbar), the title compound as a white solid (86 mg, 80%). HPLC (method LCMS_gradient) $t_R$=1.4 min. $^1$H NMR (d6-DMSO, 300 MHz): δ 1.69 (s, 3H), 1.71 (s, 3H), 1.74 (s, 3H), 2.38-2.42 (m, 1H), 2.55-2.80 (m, 1H), 3.42 (br s, 2H), 3.46-3.70 (m, 2H), 4.04-4.12 (m, 1H), 6.83 (br s, 1H), 7.85 (dd, J=8.9, 11.5 Hz, 1H), 8.20-8.30 (m, 2H), 8.47 (dd, J=2.0, 8.1 Hz, 1H), 9.14-9.17 (m, 1H), 10.51 (s, 1H). MS (ES+) m/z 525.1 [M+H].

N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-(difluoromethoxy)picolinamide (45AA)

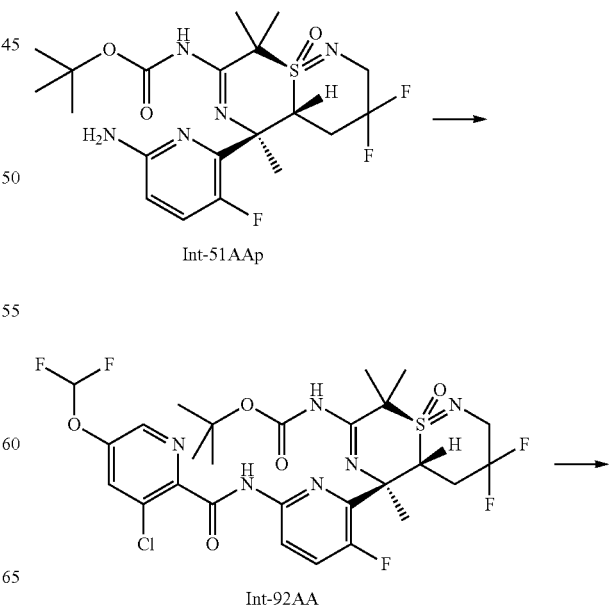

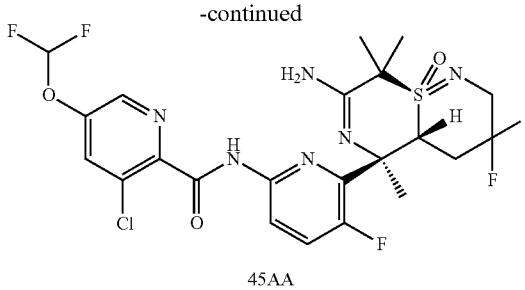

45AA

Step 1: tert-Butyl ((4aR,5R,9R)-5-(6-(3-chloro-5-(difluoromethoxy)picolinamido)-3-fluoropyridin-2-yl)-3,3-difluoro-5,8,8-trimethyl-9-oxido-2,3,4,4a,5,8-hexahydro-[1,4]thiazino-[2,1-f][1,2]thiazin-7-yl)carbamate (Int-92AA)

3-Chloro-5-(difluoromethoxy)picolinic acid (56.3 mg, 252 μmol) was suspended in dichloromethane (3 mL), the suspension was cooled to 0-5° C. (ice bath) and oxalyl chloride (44.8 mg, 30.9 μL, 353 mol) as well as dimethylformamide (0.242 M in toluene, 26 μL, 6.3 μmol) were added. The mixture was stirred for 15 h at room temperature. Then, it was concentrated in vacuo (40° C., 5 mbar) to afford 3-chloro-5-(difluoromethoxy)picolinoyl chloride as red oil (58.4 mg, quant.). After that, tert-butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AAp, 80 mg, 168 μmol) was dissolved in dichloromethane (5 mL), the solution cooled to 0-5° C. (ice bath) and N,N-diisopropylethylamine (41.3 mg, 55.8 tμL, 320 μmol) was added, followed by a solution of 3-chloro-5-(difluoromethoxy)picolinoyl chloride (vide supra, 58.4 mg, 252 μmol) in dichloromethane (3 mL). The reaction mixture was stirred for 45 min at 0-5° C. Then, methanol (5 mL) was added, the mixture was stirred for 15 min at room temperature, and concentrated in vacuo. The crude was purified by column chromatography (silica gel, 12 g, eluting with ethyl acetate/n-heptane, gradient 10:90 to 35:65) to yield, after drying in vacuo (40° C., 5 mbar), the title compound as an off-white solid (109 mg, 95%). HPLC (method LCMS_fglm) $t_R$=1.49 min. MS (ES+) m/z 681.3 [M+H].

Step 2: N-(6-((4aR,5R,9R)-7-Amino-3,3-difluoro-5,8,8-trimethyl-9-oxido-2,3,4,4a,5,8-hexahydro-[1,4]thiazino[2,1-f]j[1,2]thiazin-5-yl)-5-fluoropyridin-2-yl)-3-chloro-5-(difluoro-methoxy)picolinamide (45AA)

tert-Butyl ((4aR,5R,9R)-5-(6-(3-chloro-5-(difluoromethoxy)picolinamido)-3-fluoropyridin-2-yl)-3,3-difluoro-5,8,8-trimethyl-9-oxido-2,3,4,4a,5,8-hexahydro-[1,4]thiazino-[2,1-f][1,2]thiazin-7-yl)carbamate (Int-92AA, 109 mg, 160 μmol) was dissolved in dichloromethane (10 mL) and trifluoroacetic acid (384 mg, 259 gμL, 3.36 mmol) was added. The solution was stirred for 17 h at room temperature. After that, the mixture was cooled to 0-5° C. (ice bath), water (20 mL) and aqueous ammonia (2 M, 6 mL) was added cautiously upon stirring, until the pH of the aqueous layer was 11-12. After phase separation, the aqueous layer was extracted with dichloromethane (2×50 mL), the combined extracts were dried (sodium sulfate) and concentrated in vacuo. The residue was purified by column chromatography (silica gel, 12 g, eluting with 2 M ammonia in methanol/dichlormethane, gradient 2:98 to 5:95) to yield, after drying in vacuo (40° C., 5 mbar), the title compound as a white powder (91 mg, 98%). For transfer purpose, the material was dissolved in dichloromethane (1 mL) and tert-butylmethyl ether (3 mL) and concentrated and dried in vacuo at 40° C./5 mbar. HPLC (method LCMS_gradient) $t_R$=1.6 min. $^1$H NMR (CDCl$_3$, 300 MHz): δ 1.78 (s, 3H), 1.82 (s, 3H), 1.83 (s, 3H), 2.31-2.46 (m, 1H), 2.55-2.78 (m, 1H), 3.58-3.87 (m, 2H), 4.18-4.29 (m, 1H), 4.40 (br s, 2H), 6.68 (t, J=71.2 Hz, 1H), 7.50 (dd, J=8.9, 10.9 Hz, 1H), 7.71 (d, J=2.2 Hz, 1H), 8.39 (dd, J=3.0, 8.9 Hz, 1H), 8.49 (d, J=2.4 Hz, 1H), 10.19 (s, 1H). MS (ES+) m/z 581.2 [M+H].

N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2-difluoroethoxy)pyrazine-2-carboxamide (46AA)

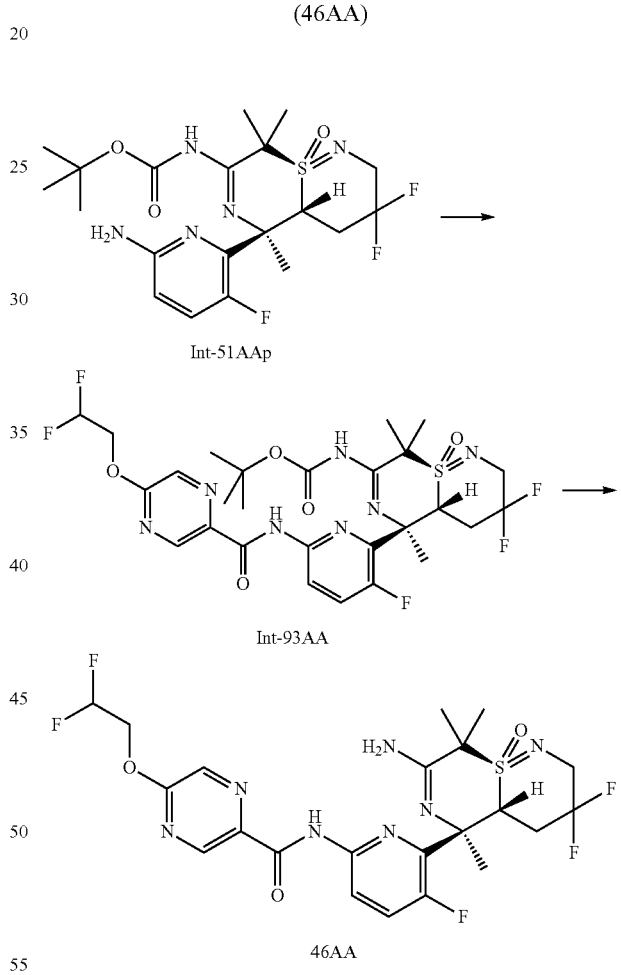

Step 1: tert-Butyl ((4aR,5R,9R)-5-(6-(5-(2,2-difluoroethoxy)pyrazine-2-carboxamido)-3-fluoropyridin-2-yl)-3,3-difluoro-5,8,8-trimethyl-9-oxido-2,3,4,4a,5,8-hexahydro-[1,4]thiazino-[2,1-f][1,2]thiazin-7-yl)carbamate (Int-93AA)

5-(2,2-Difluoroethoxy)pyrazine-2-carboxylic acid (51.4 mg, 252 mol) was suspended in dichloromethane (3 mL), the suspension was cooled to 0-5° C. (ice bath) and oxalyl chloride (44.8 mg, 30.9 μL, 353 gμmol) as well as dimethylformamide (0.242 M in toluene, 26 μL, 6.3 μmol) were added. The mixture was stirred for 2 h at room temperature. Then, it was concentrated in vacuo (40° C., 5 mbar) to afford 5-(2,2-difluoroethoxy)pyrazine-2-carboxylic acid chloride as yellow oil (56.1 mg, quant.). After that, tert-butyl ((4aR, 5R,9R)-5-(6-amino-3-fluoropyridin-2-yl)-3,3-difluoro-5,8, 8-trimethyl-9-oxido-2,3,4,4a,5,8-hexahydro-[1,4]thiazino [2,1-f][1,2]thiazin-7-yl)carbamate (Int-51AAp, 80 mg, 168 mol) was dissolved in dichloromethane (5 mL), the solution cooled to 0-5° C. (ice bath) and N,N-diisopropylethylamine (41.3 mg, 55.8 μL, 320 μmol) was added, followed by a solution of 5-(2,2-difluoroethoxy)pyrazine-2-carboxylic acid chloride (vide supra, 56.1 mg, 252 μmol) in dichloromethane (3 mL). The reaction mixture was stirred for 75 min at 0-5° C. Then, methanol (5 mL) was added, the mixture was stirred for 15 min at room temperature, and concentrated in vacuo. The crude was purified by column chromatography (silica gel, 12 g, eluting with ethyl acetate/ n-heptane, gradient 10:90 to 35:65) to yield, after drying in vacuo (40° C., 5 mbar), the title compound as an off-white solid (104 mg, 94%). HPLC (method LCMS_fglm) $t_R$=1.49 min. MS (ES+) m/z 662.3 [M+H].

Step 2: N-(6-((4aR,5R,9R)-7-Amino-3,3-difluoro-5, 8,8-trimethyl-9-oxido-2,3,4,4a,5,8-hexahydro-[1,4] thiazino[2,1-f][1,2]thiazin-5-yl)-5-fluoropyridin-2-yl)-5-(2,2-difluoroethoxy)-pyrazine-2-carboxamide (46AA)

tert-Butyl ((4aR,5R,9R)-5-(6-(5-(2,2-difluoroethoxy) pyrazine-2-carboxamido)-3-fluoropyridin-2-yl)-3,3-difluoro-5,8,8-trimethyl-9-oxido-2,3,4,4a,5,8-hexahydro-[1,4] thiazino[2,1-f][1,2]thiazin-7-yl)carbamate (Int-93AA, 104 mg, 157 μmol) was dissolved in dichloromethane (10 mL) and trifluoroacetic acid (384 mg, 259 μL, 3.36 mmol) was added. The solution was stirred for 17 h at room temperature. After that, the mixture was cooled to 0-5° C. (ice bath), water (20 mL) and aqueous ammonia (2 M, 6 mL) was added cautiously upon stirring, until the pH of the aqueous layer was 11-12. After phase separation, the aqueous layer was extracted with dichloromethane (2×50 mL), the combined extracts were dried (sodium sulfate) and concentrated in vacuo. The residue was purified by column chromatography (silica gel, 12 g, eluting with 2 M ammonia in methanol/dichlormethane, gradient 2:98 to 5:95) to yield, after drying in vacuo (40° C., 5 mbar), the title compound as a white powder (88 mg, 99%). HPLC (method LCMS_gradient) $t_R$=1.7 min. $^1$H NMR (CDCl$_3$, 300 MHz): δ 1.79 (s, 3H), 1.83 (s, 3H), 1.84 (s, 3H), 2.29-2.44 (m, 1H), 2.55-2.79 (m, 1H), 3.57-3.87 (m, 2H), 4.16-4.27 (m, 1H), 4.41 (br s, 2H), 4.68 (dt, J=4.0, 13.3 Hz, 2H), 6.18 (tt, J=4.0, 55.0 Hz, 1H), 7.51 (dd, J=9.0, 10.8 Hz, 1H), 8.34 (d, J=1.4 Hz, 1H), 8.38 (dd, J=3.0, 8.9 Hz, 1H), 9.04 (d, J=1.2 Hz, 1H), 9.94 (s, 1H). MS (ES+) m/z 562.3 [M+H].

N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(prop-1-yn-1-yl)picolinamide (47AA)

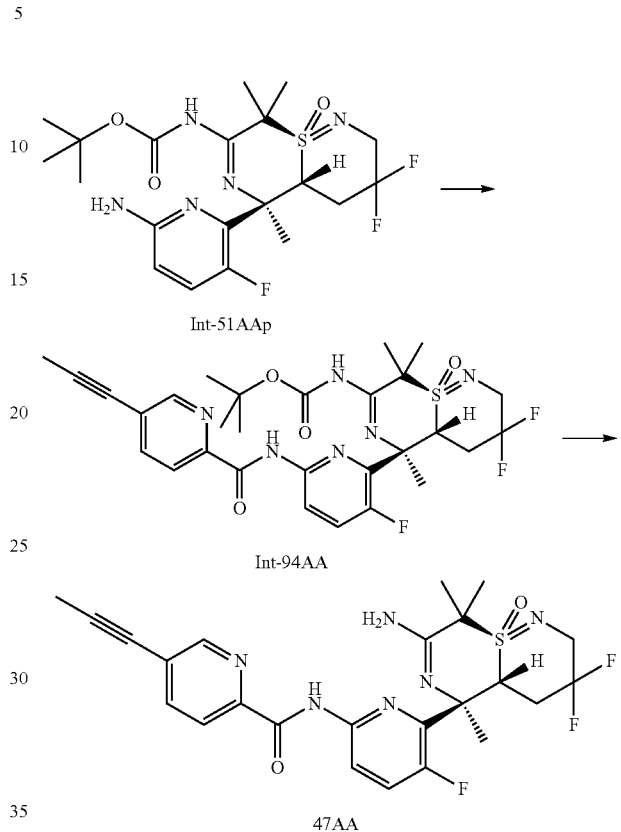

Step 1: tert-Butyl ((4aR,5R,9R)-3,3-difluoro-5-(3-fluoro-6-(5-(prop-1-yn-1-yl)picolinamido)-pyridin-2-yl)-5,8,8-trimethyl-9-oxido-2,3,4,4a,5,8-hexahydro-[1,4]thiazino[2,1-f][1,2]thiazin-7-yl) carbamate (Int-94AA)

5-(Prop-1-yn-1-yl)picolinic acid (30.5 mg, 189 μmol) was suspended in dichloromethane (3 mL), the suspension was cooled to 0-5° C. (ice bath) and oxalyl chloride (33.6 mg, 23.2 μL, 265 μmol) as well as dimethylformamide (0.242 M in toluene, 19.5 μL, 4.7 μmol) were added. The mixture was stirred for 3 h at room temperature. Then, it was concentrated in vacuo (40° C., 5 mbar) to afford 5-(prop-1-yn-1-yl)picolinoyl chloride as yellow oil (34 mg, quant.). After that, tert-butyl ((4aR,5R,9R)-5-(6-amino-3-fluoropyridin-2-yl)-3,3-difluoro-5,8,8-trimethyl-9-oxido-2,3,4,4a,5,8-hexahydro-[1,4]thiazino[2,1-f][1,2]thiazin-7-yl)carbamate (Int-51AAp, 60 mg, 126 μmol) was dissolved in dichloromethane (5 mL), the solution cooled to 0-5° C. (ice bath) and N,N-diisopropylethylamine (31 mg, 41.9 μL, 240 μmol) was added, followed by a solution of 5-(prop-1-yn-1-yl)picolinoyl chloride (vide supra, 34 mg, 189 μmol) in dichloromethane (3 mL). The reaction mixture was stirred for 75 min at 0-5° C. Then, methanol (5 mL) was added, the mixture was stirred for 15 min at room temperature, and concentrated in vacuo. The crude was purified by column chromatography (silica gel, 12 g, eluting with ethyl acetate/ n-heptane, gradient 10:90 to 35:65) to yield, after drying in vacuo (40° C., 5 mbar), the title compound as a white solid (85 mg), that was used in the next without further purification. HPLC (method LCMS_fglm) $t_R$=1.57 min. MS (ES+) m/z 619.3 [M+H].

Step 2: N-(6-((4aR,5R,9R)-7-Amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(prop-1-yn-1-yl)picolinamide (47AA)

tert-Butyl ((4aR,5R,9R)-3,3-difluoro-5-(3-fluoro-6-(5-(prop-1-yn-1-yl)picolinamido)pyridin-2-yl)-5,8,8-trimethyl-9-oxido-2,3,4,4a,5,8-hexahydro-[1,4]thiazino[2,1-f][1,2]thiazin-7-yl)carbamate (Int-94AA, 85 mg, see preceeding step, 126 µmol) was dissolved in dichloromethane (10 mL) and trifluoroacetic acid (288 mg, 194 µL, 2.52 mmol) was added. The solution was stirred for 17 h at room temperature. After that, the mixture was cooled to 0-5° C. (ice bath), water (20 mL) and aqueous ammonia (2 M, 6 mL) was added cautiously upon stirring, until the pH of the aqueous layer was 11-12. After phase separation, the aqueous layer was extracted with dichloromethane (2×50 mL), the combined extracts were dried (sodium sulfate) and concentrated in vacuo. The residue was purified by column chromatography (silica gel, 12 g, eluting with 2 M ammonia in methanol/dichlormethane, gradient 0:100 to 7:93) to yield, after drying in vacuo (40° C., 5 mbar), the title compound as a white solid (61 mg, 93% over 2 steps). HPLC (method LCMS_gradient) $t_R$=1.9 min. $^1$H NMR (CDCl$_3$, 300 MHz): δ 1.79 (s, 3H), 1.84 (2s, 6H), 2.14 (s, 3H), 2.29-2.45 (m, 1H), 2.56-2.79 (m, 1H), 3.58-3.88 (m, 2H), 4.16-4.26 (m, 1H), 4.41 (br s, 2H), 7.50 (dd, J=8.9, 10.9 Hz, 1H), 7.88 (dd, J=1.9, 8.2 Hz, 1H), 8.22 (d, J=8.1 Hz, 1H), 8.40 (dd, J=3.0, 8.9 Hz, 1H), 8.66 (d, J=1.4 Hz, 1H), 10.35 (s, 1H). MS (ES+) m/z 519.3 [M+H].

N-(6-((4aR,5R,9R)-7-Amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-5-cyano-3-methylpicolinamide (48AA)

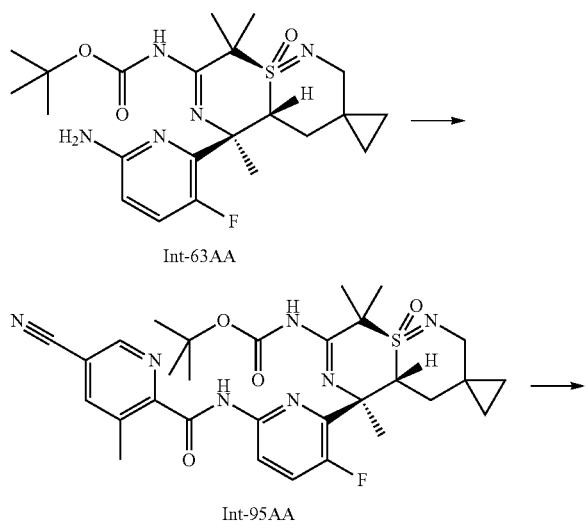

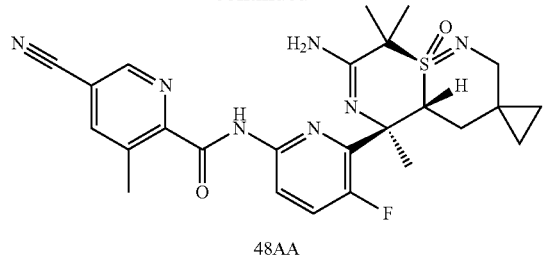

48AA

Step 1: tert-Butyl ((4aR,5R,9R)-5-(6-(5-cyano-3-methylpicolinamido)-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-95AA)

5-Cyano-3-methylpicolinic acid (52.2 mg, 322 mol) was suspended in dichloromethane (3 mL), the suspension was cooled to 0-5° C. (ice bath) and oxalyl chloride (57.2 mg, 39.5 µL, 451 µmol) as well as dimethylformamide (0.242 M in toluene, 33 µL, 8.0 µmol) were added. The mixture was stirred for 15 h at room temperature. Then, it was concentrated in vacuo (40° C., mbar) to afford 5-cyano-3-methylpicolinoyl chloride as red oil (58.2 mg, quant.). After that, tert-butyl ((4aR,5R,9R)-5-(6-amino-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-63AA, 100 mg, 215 µmol) was dissolved in dichloromethane (5 mL), the solution cooled to 0-5° C. (ice bath) and N,N-diisopropylethylamine (55.5 mg, 75 µL, 430 µmol) was added, followed by a solution of 5-cyano-3-methylpicolinoyl chloride (vide supra, 58.2 mg, 322 mol) in dichloromethane (3 mL). The reaction mixture was stirred for 45 min at 0-5° C. Then, methanol (5 mL) was added, the mixture was stirred for 15 min at room temperature, and concentrated in vacuo. The crude was purified by column chromatography (silica gel, 12 g, eluting with ethyl acetate/n-heptane, gradient 10:90 to 60:40) to yield, after drying in vacuo (40° C., 5 mbar), the title compound as a white solid (137 mg), that was used in the next step without further purification. HPLC (method LCMS_fglm) $t_R$=1.45 min. MS (ES+) m/z 610.3 [M+H].

Step 2: N-(6-((4aR,5R,9R)-7-Amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-5-cyano-3-methylpicolinamide (48AA)

tert-Butyl ((4aR,5R,9R)-5-(6-(5-cyano-3-methylpicolinamido)-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-95AA, 137 mg, 215 mol, see preceding step) was dissolved in dichloromethane (10 mL) and trifluoroacetic acid (490 mg, 331 µL, 4.3 mmol) was added. The solution was stirred for 17 h at room temperature. After that, the mixture was cooled to 0-5° C. (ice bath), water (20 mL) and aqueous ammonia (2 M, 6 mL) was added cautiously upon stirring, until the pH of the aqueous layer was 11-12. After phase separation, the aqueous layer was extracted with dichloromethane (2×50 mL), the combined extracts were dried (sodium sulfate) and concentrated in vacuo. The residue was purified by column chromatography (silica gel, 12 g, eluting with 2 M ammonia in methanol/dichlormethane, gradient 2:98 to 7:93) to yield, after drying in vacuo (40° C., 5 mbar), the title compound as a white powder (100 mg). Enantiomeric purification was performed by chiral preparative HPLC (Chiralpak AD, 250*4.6 mm*5 μm, isocratic, n-heptane/(ethanol+0.01% ammonium acetate) 60/40, flow 1.0 mL/min) to yield the desired major, first eluting enantiomer as a white solid (58 mg, 52% over 2 steps), and the opposite, minor enantiomer as a white solid (28 mg, 25%). HPLC (method LCMS_gradient) $t_R$=1.6 min. $^1$H NMR (CDCl$_3$, 300 MHz): δ 0.07-0.17 (m, 1H), 0.26-0.35 (m, 1H), 0.39-0.48 (m, 1H), 0.53-0.62 (m, 1H), 0.89-0.99 (m, 1H), 1.83 (s, 3H), 1.90 (s, 3H), 1.92 (s, 3H), 2.46 (dd, J=1.8, 13.1 Hz, 1H), 2.80 (dd, J=13.2, 13.2 Hz, 1H), 2.87 (s, 3H), 3.96-4.08 (m, 2H), 5.15 (br s, 2H), 7.52 (dd, J=8.9, 10.9 Hz, 1H), 7.96-7.99 (m, 1H), 8.35 (dd, J=3.0, 8.9 Hz, 1H), 8.78-8.81 (m, 1H), 10.43 (s, 1H). MS (ES+) m/z 510.3 [M+H].

N-(6-((4aS,5R,9R)-7-Amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-5-cyano-3-methylpicolinamide (48AB)

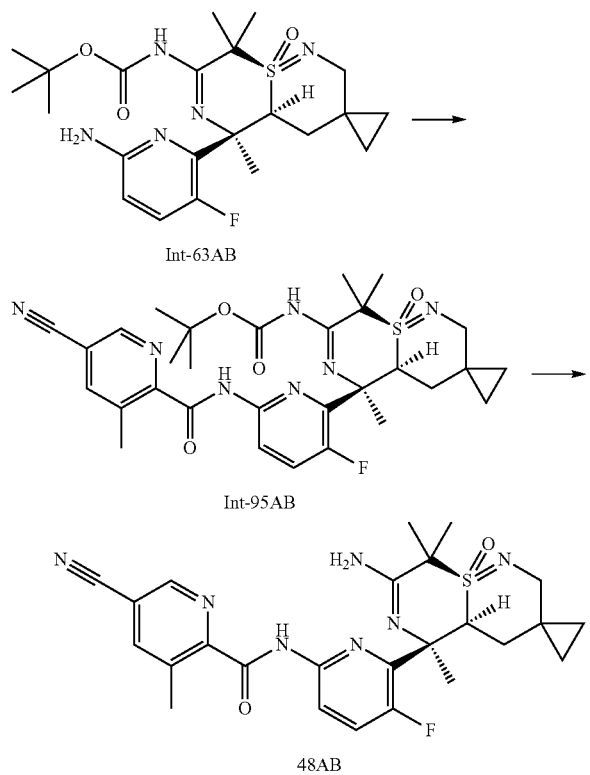

Step 1: tert-Butyl ((4aS,5R,9R)-5-(6-(5-cyano-3-methylpicolinamido)-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-95AB)

5-Cyano-3-methylpicolinic acid (51.1 mg, 377 mol) was suspended in dichloromethane (3 mL), the suspension was cooled to 0-5° C. (ice bath) and oxalyl chloride (67 mg, 46 μL, 528 μmol) as well as dimethylformamide (0.242 M in toluene, 39 μL, 9.4 μmol) were added. The mixture was stirred for 15 h at room temperature. Then, it was concentrated in vacuo (40° C., 5 mbar) to afford 5-cyano-3-methylpicolinoyl chloride as red oil (68.1 mg, quant.). After that, tert-butyl ((4aS,5R,9R)-5-(6-amino-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-63AB, 117 mg, 251 mol) was dissolved in dichloromethane (5 mL), the solution cooled to 0-5° C. (ice bath) and N,N-diisopropylethylamine (65 mg, 88 μL, 503 μmol) was added, followed by a solution of 5-cyano-3-methylpicolinoyl chloride (vide supra, 68.1 mg, 377 mol) in dichloromethane (3 mL). The reaction mixture was stirred for 90 min at 0-5° C. Then, methanol (5 mL) was added, the mixture was stirred for 15 min at room temperature. The resulting suspension was filtered, the precipitate was washed with dichloromethane (3×5 mL) and dried to give the first crop of the title compound. The combined filtrate was concentrated in vacuo. The crude was purified by column chromatography (silica gel, 12 g, eluting with 2 M ammonia in methanol/dichlormethane, gradient 1:99 to 3:97) to yield, after drying in vacuo (40° C., 5 mbar), the second crop of the title compound. Both crops were combined to give the title compound as a light brown solid (141 mg, 92%). HPLC (method LCMS_fglm) $t_R$=1.40 min. MS (ES+) m/z 610.3 [M+H].

Step 2: N-(6-((4aS,5R,9R)-7-Amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-5-cyano-3-methylpicolinamide (48AB)

tert-Butyl ((4aS,5R,9R)-5-(6-(5-cyano-3-methylpicolinamido)-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-95AB, 141 mg, 231 μmol) was dissolved in dichloromethane (10 mL) and trifluoroacetic acid (573 mg, 387 μL, 5.0 mmol) was added. The solution was stirred for 17 h at room temperature. After that, the mixture was cooled to 0-5° C. (ice bath), water (20 mL) and aqueous ammonia (2 M, 6 mL) was added cautiously upon stirring, until the pH of the aqueous layer was 11-12. After phase separation, the aqueous layer was extracted with dichloromethane (2×50 mL), the combined extracts were dried (sodium sulfate) and concentrated in vacuo. The residue was purified by column chromatography (silica gel, 12 g, eluting with 2 M ammonia in methanol/dichlormethane, gradient 2:98 to 7:93) to yield, after drying in vacuo (40° C., 5 mbar), the title compound as a white solid (110 mg). Enantiomeric purification was performed by chiral preparative HPLC (Reprosil Chiral NR, 250*4.6 mm*5 m, isocratic, n-heptane/(ethanol+0.01% ammonium acetate) 60/40, flow 1.0 mL/min) to yield the desired (+)-rotating second eluting enantiomer as a light brown solid (68 mg, 57%), and the opposite (−)-rotating first eluting enantiomer as a light brown solid (22 mg, 18%). HPLC (method LCMS_gradient) $t_R$=0.86 min. $^1$H NMR (CDCl$_3$, 300 MHz): δ 0.29-0.49 (m, 3H), 0.69-0.83 (m, 2H), 1.81 (s, 3H), 1.93 (s, 3H), 1.98 (s, 3H), 2.40 (dd, J=13.9, 13.9 Hz, 1H), 2.79-2.86 (m, 1H), 2.83 (s, 3H), 3.83-3.92 (m, 2H), 6.17 (br s, 2H), 7.55 (dd, J=9.1, 10.3 Hz, 1H), 7.95-7.98 (m, 1H), 8.44 (dd, J=3.0, 8.9 Hz, 1H), 8.80 (d, J=1.4 Hz, 1H), 11.00 (s, 1H). MS (ES+) m/z 510.2 [M+H].

N-(6-((4aR,5R,9R)-7-Amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-3-chloro-5-cyanopicolinamide (49AA)

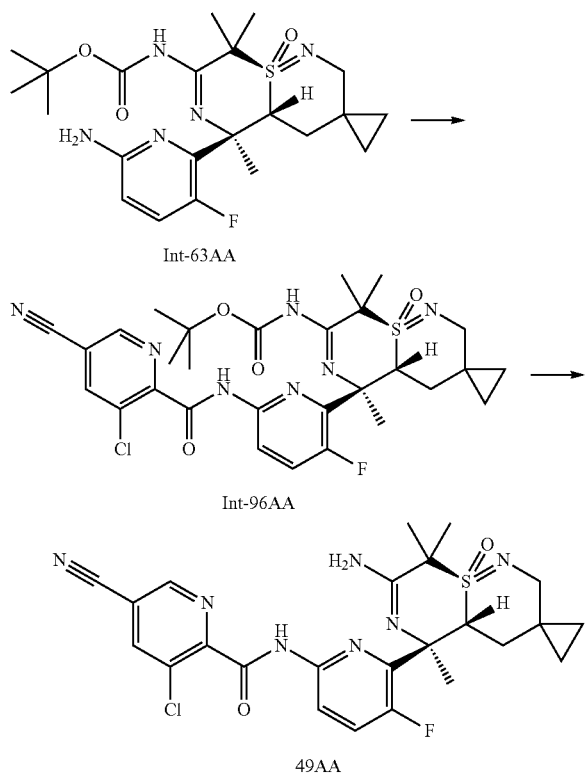

Int-63AA

Int-96AA

49AA

Step 1: tert-Butyl ((4aR,5R,9R)-5-(6-(3-chloro-5-cyanopicolinamido)-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-96AA)

3-Chloro-5-cyanopicolinic acid (58.8 mg, 322 μmol) was suspended in dichloromethane (3 mL), the suspension was cooled to 0-5° C. (ice bath) and oxalyl chloride (57.2 mg, 39.5 μL, 451 μmol) as well as dimethylformamide (0.242 M in toluene, 33 μL, 8 μmol) were added. The mixture was stirred for 2 h at room temperature. Then, it was concentrated in vacuo (40° C., 5 mbar) to afford 3-chloro-5-cyanopicolinoyl chloride as brown oil (64.8 mg, quant.). After that, tert-butyl ((4aR,5R,9R)-5-(6-amino-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-63AA, 100 mg, 215 μmol) was dissolved in dichloromethane (5 mL), the solution cooled to 0-5° C. (ice bath) and N,N-diisopropylethylamine (55.5 mg, 75 μL, 430 μmol) was added, followed by a solution of 3-chloro-5-cyanopicolinoyl chloride (vide supra, 64.8 mg, 322 mol) in dichloromethane (3 mL). The reaction mixture was stirred for 45 min at 0-5° C. Then, methanol (5 mL) was added, the mixture was stirred for 15 min at room temperature, and concentrated in vacuo. The crude was purified by column chromatography (silica gel, 12 g, eluting with ethyl acetate/n-heptane, gradient 10:90 to 70:30) to yield, after drying in vacuo (40° C., 5 mbar), the title compound as a light yellow solid (137 mg, 99%). HPLC (method LCMS_fglm) $t_R$=1.38 min. MS (ES+) m/z 630.3 [M+H].

Step 2: N-(6-((4aR,5R,9R)-7-Amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-3-chloro-5-cyanopicolinamide (49AA)

tert-Butyl ((4aR,5R,9R)-5-(6-(3-chloro-5-cyanopicolinamido)-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-96AA, 137 mg, 214 mol) was dissolved in dichloromethane (10 mL) and trifluoroacetic acid (490 mg, 331 μL, 4.3 mmol) was added. The solution was stirred for 17 h at room temperature. After that, the mixture was cooled to 0-5° C. (ice bath), water (20 mL) and aqueous ammonia (2 M, 6 mL) was added cautiously upon stirring, until the pH of the aqueous layer was 11-12. After phase separation, the aqueous layer was extracted with dichloromethane (2×50 mL), the combined extracts were dried (sodium sulfate) and concentrated in vacuo. The residue was purified by column chromatography (silica gel, 12 g, eluting with 2 M ammonia in methanol/dichlormethane, gradient 0:100 to 8:92) to yield, after drying in vacuo (40° C., 5 mbar), the title compound as a white solid (97 mg). Enantiomeric purification was performed by chiral preparative HPLC (Chiralpak AD, 250*4.6 mm*5 μm, isocratic, n-heptane/(ethanol+0.01% ammonium acetate) 60/40, flow 1.0 mL/min) to yield the desired first eluting enantiomer as an off-white solid (67 mg, 58%), and the opposite second eluting enantiomer as a light brown solid (26 mg, 22%). HPLC (method LCMS_gradient) $t_R$=1.5 min. $^1$H NMR (CDCl$_3$, 300 MHz): δ 0.02-0.10 (m, 1H), 0.27-0.36 (m, 1H), 0.40-0.49 (m, 1H), 0.51-0.60 (m, 1H), 0.84-0.96 (m, 1H), 1.87 (s, 3H), 1.91 (s, 3H), 1.95 (s, 3H), 2.42-2.51 (m, 1H), 2.80 (dd, J=13.2, 13.2 Hz, 1H), 3.92-4.02 (m, 2H), 4.62 (br s, 2H), 7.57 (dd, J=9.0, 11.0 Hz, 1H), 8.21 (d, J=1.8 Hz, 1H), 8.41 (dd, J=3.0, 8.9 Hz, 1H), 8.85 (d, J=1.8 Hz, 1H), 10.16 (s, 1H). MS (ES+) m/z 530.3 [M+H].

N-(6-((4aR,5R,9R)-7-Amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-3-chloro-5-(difluoromethoxy)picolinamide (50AA)

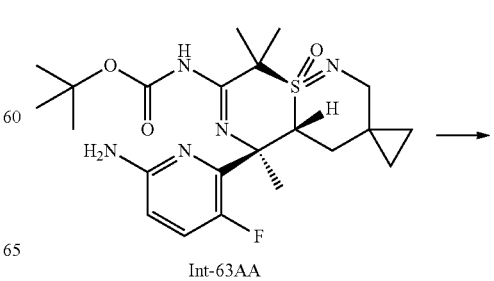

Int-63AA

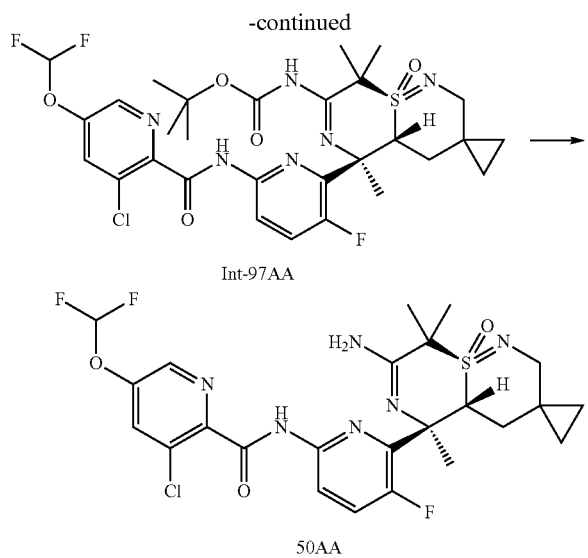

Int-97AA

50AA

Step 1: tert-Butyl ((4aR,5R,9R)-5-(6-(3-chloro-5-(difluoromethoxy)picolinamido)-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-97AA)

3-Chloro-5-(difluoromethoxy)picolinic acid (72 mg, 322 μmol) was suspended in dichloromethane (3 mL), the suspension was cooled to 0-5° C. (ice bath) and oxalyl chloride (57.2 mg, 39.5 μL, 451 μmol) as well as dimethylformamide (0.242 M in toluene, 33 μL, 8 mol) were added. The mixture was stirred for 2 h at room temperature. Then, it was concentrated in vacuo (40° C., 5 mbar) to afford 3-chloro-5-(difluoromethoxy)picolinoyl chloride as yellow oil (78 mg, quant.). After that, tert-butyl ((4aR,5R,9R)-5-(6-amino-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-63AA, 100 mg, 215 μmol) was dissolved in dichloromethane (5 mL), the solution cooled to 0-5° C. (ice bath) and N,N-diisopropylethylamine (55.5 mg, 75 μL, 430 μmol) was added, followed by a solution of 3-chloro-5-(difluoromethoxy)picolinoyl chloride (vide supra, 78 mg, 322 μmol) in dichloromethane (3 mL). The reaction mixture was stirred for 45 min at 0-5° C. Then, methanol (5 mL) was added, the mixture was stirred for 15 min at room temperature, and concentrated in vacuo. The crude was purified by column chromatography (silica gel, 12 g, eluting with ethyl acetate/n-heptane, gradient 10:90 to 60:40) to yield, after drying in vacuo (40° C., 5 mbar), the title compound as an off-white solid (137 mg, 95%). HPLC (method LCMS_fglm) $t_R$=1.48 min. MS (ES+) m/z 671.3 [M+H].

Step 2: N-(6-((4aR,5R,9R)-7-Amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-3-chloro-5-(difluoromethoxy)picolinamide (50AA)

tert-Butyl ((4aR,5R,9R)-5-(6-(3-chloro-5-(difluoromethoxy)picolinamido)-3-fluoropyridin-2-yl)-5,8,8-trimethyl-9-oxido-4,4a,5,8-tetrahydro-2H-spiro[[1,4]thiazino[2,1-f][1,2]thiazine-3,1'-cyclopropan]-7-yl)carbamate (Int-97AA, 137 mg, 204 μmol) was dissolved in dichloromethane (10 mL) and trifluoroacetic acid (490 mg, 331 μL, 4.3 mmol) was added. The solution was stirred for 17 h at room temperature. After that, the mixture was cooled to 0-5° C. (ice bath), water (20 mL) and aqueous ammonia (2 M, 6 mL) was added cautiously upon stirring, until the pH of the aqueous layer was 11-12. After phase separation, the aqueous layer was extracted with dichloromethane (2×50 mL), the combined extracts were dried (sodium sulfate) and concentrated in vacuo The residue was purified by column chromatography (silica gel, 12 g, eluting with 2 M ammonia in methanol/dichlormethane, gradient 0:100 to 8:92) to yield, after drying in vacuo (40° C., 5 mbar), the title compound as a white solid (108 mg). Enantiomeric purification was performed by chiral preparative HPLC (Chiralpak AD, 250*4.6 mm*5 μm, isocratic, n-heptane/(ethanol+0.01% ammonium acetate) 60/40, flow 1.0 mL/min) to yield the desired first eluting enantiomer as an off-white solid (80 mg, 69%), and the opposite second eluting enantiomer as a light brown solid (25 mg, 21%). HPLC (method LCMS_gradient) $t_R$=1.8 min. $^1$H NMR (CDCl$_3$, 300 MHz): δ 0.06-0.16 (m, 1H), 0.26-0.36 (m, 1H), 0.39-0.47 (m, 1H), 0.52-0.61 (m, 1H), 0.89-0.98 (m, 1H), 1.83 (s, 3H), 1.90 (s, 3H), 1.92 (s, 3H), 2.42-2.49 (m, 1H), 2.79 (dd, J=13.3, 13.3 Hz, 1H), 3.96-4.06 (m, 2H), 5.67 (br s, 2H), 6.68 (t, J=71.1 Hz, 1H), 7.52 (dd, J=8.9, 10.9 Hz, 1H), 7.72 (d, J=2.4 Hz, 1H), 8.39 (dd, J=3.0, 8.9 Hz, 1H), 8.48 (d, J=2.2 Hz, 1H), 10.19 (s, 1H). MS (ES+) m/z 571.2 [M+H].

N-(6-((3aS,4R,8R)-6-Amino-4,7,7-trimethyl-8-oxido-3,3a,4,7-tetrahydro-2H-isothiazolo[1,5-a][1,4]thiazin-4-yl)-5-fluoropyridin-2-yl)-4-chloro-1-(difluoromethyl)-1H-pyrazole-3-carboxamide (51AB)

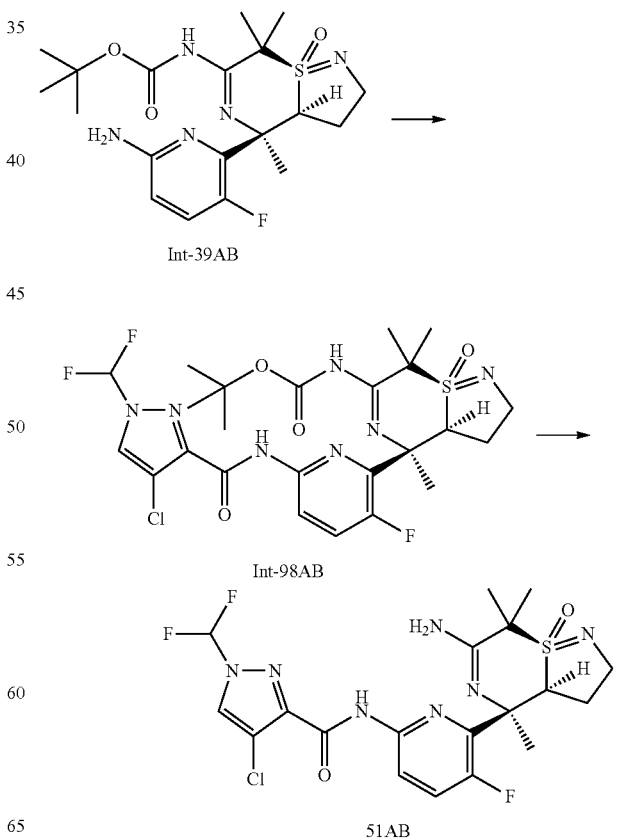

Int-39AB

Int-98AB

51AB

Step 1: tert-Butyl ((3aS,4R,8R)-4-(6-(4-chloro-1-(difluoromethyl)-1H-pyrazole-3-carboxamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-98AB)

4-Chloro-1-(difluoromethyl)-1H-pyrazole-3-carboxylic acid (111 mg, 565 μmol) was suspended in dichloromethane (5 mL), the suspension was cooled to 0-5° C. (ice bath) and oxalyl chloride (100 mg, 791 μmol) as well as dimethylformamide (0.308 M in toluene, 76 μL, 23 μmol) were added. The mixture was stirred for 3.5 h at room temperature. Then, it was concentrated in vacuo (40° C., 5 mbar) and dried azeotropically by addition of toluene (5 mL) followed by concentration in vacuo to afford 4-chloro-1-(difluoromethyl)-1H-pyrazole-3-carbonyl chloride as light yellow oil (121 mg, quant.). After that, tert-butyl ((3aS,4R,8R)-4-(6-amino-3-fluoropyridin-2-yl)-4,7,7-trimethyl-8-oxido-3,3a,4,7-tetrahydro-2H-isothiazolo[1,5-a][1,4]thiazin-6-yl)carbamate (Int-39AB, 100 mg, 235 mol) was dissolved in dichloromethane (5 mL), the solution cooled to 0-5° C. (ice bath) and N,N-diisopropylethylamine (46 mg, 62 μL, 353 μmol) and 4-(dimethylamino)pyridine (2.9 mg, 23.5 μmol) were added, followed by a solution of 4-chloro-1-(difluoromethyl)-1H-pyrazole-3-carbonyl chloride (vide supra, 61 mg, 282 mol) in dichloromethane (5 mL). The reaction mixture was stirred for 75 min at room temperature. Then, additional portions of N,N-diisopropylethylamine (46 mg, 62 μL, 353 mol) and a solution of 4-chloro-1-(difluoromethyl)-1H-pyrazole-3-carbonyl chloride (vide supra, 60 mg, 280 μmol) in dichloromethane (5 mL) were added, the mixture was stirred for 16 h at room temperature. After that, a third portion of N,N-diisopropylethylamine (46 mg, 62 μL, 353 mol) and a solution of 4-chloro-1-(difluoromethyl)-1H-pyrazole-3-carbonyl chloride (vide supra, 61 mg, 282 mol) in dichloromethane (5 mL) were added, the mixture was stirred for a further 1 h at room temperature. Aqueous sodium carbonate solution (10% m/m, 25 mL) was added, the aqueous phase was extracted with dichloromethane (2×25 mL), the combined organic extracts were dried (sodium sulfate) and concentrated in vacuo. The crude was purified by column chromatography (silica gel, 24 g, eluting with ethyl acetate/dichloromethane, gradient 35:65 to 100:0) to yield, after drying in vacuo (40° C., 5 mbar), the title compound as an off-white solid (71 mg, 50% yield). HPLC (method LCMS_fglm) $t_R$=1.31 min. MS (ES+) m/z 604.4 [M+H].

Step 2: N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-4-chloro-1-(difluoromethyl)-1H-pyrazole-3-carboxamide (51AB)

tert-Butyl ((3aS,4R,8R)-4-(6-(4-chloro-1-(difluoromethyl)-1H-pyrazole-3-carboxamido)-3-fluoropyridin-2-yl)-4,7,7-trimethyl-8-oxido-3,3a,4,7-tetrahydro-2H-isothiazolo[1,5-a][1,4]thiazin-6-yl)carbamate (Int-98AB, 71 mg, 118 μmol) was dissolved in dichloromethane (5 mL) and trifluoroacetic acid (268 mg, 181 μL, 2.35 mmol) was added. The solution was stirred for 18 h at room temperature. After that, the mixture was concentrated in vacuo, the residue was redissolved in methanol (5 mL), aqueous ammonia (25% m/m, 200 μL) was added, stirred for 5 min at room temperature, and concentrated in vacuo. The crude was purified by column chromatography (silica gel, 12 g, eluting with 2 M ammonia in methanol/dichlormethane, gradient 1:99 to 6:94) to yield, after drying in vacuo (40° C., 5 mbar), the title compound as a white solid (60 mg). Enantiomeric purification was performed by chiral preparative HPLC (Chiralpak AD, 250*4.6 mm*5 μm, isocratic, n-heptane/(ethanol+0.01% ammonium acetate) 80/20, flow 1.0 mL/min) to yield the desired second eluting enantiomer as an off-white powder (40 mg, 67%), and the opposite first eluting enantiomer as an off white powder (10 mg, 17%). HPLC (method LCMS_gradient) $t_R$=1.4 min. $^1$H NMR (CDCl$_3$, 300 MHz): δ 1.62-1.78 (m, 1H), 1.80 (s, 3H), 1.93 (s, 3H), 2.03-2.14 (m, 1H), 2.06 (s, 3H), 3.52 (dd, J=7.5, 10.5 Hz, 1H), 3.71 (ddd, J=5.0, 10.6, 10.6 Hz, 1H), 4.23 (ddd, J=2.1, 7.1, 12.4 Hz, 1H), 7.24 (t, J=59.8 Hz, 1H), 7.58 (dd, J=8.9, 10.3 Hz, 1H), 7.97 (s, 1H), 8.43 (dd, J=3.0, 8.9 Hz, 1H), 9.35 (s, 1H). MS (ES+) m/z 504.3 [M+H].

Examples 2BB, 3AB, 3BA, 3BB, 4AB, 4BA, 4BB, 5AA, 5AB, 5BA, 5BB, 6AB, 6BA, 6BB, 7AB, 7BA, 7BB, 8AB, 8BA, 8BB, 17AB, 17BA, 17BB, 18AA, 18AB, 18BA, 18BB, 19AA, 19AB, 19BA, 20AA, 20AB, 20BA, 20BB, 21AA, 21AB, 21BA, 21BB, 22AA, 22AB, 22BA, 22BB, 23AA, 23AB, 23BA, 23BB, 24AA, 24AB, 24BA and 24BB can analogously be synthesized.

The invention claimed is:
1. A compound of formula I:

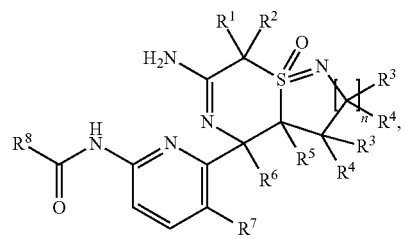

wherein:
n is 1, 2 or 3;
$R^1$ is selected from the group consisting of
  i) $C_{1-6}$-alkyl and
  ii) halogen-$C_{1-6}$-alkyl;
$R^2$ is selected from the group consisting of
  i) $C_{1-6}$-alkyl, and
  ii) halogen-$C_{1-6}$-alkyl;
or $R^1$ and $R^2$ form together with the C-atom they are attached to, a $C_{3-6}$-cycloalkyl-, wherein the $C_{3-6}$-cycloalkyl- is optionally substituted by one or more substituents selected from the group consisting of halogen and hydroxyl;
$R^3$ is each independently selected from the group consisting of
  i) hydrogen,
  ii) $C_{1-6}$-alkyl, and
  iii) halogen;
$R^4$ is each independently selected from the group consisting of
  i) hydrogen,
  ii) $C_{1-6}$-alkyl, and
  iii) halogen;
or wherein $R^3$ and $R^4$ together are $(CH_2)_m$—, wherein m is 2, 3, 4 or 5, R⁵ is hydrogen,
R⁶ is selected from the group consisting of
  i) $C_{1-6}$-alkyl, and
  ii) halogen-$C_{1-6}$-alkyl;
R⁷ is selected from the group consisting of
  i) hydrogen, and
  ii) halogen;
R⁸ is selected from the group consisting of
  i) aryl,
  ii) aryl substituted by 1-4 substituents individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, COOR⁹, wherein R⁹ is H or $C_{1-6}$-alkyl, CONR¹⁰R¹¹, wherein R¹⁰ is H or $C_{1-6}$-alkyl $C_{3-6}$-cycloalkyl and R¹¹ is H or $C_{1-6}$-alkyl, $C_{3-6}$-cycloalkyl that is optionally substituted by 1 to 4 substituents individually selected from the group consisting of halogen, cyano, $C_{1-6}$-alkyl and $C_{1-6}$-alkoxy, $C_{3-6}$-cycloalkyl-$C_{1-6}$-alkoxy and $C_{3-6}$-cycloalkyl-$C_{1-6}$-alkoxy, wherein the cycloalkyl unit is substituted by 1 to 4 substituents individually selected from the group consisting of halogen, cyano, $C_{1-6}$-alkyl and $C_{1-6}$-alkoxy;
  iii) heteroaryl, and
  iv) heteroaryl substituted by 1-4 substituents individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, COOR⁹, wherein R⁹ is H or $C_{1-6}$-alkyl, CONR¹⁰R¹¹, wherein R¹⁰ is H or $C_{1-6}$-alkyl $C_{3-6}$-cycloalkyl and R¹¹ is H or $C_{3-6}$-cycloalkyl that is optionally substituted by 1 to 4 substituents individually selected from the group consisting of halogen, cyano, $C_{1-6}$-alkyl and $C_{1-6}$-alkoxy, $C_{3-6}$-cycloalkyl-$C_{1-6}$-alkoxy and $C_{3-6}$-cycloalkyl-$C_{1-6}$-alkoxy, wherein the cycloalkyl unit is substituted by 1 to 4 substituents individually selected from the group consisting of halogen, cyano, $C_{1-6}$-alkyl and $C_{1-6}$-alkoxy;
or pharmaceutically acceptable salts thereof.

2. The compound according to claim 1, wherein
n is 1, 2 or 3;
R¹ is selected from the group consisting of
  i) $C_{1-6}$-alkyl and
  ii) halogen-$C_{1-6}$-alkyl;
R² is selected from the group consisting of
  i) $C_{1-6}$-alkyl, and
  ii) halogen-$C_{1-6}$-alkyl;
or R¹ and R² form together with the C-atom they are attached to, a $C_{3-6}$-cycloalkyl-, wherein the $C_{3-6}$-cycloalkyl- is optionally substituted by one or more substituents selected from the group consisting of halogen and hydroxyl;
R³ is each independently selected from the group consisting of
  i) hydrogen,
  ii) $C_{1-6}$-alkyl, and
  iii) halogen;
R⁴ is each independently selected from the group consisting of
  i) hydrogen,
  ii) $C_{1-6}$-alkyl, and
  iii) halogen;
R⁵ is hydrogen
R⁶ is selected from the group consisting of
  i) $C_{1-6}$-alkyl, and
  ii) halogen-$C_{1-6}$-alkyl;
R⁷ is selected from the group consisting of
  i) hydrogen, and
  ii) halogen;
R⁸ is selected from the group consisting of
  i) aryl,
  ii) aryl substituted by 1-4 substituents individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, $C_{3-6}$-cycloalkyl, $C_{3-6}$-cycloalkyl that is optionally substituted by 1 to 4 substituents individually selected from the group consisting of halogen, cyano, $C_{1-6}$-alkyl and $C_{1-6}$-alkoxy, $C_{3-6}$-cycloalkyl-$C_{1-6}$-alkoxy and $C_{3-6}$-cycloalkyl-$C_{1-6}$-alkoxy, wherein the cycloalkyl unit is substituted by 1 to 4 substituents individually selected from the group consisting of halogen, cyano, $C_{1-6}$-alkyl and $C_{1-6}$-alkoxy;
  iii) heteroaryl, and
  iv) heteroaryl substituted by 1-4 substituents individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{3-6}$-cycloalkyl that is optionally substituted by 1 to 4 substituents individually selected from the group consisting of halogen, cyano, $C_{1-6}$-alkyl and $C_{1-6}$-alkoxy, $C_{3-6}$-cycloalkyl-$C_{1-6}$-alkoxy and $C_{3-6}$-cycloalkyl-$C_{1-6}$-alkoxy, wherein the cycloalkyl unit is substituted by 1 to 4 substituents individually selected from the group consisting of halogen, cyano, $C_{1-6}$-alkyl and $C_{1-6}$-alkoxy;
or pharmaceutically acceptable salts thereof.

3. The compound according to claim 1, which is of formula Ia:

wherein n, R¹, R², R³, R⁴, R⁵, R⁶, R⁷ and R⁸ are as described in claim 1.

4. The compound according to claim 1, wherein R¹ is methyl.

5. The compound according to claim 1, wherein R² is methyl.

6. The compound according to claim 1, wherein R³ is hydrogen.

7. The compound according to claim 1, wherein R⁴ is hydrogen.

8. The compound according to claim 1, wherein R³ and R⁴ together are —(CH₂)₂—.

9. The compound according to claim 1, wherein R⁵ is hydrogen.

10. The compound according to claim 1, wherein $R^6$ is methyl.

11. The compound according to claim 1, wherein $R^7$ is F.

12. The compound according to claim 1, wherein $R^8$ is aryl substituted by 1-2 substituents individually selected from cyano and halogen.

13. The compound according to claim 1, wherein $R^8$ is phenyl substituted by 1-2 substituents individually selected from cyano and Cl.

14. The compound according to claim 1, wherein $R^8$ is heteroaryl, substituted by 1-2 substituents individually selected from cyano, halogen, halogen-$C_{1-6}$-alkoxy, halogen-$C_{1-6}$-alkyl, $C_{1-6}$-alkoxy, $C_{2-6}$-alkylnyl and $C_{1-6}$-alkyl.

15. The compound according to claim 1, wherein $R^8$ is heteroaryl, substituted by 1-2 substituents individually selected from cyano, halogen, halogen-$C_{1-6}$-alkoxy, $C_{1-6}$-alkoxy and $C_{1-6}$-alkyl.

16. The compound according to claim 1, wherein $R^8$ is 1H-pyrazolyl, pyridinyl, pyrazinyl or imidazo[1,2-a]pyridinyl, substituted by 1-2 substituents individually selected from cyano, halogen, halogen-$C_{1-6}$-alkoxy, halogen-$C_{1-6}$-alkyl, $C_{1-6}$-alkoxy, $C_{2-6}$-alkylnyl and $C_{1-6}$-alkyl.

17. The compound according to claim 1, wherein $R^8$ is pyridinyl, pyrazinyl or imidazo[1,2-a]pyridinyl, each substituted by 1-2 substituents individually selected from cyano, halogen, halogen-$C_{1-6}$-alkoxy, $C_{1-6}$-alkoxy and $C_{1-6}$-alkyl.

18. The compound according to claim 1, wherein n is 1 or 2.

19. The compound according to claim 1, selected from the group consisting of:
- N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide,
- N-(6-(3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide,
- N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide,
- N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide,
- N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide,
- N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide,
- N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide,
- N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide,
- N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide,
- N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide,
- N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide,
- N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide,
- N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide,
- N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide,
- N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide,
- N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide,
- N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide,
- N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide,
- N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoropicolinamide,
- N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide,
- N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide,
- N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide,
- N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide,
- N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide,
- N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide,
- N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-(difluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3,5-dichloropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-4-cyanobenzamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-2-chloro-4-cyanobenzamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-cyanopicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)-picolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-fluoropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-chloro-3-methylpicanamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-chloropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-(difluoromethoxy)-picolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2-difluoroethoxy)pyrazine-2-carboxamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(prop-1-yn-1-yl)picolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-7-chloro-3-methylimidazo[1,2-a]pyridine-2-carboxamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-7-chloro-3-methylimidazo[1,2-a]pyridine-2-carboxamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-7-chloro-3-methylimidazo[1,2-a]pyridine-2-carboxamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-7-chloro-3-methylimidazo[1,2-a]pyridine-2-carboxamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((4aR,5R,9R)-7-amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-5-cyano-3-methylpicolinamide, N-(6-((4aS,5R,9R)-7-amino-5,8,8-trimethyl-9-oxido-4,4a,5,8-tetrahydro-2H-spiro[[1,4]-thiazino[2,1-f][1,2]thiazine-3,1'-cyclopropan]-5-yl)-5-fluoropyridin-2-yl)-5-cyano-3-methylpicolinamide, N-(6-((4aR,5R,9R)-7-amino-5,8,8-trimethyl-9-oxido-4,4a,5,8-tetrahydro-2H-spiro[[1,4]-thiazino[2,1-f][1,2]thiazine-3,1'-cyclopropan]-5-yl)-5-fluoropyridin-2-yl)-3-chloro-5-cyanopicolinamide, N-(6-((4aR,5R,9R)-7-amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-3-chloro-5-(difluoro-methoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-4-chloro-1-(difluoromethyl)-1H-pyrazole-3-carboxamide, and 6-((6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)carbamoyl)nicotinic acid, or pharmaceutically acceptable salts thereof.

20. The compound according to claim 1, selected from the group consisting of:

N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-((3aR,4R,8S)-6-amino-4,7,7-trimethyl-8-oxido-3,3a, 4,7-tetrahydro-2H-isothiazolo[1,5-a][1,4]thiazin-4-yl)-5-fluoropyridin-2-yl)-5-chloro-3-methylpicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-(difluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3,5-dichloropicolinamide, N-(6-((3aS,4R,8R)-6-amino-4,7,7-trimethyl-8-oxido-3,3a,4,7-tetrahydro-2H-isothiazolo[1,5a][1,4]thiazin-4-yl)-5-fluoropyridin-2-yl)-4-cyanobenzamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-2-chloro-4-cyanobenzamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-cyanopicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)-picolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-fluoropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-chloro-3-methylpicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-chloropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-(difluoromethoxy)-picolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2-difluoroethoxy)pyrazine-2-carboxamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(prop-1-yn-1-yl)picolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-7-chloro-3-methylimidazo[1,2-a]pyridine-2-carboxamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9R)-7-amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-5-cyano-3-methylpicolinamide, N-(6-((4aS,5R,9R)-7-amino-5,8,8-trimethyl-9-oxido-4,4a,5,8-tetrahydro-2H-spiro[[1,4]-thiazino[2,1-f][1,2]thiazine-3,1'-cyclopropan]-5-yl)-5-fluoropyridin-2-yl)-5-cyano-3-methylpicolinamide, N-(6-((4aR,5R,9R)-7-amino-5,8,8-trimethyl-9-oxido-4,4a,5,8-tetrahydro-2H-spiro[[1,4]-thiazino[2,1-f][1,2]thiazine-3,1'-cyclopropan]-5-yl)-5-fluoropyridin-2-yl)-3-chloro-5-cyanopicolinamide, N-(6-((4aR,5R,9R)-7-amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-3-chloro-5-(difluoro-methoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-4-chloro-1-(difluoromethyl)-1H-pyrazole-3-carboxamide, and 6-((6-44aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)carbamoyl) nicotinic acid, or pharmaceutically acceptable salts thereof.

21. The compound according to claim 1, selected from the group consisting of:

N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aS,5R,9R)-7-amino-5,8,8-trimethyl-9-oxido-2,3,4,4a,5,8-hexahydro[1,4]thiazino[2,1-f][1,2]thiazin-5-yl)-5-fluoropyridin-2-yl)-5-cyano-3-methylpicolinamide, N-(6-((4aR,5R,9S)-7-amino-5,8,8-trimethyl-9-oxido-2,3,4,4a,5,8-hexahydro[1,4]thiazino[2,1-f][1,2]thiazin-5-yl)-5-fluoropyridin-2-yl)-5-cyano-3-methylpicolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aS,5R,9R)-7-amino-5,8,8-trimethyl-9-oxido-2,3,4,4a,5,8-hexahydro[1,4]thiazino[2,1-f][1,2]thiazin-5-yl)-5-fluoropyridin-2-yl)-3,5-dichloropicolinamide, N-(6-((4aR,5R,9S)-7-amino-5, 8,8-trimethyl-9-oxido-2,3,4,4a,5,8-hexahydro[1,4]thiazino[2,1-f][1,2]thiazin-5-yl)-5-fluoropyridin-2-yl)-3,5-dichloropicolinamide, N-(6-((4aS,5R,9S)-7-amino-5,8,8-trimethyl-9-oxido-2,3,4,4a,5,8-hexahydro[1,4]thiazino[2,1-f][1,2]thiazin-5-yl)-5-fluoropyridin-2-yl)-3,5-dichloropicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-7-chloro-3-methylimidazo[1,2-a]pyridine-2-carboxamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-7-chloro-3-methylimidazo[1,2-a]pyridine-2-carboxamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-7-chloro-3-methylimidazo[1,2-a]pyridine-2-carboxamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-7-chloro-3-methylimidazo[1,2-a]pyridine-2-carboxamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9R)-7-amino-5,8,8-trimethyl-9-oxido-2,3,4,4a,5,8-hexahydro[1,4]thiazino[2,1-f][1,2]thiazin-5-yl)-5-fluoropyridin-2-yl)-5-(2,2,3,3-tetrafluoropropoxy)picolinamide, N-(6-((4aS,5R,9R)-7-amino-5,8,8-trimethyl-9-oxido-2,3,4,4a,5,8-hexahydro[1,4]thiazino[2,1-f][1,2]thiazin-5-yl)-5-fluoropyridin-2-yl)-5-(2,2,3,3-tetrafluoropropoxy)picolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, N-(6-((3aR,4R,8S)-6-amino-4,7,7-trimethyl-8-oxido-3,3a,4,7-tetrahydro-2H-isothiazolo[1, 5-a][1,4]thiazin-4-yl)-5-fluoropyridin-2-yl)-5-cyano-3-methylpicolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-43aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aS,4R,8S)-6-amino-4,7,7-trimethyl-8-oxido-3,3a,4,7-tetrahydro-2H-isothiazolo[1,5a][1,4]thiazin-4-yl)-5-fluoropyridin-2-yl)-5-(difluoromethoxy)picolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aR,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, N-(6-((3aS,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5 aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aR,6R,10S)-8-amino-6,9,9-trimethyl-10-oxido-3,4,5,5a, 6,9-hexahydro-2H-[1,4]thiazino[2,1-g][1,2]thiazepin-6-yl)-5-fluoropyridin-2-yl)-5-fluoro-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aR,6R,10R)-8-amino-6,9,9-trimethyl-10-oxido-3,4,5,5a,6,9-hexahydro-2H-[1,4]thiazino[2, 1-g][1,2]thiazepin-6-yl)-5-fluoropyridin-2-yl)-5-chloro-3-methylpicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5 aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5 aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aS,6R,10R)-8-amino-6,9,9-trimethyl-10-oxido-3,4, 5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5 aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5 aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, and N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide or pharmaceutically acceptable salts thereof.

22. The compound according to claim 1, selected from the group consisting of:

N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aR,4R,8S)-6-amino-4,7,7-trimethyl-8-oxido-3,3a,4,7-tetrahydro-2H-isothiazolo[1,5a][1,4]thiazin-4-yl)-5-fluoropyridin-2-yl)-5-methoxypyrazine-2-carboxamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide, N-(6-((3aR,4R,8S)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-cyano-3-methylpicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-cyanopicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoro-3-methylpicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-fluoropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-chloro-3-methylpicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(fluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(2,2,3,3-tetrafluoropropoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-methoxypyrazine-2-carboxamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-(difluoromethoxy)pyrazine-2-carboxamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-5-fluoropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3-chloro-5-(difluoromethoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-3,5-dichloropicolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-4-cyanobenzamide, N-(6-((3aS,4R,8R)-6-amino-4,7,7-trimethyl-8-oxido-3,3a,4,7-tetrahydro-2H-isothiazolo[1,5a][1,4]thiazin-4-yl)-5-fluoropyridin-2-yl)-2-chloro-4-cyanobenzamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-cyanopicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)-picolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-fluoropicolinamide, N-(6-((4aR,5R,9R)-7-amino-3,3-difluoro-5,8,8-trimethyl-9-oxido-2,3,8-hexahydro-[1,4]thiazino[2,1-f][1,2]thiazin-5-yl)-5-fluoropyridin-2-yl)-5-chloro-3-methylpicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-chloropicolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-(difluoromethoxy)-picolinamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2-difluoroethoxy)pyrazine-2-carboxamide, N-(6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)-5-(prop-1-yn-1-yl)picolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aR,5R,9R)-7-amino-5,8,8-trimethyl-9-oxido-2,3,4,4a,5,8-hexahydro-[1, 4]thiazino[2,1-f][1,2]thiazin-5-yl)-5-fluoropyridin-2-yl)-5-fluoro-3-methylpicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-6-chloro-3-methylimidazo[1,2-a]pyridine-2-carboxamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-6-chloro-3-methylimidazo[1,2-a]pyridine-2-carboxamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aR,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-6-chloro-3-methylimidazo[1,2-a]pyridine-2-carboxamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(difluoromethoxy)picolinamide, N-(6-((4aS,5R,9R)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-cyano-3-methylpicolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-methoxypyrazine-2-carboxamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3,5-dichloropicolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-fluoro-3-methylpicolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-3-chloro-5-cyanopicolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-6-chloro-3-methylimidazo[1,2-a]pyridine-2-carboxamide, N-(6-((4aS,5R,9S)-7-amino-5,8,8-trimethyl-9-oxido-2,3a,4a,5,8-hexahydro-[1,4]thiazino[2,1-f][1,2]thiazin-5-yl)-5-fluoropyridin-2-yl)-5-(difluoromethoxy)picolinamide, N-(6-((4aS,5R,9S)-7-amino-5,8,8-trimethyl-9-oxido-2,3,4,4a,5,8-hexahydro-[1,4]thiazino[2,1-f][1,2]thiazin-5-yl)-5-fluoropyridin-2-yl)-5-(2,2,3,3-tetrafluoropropoxy)picolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aR,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5 aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5 aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-45aR,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aS,6R,10R)-8-amino-6,9,9-trimethyl-10-oxido-3,4, 5,5a,6,9-hexahydro-2H-[1,4]thiazino[2,1-g][1,2]thiazepin-6-yl)-5-fluoropyridin-2-yl)-3-chloro-5-fluoropicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aS,6R,10R)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-cyano-3-methylpicolinamide, N-(6-((5aS,6R,10S)-8-amino-6,9,9-trimethyl-1-oxido-3,4,5,5a,6,9-hexahydro-2H-[1,4]thiazino[2,1-g][1,2]thiazepin-6-yl)-5-fluoropyridin-2-yl)-5-fluoro-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-3-chloro-5-fluoropicolinamide, N-(6-45aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-chloro-3-methylpicolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(fluoromethoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(difluoromethoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-(2,2,3,3-tetrafluoropropoxy)picolinamide, N-(6-((5aS,6R,10S)-8-amino-6,9,9-trimethyl-10-oxido-3,4,5,5a,6,9-hexahydro-2H-[1,4]thiazino[2,1-g][1,2]thiazepin-6-yl)-5-fluoropyridin-2-yl)-5-methoxypyrazine-2-carboxamide, N-(6-((4aR,5R,9R)-7-amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-5-cyano-3-methylpicolinamide, N-(6-((4aS,5R,9R)-7-amino-5,8,8-trimethyl-9-oxido-4,4a,5,8-tetrahydro-2H-spiro[[1,4]-thiazino[2,1-f][1,2]thiazine-3,1'-cyclopropan]-5-yl)-5-fluoropyridin-2-yl)-5-cyano-3-methylpicolinamide, N-(6-((4aR,5R,9R)-7-amino-5,8,8-trimethyl-9-oxido-4,4a,5,8-tetrahydro-2H-spiro[[1,4]-thiazino[2,1-f][1,2]thiazine-3,1'-cyclopropan]-5-yl)-5-fluoropyridin-2-yl)-3-chloro-5-cyanopicolinamide, N-(6-((4aR,5R,9R)-7-amino-5,8,8-trimethyl-9-oxido-4,4a,5,8-tetrahydro-2H-spiro[[1,4]thiazino[2,1-f][1,2]thiazine-3,1'-cyclopropan]-5-yl)-5-fluoropyridin-2-yl)-3-chloro-5-(difluoro-methoxy)picolinamide, N-(6-((3aS,4R,8R)-6-amino-4,7,7-trimethyl-8-oxido-3,3a,4,7-tetrahydro-2H-isothiazolo[1,5-a][1,4]thiazin-4-yl)-5-fluoropyridin-2-yl)-4-chloro-1-(difluoromethyl)-1H-pyrazole-3-carboxamide, and 6-((6-((4aR,5R,9R)-7-amino-3,3-difluoro-5,8,8-trimethyl-9-oxido-2,3,4,4a,5,8-hexahydro-[1,4]thiazino[2,1-f][1,2]thiazin-5-yl)-5-fluoropyridin-2-yl)carbamoyl)nicotinic acid, or pharmaceutically acceptable salts thereof.

23. A pharmaceutical composition, comprising a therapeutically effective amount of a compound according to claim 1 and a pharmaceutically acceptable carrier.

24. A method for treating Alzheimer's disease, comprising the step of administering a therapeutically effective amount of a compound of a compound according to claim 1 to a human being or animal in need thereof.

* * * * *